US006645990B2

(12) United States Patent
Askew et al.

(10) Patent No.: US 6,645,990 B2
(45) Date of Patent: Nov. 11, 2003

(54) THIAZOLYL UREA COMPOUNDS AND METHODS OF USES

(75) Inventors: Benny C. Askew, Newbury Park, CA (US); Frenel F. De Morin, Thousand Oaks, CA (US); Andrew Hague, Camarillo, CA (US); Ellen Laber, Ventura, CA (US); Aiwen Li, Westlake Village, CA (US); Gang Liu, Oak Park, CA (US); Patricia Lopez, Northridge, CA (US); Rana Nomak, Westlake Village, CA (US); Vincent Santora, Ladera Ranch, CA (US); Christopher Tegley, Thousand Oaks, CA (US); Kevin Yang, San Gabriel, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 10/077,124

(22) Filed: Feb. 15, 2002

(65) Prior Publication Data

US 2002/0193405 A1 Dec. 19, 2002

Related U.S. Application Data

(63) Continuation-in-part of application No. 09/930,753, filed on Aug. 14, 2001.
(60) Provisional application No. 60/225,793, filed on Aug. 15, 2000.

(51) Int. Cl.[7] .................. C07D 211/26; A61K 31/44
(52) U.S. Cl. .............. 514/342; 514/241; 514/247; 514/256; 514/315; 544/162; 544/180; 544/182; 544/224; 544/333; 546/229; 546/268.7
(58) Field of Search ................ 546/229, 268.7; 544/162, 180, 182, 224, 338, 333; 514/241, 247, 256, 315

(56) References Cited

U.S. PATENT DOCUMENTS

| | | | |
|---|---|---|---|
| 4,260,765 A | 4/1981 | Harrison et al. | |
| 5,208,248 A | 5/1993 | Baker et al. | |
| 5,294,596 A | 3/1994 | Haas et al. | |
| 5,364,871 A | 11/1994 | Takasugi et al. | |
| 5,395,818 A | 3/1995 | Haas et al. | |
| 5,693,667 A | 12/1997 | Phillion et al. | |
| 5,821,245 A | 10/1998 | Howard, Jr. | |
| 5,945,380 A | 8/1999 | Gallenkamp et al. | |

FOREIGN PATENT DOCUMENTS

| | | |
|---|---|---|
| DE | 4204 492 A1 | 8/1992 |
| EP | 0 468 695 A1 | 1/2002 |
| GB | 2 263 109 A | 7/1993 |
| GB | 2 293 380 A | 3/1996 |
| HU | 1 437 895 | 6/1976 |
| WO | WO 89/00568 | 1/1989 |
| WO | WO 96/23783 | 8/1996 |
| WO | WO 97/01552 | 1/1997 |
| WO | WO 98/52558 | 11/1998 |
| WO | WO 98/57969 | 12/1998 |
| WO | WO 99/00357 | 1/1999 |
| WO | WO 99/21555 | 5/1999 |
| WO | WO 99/23091 | 5/1999 |
| WO | WO 99/24416 | 5/1999 |
| WO | WO 99/32106 | 7/1999 |
| WO | WO 99/32110 | 7/1999 |
| WO | WO 99/32111 | 7/1999 |
| WO | WO 99 /32436 | 7/1999 |
| WO | WO 99/32455 | 7/1999 |
| WO | WO 99/32463 | 7/1999 |
| WO | WO 99/46244 | 9/1999 |
| WO | WO 99/58502 | 11/1999 |
| WO | WO 99/65884 | 12/1999 |
| WO | WO 00/24735 | 5/2000 |
| WO | WO 00/24739 | 5/2000 |
| WO | WO 00/26203 | 5/2000 |

OTHER PUBLICATIONS

Maccioni et al., "The protein kinase Cdk5 Structural aspects, roles in neurogenesis and involvement in Alzheimer's patholgy" Eur. J. Biochem., 268;1518–1527 (2001).
Noguchi et al., "Involvement of Cyclins in Cell Proliferation and Their Clinical Implications in Soft Tissue Smooth Muscle Tumors." Amer. J. of Pathology, 156:6, 2135–2147 (2000).
Paglini et al., "The role of the Cdk5–p35 kinase in neuronal development." Eur. J. Biochem., 268: 1528–1533 (2001).
Senderowicz et al., "Preclinical and Clinical development of cyclin–dependent kinase modulators." J. of the Natl. Cancer Inst., 92:5, 376–387 (2000).

Primary Examiner—Joseph K. McKane
Assistant Examiner—Kamal Saeed
(74) Attorney, Agent, or Firm—Joseph W. Bulock; Ron K. Levy; Stuart L. Watt

(57) ABSTRACT

Selected novel urea compounds are effective for prophylaxis and treatment of diseases, such as cell proliferation or apoptosis mediated diseases. The invention encompasses novel compounds, analogs, prodrugs and pharmaceutically acceptable salts thereof, pharmaceutical compositions and methods for prophylaxis and treatment of diseases and other maladies or conditions involving stoke, cancer and the like. The subject invention also relates to processes for making such compounds as well as to intermediates useful in such processes.

18 Claims, No Drawings

THIAZOLYL UREA COMPOUNDS AND METHODS OF USES

RELATED APPLICATIONS

This application is a continuation in part application of application Ser. No. 09/930,753, filed Aug. 14, 2001 which claims the benefit of U.S. Provisional Application No. 60/225,793, filed Aug. 15, 2000, which are hereby incorporated by reference.

This application is a continuation in part application of application Ser. No. 09/930,753, filed Aug. 14, 2001, which claims priority to provisional application No. 60/225,793, filed Aug. 15, 2000.

FIELD OF THE INVENTION

This invention is in the field of pharmaceutical agents and specifically relates to compounds, compositions, uses and methods for treating cell proliferation-related disorders, cell death and apoptosis-related disorders.

BACKGROUND OF THE INVENTION

Identification of therapeutic agents effective in the treatment of neoplastic diseases or for the treatment of neurological disorders is the subject of significant research efforts.

Protein kinases represent a large family of proteins which play a central role in the regulation of a wide variety of cellular processes and maintaining control over cellular function. A partial list of such kinases includes ab1, Akt, bcr-abl, Blk, Brk, Btk, c-kit, c-met, c-src, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, FLK-4, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. As such, inhibition of kinases has become an important therapeutic target.

Cell proliferation is the rapid reproduction of cells, such as by cell division The cell cycle, which controls cell proliferation, is itself controlled by a family of serine-threonine kinases called cyclin dependent kinases (CDKs). The regulation of CDK activation is complex, and requires the association of the CDK with a member of the cyclin family of regulatory subunits. A further level of regulation occurs through both activating and inactivating phosphorylations of the CDK subunit. The coordinate activation and inactivation of different cyclin/CDK complexes is necessary for normal progression through the cell cycle. Both the critical G1-S and G2-M transitions are controlled by the activation of different cyclin/CDK activities. Loss of control of CDK regulation is a frequent event in hyperproliferative diseases and cancer. (T. Noguchi et al., Am. J. Pathol., 156, 2135–47 (2000)) As such, inhibition of CDKs has become an important target in the study of chemotherapeutics (A. Senderowicz and E. Sausville, J. Nat. Canc. Instit., 92, 376–87 (2000))

Kinases have also been implicated in diseases and disorders of the central nervous system. For example, patients suffering from stroke, Alzheimer's disease or Parkinson's disease would benefit from the inhibition of kinases. Cdk5 has been shown to be involved in Alzheimer's pathology (R. Maccioni, et al., Eur. J. Biochem., 268, 1518–27 (2001)) and with neuronal development (G. Paglini and A. Caceres, Eur. J. Biochem., 268, 1528–33 (2001)).

Protein kinases also control programmed cell death, also known as apoptosis. Apoptosis is a ubiquitous physiological process used to eliminate damaged or unwanted cells in multicellular organisms. Disregulation of apoptosis is believed to be involved in the pathogenesis of many human diseases. The failure of apoptotic cell death has been implicated in various cancers, as well as autoimmune disorders. Conversely, increased apoptosis is associated with a variety of diseases involving cell loss such as neurodegenerative disorders and AIDS. As such, inhibition of apoptosis has become an important therapeutic target. Cdk5 has been shown to be involved in apoptosis pathology (A. Catania et al., Neuro-Oncology, 89–98 (April 2001)).

Substituted heterocyclic compounds are known in the pesticide art. WO00/24735, published May 4, 2000, describes 1-pyridyl-1,2,4-triazoles as pesticides. WO00/24739, published May 4, 2000, describes substituted 1,2,4-triazoles as pesticides. WO97/01552, published Jan. 16, 1997, describes substituted 1,2,4-triazoles as antifungal agents. DE4204492 describes substituted benzamides as pesticides. WO98/57969, published Dec. 23, 1998, describes heterocyclylpyridines as pesticides. GB2293380, published Mar. 27, 1996, describes the use of heterocyclic compounds as pesticides. U.S. Pat. No. 5,693,667, issued Dec. 2, 1997, describes heterocyclic compounds for the treatment of take-all disease. EP468695 describes fungicide compounds. U.S. Pat. No. 5,294,596, issued Mar. 15, 1994, describes herbicidal triazolinones. U.S. Pat. No. 5,395,818, issued Mar. 7, 1995, describes herbicidal triazolinones.

Substituted thiazoles also are known in the pesticide art. U.S. Pat. No. 4,260,765, issued Apr. 7, 1981, describes 2-(3-pyridyl)-5-thiazolecarboxamides for the treatment of aphids. U.S. Pat. No. 5,945,380, issued Aug. 31, 1999, describes 4-(4-pyridyl)pyrazoles as insecticides. WO89/00568, published Jan. 26, 1989, describes nicotine derivatives as fungicides.

Heterocyclic ureas are known in the pharmaceutical art. WO99/23091, published May 14, 1999, describes heterocyclic compounds as anti-inflammatories. WO99/32455, published Jul. 1, 1999, describes heterocyclic ureas as RAF kinase inhibitors. WO99/32110, published Jul. 1, 1999, describes heterocyclic ureas as p38 kinase inhibitors. WO99/32106, published Jul. 1, 1999, describes heterocyclic ureas as RAF kinase inhibitors. WO99/32111, published Jul. 1, 1999, describes heterocyclic ureas as p38 kinase inhibitors. WO99/32436, published Jul. 1, 1999, describes urea compounds as inhibitors of RAF kinase. WO99/32463, published Jul. 1, 1999, describes urea compounds that inhibit p38 kinase. WO98/52558, published Nov. 26, 1998, describes urea compounds for the inhibition of p38 kinase. WO99/00357, published Jan. 7, 1999, describes the use of urea compounds as inhibitors of p38 kinase. WO99/58502, published Nov. 18, 1999, describes urea compounds as inhibitors of p38 kinase. U.S. Pat. No. 5,821,245, issued Oct. 13, 1998, describes substituted naphthalene derivatives for treating cell growth. GB patent 1,437,895 describes 2-thiazolyl ureas for the treatment of ulcers. U.S. Pat. No. 5,364,871, issued Nov. 15, 1994 describes thiazoles as anti-ulcer compounds. WO99/21555, published May 6, 1999, describes pyridyl-substituted thiazoles as adenosine A3 receptor antagonists. WO96/23783 describes indole derivatives as 5-HT receptor antagonists. U.S. Pat. No. 5,208,248 describes indazole derivatives as 5-HT receptor antagonists. WO99/46244, published Sep. 16, 1999 describes heterocyclic compounds as tyrosine phosphatases. GB patent 2,263,109, published Jul. 14, 1993, describes pyridylthiazoles as PAF-receptor antagonists.

Thiazole compounds have also been described as inhibitors of CDK. WO00/26203, published May 11, 2000, describes 2-ureidothiazoles as inhibitors of cdk. WO99/65884 describes 2-aminothiazoles as inhibitors of CDK. WO99/24416 describes 2-aminothiazoles as inhibitors of CDK.

However, compounds of the current invention have not been described as inhibitors of cell proliferation or apoptosis such as for the treatment of cancer or stroke.

DESCRIPTION OF THE INVENTION

A class of compounds useful in treating cell proliferative disorders, neurological disorders and apoptosis is defined by Formula I

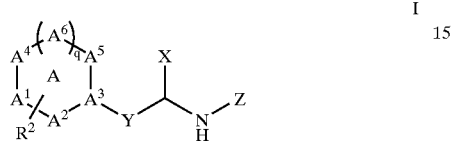

wherein each of $A^1$–$A^6$ is selected from $CH_2$, CH, C, O, S, NH and N; wherein $A^1$–$A^6$ together form a ring A selected from
a) additionally substituted or unsubstituted 5- or 6-membered heterocyclyl,
preferably 5- or 6-membered heteroaryl,
more preferably 5-membered heteroaryl selected from thiazolyl, oxazolyl, imidazolyl, pyrrolyl, pyrazolyl, isoxazolyl, triazolyl and isothiazolyl, and
6-membered heteroaryl selected from pyridyl, pyrazinyl, pyrimidinyl and pyridazinyl,
even more preferably 5-membered heteroaryl selected from thiazolyl, oxazolyl and imidazolyl, and 6-membered heteroaryl selected from pyridyl, and pyrimidinyl,
b) additionally substituted or unsubstituted 5- or 6-membered heteroaryl fused with a phenyl group,
c) additionally substituted or unsubstituted 5- or 6-membered cycloalkenyl,
preferably 5-membered cycloalkenyl,
more preferably cyclopentadienyl or cyclopentenyl, and
d) additionally substituted or unsubstituted phenyl,
wherein A is additionally substituted with one or more substituents independently selected from halo, —$OR^3$, —$SR^3$, —$CO_2R^3$, —$CO_2NR^3R^3$, —$COR^3$, —$NR^3R^3$, —$SO_2NR^3R^3$, —$NR^3C(O)OR^3$, —$NR^3C(O)R^3$, cycloalkyl, optionally substituted phenylalkylenyl, optionally substituted 5–6 membered heterocyclyl, optionally substituted heteroarylalkylenyl, optionally substituted phenyl, lower alkyl, cyano, lower hydroxyalkyl, nitro, lower alkenyl, lower alkynyl and lower haloalkyl,
preferably one or more substituents independently selected from halo, —$OR^3$, —$SR^3$, —$S(O)R^3$, —$CO_2R^3$, —$CO_2NR^3R^3$, —$COR^3$, —$NR^3R^3$, —$SO_2NR^3R^3$—$NR^3C(O)OR^3$, —$NR^3C(O)R^3$, $C_1$–$C_2$ alkyl, cyano, $C_1$–$C_2$ hydroxyalkyl, nitro, $C_2$–$C_3$ alkenyl, $C_2$–$C_3$ alkynyl and $C_1$–$C_2$ haloalkyl,
more preferably one or more substituents independently selected from fluoro, hydroxy, methoxy, amino and methyl;
wherein X and Z taken together form a nitrogen containing ring selected from
unsubstituted 5–6 membered heterocyclyl,
unsubstituted 5–6 membered heterocyclyl fused with a phenyl group,
5–6 membered heterocyclyl substituted with one or more substituents independently selected from $R^1$, and
5–6 membered nitrogen-containing heterocyclyl, fused with a phenyl group, substituted with one or more substituents independently selected from $R^1$,
preferably a ring selected from substituted or unsubstituted 5- or 6-membered nitrogen-containing heteroaryl, and substituted or unsubstituted 5- or 6-membered nitrogen-containing heteroaryl fused with a phenyl group,
more preferably substituted or unsubstituted thiazolyl, pyridyl, pyrazinyl, pyrimidinyl, pyridazinyl, triazinyl, isoindolyl, indolyl, indazolyl, purinyl, [1,6]naphthyridinyl, 5,6,7,8-tetrahydro[1,6]naphthyridinyl, isoquinolyl and quinolyl,
even more preferably pyridyl, pyrazinyl, pyrimidinyl, pyridazinyl, [1,6]naphthyridinyl and 5,6,7,8-tetrahydro[1,6]naphthyridinyl,
most preferably pyridyl, pyrazinyl, pyrimidinyl and pyridazinyl,
most preferred pyridyl;
wherein $R^1$ is independently selected from H, halo, —$OR^3$, —$SR^3$, —$CO_2R^3$, —$CO_2NR^3R^3$, —$COR^3$, —$CONR^3R^3$, —$NR^3R^3$, —$C(S)NR^3R^3$, —$SO_2NR^3R^3$, —$NR^3C(O)OR^3$, —$NR^3C(O)R^3$ cycloalkyl, optionally substituted phenylalkylenyl, optionally substituted 4–10 membered heterocyclyl, optionally substituted 4–10 membered heterocyclylalkyl, optionally substituted phenyl, optionally substituted phenoxy, lower alkyl, lower cyano, lower alkenyl, lower alkynyl and lower haloalkyl,
preferably optionally substituted pyrrolidinyl, optionally substituted piperazinyl, optionally substituted piperidinyl, morpholinyl, optionally substituted pyridyl, 1,4-dioxa-8-aza-spiro[4.5]decyl, optionally substituted phenyl, $C_1$–$C_4$ alkyl, $C_1$–$C_2$ haloalkyl, halo, $C_1$–$C_4$-hydroxyalkyl, amino, $C_1$–$C_4$-azidoalkyl, $C_1$–$C_4$-cyanoalkyl, $C_1$–$C_4$-aminoalkyl, hydroxy, $C_1$–$C_4$-alkoxy-$C_1$–$C_4$-alkyl, $C_1$–$C_4$-alkylamino-$C_1$–$C_4$-alkyl, $C_1$–$C_4$-hydroxyalkylamino-$C_1$–$C_4$-alkyl, amino-$C_1$–$C_4$-alkoxy-$C_1$–$C_4$-alkyl, $C_1$–$C_4$-alkylamino-$C_1$–$C_4$-alkylamino-$C_1$–$C_4$-alkyl, (optionally substituted pyrrolidinyl)-$C_1$–$C_2$alkyl, (optionally substituted piperidinyl)-$C_1$–$C_2$-alkyl, (optionally substituted piperazinyl)-$C_1$–$C_2$-alkyl, 4-morpholinyl-$C_1$–$C_2$-alkyl, (optionally substituted imidazolyl)-$C_1$–$C_2$-alkyl, phthalimidylethyl, optionally substituted azepanyl-$C_1$–$C_2$-alkyl, 1,4-dioxa-8-aza-spiro[4.5]decyl-$C_1$–$C_2$-alkyl, optionally substituted pyridyloxy, optionally substituted phenoxy, tetrahydrofuryl-O-, (1-aza-bicyclo[2.2.2]oct-3-yl)-oxy, optionally substituted phenoxy-$C_1$–$C_2$-alkyl, optionally substituted pyrrolidinyl-$C_1$–$C_4$-alkoxy, optionally substituted azetidinyl-$C_1$–$C_4$-alkoxy, optionally substituted piperidinyl-$C_1$–$C_4$-alkoxy, tetrahydrofuryl-$C_1$–$C_4$-alkoxy, $C_1$–$C_4$-alkylamino-$C_1$–$C_4$alkoxy morpholinyl-$C_1$–$C_4$-alkylenylaminocarbonyl, $C_1$–$C_4$-alkoxycarbonyl, 5–6-membered heterocyclyl-$C_1$–$C_4$-alkylaminocarbonyl, 5–6-membered N-containing heterocyclylcarbonyl, $C_1$–$C_4$-alkylaminocarbonyl, $C_1$–$C_4$-alkylamino-$C_1$–$C_4$-alkylaminocarbonyl, 5-6-membered N-containing heterocyclyl-$C_1$–$C_4$-alkylamino, aminocarbonyl, $C_1$–$C_3$-alkylaminothiocarbonyl, $C_1$–$C_4$-alkylamino and $C_1$–$C_4$-alkylamino-$C_1$–$C_4$-alkylamino,
more preferably 3-(N,N-dimethylamino)-1-pyrrolidinyl, 1-methyl-4-piperazinyl, 1-benzyl-4-piperazinyl, 1-(2- pyrimidinyl)-4-piperazinyl, 1-(2-pyridyl)-4-piperazinyl, 1-ethyl-4-piperazinyl, piperidinyl, morpholinyl, 4-amino-1-piperidinyl, 4-(N-hydroxyethylamino)-1-piperidinyl, 4-(N-propylamino)-1-piperidinyl, 4-(N-benzylamino)-1-piperidinyl, 4-oxo-piperidinyl, 4-(hydroxyimino)-piperidinyl, 4-morpholinyl, 1,4-dioxa-8-aza-spiro[4.5]decyl, pyridyl, phenyl, methyl, ethyl, propyl, isopropyl, butyl, sec-butyl, isobutyl, tert-butyl, amino, azidomethyl, hydroxymethyl, trifluoromethyl, difluoromethyl, pentafluoroethyl, fluoro, chloro, bromo, aminoethyl, aminomethyl, cyanomethyl, 1-pyrrolidinyl-$CH_2$—, 2-methoxycarbonyl-1-pyrrolidinyl-$CH_2$—, 2-carboxy-1-pyrrolidinyl-$CH_2$—, 2-hydroxymethyl-1-pyrrolidinyl-$CH_2$—, 1-piperidinyl-$CH_2$—, 4-methyl-1-piperidinyl-$CH_2$—, 3-methyl-1-piperidinyl-$CH_2$—, 2-methyl-1-piperidinyl-$CH_2$—, 3,5-dimethyl-1-piperidinyl-$CH_2$—, 4-oxo-1-piperidinyl-$CH_2$—, 4-hydroxy-1-piperidinyl-$CH_2$—, 3-hydroxy-1-piperidinyl-$CH_2$—, 2-ethoxycarbonyl-1-piperidinyl-$CH_2$—, 3-ethoxycarbonyl-1-piperidinyl-$CH_2$—, 3-carboxy-1-piperidinyl-$CH_2$—, 4-ethoxycarbonyl-1-piperidinyl-$CH_2$—, 4-carboxy-1-piperidinyl-$CH_2$—, 4-(1-pyrrolidinyl)-1-piperidinyl-$CH_2$—, 4-(N-hydroxyethylamino)-1-piperidinyl-$CH_2$—, 4-(N-propylamino)-1-piperidinyl-$CH_2$—, 1-methyl-4-piperazinyl-$CH_2$—, 4-morpholinyl-$CH_2$—, (2-methyl-1-imidazolyl-$CH_2$—, 3-(N,N-diethylamino)carbonyl-1-piperidinyl-$CH_2$—, phthalimidylethylenyl, 1-azepanyl-$CH_2$—, 1,4-dioxa-8-aza-spiro[4.5]decyl-$CH_2$—, 4-(methyl)phenoxymethylenyl, 4-(N,N-dimethylaminomethylenyl)phenoxymethylenyl, methylaminothiocarbonyl, methoxymethylenyl, ethylaminothiocarbonyl, N,N-dimethylaminoethylenyl, N,N-diethylaminomethylenyl, N-methylaminoethylenyl, N-methylaminomethylenyl, N-(hydroxypropyl)aminomethylenyl, N-ethylaminomethylenyl, Boc-aminoethoxymethylenyl, aminoethoxymethylenyl, (1-aza-bicyclo[2.2.2]oct-3-yl)-oxy, 2-pyrrolidinylmethoxy, 1-methyl-2-pyrrolidinylmethoxy, azetidin-3-ylmethoxy, N-Boc-azetidin-3-ylmethoxy, N-Boc-piperidin-4-ylethoxy, 1-methyl-4-piperidinylethoxy, 4-piperidinylethoxy, 4-piperidinylmethoxy, N,N-dimethylaminoethoxy, 3-tetrahydrofuryl-O—, 3-tetrahydrofurylmethoxy, 4-tetrahydrofurylmethoxy, 4-methylphenoxy, 4-(aminoethyl)phenoxy, 4-(1-imidazolyl)phenoxy, 2,4dimethylphenoxy, phenoxy, 4-cyanophenoxy, 4-[1,3]dioxolan-2-ylphenoxy, 4-fluorophenoxy, 3,4-difluorophenoxy, ethoxycarbonyl, morpholinylethylenylaminocarbonyl, morpholinylpropylenylaminocarbonyl, 1-piperidinylcarbonyl, methylaminocarbonyl, ethylaminocarbonyl, N,N-diethylaminocarbonyl, N-(N',N'-dimethylaminoethylenyl)aminocarbonyl, aminocarbonyl, morpholinylethylenylamino, morpholinylpropylenylamino, N,N-diethylamino, N,N-dimethylamino, N,N-diethylamino(2-propylenyl)aminomethylenyl, N,N-diethylamino(1-propylenyl)aminomethylenyl and N-(N',N'-dimethylaminoethylenyl)amino;

wherein Y is selected from

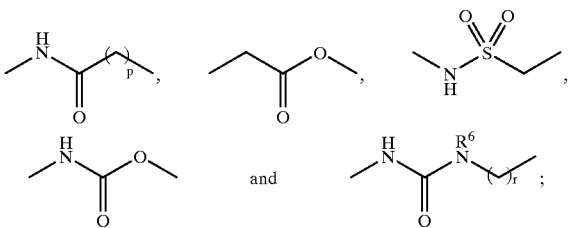

preferably Y is selected from

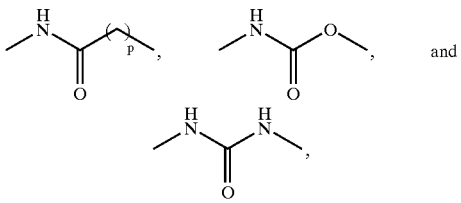

more preferably Y is selected from

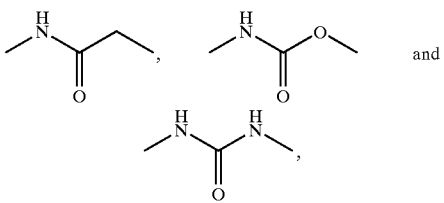

even more preferably Y is

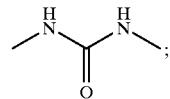

wherein $R^2$ is selected from
  a) lower alkylaminoalkynyl,
  b) cycloalkenyl-$C_{2-3}$-alkynyl,
  c) cycloalkyl-$C_{2-3}$-alkynyl,
  d) phenyl-$C_{2-3}$-alkynyl,
  e) 5–6 membered heterocyclyl-$C_{2-3}$-alkynyl,
  f) substituted or unsubstituted cycloalkenyl,
  g) substituted or unsubstituted phenyl,
  h) substituted or unsubstituted 5–6 membered heterocyclyl, and
  i) substituted or unsubstituted 5–6 membered heterocyclyl bridged with a phenyl group,
  preferably substituted phenyl, substituted or unsubstituted 5–6 membered nitrogen-containing heteroaryl, and substituted or unsubstituted 5–6 membered nitrogen-containing heteroaryl fused with a phenyl group,
  more preferably substituted or unsubstituted substituted phenyl or a substituted or unsubstituted heterocyclyl substituent selected from thiazolyl, pyridyl, pyrazinyl, pyrimidinyl, pyridazinyl, triazinyl, isoindolyl, indolyl, indazolyl, purinyl, isoquinolyl and quinolyl,
  even more preferably phenyl, pyridyl, pyrazinyl, pyrimidinyl, pyridazinyl, purinyl, isoquinolyl and quinolyl, most preferably pyridyl, pyrazinyl, pyrimidinyl and pyridazinyl, preferred pyridyl;

wherein substituted $R^2$ is substituted with one or more substituents independently selected from halo, —$OR^3$, —$SR^3$, —$CO_2R^3$, —$CO_2NR^3R^3$, —$COR^3$, —$NR^3R^3$, —$C(O)NR^3R^3$, —$SO_2NR\ R^3$, —$NR^3C(O)R^3$, —NHC(O) $R^3$, —$SO_2NHC(O)R^3$, —$C(S)NR^3R^3$, nitro, cycloalkyl, optionally substituted phenylalkylenyl, optionally substituted 4–7 membered heterocyclyl, optionally substituted heterocyclylalkylenyl, optionally substituted phenyl, optionally substituted phenoxyalkylenyl, optionally substituted heterocyclyloxyalkyl, lower alkyl, cyano, lower hydroxyalkyl, lower alkoxyalkyl, lower azidoalkyl, lower aminoalkyl, lower (hydroxyalkyl)aminoalkyl, lower alkylaminoalkyl, lower alkylaminoalkoxy, lower aminoalkoxyalkyl, lower (alkylaminoalkyl)amino lower ((alkylamino)alkylamino)alkyl, lower alkylaminoalkylaminocarbonyl, lower cyanoalkyl, lower alkenyl, lower alkynyl and lower haloalkyl, preferably selected from $C_1$–$C_4$ alkyl, $C_1$–$C_2$ haloalkyl, halo, amino, $C_1$–$C_2$-alkoxy, $C_1$–$C_2$-alkoxy-$C_1$–$C_2$-alkyl, hydroxy, $C_1$–$C_2$-alkylthio, cyano, $C_1$–$C_2$-haloalkyloxy, aminosulfonyl, (6-membered N-containing heterocyclyl) sulfonyl, $C_1$–$C_2$-haloalkylaminocarbonyl, nitro, $C_1$–$C_2$-haloalkylcarbonylaminosulfonyl, $C_1$–$C_2$-alkylaminosulfonyl, $C_3$–$C_6$-cycloalkylaminosulfonyl, phenyl-$C_1$–$C_2$-alkylaminosulfonyl, (optionally substituted phenyl) aminosulfonyl, piperidinyl, morpholinyl, $C_1$–$C_2$ alkylpiperazinyl, $C_1$–$C_3$ alkylaminothiocarbonyl, $C_1$–$C_2$-alkylamino-$C_1$–$C_4$-alkylenyl, morpholinyl-$C_1$–$C_4$-alkylenylaminocarbonyl, aminocarbonyl, $C_1$–$C_2$-alkylcarbonylamino, morpholinyl-$C_1$–$C_4$-alkylenylamino, $C_1$–$C_2$-alkylamino and $C_1$–$C_2$-alkylamino-$C_1$–$C_4$-alkylenylamino, more preferably selected from nitro, methylcarbonylamino, aminosulfonyl, phenylsulfonylamino, morpholinylsulfonyl, trifluoroacetylaminosulfonyl, (4-chlorophenyl)aminosulfonyl, hydroxy, methylthio, cyano, trifluoromethoxy, bromo, chloro, fluoro, amino, methoxy, ethoxy, ethoxymethyl, trifluoromethylcarbonylamino, trifluoroethoxy, pyridyl, phenyl, methyl, ethyl, propyl, isopropyl, butyl, sec-butyl, isobutyl, tert-butyl, trifluoromethyl, difluoromethyl, pentafluoroethyl, carboxy, methylthio, piperidinyl, morpholinyl, N-methylpiperazinyl, N-ethylpiperazinyl, methylaminothiocarbonyl, N-methylamino-methylenyl, N,N-dimethylaminoethylenyl, N,N-diethylaminomethylenyl, N,N-dimethylamino, N-methylaminoethylenyl, N,N-diethylamino, morpholinylethylenylaminocarbonyl, morpholinylpropylenylaminocarbonyl, aminocarbonyl, morpholinylethylenylamino, morpholinylpropylenylamino, N,N-dimethylamino and N,N-di-methylaminoethylenylamino;

wherein $R^3$ is selected from H, lower alkyl, optionally substituted phenyl, optionally substituted phenylalkyl, optionally substituted heterocyclyl, optionally substituted heterocyclylalkyl, $C_3$–$C_6$ cycloalkyl, and lower haloalkyl, preferably H, $C_1$–$C_3$ alkyl, phenyl, 5–6 membered heteroaryl, $C_5$–$C_6$ cycloalkyl, and $C_1$–$C_3$ haloalkyl;

more preferably H, methyl, ethyl, optionally substituted phenyl, benzyl, and trifluoromethyl;

wherein $R^6$ is selected from H, alkyl, 5–6 membered heterocyclylalkylenyl and alkylamino, preferably H;

wherein p is 1–2, preferably p is 1;

wherein q is 0 or 1; and wherein r is 0, 1, 2 or 3, preferably 0 or 1, more preferably 0;

and pharmaceutically acceptable salts thereof;

provided A is not thiazol-2-yl when Y is ureido; further provided A is not phenyl when $R^2$ is pyridyl or pyrimidyl when Y is ureido and when X and Z taken together form 1-methylindolyl; further provided A is not 1-phenylpyrazol-4-yl when Y is ureido when X and Z taken together form pyrazolyl and when $R^2$ is pyrrol-1-yl; further provided A is not thiazolyl or dihydrothiazolyl when $R^2$ is indolyl when Y is ureido and when X and Z taken together form thiazolyl or dihydrothiazolyl; provided A is not thiazolyl when $R^2$ is 3-pyridyl when Y is ureido and when X and Z taken together form 2-(3-pyridyl)thiazol-4-yl; and further provided A is not thien-3-yl when Y is ureido when X and Z taken together form thienyl and when $R^2$ is pyrrol-1-yl.

The invention also relates to compounds of Formula Ia

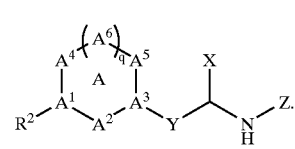

The invention also relates to compounds of Formula I wherein A is selected from

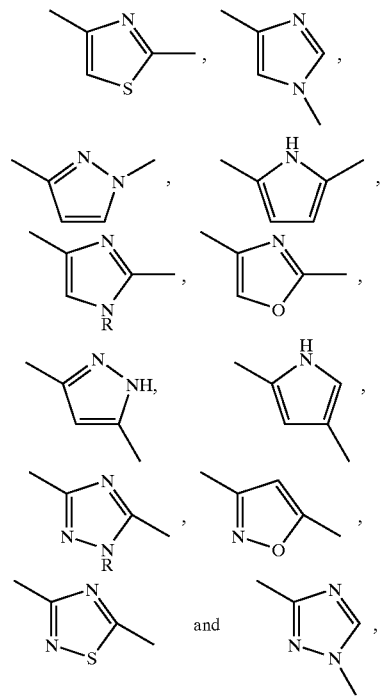

preferably A is

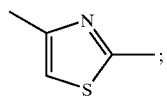

and
wherein R is selected from H and $C_1$–$C_3$ alkyl; and pharmaceutically acceptable salts thereof.

The invention also relates to compounds of Formula II

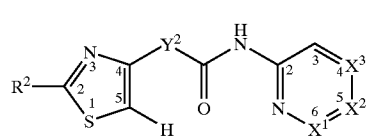

wherein $X^1$ is $CR^1$ or N; wherein x is $CR^1$ or N; wherein $X^3$ is CH or N; provided only one of $X^1$, $X^2$ and $X^3$ can be N;

wherein $R^1$ is one or more substituents selected from H, optionally substituted pyrrolidinyl, optionally substituted piperazinyl, optionally substituted piperidinyl, morpholinyl, 1,4-dioxa-8-aza-spiro[4.5]decyl, pyridyl, phenyl, $C_1$–$C_6$-alkyl, $C_1$–$C_2$-haloalkyl, $C_1$–$C_4$-hydroxyalkyl, amino, $C_1$–$C_4$-azidoalkyl, $C_1$–$C_4$-cyanoalkyl, $C_1$–$C_4$-aminoalkyl, halo, hydroxy, (optionally substituted pyrrolidinyl)-$C_1$–$C_2$-alkyl, (optionally substituted piperidinyl)-$C_1$–$C_2$-alkyl, (optionally substituted piperazinyl)-$C_1$–$C_2$-alkyl, morpholinyl-$C_1$–$C_2$-alkyl, (optionally substituted imidazolyl)-$C_1$–$C_2$-alkyl, phthalimidyl-$C_1$–$C_2$-alkyl, optionally substituted azepanyl-$C_1$–$C_2$-alkyl, 1,4-dioxa-8-aza-spiro[4.5]decyl-$C_1$–$C_2$-alkyl, optionally substituted phenoxy-$C_1$–$C_2$-alkyl, $C_1$–$C_4$-alkylaminothiocarbonyl, $C_1$–$C_4$-alkoxy-$C_1$–$C_4$-alkyl, $C_1$–$C_4$-alkylamino-$C_1$–$C_4$-alkyl, $C_1$–$C_4$-hydroxyalkylamino-$C_1$–$C_4$-alkyl, amino-$C_1$–$C_4$-alkoxy-$C_1$–$C_4$-alkyl, (1-aza-bicyclo[2.2.2]oct-3-yl)-oxy, optionally substituted pyrrolidinyl-$C_1$–$C_4$-alkoxy, optionally substituted azetidinyl-$C_1$–$C_4$-alkoxy, optionally substituted piperidinyl-$C_1$–$C_4$-alkoxy, $C_1$–$C_4$-alkylamino-$C_1$–$C_4$-alkoxy, tetrahydrofuryl-O—, tetrahydrofuryl-$C_1$–$C_4$-alkoxy, optionally substituted pyridyloxy, optionally substituted phenoxy, $C_1$–$C_4$-alkoxycarbonyl, 5–6-membered heterocyclyl-$C_1$–$C_4$-alkylaminocarbonyl, 5–6-membered N-containing heterocyclylcarbonyl, $C_1$–$C_4$-alkylaminocarbonyl, $C_1$–$C_4$-alkylamino-$C_1$–$C_4$-alkylaminocarbonyl, aminocarbonyl, 5–6-membered N-containing heterocyclyl-$C_1$–$C_4$-alkylamino, $C_1$–$C_4$-alkylamino, $C_1$–$C_4$-alkylamino-$C_1$–$C_4$-alkylamino-$C_1$–$C_4$-alkyl, and $C_1$–$C_4$-alkylamino-$C_1$–$C_4$-alkylamino;

wherein $R^2$ is selected from halo, $C_1$–$C_4$-alkyl, $C_1$–$C_4$-alkylamino-$C_2$–$C_4$-alkynyl, $C_3$–$C_6$-cycloalkyl, optionally substituted benzodioxolyl, optionally substituted indolyl, optionally substituted phenoxy, unsubstituted 5-membered oxygen or sulfur containing heteroaryl, unsubstituted 6-membered nitrogen-containing heterocyclyl, phenyl optionally substituted with one or two substituents selected
from halo, $C_1$–$C_4$-alkylamino, amino, nitro, $C_1$–$C_4$-alkoxy, $C_1$–$C_2$-haloalkyl, hydroxy, $C_1$–$C_4$-alkylthio, $C_1$–$C_4$-alkylcarbonylamino, (optionally substituted phenyl)sulfonylamino, cyano, $C_1$–$C_2$-haloalkoxy, 5- or 6-membered N-containing heterocyclyl, aminosulfonyl, (6-membered N-containing heterocyclyl)sulfonyl, $C_1$–$C_2$-haloalkylcarbonylaminosulfonyl and (optionally substituted phenyl)aminosulfonyl, and 6-membered nitrogen-containing heterocyclyl substituted with one or more substituents independently selected from pyridyl, phenyl,
$C_1$–$C_4$ alkyl, $C_1$–$C_2$ haloalkyl, $C_1$–$C_2$ alkoxy, amino, halo, piperidinyl, morpholinyl, $C_1$–$C_2$ alkylpiperazinyl, $C_1$–$C_3$ alkylaminothiocarbonyl, N,N-di-$C_1$–$C_2$-alkylamino-$C_1$–$C_4$-alkylenyl, N—$C_1$–$C_2$ alkylamino-$C_1$–$C_4$-alkylenyl, morpholinyl-$C_1$–$C_4$-alkylenylaminocarbonyl, aminocarbonyl, $C_1$–$C_2$-haloalkylcarbonylamino, morpholinyl-$C_1$–$C_4$-alkylenylamino, N,N-di-$C_1$–$C_2$-alkylamino and N,N-di-$C_1$–$C_2$-alkylamino-$C_1$–$C_4$-alkylenylamino; and wherein $Y^2$ is selected from O, NH and $CH_2$;
and pharmaceutically acceptable salts thereof.

The invention also relates to compounds of Formula III

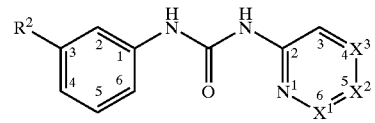

wherein $X^1$ is $CR^1$ or N; wherein $X^2$ is $CR^1$ or N; wherein $X^3$ is CH or N; provided only one of $X^1$, $X^2$ and $X^3$ can be N; preferably $X^1$ is $CR^1$; $X^2$ is $CR^1$; $X^3$ is CH; provided $X^2$ is CH when $X^1$ is not CH;

wherein $R^1$ is one or more substituents independently selected from H, optionally substituted pyrrolidinyl, optionally substituted piperazinyl, optionally substituted piperidinyl, morpholinyl, 1,4-dioxa-8-aza-spiro[4.5] decyl, pyridyl, phenyl, $C_1$–$C_6$-alkyl, $C_1$–$C_2$-haloalkyl, $C_1$–$C_4$-hydroxyalkyl, amino, $C_1$–$C_4$-azidoalkyl, $C_1$–$C_4$-cyanoalkyl, $C_1$–$C_4$-aminoalkyl, halo, hydroxy, (optionally substituted pyrrolidinyl)-$C_1$–$C_2$-alkyl, (optionally substituted piperidinyl)-$C_1$–$C_2$-alkyl, (optionally substituted piperazinyl)-$C_1$–$C_2$-alkyl, morpholinyl-$C_1$–$C_2$-alkyl, (optionally substituted imidazolyl)-$C_1$–$C_2$-alkyl, phthalimidyl-$C_1$–$C_2$-alkyl, optionally substituted azepanyl-$C_1$–$C_2$-alkyl, 1,4-dioxa-8-aza-spiro[4.5]decyl-$C_1$–$C_2$-alkyl, optionally substituted phenoxy-$C_1$–$C_2$-alkyl, $C_1$–$C_4$-alkylaminothiocarbonyl, $C_1$–$C_4$-alkoxy-$C_1$–$C_4$-alkyl, $C_1$–$C_4$-alkylamino-$C_1$–$C_4$-alkyl, $C_1$–$C_4$-hydroxyalkylamino-$C_1$–$C_4$-alkyl, amino-$C_1$–$C_4$-alkoxy-$C_1$–$C_4$-alkyl, (1-aza-bicyclo[2.2.2]oct-3-yl)-oxy, optionally substituted pyrrolidinyl-$C_1$–$C_4$-alkoxy, optionally substituted azetidinyl-$C_1$–$C_4$-alkoxy, optionally substituted piperidinyl-$C_1$–$C_4$-alkoxy, $C_1$–$C_4$-alkylamino-$C_1$–$C_4$-alkoxy, tetrahydrofuryl-O—, tetrahydrofuryl-$C_1$–$C_4$-alkoxy, optionally substituted pyridyloxy, optionally substituted phenoxy, $C_1$–$C_4$-alkoxycarbonyl, 5–6-membered heterocyclyl-$C_1$–$C_4$-alkylaminocarbonyl, 5–6-membered N-containing heterocyclylcarbonyl, $C_1$–$C_4$-alkylaminocarbonyl, $C_1$–$C_4$-alkylamino-$C_1$–$C_4$-alkylaminocarbonyl, aminocarbonyl, 5–6-membered N-containing heterocyclyl-$C_1$–$C_4$-alkylamino, $C_1$–$C_4$-alkylamino, $C_1$–$C_4$-alkylamino-$C_1$–$C_4$-alkylamino-$C_1$–$C_4$-alkyl, and $C_1$–$C_4$-alkylamino-$C_1$–$C_4$-alkylamino, preferably H, methyl, ethyl, propyl, 1-methyl-4-piperazinyl, l-benzyl-4-piperazinyl, 1-(2-pyrimidinyl)-4-piperazinyl, 1-(2-pyridyl)-4-piperazinyl, 1-ethyl-4-piperazinyl, 1-piperidinyl-$CH_2$—, 4-methyl-1-piperidinyl-$CH_2$—, 3-methyl-1-piperidinyl-$CH_2$—, 2-methyl-1-piperidinyl- $CH_2$—, 3,5-dimethyl-1-piperidinyl-$CH_2$—, 4-oxo-1-piperidinyl-$CH_2$—, 4-hydroxy-1-piperidinyl-$CH_2$—, 3-hydroxy-1-piperidinyl-$CH_2$—, 2-ethoxycarbonyl-1-piperidinyl-$CH_2$—, 3-ethoxycarbonyl-1-piperidinyl-$CH_2$—, 3-carboxy-1-piperidinyl-$CH_2$—, 4-ethoxycarbonyl-1-piperidinyl-$CH_2$—, 4-carboxy-1-piperidinyl-$CH_2$—, 4-(1-pyrrolidinyl)-1-piperidinyl-$CH_2$—, 4-(N-hydroxyethylamino)-1-piperidinyl-$CH_2$—, 4-(N-propylamino)-1-piperidinyl-$CH_2$—, 3-(N,N-diethylamino)carbonyl-1-piperidinyl-$CH_2$—, 4-morpholinyl-$CH_2$—, N,N-dimethylaminoethylenyl, N,N-diethylaminomethylenyl, N-methylaminomethylenyl, N-ethylaminomethylenyl and N,N-diethylamino, more preferably ethyl, propyl, 1-methyl-4-piperazinyl, 1-piperidinyl-$CH_2$—, 4-morpholinyl-$CH_2$—, N,N-diethylaminomethylenyl and N,N-diethylamino; and wherein $R^2$ is selected from halo, $C_1$–$C_4$-alkyl, $C_1$–$C_4$-alkylamino-$C_2$–$C_4$-alkynyl, $C_3$–$C_6$-cycloalkyl, optionally substituted benzodioxolyl, optionally substituted indolyl, optionally substituted phenoxy, unsubstituted 5-membered oxygen or sulfur containing heteroaryl, unsubstituted 5- or 6-membered nitrogen-containing heterocyclyl, phenyl optionally substituted with one or two substituents selected from halo, $C_1$–$C_4$-alkylamino, amino, nitro, $C_1$–$C_4$-alkoxy, $C_1$–$C_2$-haloalkyl, hydroxy, $C_1$–$C_4$-alkylthio, $C_1$–$C_4$-alkylcarbonylamino, (optionally substituted phenyl)sulfonylamino, cyano, $C_1$–$C_2$-haloalkoxy, 5- or 6-membered N-containing heterocyclyl, aminosulfonyl, (6-membered N-containing heterocyclyl)sulfonyl, $C_1$–$C_2$-haloalkylcarbonylaminosulfonyl and (optionally substituted phenyl)aminosulfonyl, and 6-membered nitrogen-containing heterocyclyl substituted with one or more substituents independently selected from pyridyl, phenyl, $C_1$–$C_4$ alkyl, $C_1$–$C_2$ haloalkyl, $C_1$–$C_2$ alkoxy, amino, halo, piperidinyl, morpholinyl, $C_1$–$C_2$ alkylpiperazinyl, $C_1$–$C_3$ alkylaminothiocarbonyl, N,N-di-$C_1$–$C_2$-alkylamino-$C_1$–$C_4$-alkylenyl, N—$C_1$–$C_2$-alkylamino-$C_1$–$C_4$-alkylenyl, morpholinyl-$C_1$–$C_4$-alkylenylaminocarbonyl, aminocarbonyl, $C_1$–$C_2$-haloalkylcarbonylamino, morpholinyl-$C_1$–$C_4$-alkylenylamino, N,N-di-$C_1$–$C_2$ alkylamino and N,N-di-$C_1$–$C_2$-alkylamino-$C_1$–$C_4$-alkylenylamino, preferably 3-(N,N-dimethylamino)-1-propynyl, 3-fluorophenyl, 4-fluorophenyl, 4-(N,N-dimethylamino)phenyl, 3-(methylcarbonylamino) phenyl, phenyl, 3-trifluoromethylphenyl, 4-trifluoromethylphenyl, 4-aminophenyl, 3-aminophenyl, 4-aminosulfonylphenyl, 4-(4-morpholinylsulfonyl)phenyl, 4-(trifluoroacetylaminosulfonyl)phenyl, 4-(trifluoromethylcarbonylaminosulfonyl)phenyl, 4-[(4-chlorophenyl)aminosulfonyl]phenyl, 3-(phenylsulfonylamino)phenyl, 2,4-difluorophenyl, 2,4-dimethoxyphenyl, 3-hydroxyphenyl, 4-hydroxyphenyl, 4-ethoxyphenyl, 3,4-dimethoxyphenyl, 4-methylthiophenyl, 4-cyanophenyl, 4-trifluoromethoxyphenyl, 4-methoxyphenyl, 3-nitrophenyl, 3-methoxyphenyl, 2-methoxyphenyl, 2-thiazolyl, 2-pyrazinyl, 5-pyrimidinyl, 4-methyl-1-piperazinyl, 4-morpholinyl, 6-methoxy-3-pyridyl, 2-methoxy-3-pyridyl, 2-ethoxy-3-pyridyl, 3,4-dichloro-4-pyridyl, 6-(trifluoromethylcarbonylamino)-3-pyridyl, 6-amino-3-pyridyl, 3,5-dichloro-4-pyridyl, 2-chloro-4-pyridyl, 3-pyridyl and 4-pyridyl, more preferably 5-pyrimidinyl, 2-pyrazinyl, morpholinyl, 4-methylpiperazinyl, 4-fluorophenyl, 4-(N,N-dimethylamino)propynyl, 3-nitrophenyl, 3-aminophenyl, 4-aminosulfonylphenyl, 3-aminosulfonylphenyl, 3-(phenylsulfonylamino) phenyl, 3-(methylcarbonylamino)phenyl, 4-[(trifluoromethylcarbonyl)aminosulfonyl]phenyl, 4-hydroxyphenyl, 4-methoxyphenyl, 2-thiazolyl, 6-(trifluoromethylcarbonylamino)-3-pyridyl, 6-amino-3-pyridyl, 3-pyridyl and 4-pyridyl;

and pharmaceutically acceptable salts thereof.

The invention also relates to compounds of Formula IV

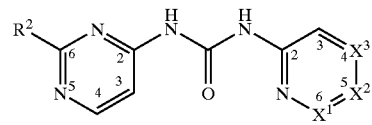

IV wherein $X^1$ is $CR^1$ or N; wherein $X^2$ is $CR^1$ or N; wherein $X^3$ is CH or N; provided only one of $X^1$, $X^2$ and $X^3$ can be N; preferably $X^1$ is $CR^1$; X is $CR^1$; X is CH; provided $X^2$ is CH when $X^1$ is not CH;

wherein $R^1$ is one or more substituents selected from H, optionally substituted pyrrolidinyl, optionally substituted piperazinyl, optionally substituted piperidinyl, morpholinyl, 1,4-dioxa-8-aza-spiro[4.5]decyl, pyridyl, phenyl, $C_1$–$C_6$-alkyl, $C_1$–$C_2$-haloalkyl, $C_1$–$C_4$-hydroxyalkyl, amino, $C_1$–$C_4$-azidoalkyl, $C_1$–$C_4$-cyanoalkyl, $C_1$–$C_4$-aminoalkyl, halo, hydroxy, (optionally substituted pyrrolidinyl)-$C_1$–$C_2$-alkyl, (optionally substituted piperidinyl)-$C_1$–$C_2$-alkyl, (optionally substituted piperazinyl)-$C_1$–$C_2$-alkyl, morpholinyl-$C_1$–$C_2$-alkyl, (optionally substituted imidazolyl)-$C_1$–$C_2$-alkyl, phthalimidyl-$C_1$–$C_2$-alkyl, optionally substituted azepanyl-$C_1$–$C_2$-alkyl, 1,4-dioxa-8-aza-spiro[4.5]decyl-$C_1$–$C_2$-alkyl, optionally substituted -phenoxy-$C_1$–$C_2$-alkyl, $C_1$–$C_4$-alkylaminothiocarbonyl, $C_1$–$C_4$-alkoxy-$C_1$–$C_4$-alkyl, $C_1$–$C_4$-alkylamino-$C_1$–$C_4$-alkyl, $C_1$–$C_4$-hydroxyalkylamino-$C_1$–$C_4$-alkyl, amino-$C_1$–$C_4$-alkoxy-$C_1$–$C_4$-alkyl, (1-aza-bicyclo[2.2.2]oct-3-yl)-oxy, optionally substituted pyrrolidinyl-$C_1$–$C_4$-alkoxy, optionally substituted azetidinyl-$C_1$–$C_4$-alkoxy, optionally substituted piperidinyl-$C_1$–$C_4$-alkoxy, $C_1$–$C_4$-alkylamino-$C_1$–$C_4$-alkoxy, tetrahydrofuryl-O—, tetrahydrofuryl-$C_1$–$C_4$-alkoxy, optionally substituted pyridyloxy, optionally substituted phenoxy, $C_1$–$C_4$-alkoxycarbonyl, 5–6-membered heterocyclyl-$C_1$–$C_4$-alkylaminocarbonyl, 5–6-membered N-containing heterocyclylcarbonyl, $C_1$–$C_4$-alkylaminocarbonyl, $C_1$–$C_4$-alkylamino-$C_1$–$C_4$-alkylaminocarbonyl, aminocarbonyl, 5–6-membered N-containing heterocyclyl-$C_1$–$C_4$-alkylamino, $C_1$–$C_4$-alkylamino, $C_1$–$C_4$-alkylamino-$C_1$–$C_4$-alkylamino-$C_1$–$C_4$-alkyl, and $C_1$–$C_4$-alkylamino-$C_1$–$C_4$-alkylamino, preferably methyl, ethyl, propyl, 1-methyl-4-piperazinyl, 1-benzyl-4-piperazinyl, 1-(2-pyrimidinyl)-4-piperazinyl, 1-(2-pyridyl)-4-piperazinyl, 1-ethyl-4-piperazinyl, 1-piperidinyl-$CH_2$—, 4-methyl-1-piperidinyl-$CH_2$—, 3-methyl-1-piperidinyl-$CH_2$—, 2-methyl-1-piperidinyl-$CH_2$—, 3,5-dimethyl-1-piperidinyl-$CH_2$—, 4-oxo-1-piperidinyl-$CH_2$—, 4-hydroxy-1-piperidinyl-$CH_2$—, 3-hydroxy-1-piperidinyl-$CH_2$—, 2-ethoxycarbonyl-1-piperidinyl- CH$_2$—, 3-ethoxycarbonyl-1-piperidinyl-CH$_2$—, 3-carboxy-1-piperidinyl-CH$_2$—, 4-ethoxycarbonyl-1-piperidinyl-CH$_2$—, 4-carboxy-1-piperidinyl-CH$_2$—, 4-(1-pyrrolidinyl)-1-piperidinyl-CH$_2$—, 4-(N-hydroxyethylamino)-1-piperidinyl-CH$_2$—, 4-(N-propylamino)-1-piperidinyl-CH$_2$—, 3-(N,N-diethylamino)carbonyl-1-piperidinyl-CH$_2$—, 4-morpholinyl-CH$_2$—, N,N-dimethylaminoethylenyl, N,N-diethylaminomethylenyl, N-methylaminomethylenyl, N-ethylaminomethylenyl and N,N-diethylamino, and more preferably ethyl, propyl and 1-methyl-4-piperazinyl; and wherein R$^2$ is halo, C$_1$–C$_4$-alkyl, C$_1$–C$_4$-alkylamino-C$_2$–C$_4$-alkynyl, C$_3$–C$_6$-cycloalkyl, optionally substituted benzodioxolyl, optionally substituted indolyl, optionally substituted phenoxy, 5-membered oxygen or sulfur containing heteroaryl, 5- or 6-membered nitrogen-containing heterocyclyl, phenyl optionally substituted with one or two substituents selected from halo, C$_1$–C$_4$-alkylamino, amino, C$_1$–C$_4$-alkoxy, C$_1$–C$_2$-haloalkyl, hydroxy, C$_1$–C$_4$-alkylthio, cyano, C$_1$–C$_2$-haloalkyloxy, aminosulfonyl, (6-membered N-containing heterocyclyl)sulfonyl, C$_1$–C$_2$-haloalkylcarbonylaminosulfonyl, and (optionally substituted phenyl)aminosulfonyl, and 6-membered nitrogen-containing heterocyclyl substituted with one or more substituents independently selected from pyridyl, phenyl, C$_1$–C$_4$ alkyl, C$_1$–C$_2$ haloalkyl, C$_1$–C$_2$ alkoxy, halo, piperidinyl, morpholinyl, C$_1$–C$_2$ alkylpiperazinyl, C$_1$–C3 alkylaminothiocarbonyl, N,N-di-C$_1$–C$_2$ alkylamino-C$_1$–C$_4$-alkylenyl, N—C$_1$–C$_2$-alkylamino-C$_1$–C$_4$-alkylenyl, morpholinyl-C$_1$–C$_4$-alkylenylaminocarbonyl, aminocarbonyl, morpholinyl-C$_1$–C$_4$-alkylenylamino, N,N-di-C$_1$–C$_2$-alkylamino and N,N-di-C$_1$–C$_2$-alkylamino-C$_1$–C$_4$-alkylenylamino, preferably 3-fluorophenyl, 4-fluorophenyl, 4-(N,N-dimethylamino)phenyl, 3-(methylcarbonylamino)phenyl, phenyl, 3-trifluoromethylphenyl, 4-trifluoromethylphenyl, 4-aminophenyl, 3-aminophenyl, 4-aminosulfonylphenyl, 4-(4-morpholinylsulfonyl)phenyl, 4-(trifluoroacetylaminosulfonyl)phenyl, 4-(trifluoromethylcarbonylaminosulfonyl)phenyl, 4-[(4-chlorophenyl)aminosulfonyl]phenyl, 3-(phenylsulfonylamino)phenyl, 2,4-difluorophenyl, 2,4-dimethoxyphenyl, 3-hydroxyphenyl, 4-hydroxyphenyl, 3-ethoxyphenyl, 3,4-dimethoxyphenyl, 4-methylthiophenyl, 4-cyanophenyl, 4-trifluoromethoxyphenyl, 4-methoxyphenyl, 3-nitrophenyl, 3-methoxyphenyl, 2-methoxyphenyl, 2-thiazolyl, 2-pyrazinyl, 5-pyrimidinyl, 4-methyl-1-piperazinyl, 4-morpholinyl, 6-methoxy-3-pyridyl, 2-methoxy-3-pyridyl, 2-ethoxy-3-pyridyl, 3,4-dichloro-4-pyridyl, 6-(trifluoromethylcarbonylamino)-3-pyridyl, 6-amino-3-pyridyl, 3,5-dichloro-4-pyridyl, 2-chloro-4-pyridyl, 3-pyridyl and 4-pyridyl, and more preferably 4-pyridyl;

and pharmaceutically acceptable salts thereof.

The invention also relates to compounds of Formula V wherein R$^7$ is selected from halo, C$_1$–C$_4$-alkyl, C$_3$–C$_6$-cycloalkyl, optionally substituted benzodioxolyl, optionally substituted indolyl, optionally substituted phenoxy, 5-membered oxygen or sulfur containing heteroaryl, 6-membered nitrogen-containing heterocyclyl, phenyl optionally substituted with one or two substituents selected from halo, C$_1$–C$_4$-alkylamino, amino, C$_1$–C$_4$-alkoxy, C$_1$–C$_2$-haloalkyl, hydroxy, C$_1$–C$_4$-alkylthio, cyano, C$_1$–C$_2$-haloalkyloxy, aminosulfonyl, (6-membered N-containing heterocyclyl) sulfonyl, C$_1$–C$_2$haloalkylcarbonylaminosulfonyl, and (optionally substituted phenyl)aminosulfonyl, and 6-membered nitrogen-containing heterocyclyl substituted with one or more substituents independently selected from pyridyl, phenyl, C$_1$–C$_4$ alkyl, C$_1$–C$_2$ haloalkyl, C$_1$–C$_2$ alkoxy, halo, piperidinyl, morpholinyl, C$_1$–C$_2$ alkylpiperazinyl, C$_1$–C3 alkylaminothiocarbonyl, N,N-di-C$_1$–C$_2$ alkylamino-C$_1$–C$_4$-alkylenyl, N—C$_1$–C$_2$-alkylamino-C$_1$–C$_4$-alkylenyl, morpholinyl-C$_1$–C$_4$-alkylenylaminocarbonyl, aminocarbonyl, morpholinyl-C$_1$–C$_4$-alkylenylamino, N,N-di-C$_1$–C$_2$-alkylamino and N,N-di-C$_1$–C$_2$-alkylamino-C$_1$–C$_4$-alkylenylamino, preferably halo, C$_1$–C$_4$-alkyl, C$_3$–C$_6$-cycloalkyl, optionally substituted pyrimidinyl, morpholinyl, optionally substituted piperidinyl, optionally substituted benzodioxolyl, optionally substituted indolyl, optionally substituted phenoxy, optionally substituted thienyl, phenyl optionally substituted with one or two substituents selected from halo, C$_1$–C$_4$-alkylamino, Boc-amino, amino, C$_1$–C$_4$-alkoxy, C$_1$–C$_2$-haloalkyl, hydroxy, C$_1$–C$_4$-alkylthio, cyano, C$_1$–C$_2$-haloalkyloxy, aminosulfonyl, (6-membered N-containing heterocyclyl)sulfonyl, C$_1$–C$_2$-haloalkylcarbonylaminosulfonyl, and (optionally substituted phenyl)aminosulfonyl, and pyridyl optionally substituted with one or two substituents selected from C$_1$–C$_3$ alkyl, C$_1$–C$_4$-alkoxy and halo, more preferably bromo, chloro, fluoro, C$_1$–C$_3$-alkyl, C$_3$–C$_6$-cycloalkyl, optionally substituted pyrimidinyl, morpholinyl, piperidinyl, -benzodioxolyl, indolyl, phenoxy, thienyl, phenyl optionally substituted with one or two substituents selected from fluoro, N,N-dimethylamino, amino, methoxy, trifluoromethyl, Boc-amino, hydroxy, ethoxy, methylthio, cyano, trifluoromethoxy, aminosulfonyl, 4-morpholinylsulfonyl, trifluoroacetylaminosulfonyl, and (4-chlorophenyl)aminosulfonyl, and pyridyl optionally substituted with one or two substituents selected from C$_1$–C$_3$ alkyl, methoxy, ethoxy and chloro, even more preferably bromo, methyl, ethyl, cyclopropyl, cyclohexyl, 3-fluorophenyl, 4-fluorophenyl, 4-(N,N-dimethylamino phenyl, phenyl, 3-trifluoromethylphenyl, 4-trifluoromethylphenyl, 4-aminophenyl, 3-aminophenyl, 4-Boc-aminophenyl, 4-aminosulfonylphenyl, 4-(4-morpholinylsulfonyl) phenyl, 4-(trifluoroacetylaminosulfonyl)phenyl, 4-[(4-chlorophenyl)aminosulfonyl]phenyl, 2,4-difluorophenyl, 5-benzodioxolyl, 2,4-dimethoxyphenyl, 3-hydroxyphenyl, 3-ethoxyphenyl, 3,4-dimethoxyphenyl, 4-methylthiophenyl, 5-indolyl, 4-cyanophenyl, 4-trifluoromethoxyphenyl, 4-methoxyphenyl, 3-methoxyphenyl, 2-methoxyphenyl, phenoxy, 2-thienyl, 4-pyrimidinyl, 2-methylthio-4-pyrimidinyl, morpholinyl, 4-piperidinyl, 6-methoxy-3-pyridyl, 2-methoxy-3-pyridyl, 2-ethoxy-3-pyridyl, 3,4-dichloro-4-pyridyl, 3,5-dichloro-4-pyridyl, 2-chloro-4-pyridyl, 3-pyridyl and 4-pyridyl; and wherein $R^8$ is selected from

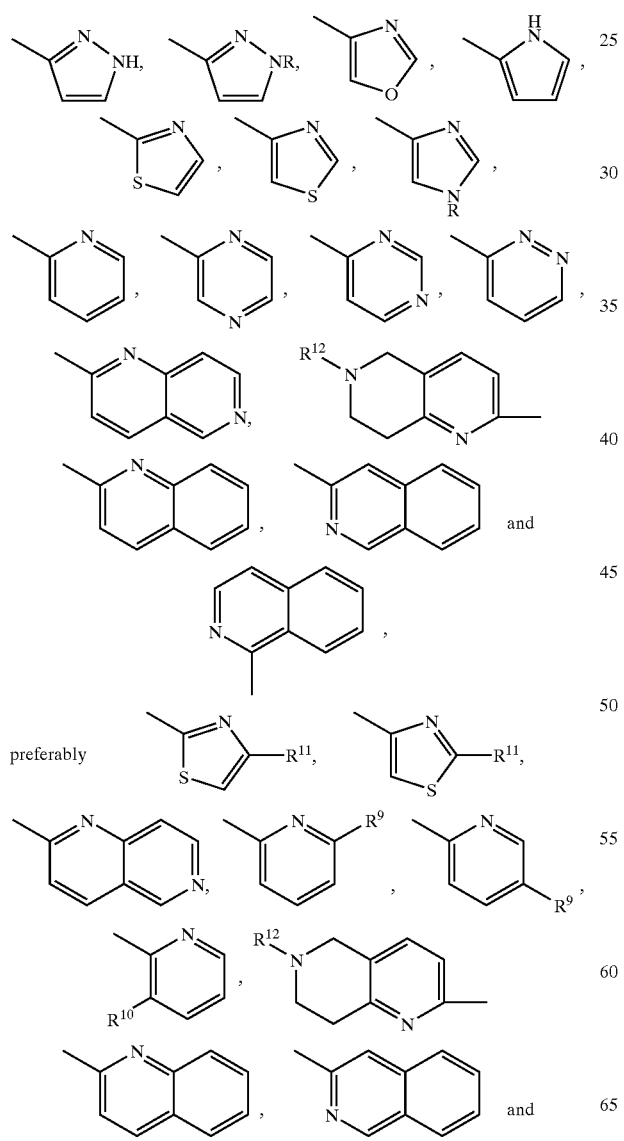

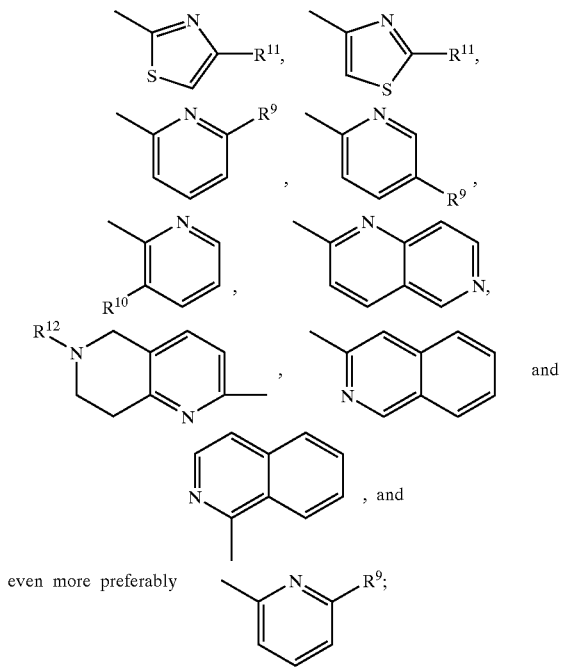

wherein $R^8$ is optionally substituted with one or two substituents independently selected from H, optionally substituted pyrrolidinyl, optionally substituted piperazinyl, optionally substituted piperidinyl, morpholinyl, 1,4-dioxa-8-aza-spiro[4.5]decyl, pyridyl, phenyl, $C_1$–$C_6$-alkyl, $C_1$–$C_2$-haloalkyl, $C_1$–$C_4$-hydroxyalkyl, amino, $C_1$–$C_4$-azidoalkyl, $C_1$–$C_4$-cyanoalkyl, $C_1$–$C_4$-aminoalkyl, halo, hydroxy, ((optionally substituted pyrrolidinyl)-$C_1$–$C_2$-alkyl, (optionally substituted piperidinyl)-$C_1$–$C_2$-alkyl, (optionally substituted piperazinyl)-$C_1$–$C_2$-alkyl, morpholinyl-$C_1$–$C_2$-alkyl, (optionally substituted imidazolyl)-$C_1$–$C_2$-alkyl, phthalimidyl-$C_1$–$C_2$-alkyl, optionally substituted azepanyl-$C_1$–$C_2$-alkyl, 1,4-dioxa-8-aza-spiro[4.5]decyl-$C_1$–$C_2$-alkyl, optionally substituted phenoxy-$C_1$–$C_2$-alkyl, $C_1$–$C_4$-alkylaminothiocarbonyl, $C_1$–$C_4$-alkoxy-$C_1$–$C_4$-alkyl, $C_1$–$C_4$-alkylamino-$C_1$–$C_4$-alkyl, $C_1$–$C_4$-hydroxyalkylamino-$C_1$–$C_4$-alkyl, amino-$C_1$–$C_4$-alkoxy-$C_1$–$C_4$-alkyl, (1-aza-bicyclo[2.2.2]oct-3-yl)-oxy, optionally substituted pyrrolidinyl-$C_1$–$C_4$-alkoxy, optionally substituted azetidinyl-$C_1$–$C_4$-alkoxy, optionally substituted -piperidinyl-$C_1$–$C_4$-alkoxy, $C_1$–$C_4$-alkylamino-$C_1$–$C_4$-alkoxy, tetrahydrofuryl-O—, tetrahydrofuryl-$C_1$–$C_4$-alkoxy, optionally substituted pyridyloxy, optionally substituted phenoxy, $C_1$–$C_4$-alkoxycarbonyl, 5–6-membered heterocyclyl-$C_1$–$C_4$-alkylaminocarbonyl, 5–6-membered N-containing heterocyclylcarbonyl, $C_1$–$C_4$-alkylaminocarbonyl, $C_1$–$C_4$-alkylamino-$C_1$–$C_4$-alkylaminocarbonyl, aminocarbonyl, 5–6-membered N-containing heterocyclyl-$C_1$–$C_4$-alkylamino, $C_1$–$C_4$-alkylamino, $C_1$–$C_4$-alkylamino-$C_1$–$C_4$-alkylamino-$C_1$–$C_4$-alkyl, and $C_1$–$C_4$-alkylamino-$C_1$–$C_4$-alkylamino, preferably unsubstituted or substituted with one or more substituents selected from pyridyl, phenyl, $C_1$–$C_4$ alkyl, $C_1$–$C_2$ haloalkyl, halo, piperidinyl, morpholinyl, methylpiperazinyl, methylaminothiocarbonyl, N,N-diethylaminomethylenyl, N-methylaminomethylenyl, morpholinylpropylenylaminocarbonyl, aminocarbonyl morpholinylpropylenylamino, N,N-diethylamino and N,N-dimethylaminoethylenylamino;

wherein $R^9$ is selected from optionally substituted pyrrolidinyl, optionally substituted piperazinyl, optionally substituted piperidinyl, morpholinyl, 1,4-dioxa-8-aza-spiro[4.5]decyl, pyridyl, phenyl, $C_1$–$C_4$ alkyl, $C_1$–$C_2$ haloalkyl, $C_1$–$C_2$ hydroxyalkyl, amino, $C_1$–$C_2$ azidoalkyl, $C_1$–$C_2$ cyanoalkyl, $C_1$–$C_2$ aminoalkyl, halo, (optionally substituted pyrrolidinyl)$CH_2$—, (optionally substituted piperidinyl)-$CH_2$—, (optionally substituted piperazinyl)-$CH_2$—, 4-morpholinyl-$CH_2$—, (optionally substituted imidazolyl)-$CH_2$—, phthalimidylethyl, optionally substituted azepanyl-$CH_2$—, 1,4-dioxa-8-aza-spiro[4.5]decyl-$CH_2$—, optionally substituted phenoxy-$CH_2$—, $C_1$–$C_4$-alkylaminothiocarbonyl, $C_1$–$C_4$-alkoxy-$C_1$–$C_4$-alkyl, $C_1$–$C_4$-alkylamino-$C_1$–$C_4$-alkyl, $C_1$–$C_4$-hydroxyalkylamino-$C_1$–$C_4$-alkyl, Boc-aminoethoxymethylenyl, amino-$C_1$–$C_4$-alkoxy-$C_1$–$C_4$-alkyl, (1-aza-bicyclo[2.2.2]oct-3-yl)-oxy, optionally substituted pyrrolidinyl-$C_1$–$C_4$-alkoxy, optionally substituted azetidinyl-$C_1$–$C_4$-alkoxy, optionally substituted piperidinyl-$C_1$–$C_4$-alkoxy, $C_1$–$C_4$-alkylamino-$C_1$–$C_4$-alkoxy, tetrahydrofuryl-O—, tetrahydrofuryl-$C_1$–$C_4$-alkoxy, optionally substituted phenoxy, $C_1$–$C_4$-alkoxycarbonyl, heterocyclyl-$C_1$–$C_4$-alkylaminocarbonyl, 1-piperidinylcarbonyl, $C_1$–$C_4$-alkylaminocarbonyl, $C_1$–$C_4$-alkylamino-$C_1$–$C_4$-alkylaminocarbonyl, aminocarbonyl, morpholinyl-$C_1$–$C_4$-alkylamino, $C_1$–$C_4$-alkylamino, $C_1$–$C_4$-alkylamino-$C_1$–$C_4$-alkylamino-$C_1$–$C_4$-alkyl, and $C_1$–$C_4$-alkylamino-$C_1$–$C_4$-alkylamino, preferably 3-(N,N-dimethylamino)-1-pyrrolidinyl, 1-methyl-4-piperazinyl, 1-benzyl-4-piperazinyl, 1-(2-pyrimidinyl)-4-piperazinyl, 1-(2-pyridyl)-4-piperazinyl, 1-ethyl-4-piperazinyl, 4-amino-1-piperidinyl, 4-(N-hydroxyethylamino)-1-piperidinyl, 4-(N-propylamino)-1-piperidinyl, 4-(N-benzylamino)-1-piperidinyl, 4-oxo-piperidinyl, 4-(hydroxyimino)-piperidinyl, 4-morpholinyl, 1,4-dioxa-8-aza-spiro[4.5]decyl, pyridyl, phenyl, methyl, ethyl, propyl, amino, azidomethyl, hydroxymethyl, trifluoromethyl, fluoro, chloro, bromo, aminoethyl, aminomethyl, cyanomethyl, 1-pyrrolidinyl-$CH_2$—, 2-methoxycarbonyl-1-pyrrolidinyl-$CH_2$—, 2-carboxy-1-pyrrolidinyl-$CH_2$—, 2-hydroxymethyl-1-pyrrolidinyl-$CH_2$—, 1-piperidinyl-$CH_2$—, 4-methyl-1-piperidinyl-$CH_2$—, 3-methyl-1-piperidinyl-$CH_2$—, 2-methyl-1-piperidinyl-$CH_2$—, 3,5-dimethyl-1-piperidinyl-$CH_2$—, 4-oxo-1-piperidinyl-$CH_2$—, 4-hydroxy-1-piperidinyl-$CH_2$—, 3-hydroxy-1-piperidinyl-$CH_2$—, 2-ethoxycarbonyl-1-piperidinyl-$CH_2$—, 3-ethoxycarbonyl-1-piperidinyl-$CH_2$—, 3-carboxy-1-piperidinyl-$CH_2$—, 4-ethoxycarbonyl-1-piperidinyl-$CH_2$—, 4-carboxy-1-piperidinyl-$CH_2$—, 4-(1-pyrrolidinyl)-1-piperidinyl-$CH_2$—, 4-(N-hydroxyethylamino)-1-piperidinyl-$CH_2$—, 4-(N-propylamino)-1-piperidinyl-$CH_2$—, 1-methyl-4-piperazinyl-$CH_2$—, 4-morpholinyl-$CH_2$—, (2-methyl-1-imidazolyl-$CH_2$—, 3-(N,N-diethylamino)carbonyl-1-piperidinyl-$CH_2$—, phthalimidylethyleneyl, 1-azepanyl-$CH_2$—, 1,4-dioxa-8-aza-spiro[4.5]decyl-$CH_2$—, 4-(methyl)phenoxymethylenyl, 4-(N,N-dimethylaminomethylenyl)phenoxymethylenyl, methylaminothiocarbonyl, methoxymethylenyl, ethylaminothiocarbonyl, N,N-dimethylaminoethylenyl, N,N-diethylaminomethylenyl, N-methylaminomethylenyl, N-(hydroxypropyl)aminomethylenyl, N-ethylaminomethylenyl, Boc-aminoethoxymethylenyl, aminoethoxymethylenyl, (1-aza-bicyclo[2.2.2]oct-3-yl)-oxy, 2-pyrrolidinylmethoxy, 1-methyl-2-pyrrolidinylmethoxy, azetidin-3-ylmethoxy, N-Boc-azetidin-3-ylmethoxy, N-Boc-piperidin-4-ylethoxy, 1-methyl-4-piperidinylethoxy, 4-piperidinylethoxy, 4-piperidinylmethoxy, N,N-dimethylaminoethoxy, 3-tetrahydrofuryl-O—, 3-tetrahydrofurylmethoxy, 4-tetrahydrofurylmethoxy, 4-methylphenoxy, 4-(aminoethyl)phenoxy, 4-(1-imidazolyl)phenoxy, 2,4-dimethylphenoxy, phenoxy, 4-cyanophenoxy, 4-[1,3]dioxolan-2-ylphenoxy, 4-fluorophenoxy, 3,4-difluorophenoxy, ethoxycarbonyl, morpholinylpropylenylaminocarbonyl, 1-piperidinylcarbonyl, methylaminocarbonyl, ethylaminocarbonyl, N,N-diethylaminocarbonyl, N-(N',N'-dimethylaminoethylenyl)aminocarbonyl, aminocarbonyl, morpholinylpropylenylamino, N,N-diethylamino, N,N-diethylamino(2-propylenyl)aminomethylenyl, N,N-diethylamino(1-propylenyl)aminomethylenyl and N-(N',N'-dimethylaminoethylenyl)amino;

wherein $R^{10}$ is selected from H, hydroxy, and amino;
wherein $R^{11}$ is selected from pyridyl and pyrimidinyl, preferably pyridyl; and
wherein $R^{12}$ is selected from H, and $C_1$–$C_4$ alkyl, preferably H, methyl, ethyl and propyl;
and pharmaceutically acceptable salts thereof.

The invention also relates to compounds of Formula VI

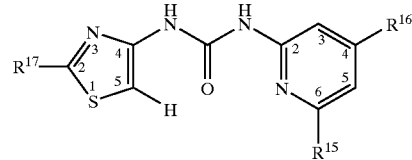

VI wherein $R^{15}$ is one or more substituents selected from H, optionally substituted heterocyclyl, phenyl, $C_1$–$C_6$-alkyl, $C_1$–$C_2$-haloalkyl, $C_1$–$C_4$-hydroxyalkyl, amino, $C_1$–$C_4$-azidoalkyl, $C_1$–$C_4$-cyanoalkyl, $C_1$–$C_4$-aminoalkyl, halo, hydroxy, (optionally substituted heterocyclyl)-$C_1$–$C_4$-alkyl, optionally substituted phenoxy-$C_1$–$C_2$-alkyl, $C_1$–$C_4$-alkoxy-$C_1$–$C_4$-alkyl, $C_1$–$C_4$-alkylamino-$C_1$–$C_4$-alkyl, $C_1$–$C_4$-hydroxyalkylamino, amino-$C_1$–$C_4$-alkoxy-$C_1$–$C_4$-alkyl, optionally substituted heterocyclyloxy, optionally substituted heterocyclyl-$C_1$–$C_4$-alkoxy, $C_1$–$C_4$-alkylamino-$C_1$–$C_4$-alkoxy, optionally substituted phenoxy, $C_1$–$C_4$-alkoxycarbonyl, 5–6-membered heterocyclyl-$C_1$–$C_4$-alkylaminocarbonyl, 5–6-membered N-containing heterocyclylcarbonyl, $C_1$–$C_4$-alkylaminocarbonyl, $C_1$–$C_4$-alkylaminothiocarbonyl, $C_1$–$C_4$-alkylamino-$C_1$–$C_4$-alkylaminocarbonyl, aminocarbonyl, 5–6-membered N-containing heterocyclyl-sulfonyl-$C_1$–$C_4$-alkyl, 5–6-membered N-containing heterocyclyl-$C_1$–$C_4$-alkylamino, $C_1$–$C_4$-alkylamino, $C_1$–$C_4$-alkylamino-$C_1$–$C_4$-alkylamino-$C_1$–$C_4$-alkyl, and $C_1$–$C_4$-alkylamino-$C_1$–$C_4$-alkylamino; preferably H, optionally substituted pyrrolidinyl, optionally substituted piperazinyl, optionally substituted piperidinyl, morpholinyl, 1,2,3,6-tetrahydro-pyridinyl, (optionally substituted pyrrolidinyl)-$C_1$–$C_2$-alkyl, (optionally substituted piperidinyl)-$C_1$–$C_2$-alkyl, (optionally substituted piperazinyl)-$C_1$–$C_2$-alkyl, morpholinyl-$C_1$–$C_2$-alkyl, $C_1$–$C_4$-alkylamino-$C_1$–$C_4$-alkyl, $C_1$–$C_4$-hydroxyalkylamino, (optionally substituted pyrrolidinyl)-$C_1$–$C_2$-alkylamino, (optionally substituted piperidinyl)-$C_1$–$C_2$-alkylamino, (optionally substituted piperazinyl)-$C_1$–$C_2$-alkylamino, morpholinyl-$C_1$–$C_2$-alkylamino, optionally substituted pyrrolidinyl-$C_1$–$C_4$-alkoxy, optionally substituted azetidinyl-$C_1$–$C_4$-alkoxy, tetrahydrofuryl-$C_1$–$C_4$-alkoxy, optionally substituted piperidinyl-$C_1$–$C_4$-alkoxy, $C_1$–$C_4$-alkylamino-$C_1$–$C_4$-alkoxy, tetrahydrofuryloxy, optionally substituted piperidinyloxy, optionally substituted phenoxy, $C_1$–$C_4$-alkylaminocarbonyl and $C_1$–$C_4$-alkylaminothiocarbonyl;

more preferably H, tetrahydro-furanyloxy, 1-methylpyrrolidin-2-ylmethoxy, 2-pyrrolidinylmethoxy, 3-pyrrolidinylmethoxy, 1-Boc-pyrrolidin-2-ylmethoxy, 4-piperidinylmethoxy, 1-Boc-piperidin-4-ylmethoxy, 1-Boc-piperidin-4-ylethoxy, piperidin-4-ylethoxy, 1-methyl-piperidin-4-ylmethoxy, 1-Boc-azetidin-3-ylmethoxy, 1-methyl-azetidin-3-ylmethoxy, 3-azetidinylmethoxy, 1-methyl-piperidin-4-yloxy, phenyloxy, 4-(pyrrolidin-1-ylmethyl)phenoxy, dimethylaminoethoxy, piperidinylethylamino, 1-piperidinylmethyl, 1-(piperidin-1-yl) ethyl, 3-methylpiperidin-1-ylmethyl, 1-pyrrolidinylmethyl, 2,2,6,6-tetramethylpiperidin-1-ylmethyl, 2,6-dimethylpiperidin-1-ylmethyl, dimethylaminomethyl, diethylaminomethyl, diethylaminothiocarbonyl, diethylaminocarbonyl, N-Boc-N-isopropylaminomethyl, isopropylaminomethyl, 2-thienylsulfonylmethyl, hydroxypropylamino, 4-ethyl-piperidin-1-yl, 4-(2-pyridyl)piperidin-1-yl, 1-methylpiperidin-4-yl, 4-(2-pyrazinyl)piperidin-1-yl, 1-methyl-1,2,3,6-tetrahydro-pyridin-4-yl, 1,2,3,6-tetrahydro-pyridin-4-yl, and 1-Boc-1,2,3,6-tetrahydro-pyridin-4-yl;

wherein $R^{16}$ is selected from H, heterocyclylcarbonyl, alkylaminocarbonyl, alkylaminomethyl, and heterocyclylmethyl;

preferably H, 5–6-membered nitrogen containing heterocyclylcarbonyl, $C_1$–$C_4$-alkylaminocarbonyl, $C_1$–$C_4$-alkylaminomethyl, and 5–6-membered nitrogen containing heterocyclylmethyl;

more preferably H, 1-piperidinylcarbonyl, diethylaminocarbonyl, diethylaminomethyl, 1-piperidinylmethyl; and wherein $R^{17}$ is selected from halo, and preferably chloro and bromo, $C_1$–$C_3$-alkyl, preferably $C_1$–$C_2$-alkyl, and more preferably methyl, cycloalkylalkynyl, preferably $C_3$–$C_6$-cycloalkyl-$C_2$–$C_4$-alkynyl, and more preferably cyclopropylethynyl, cycloalkyl, preferably $C_3$–$C_6$-cycloalkyl, and more preferably cyclopropyl, optionally substituted heteroarylsulfonyl-$C_1$–$C_4$-alkyl, and preferably optionally substituted 5–6-membered heteroarylsulfonyl-$C_1$–$C_2$-alkyl, optionally substituted indolyl, and preferably 1-Boc-indol-5-yl, optionally substituted phenoxy, optionally substituted indazolyl, and preferably 5-indazolyl, unsubstituted 5-membered oxygen or sulfur containing heteroaryl, and preferably unsubstituted thienyl, and 5-tert-butyloxazol-2-yl, unsubstituted 6-membered nitrogen-containing heterocyclyl, phenyl optionally substituted with one or two substituents selected from halo, $C_1$–$C_4$-alkylamino, amino, nitro, $C_1$–$C_4$-alkoxy, $C_1$–$C_2$-haloalkyl, hydroxy, $C_1$–$C_4$-alkylthio, $C_1$–$C_4$-alkylcarbonylamino, (optionally substituted phenyl)sulfonylamino, cyano, $C_1$–$C_2$-haloalkoxy, 5- or 6-membered N-containing heterocyclyl, aminosulfonyl, (6-membered N-containing heterocyclyl)sulfonyl, $C_1$–$C_2$-haloalkylcarbonylaminosulfonyl and (optionally substituted phenyl)aminosulfonyl, and preferably optionally substituted with one or two substituents selected from halo, $C_1$–$C_4$-alkylamino, amino, nitro, $C_1$–$C_4$-alkoxy, $C_1$–$C_2$-haloalkyl, hydroxy, $C_1$–$C_4$-alkylthio, $C_1$–$C_4$-alkylcarbonylamino, (optionally substituted phenyl)sulfonylamino, cyano, $C_1$–$C_2$-haloalkoxy, 5- or 6-membered N-containing heterocyclyl, aminosulfonyl, (6-membered N-containing heterocyclyl)sulfonyl, $C_1$–$C_2$-haloalkylcarbonylaminosulfonyl and (optionally substituted phenyl)aminosulfonyl; and more preferably and phenyl optionally substituted with aminosulfonyl, and 6-membered nitrogen-containing heterocyclyl substituted with one or more substituents independently selected from pyridyl, phenyl, $C_1$–$C_4$ alkyl, $C_1$–$C_4$ haloalkyl, $C_1$–$C_4$ alkoxy, amino, halo, piperidinyl, morpholinyl, $C_1$–$C_4$ alkylpiperazinyl, $C_1$–$C_4$ alkylaminothiocarbonyl, N,N-di-$C_1$–$C_4$-alkylamino-$C_1$–$C_4$-alkylenyl, N—$C_1$–$C_4$-alkylamino-$C_1$–$C_4$-alkylenyl, morpholinyl-$C_1$–$C_4$-alkylenylaminocarbonyl, aminocarbonyl, $C_1$–$C_4$-haloalkylcarbonylamino, morpholinyl-$C_1$–$C_4$-alkylenylamino, N,N-di-$C_1$–$C_2$-alkylamino and N,N-di-$C_1$–$C_2$-alkylamino-$C_1$–$C_4$-alkylenylamino;

preferably pyridyl, phenyl, $C_1$–$C_4$ alkyl, $C_1$–$C_2$ haloalkyl, $C_1$–$C_2$ alkoxy, amino, halo, piperidinyl, morpholinyl, $C_1$–$C_2$ alkylpiperazinyl, $C_1$–$C_3$ alkylaminothiocarbonyl, N,N-di-$C_1$–$C_2$-alkylamino-$C_1$–$C_4$-alkylenyl, N—$C_1$–$C_2$-alkylamino-$C_1$–$C_4$-alkylenyl, morpholinyl-$C_1$–$C_4$-alkylenylaminocarbonyl, aminocarbonyl, $C_1$–$C_2$-haloalkylcarbonylamino, morpholinyl-$C_1$–$C_4$-alkylenylamino, N,N-di-$C_1$–$C_2$-alkylamino and N,N-di-$C_1$–$C_2$-alkylamino-$C_1$–$C_4$-alkylenylamino, and more preferably 4-pyridyl substituted with one or more substituents independently selected from methoxy and chloro;

and pharmaceutically acceptable derivatives thereof; provided only one of $R^{15}$ and $R^{16}$ is H.

A family of specific compounds of particular interest within Formula I consists of compounds and pharmaceutically-acceptable salts thereof as follows:

1-[6-(3-Methyl-piperidin-1-ylmethyl)-pyridin-2-yl]-3-(2-phenyl-thiazol-4-yl)-urea;

1-[4-(Piperidine-1-carbonyl)-pyridin-2-yl]-3-(2-pyridin-4-yl-thiazol-4-yl)-urea;

1-(2-Chloro-thiazol-4-yl)-3-[4-(piperidine-1-carbonyl)-pyridin-2-yl]-urea;

N,N-Diethyl-2-[3-(2-pyridin-4-yl-thiazol-4-yl)-ureido]-isonicotinamide;
N,N-Diethyl-2-[3-(2-phenyl-thiazol-4-yl)-ureido]-isonicotinamide;
2-[3-(2-Bromo-thiazol-4-yl)-ureido]-N,N-diethyl-isonicotinamide;
1-(4-Diethylaminomethyl-pyridin-2-yl)-3-(2-pyridin-4-yl-thiazol-4-yl)-urea;
1-[6-(2,6-Dimethyl-piperidin-1-ylmethyl)-pyridin-2-yl]-3-(2-pyridin-4-yl-thiazol-4-yl)-urea;
1-[6-(1-Piperidin-1-yl-ethyl)-pyridin-2-yl]-3-(2-pyridin-4-yl-thiazol-4-yl)-urea;
2-({6-[3-(2-Pyridin-4-yl-thiazol-4-yl)-ureido]-pyridin-2-ylamino}-methyl)-piperidine-1-carboxylic acid tert-butyl ester;
1-{6-[(Piperidin-2-ylmethyl)-amino]-pyridin-2-yl}-3-(2-pyridin-4-yl-thiazol-4-yl)-urea;
(S)-1-[6-(3-Methyl-piperidin-1-ylmethyl)-pyridin-2-yl]-3-(2-pyridin-4-yl-thiazol-4-yl)-urea;
(R)-1-[6-(3-Methyl-piperidin-1-ylmethyl)-pyridin-2-yl]-3-(2-pyridin-4-yl-thiazol-4-yl)-urea;
1-(2-Chloro-thiazol-4-yl)-3-(6-piperidin-1-ylmethyl-pyridin-2-yl)-urea;
1-(2-Bromo-thiazol-4-yl)-3-[6-(2-piperidin-4-yl-ethoxy)-pyridin-2-yl]-urea;
1-(2-Chloro-thiazol-4-yl)-3-[6-(2-piperidin-4-yl-ethoxy)-pyridin-2-yl]-urea;
1-[6-(Azetidin-3-ylmethoxy)-pyridin-2-yl]-3-(2-bromo-thiazol-4-yl)-urea;
1-[6-(Azetidin-3-ylmethoxy)-pyridin-2-yl]-3-(2-chloro-thiazol-4-yl)-urea;
1-(2-Bromo-thiazol-4-yl)-3-[6-(piperidin-4-ylmethoxy)-pyridin-2-yl]-urea;
1-(2-Chloro-thiazol-4-yl)-3-[6-(piperidin-4-ylmethoxy)-pyridin-2-yl]-urea;
3-(4-{3-[6-(1-Methyl-pyrrolidin-2-ylmethoxy)-pyridin-2-yl]-ureido}-thiazol-2-yl)-benzenesulfonamide;
tert-Butyl 3-{6-[3-(2-pyridin-4-yl-thiazol-4-yl)-ureido]-pyridin-2-yloxymethyl}-pyrrolidine-1-carboxylate;
1-(2-Pyridin-4-yl-thiazol-4-yl)-3-[6-(pyrrolidin-3-ylmethoxy)-pyridin-2-yl]-urea;
1-(2-Cyclopropyl-thiazol-4-yl)-3-[6-(2-piperidin-4-yl-ethoxy)-pyridin-2-yl]-urea;
1-[6-(Isopropylamino-methyl)-pyridin-2-yl]-3-(2-pyridin-4-yl-thiazol-4-yl)-urea;
Isopropyl-{6-[3-(2-phenyl-thiazol-4-yl)-ureido-pyridin-2-ylmethyl)-carbamic acid tert-butyl ester;
1-[6-(Isopropylamino-methyl)-pyridin-2-yl]-3-(2-phenyl-thiazol-4-yl)-urea;
1-(2-Bromo-thiazol-4-yl)-3-[6-(isopropylamino-methyl)-pyridin-2-yl]-urea;
1-(2-Bromo-thiazol-4-yl)-3-[6-(1-methyl-pyrrolidin-2-ylmethoxy)-pyridin-2-yl]-urea;
1-(2-Chloro-thiazol-4-yl)-3-[6-(1-methyl-pyrrolidin-2-ylmethoxy)-pyridin-2-yl]-urea;
1-(2-phenylthiazol-4-yl)-3-(6-p-pyrrolidin-1-ylmethylphenoxypyridin-2-yl)urea;
1-(2-Pyridin-4-yl-thiazol-4-yl)-3-[6-(tetrahydro-furan-3-yloxy)-pyridin-2-yl]-urea;
1-[2-(1H-Indazol-5-yl)-thiazol-4-yl]-3-(6-piperidin-1-ylmethyl-pyridin-2-yl)-urea;
1-(1'-Methyl-1',2',3',6'-tetrahydro-[2,4']bipyridinyl-6-yl)-3-(2-pyridin-4-yl-thiazol-4-yl)-urea;
1-(2-Bromo-thizol-4-yl)-3-(1'-methyl-1',2',3',6'-tetrahydro-[2,4']bipyridinyl-6-yl)-urea;
1-(1-Methyl-1',2',3',6'-tetrahydro-2[2,4]bipyridinyl-6-yl)-3-(2-phenyl-thiazol-4-yl)-urea;
1-[6-(3-Hydroxy-propylamino)-pyridin-2-yl]-3-(2-pyridin-4-yl-thizol-4-yl)-urea;
1-(2-Bromo-thiazol-4-yl)-3-[6(3-hydroxy-propylamino)-pyridin-2-yl]-urea;
1-(1'-Methyl-1',2',3',4',5',6'-hexahydro-[2,4']bipydrinyl-6-yl)-3-(2-pyridin-4-yl-thiazol-4-yl)-urea;
1-(1-Methyl-1',2',3',4',5',6'-hexahydro-[2,4']bipyridinyl-6-yl)-3-(2-phenyl-thiazol-4-yl)-urea;
6-[3-(2-Pyridin-4-yl-thizol-4-yl)-ureido]-3',6'-dihydro-2'H-[2,4]bipyridinyl-1'-carboxylic acid tert-butylester;
1-(2-Pyridin-4-yl-thiazol-4-yl)-3-(1',2',3',6'-tetrahydro-[2,4']bipyridinyl-6-yl)-urea;
1-(2-Pyridin-4-yl-thizol-4-yl)-3-[6-(tetrahydro-furan-3-ylmethoxy)-pyridin-2-yl]-urea;
2-[6-[3-(2-Pyridin-4-yl-thiazol-4-yl)-ureido]-pyridin-2-yloxymethyl]-pyrrolidine-1-carboxylic acid tert-butyl ester;
1-(2-Pyridin-4-yl-thiazol-4-yl)-3-[6-(pyrrolidin-2-ylmethoxy)-pyridin-2-yl]-urea;
6-[3-(2-Pyridin-4-yl-thiazol-4-yl)-ureido]-pyridine-2-carbothioic acid diethylamide;
1-(2-Bromo-thiazol-4-yl)-3-[6-(3-methyl-piperidin-1-ylmethyl)-pyridin-2-yl]-urea;
1-(2-Chloro-thiazol-4-yl)-3-[6-(3-methyl-piperidin-1-ylmethyl)-pyridin-2-yl]-urea;
1-(2-Phenyl-thiazol-4-yl)-3-[4-(piperidine-1-carbonyl)-pyridin-2-yl]-urea;
1-(2-Bromo-thiazol-4-yl)-3-[4-(piperidine-1-carbonyl)-pyridin-2-yl]-urea;
1-[2-(2-Methoxy-pyridin-4-yl)-thiazol-4-yl]-3-(6-phenoxy-pyridin-2-yl)-urea;
1-[2-(2-Methoxy-pyridin-4-yl)-thiazol-4-yl]-3-[6-(1-methyl-pyrrolidin-2-ylmethoxy)-pyridin-2-yl]-urea;
1-[6-(2-Dimethylamino-ethoxy)-pyridin-2-yl]-3-[2-(2-methoxy-pyridin-4-yl)-thiazol-4-yl]-urea;
1-[6-(1-Methyl-pyrrolidin-2-ylmethoxy)-pyridin-2-yl]-3-(2-pyridin-4-yl-thiazol-4-yl)-urea;
1-(2-phenylthiazol-4-yl)-3-(6-pyrrolidin-1-ylmethyl-pyridin-2-yl)urea;
1-(6-Diethylaminomethylpyridin-2-yl)-3-(2-phenylthiazol-4-yl)urea;
(S)-1-[6-(1-Methylpyrrolidin-2-ylmethoxy)pyridin-2-yl]-3-(2-phenylthiazol-4-yl)urea;
1-[6-(2-Piperidin-4-yl-ethoxy)pyridin-2-yl]-3-[2-phenylthiazol-4-yl]urea;
1-[6-(4-Ethylpiperazin-1-yl)-pyridin-2-yl]-3-(2-phenylthiazol-4-yl)urea;
1-(2-phenylthiazol-4-yl)-3-[6-(4-pyrimidin-2-yl-piperazin-1-yl)pyridin-2-yl]urea;
Diethyl 6-[3-(2-phenylthiazol-4-yl)ureido]-pyridine-2-carboxamide;
1-(2-Pyridin-4-yl-thiazol-4-yl)-3-(6-p-pyrrolidin-1-ylmethylphenoxypyridin-2-yl)urea;
1-(2-Bromothiazol-4-yl)-3-(6-p-pyrrolidin-1-ylmethylphenoxypyridin-2-yl)urea;
1-[6-(Piperidin-4-ylmethoxy)-pyridin-2-yl]-3-(2-pyridin-4-yl-thiazol-4-yl)-urea;
1-[6-(1-Methyl-piperidin-4-ylmethoxy)-pyridin-2-yl]-3-(2-pyridin-4-yl-thiazol-4-yl)-urea;
1-[6-(1-Methyl-piperidin-4-yloxy)-pyridin-2-yl]-3-(2-pyridin-4-yl-thiazol-4-yl)-urea;
1-[6-(1-Methyl-azetidin-3-ylmethoxy)-pyridin-2-yl]-3-(2-pyridin-4-yl-thiazol-4-yl)-urea;
1-[6-(Azetidin-3-ylmethoxy)-pyridin-2-yl]-3-(2-phenyl-thiazol-4-yl)-urea;
1-[6-(1-Methyl-azetidin-3-ylmethoxy)-pyridin-2-yl]-3-(2-phenyl-thiazol-4-yl)-urea;

1-(2-Phenyl-thiazol-4-yl)-3-[6-(piperidin-4-ylmethoxy)-pyridin-2-yl]-urea;
1-[6-(1-Methyl-piperidin-4-ylmethoxy)-pyridin-2-yl]-3-(2-phenyl-thiazol-4-yl)-urea;
1-[6-(1-Methyl-piperidin-4-yloxy)-pyridin-2-yl]-3-(2-phenyl-thiazol-4-yl)-urea;
1-[6-(2-Piperidin-4-yl-ethoxy)-pyridin-2-yl]-3-(2-thiophen-2-yl-thiazol-4-yl)-urea;
1-[6-(1-Methyl-pyrrolidin-2-ylmethoxy)-pyridin-2-yl]-3-[2-(thiophene-2-sulfonylmethyl)-thiazol-4-yl]-urea;
1-[2-(2-Methoxy-pyridin-4-yl)-thiazol-4-yl]-3-(6-piperdin-1-ylmethyl-pyridin-2-yl)-urea; and
[2-(2-Chloro-pyridin-4-yl)-thiazol-4-yl]-3-(6-piperdin-1-ylmethyl-pyridin-2-yl)-urea.

Indications

Compounds of the present invention would be useful for, but not limited to, the treatment of cell proliferative diseases or of apoptosis.

The compounds of the invention are endowed with kinase inhibitory activity, such as CDK/cyclin kinase inhibitory activity and GSK inhibitory activity.

The compounds of the invention are useful in therapy as antineoplasia agents.

Compounds of the invention would be useful for the treatment of neoplasia including cancer, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-Lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

Due to the key role of CDKs in the regulation of cellular proliferation, these compounds are also useful in the treatment of a variety of cell proliferative disorders such as, for instance, blood vessel proliferative disorders including arthritis and restenosis; fibrotic disorders including hepatic cirrhosis and atherosclerosis; mesangial cell proliferative disorders including glomerulonephritis, diabetic nephropathy, malignant nephrosclerosis, thrombotic microangiopathy syndromes, transplant rejection and glomerulopathies; metabolic disorders including psoriasis, diabetes mellitus, chronic wound healing, inflammation, and diabetic retinopathy and other vision disorders; and others including benign prostate hyperplasia, familial adenomatosis polyposis, neuro-fibromatosis, pulmonary fibrosis, angiogenesis, metastasis, vascular smooth cell proliferation, post-surgical stenosis and hypertrophic scar formation, eczema, inflammatory bowel disease, endotoxic shock, and fungal infections.

The compounds of the invention are useful to prevent the phosphorylation of tau protein.

The compounds of the invention are useful in the treatment of neurological disorders, including neurological injuries and neurodegenerative diseases, such as, but not limited to, stroke, brain trauma, epilepsy, spinal cord injury, ischemia, multiple sclerosis, vision related disorders including but not limited to glaucoma and macular degeneration, hearing loss, AIDS-related dementia, retinitis pigmentosa, spinal muscular atrophy, cerebellar degeneration, amyotrophic lateral sclerosis, Parkinson's disease, Huntington's disease and Alzheimer's disease.

Compounds of Formula I–VI, as inhibitors of the CDKs, can modulate the level of cellular RNA and DNA synthesis. These agents would therefore be useful in the treatment of viral infections, including but not limited to HIV, human papilloma virus, herpesvirus, poxyirus, Epstein-Barr virus, Sindbis virus and adenovirus.

The compounds of this invention may also act as inhibitors of other protein kinases, e.g. KDR, IKK, JNK3, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

Inhibitors of certain kinases may have utility in the treatment of diseases when the kinase is not misregulated, but is nonetheless essential for maintenance of the disease state. In this case, inhibition of the kinase activity would act either as a cure or palliative for these diseases. For example, many viruses, such as human papilloma virus, disrupt the cell cycle and drive cells into the S-phase of the cell cycle. Preventing cells from entering DNA synthesis after viral infection by inhibition of essential S-phase initiating activities such as CDK2, may disrupt the virus life cycle by preventing virus replication. This same principle may be used to protect normal cells of the body from toxicity of cycle-specific chemotherapeutic agents. Inhibition of CDK2 or CDK4 will prevent progression into the cycle in normal cells and limit the toxicity of cytotoxics which act in S-phase, G2 or mitosis. Furthermore, CDK2/cyclin E activity has also been shown to regulate NF-κB: Inhibition of CDK2 activity stimulates NF-κB-dependent gene expression, an event mediated through interactions with the p300 coactivator. NF-κB regulates genes involved in inflammatory responses, (such as hematopoietic growth factors chemokines and leukocyte adhesion molecules) and may be involved in the suppression of apoptotic signals within the cell. Thus, inhibition of CDK2 may suppress apoptosis induced by cytotoxic drugs via a mechanism which involves NF-κB. Inhibition of CDK2 activity may also have utility in other cases where regulation of NF-KB plays a role in etiology of disease. A further example may be taken from fungal infections: Inhibition of the Aspergillus kinases Cdc2/CDC28 or Nim A may cause arrest or death in the fungi, improving the therapeutic outcome for patients with these infections.

The compounds of the invention are useful as modulators of apoptosis. As such they are useful in the prevention of AIDS development in HIV-infected individuals, autoimmune diseases (including but not limited to systemic lupus, erythematosus, autoimmune mediated glomerulonephritis, rheumatoid arthritis and autoimmune diabetes mellitus), myelodysplastic syndromes, aplastic anemia, ischemic injury associated with myocardial infarctions, stroke and reperfusion injury, vision related disorders including but not limited to glaucoma and macular degeneration, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis) aspirin-sensitive rhinosinusitis, cystic fibrosis, kidney diseases and cancer pain.

Definitions

The term "prevention" includes either preventing the onset of disorders altogether or delaying the onset of a preclinically evident stage of disorders in individuals. This includes prophylactic treatment of those at risk of developing a disease, such as a cancer, for example.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neuroplastic therapeutic agents prolong the survivability of the patient, inhibit the rapidly-proliferating cell growth associated with the neoplasm, or effect a regression of the neoplasm. Alternatively, effective therapeutic agents for the treatment of neurological disorders minimize the damage from injury, improve cognitive functions, and the like.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twenty carbon atoms or, preferably, one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. Even more preferred are lower alkyl radicals having one to four carbon atoms. The term "alkylenyl" embraces bridging divalent alkyl radicals such as methylenyl and ethyleneyl.

The term "alkenyl" embraces linear or branched radicals having at least one carbon—carbon double bond of two to about twenty carbon atoms or, preferably, two to about twelve carbon atoms. More preferred alkenyl radicals are "lower alkenyl" radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of tie same halo atoms or a combination of different halo radicals. "Lower haloalkyl" embraces radicals having 1–6 carbon atoms.

Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "azidoalkyl" embraces linear or branched alkyl radicals having one to about ten carbon atoms any one of which may be substituted with one or more azido ($N_3$) radicals. More preferred azidoalkyl radicals are "lower azidoalkyl" radicals having one to six carbon atoms and one azido radical. Examples of such radicals include azidomethyl. Even more preferred are lower azidoalkyl radicals having one to three carbon atoms.

The term "cyanoalkyl" embraces linear or branched alkyl radicals having one to about ten carbon atoms any one of which may be substituted with one or more cyano (CN) radicals. More preferred cyanoalkyl radicals are "lower cyanoalkyl" radicals having one to six carbon atoms and one cyano radical. Examples of such radicals include cyanomethyl. Even more preferred are lower cyanoalkyl radicals having one to three carbon atoms.

The term "phenyloxyalkyl" embraces linear or branched alkyl radicals having one to about ten carbon atoms any one of which may be substituted with one or more phenoxy radicals. More preferred phenyloxyalkyl radicals are "lower phenyloxyalkyl" radicals having one to six carbon atoms and one phenoxy radical. Examples of such radicals include phenoxymethyl.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. The "alkoxy" radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "alkoxyalkyl" embraces linear or branched alkyl radicals having one to about ten carbon atoms any one of which may be substituted with one or more alkoxy radicals. More preferred alkoxyalkyl radicals are "lower alkoxyalkyl" radicals having one to six carbon atoms and one alkoxy radical. Examples of such radicals include methoxymethyl.

The term "aminoalkoxyalkyl" embraces alkoxyalkyl radicals, as defined above, where any one carbon atom may be substituted with one amino radical. More preferred aminoalkoxyalkyl radicals are "lower aminoalkoxyalkyl" radicals having one to six carbon atoms. Examples of such radicals include aminoethoxymethyl.

The term "alkylaminoalkoxy" embraces alkoxy radicals, as defined above, substituted with an alkylamino radical. More preferred alkylaminoalkoxy radicals are "lower alkylaminoalkoxy" radicals having alkoxy groups with one to six carbon atoms and an alkylamino radical with one to six carbon atoms. Examples of such radicals include methylaminomethoxy.

The term "aryl", alone or in combination, means a carbocyclic aromatic system containing one or two rings wherein such rings may be attached together in a pendent manner or may be fused. The term "aryl" embraces aromatic radicals such as phenyl, naphthyl, tetrahydronaphthyl, indane and biphenyl. More preferred aryl is phenyl. Said "aryl" group may have 1 to 3 substituents such as lower alkyl, hydroxyl, halo, haloalkyl, nitro, cyano, alkoxy and lower alkylamino.

The term "heterocyclyl" embraces saturated, partially saturated and unsaturated heteroatom-containing ring-shaped radicals, where the heteroatoms may be selected from nitrogen, sulfur and oxygen. It does not include rings containing —O—O—, —O—S— or —S—S— portions. Said "heterocyclyl" group may have 1 to 3 substituents such as BOC, hydroxyl, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic group containing 1 to 4 nitrogen atoms [e.g. pyrrolidinyl, imidazolidinyl, piperidino, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothiophene, dihydropyran, dihydrofuran and dihydrothiazole.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, -indolizinyl, benzimidazolyl, quinolyl, isoquinolyl, indazolyl, benzotriazolyl, tetrazolopyridazinyl [e.g., tetrazolo [1,5-b] pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl].

The term also includes bridged, spiro and oxo-containing heterocyclic rings, such as 1,4-dioxa-8-aza-spiro[4.5]decyl, phthalimidyl, 1,4-dioxa-8-aza-spiro[4.5]decyl, and (1-azabicyclo[2.2.2]oct-3-yl).

Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Even more preferred heteroaryl radicals are 5- or 6-membered heteroaryl, containing one or two heteroatoms selected from sulfur nitrogen and oxygen, selected from thienyl, furanyl, pyrrolyl, thiazolyl, oxazolyl, imidazolyl, pyrazolyl, isoxazolyl, isothiazolyl, pyridyl, piperidinyl and pyrazinyl.

The term "sulfonyl", whether used alone or linked to other terms such as alkylsulfonyl, denotes respectively divalent radicals —SO$_2$—.

The terms "sulfamyl," "aminosulfonyl" and "sulfonamidyl," whether alone or used with terms such as "N-alkylaminosulfonyl", "N-arylaminosulfonyl", "N,N-dialkylaminosulfonyl" and "N-alkyl-N-arylaminosulfonyl", denotes a sulfonyl radical substituted with an amine radical, forming a sulfonamide (—SO$_2$NH$_2$).

The term "alkylaminosulfonyl" includes "N-alkylaminosulfonyl" and "N,N-dialkylaminosulfonyl" where sulfamyl radicals are substituted, respectively, with one alkyl radical, or two alkyl radicals. More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, N-ethylaminosulfonyl and N-methyl-N-ethylaminosulfonyl.

The terms "N-arylaminosulfonyl" and "N-alkyl-N-arylaminosulfonyl" denote sulfamyl radicals substituted, respectively, with one aryl radical, or one alkyl and one aryl radical. More preferred N-alkyl-N-arylaminosulfonyl radicals are "lower N-alkyl-N-arylsulfonyl" radicals having alkyl radicals of one to six carbon atoms. Even more preferred are lower N-alkyl-N-arylsulfonyl radicals having one to three carbon atoms. Examples of such lower N-alkyl-N-aryl-aminosulfonyl radicals include N-methyl-N-phenylaminosulfonyl and N-ethyl-N-phenylaminosulfonyl. Examples of such N-aryl-aminosulfonyl radicals include N-phenylaminosulfonyl, which may be optionally substituted on the phenyl ring.

The term "arylalkylaminosulfonyl" embraces aralkyl radicals as described above, attached to an aminosulfonyl radical. More preferred are lower arylalkylaminosulfonyl radicals having one to three carbon atoms.

The term "heterocyclylaminosulfonyl" embraces heterocyclyl radicals as described above, attached to an aminosulfonyl radical.

The term "heterocyclylsulfonylalkyl" embraces heterocyclyl radicals as described above, attached to an alkyl radical through a sulfonyl linker. More preferred are "lower heterocyclylsulfonylalkyl" wherein the alkyl portion is one to six carbons long. Even more preferred, the alkyl portions are 1–3 carbons long.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "aminocarbonyl" when used by itself or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula —C(=O)NH$_2$.

The term "alkoxycarbonyl" denotes an ester group wherein the carbonyl group is substituted with an alkoxy radical, as described above. The carbonyl portion is the point of attachment. More preferred are "lower alkoxycarbonyl" having lower alkoxy radicals as described above attached to a carbonyl radical.

The terms "N-alkylaminocarbonyl" and "N,N-dialkylaminocarbonyl" denote aminocarbonyl radicals which have been substituted with one alkyl radical and with two alkyl radicals, respectively. More preferred are "lower alkylaminocarbonyl" having lower alkyl radicals as described above attached to an aminocarbonyl radical.

The term "alkylamino-alkylaminocarbonyl" denotes alkylaminocarbonyl radicals which have been substituted with an alkylamino radical. More preferred are "lower alkylamino-alkylaminocarbonyl" having lower alkyl radicals, as described above.

The terms "N-arylaminocarbonyl" and "N-alkyl-N-arylaminocarbonyl" denote aminocarbonyl radicals substituted, respectively, with one aryl radical, or one alkyl and one aryl radical.

The term "heterocyclylalkylaminocarbonyl" denotes aminocarbonyl radicals substituted with a heterocyclylalkyl radical.

The term "heterocyclylcarbonyl" denotes carbonyl radicals substituted with a heterocyclyl radical.

The term "aminoalkyl" embraces alkyl radicals substituted with amino radicals.

The term "alkylaminothiocarbonyl" denotes thioamide compounds comprising thiocarbonyl radicals (—C(S)—) which have been substituted with an alkylamino radicals. More preferred are "lower alkylaminothiocarbonyl" having lower alkyl radicals as described above.

The term "alkylaminoalkyl" embraces aminoalkyl radicals having the nitrogen atom substituted with an alkyl radical. The term includes both mono- and di-substituted amines. Even more preferred are lower alkylaminoalkyl radicals having one to three carbon atoms.

The term "heterocyclylalkyl" embraces heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are lower aralkyl radicals phenyl attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "arylalkenyl" embraces aryl-substituted alkenyl radicals. Preferable arylalkenyl radicals are "lower arylalkenyl" radicals having aryl radicals attached to alkenyl radicals having two to six carbon atoms. Examples of such radicals include phenylethenyl. The aryl in said arylalkenyl may be additionally substituted with halo, alkyl, alkoxy, halkoalkyl and haloalkoxy.

The term "arylalkynyl" embraces aryl-substituted alkynyl radicals. Preferable arylalkynyl radicals are "lower arylalkynyl" radicals having aryl radicals attached to alkynyl radicals having two to six carbon atoms. Examples of such radicals include phenylethynyl. The aryl in said aralkyl may be additionally substituted with halo, alkyl, alkoxy, halkoalkyl and haloalkoxy. The terms benzyl and phenylmethyl are interchangeable.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, (CH$_3$S—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylsulfinyl" embraces radicals containing a linear or branched alkyl radical, of one to ten carbon atoms, attached to a divalent —S(=O)— atom. More preferred are lower alkylsulfinyl radicals having one to three carbon atoms.

The term "arylsulfinyl" embraces radicals containing an aryl radical, attached to a divalent —S(=O)— atom. Even more preferred are optionally substituted phenylsulfinyl radicals.

The term "haloalkylsulfinyl" embraces radicals containing a haloalkyl radical, of one to ten carbon atoms, attached to a divalent —S(=O)— atom. Even more preferred are lower haloalkylsulfinyl radicals having one to three carbon atoms.

The term "alkylamino" denotes amino groups which have been substituted with one alkyl radical and with two alkyl radicals, including terms "N-alkylamino" and "N,N-dialkylamino". More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable "alkylamino" may be mono or dialkylamino such as N-methylamino, N-ethylamino, N,N-dimethylamino, N,N-diethylamino or the like.

The term "hydroxyalkylamino" denotes amino groups which have been substituted with a hydroxyalkyl radical, as defined above.

The term "heterocyclylalkylamino" denotes alkylamino groups which have been substituted with a heterocyclyl radical, as defined above.

The tern "arylamino" denotes amino groups which have been substituted with one or two aryl radicals, such as N-phenylamino. The "arylamino" radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "aralkylamino" denotes amino groups which have been substituted with one or two aralkyl radicals. More preferred are phenyl-C$_1$–C$_3$-alkylamino radicals, such as N-benzylamino. The "aralkylamino" radicals may be further substituted on the aryl ring portion of the radical.

The terms "N-alkyl-N-arylamino" and "N-aralkyl-N-alkylamino" denote amino groups which have been substituted with one aralkyl and one alkyl radical, or one aryl and one alkyl radical, respectively, to an amino group.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "heterocyclyloxy" embraces optionally substituted heterocyclyl radicals, as defined above, attached to an oxygen atom. Examples of such radicals include pyrrolidinyloxy, piperidinyloxy, and pyridyloxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heterocyclylalkoxy" embraces oxy-containing heterocyclylalkyl radicals attached through an oxygen atom to other radicals. More preferred heterocyclyloxy radicals are "lower heterocyclyloxy "radicals having optionally substituted 5–6 membered heterocyclyl radicals attached to lower alkoxy radical as described above.

The term "cycloalkyl" includes saturated carbocyclic groups. Preferred cycloalkyl groups include $C_3$–$C_6$ rings. More preferred compounds include, for example, cyclopropyl, cyclopentyl and cyclohexyl.

The term "cycloalkenyl" includes carbocyclic groups having one or more carbon—carbon double bonds. "Cycloalkenyl" and "cycloalkyldienyl" compounds are included. Preferred cycloalkenyl groups include $C_3$–$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The present invention preferably includes compounds that selectively inhibit GSK, CDK2 and/or CDK5.

The present invention also comprises the use of a compound of the invention, or pharmaceutically acceptable salt thereof, in the manufacture of a medicament for the treatment either acutely or chronically of a cell proliferation or apoptosis mediated disease state, including those described previously. The compounds of the present invention are also useful in the manufacture of an anti-cancer medicament. The compounds of the present invention are also useful in the manufacture of a medicament to attenuate or prevent disorders through inhibition of CDKs and other kinases. The compounds of the present invention are also useful in the manufacture of a medicament to treat neurological disorders.

The present invention comprises a pharmaceutical composition comprising a therapeutically-effective amount of a compound of Formulas I–VI in association with a least one pharmaceutically-acceptable carrier, adjuvant or diluent.

The present invention also comprises a method of treating cell proliferative disorders, apoptosis mediated disorders, cancer, CDK mediated disorder or neurological disorders, in a subject, the method comprising treating the subject having or susceptible to such disorder with a therapeutically-effective amount of a compound of Formulas I–VI.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the treatment of neoplasia, such as with radiation therapy or with cytostatic or cytotoxic agents; or in the treatment of neurological disorders, such as with thrombolytic and anticoagulant agents, anti-inflammatory agents, NMDA inhibitors, anti-parkinsonian agents, and inhibitors of lipid peroxidation.

If formulated as a fixed dose, such combination products employ the compounds of this invention within the accepted dosage ranges. Compounds of Formula I–VI may also be administered sequentially with known agents when a combination formulation is inappropriate. The invention is not limited in the sequence of administration; compounds of the invention may be administered either prior to, at the same time with or after administration of the other agent.

Currently, standard treatment of primary tumors consists of surgical excision followed by either radiation or IV administered chemotherapy. The typical chemotherapy regime consists of either DNA alkylating agents, DNA intercalating agents or microtubule poisons. The chemotherapy doses used are just below the maximal tolerated dose and therefore dose limiting toxicities typically include, nausea, vomiting, diarrhea, hair loss, neutropenia and the like. Experiments performed in in vivo animal models and in in vitro cell based assays have demonstrated that combining chemotherapeutic agents with cell cycle inhibitors, such as CDK inhibitors, typically results in either decreased rate of tumor growth or, in some cases, tumor regression. Combining chemotherapy with a CDK inhibitor typically results in an increased therapeutic index and lower levels of both agents are required. This ultimately results in a decrease in toxicity and an increase in efficacy.

Schwartz et al, Clin. Can. Res., 3,1467–1472 (1997) have demonstrated that combining the CDK inhibitor flavopiridol with mitomycin-C (DNA alkylating agent) resulted in an increased rate of apoptosis in gastric and breast cancer cells. Bible et al (Bible et al., Cancer Res., 57, 3375–3380 (1997) have also demonstrated therapeutic synergy exists between flavopiridol and paclitaxel, cytarabine, topotecan, doxorubicin, and etoposide (all standard chemotherapeutic agents) when tested in cell based assays using human non-small cell lung cancer cells. Preclinical models (cell culture) suggest that a cell cycle inhibitor potentiates the effect of a cytotoxic agent when administered after the chemotherapeutic agent. The chemotherapeutic agent will induce specific DNA/mitotic damage checkpoints in normal cells which in combination with a CDK inhibitor will cause a cell cycle arrest or cytostatic effect. In contrast, tumor cells will be driven into apoptosis or cell death when a chemotherapeutic agent and a CDK inhibitor are combined due to tumor cells attempting to activate defective DNA damage and cell cycle checkpoints. In addition, scheduling of a CDK inhibitor for clinical trials should include a rest period to allow the patients normal cells to recover and reduce the potential for cytotoxic side effects.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine protein kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SR1 International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICM compound 4711, Contracan, Yakult Honsha CPT-11, crisnatol, curaderm, cytochalasin B. cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylateddehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celecoxib, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit anti-thymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SDO1 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetraexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other anti-neoplastic agents, such as other kinase inhibitors including KDR inhibitors, p38 inhibitors, TNF inhibitors, metallomatrix proteases inhibitors (MMP), COX-2 inhibitors, NSAID's, SOD mimics or $\alpha_v\beta_3$ inhibitors.

Alternatively, the present compounds may also be used in co-therapies with other treatments for neurological treatments such as thrombolytic and anticoagulant agents including tPA, urokinase and inhibitors of platelet aggregation, p38 inhibitors, IL1ra, NMDA inhibitors, antiparkinsonian agents including carbidopa and levodopa, and inhibitors of lipid peroxidation, for example.

The present invention comprises a process for the preparation of a compound of Formula I–VI.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

Compounds of the present invention can possess, in general, tautomeric forms, which are included in the family of compounds in Formula I–VI.

Also included in the family of compounds of Formula I–VI are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I–VI may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), -methanesulfonic, ethanesulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I–VI include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula I–VI.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as HCl, $H_2SO_4$ and $H_3PO_4$ and such organic acids as oxalic acid, maleic acid, succinic acid and citric acid. Other examples include salts with alkali metals or alkaline earth metals, such as sodium, potassium, calcium or magnesium or with organic bases.

Additional examples of such salts can be found in Berge et al., J. Pharm. Sci., 66, 1 (1977).

General Synthetic Procedures

The compounds of the invention can be synthesized according to the following procedures of Schemes 1–24, wherein the substituents are as defined for Formulas I–VI, above, except where further noted.

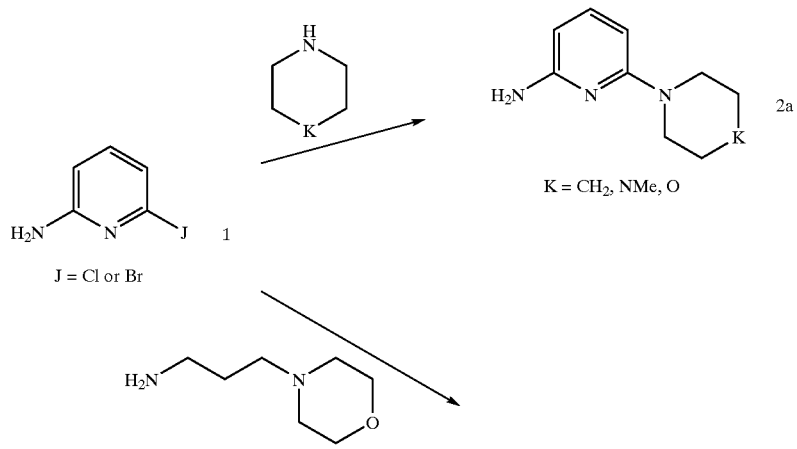

Scheme 1

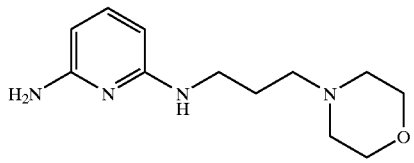

2b

Substituted pyridines can be prepared according to the method set out in Scheme 1. A mixture of halo-aniline 1, substituted amine and phenol is reacted, preferably at a temperature above RT and more preferably at temperature of about 150° C., to yield the heterocyclyl derivative 2a or substituted amine derivative 2b.

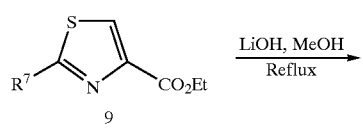

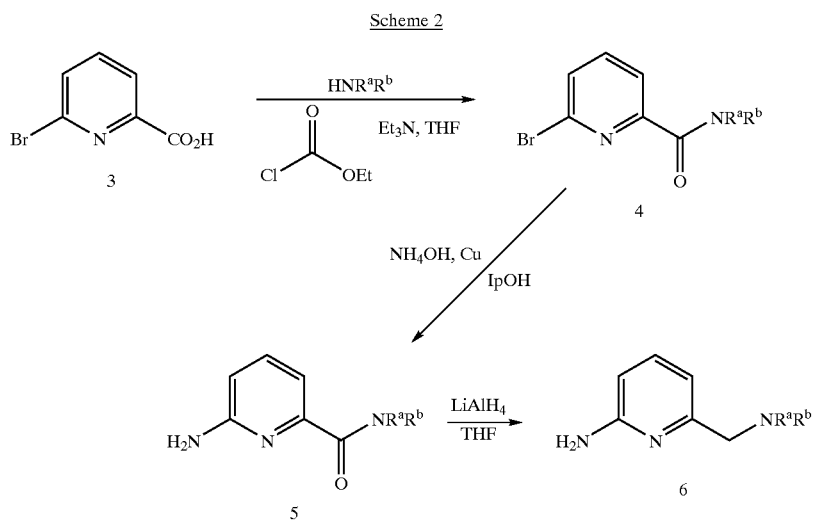

Substituted pyridines can be prepared according to the method set out in Scheme 2. A halopicolinic acid 3 is reacted with substituted amines (where $R^a$ and $R^b$ are H, alkyl, substituted alkyl, etc.) in the presence of chloroformate esters and base in a suitable solvent to form the halopyridyl amide derivatives 4. Preferably the reaction is at a temperature below RT, more preferably the reaction occurs at a temperature of about 0° C. The halopyridyl amide 4 is dehalogenated, such as with $NH_4OH$ and Cu powder in an appropriate solvent, such as IpOH to form the aniline derivative 5. Preferably the reaction occurs at a temperature above RT, more preferably the reaction occurs at about 100° C. The aniline derivative 5 is reduced, such as with $LiAlH_4$ in $Et_2O$ to form the aminoalkyl derivative 6.

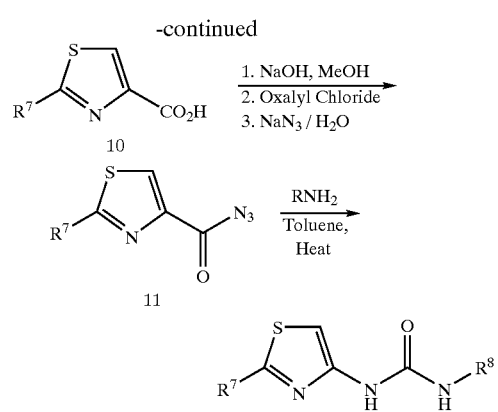

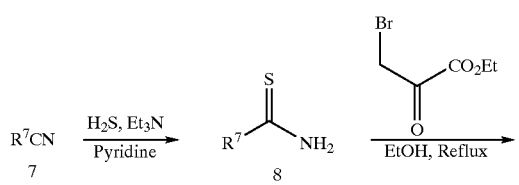

Substituted 4-thiazolylurea compounds 12 are prepared from the corresponding nitrites 7 according to the method set out in Scheme 3. Substituted nitrites 7 are added to base at about RT and $H_2S$ is bubbled through the solution, to yield the thione 8. The thione 8 is combined with ethyl bromopyruvate and heated to form the thiazolyl carboxylate ester 9. Aqueous LiOH is heated with the ester 9 at a temperature above RT and preferably at reflux to give the thiazole carboxylic acid 10. Treatment of the substituted thiazolyl carboxylic acid 10 with base in a suitable solvent at about RT yields a salt. At about 0° C., oxalyl chloride is added to a suspension of the salt in solvent followed by a catalytic amount of DMF. Afterwards, aqueous NaN$_3$ is added to yield the thiazolyl carbonyl azide 11. The carbonyl azide 11 is added to substituted amines to form the thiazolyl urea compound 12.

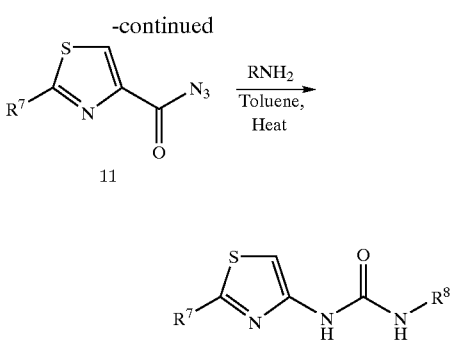

Scheme 4

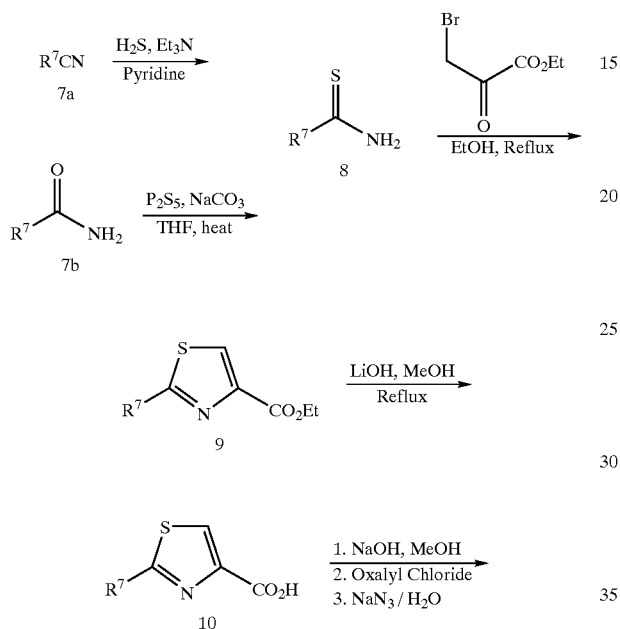

Substituted 4-thiazolylurea compounds 12 are prepared from either the corresponding nitrites 7a or the corresponding amides 7b according to the method set out in Scheme 3. Substituted nitrites 7a are added to base at about RT and H$_2$S is bubbled through the solution, to yield the thione 8. Alternatively, substituted amides 7b are treated with P$_2$S5, NaCO$_3$ in THF and heated to give 8. The thione 8 is combined with ethyl bromopyruvate and heated to form the thiazolyl carboxylate ester 9. Aqueous LiOH is heated with the ester 9 at a temperature above RT and preferably at reflux to give the thiazole carboxylic acid 10. Treatment of the substituted thiazolyl carboxylic acid 10 with base in a suitable solvent at about RT yields a salt. At about 0° C., oxalyl chloride is added to a suspension of the salt in solvent followed by a catalytic amount of DMF. Afterwards, aqueous NaN$_3$ is added to yield the thiazolyl carbonyl azide 11. The carbonyl azide 11 is added to substituted amines to form the thiazolyl urea compound 12.

Scheme 5

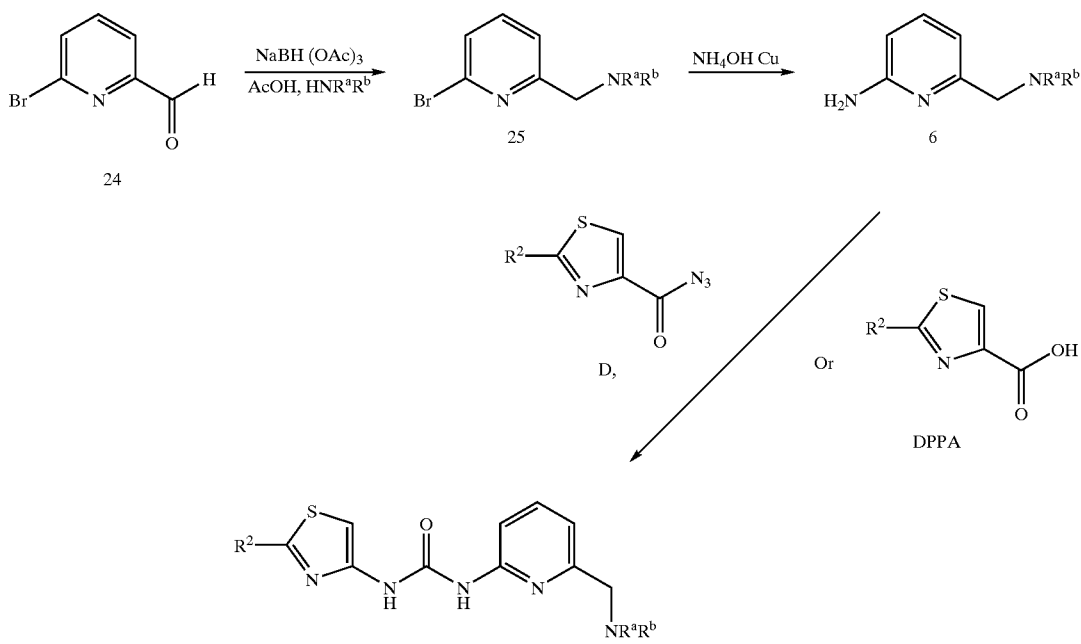

Substituted 4-thiazolylurea compounds 27 are prepared from the corresponding pyridines 24 according to the method set out in Scheme 58. Reductive amination with an amine (including nitrogen-containing heterocycles) and 6-bromo-2-pyridinecarboxaldehyde 24, is achieved such as in a halocarbon solvent such as dichloromethane, in the presence of NaBH(OAc)$_3$ and acid, such as AcOH, to give 2-aminomethyl-6-bromo-pyridine 25. The 2-aminomethyl-6-bromo-pyridine 25 is aminated, such as with NH$_4$OH in the presence of Cu powder, such as in the presence of an alcohol solvent, at a temperature above about 50° C. and preferably at about 100° C., such as in a sealed tube to give the corresponding aniline 6. A substituted thiazolylcarbonylazide, such as in dry hydrocarbon solvent such as toluene is heated at a temperature above about 50° C. and preferably above about 85° C. and reacted with the aniline 6 to give the 4-thiazolylurea compounds 27.

Alternatively, the aniline 6 can be coupled with thiazolyl carboxylic acid, such as with DPPA in the presence of base, such as TEA, and molecular sieves in a solvent like THF. The reaction can be heated at a temperature above about 50° C. and preferably at about reflux yielding the 4-thiazolylurea compounds 27.

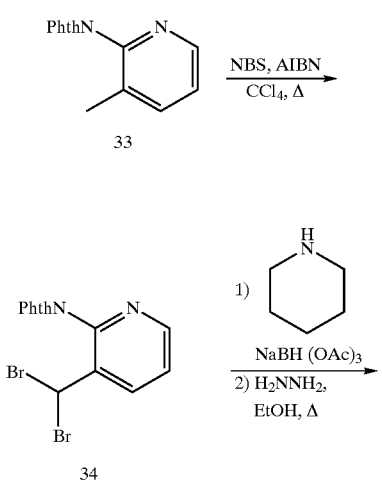

Scheme 9

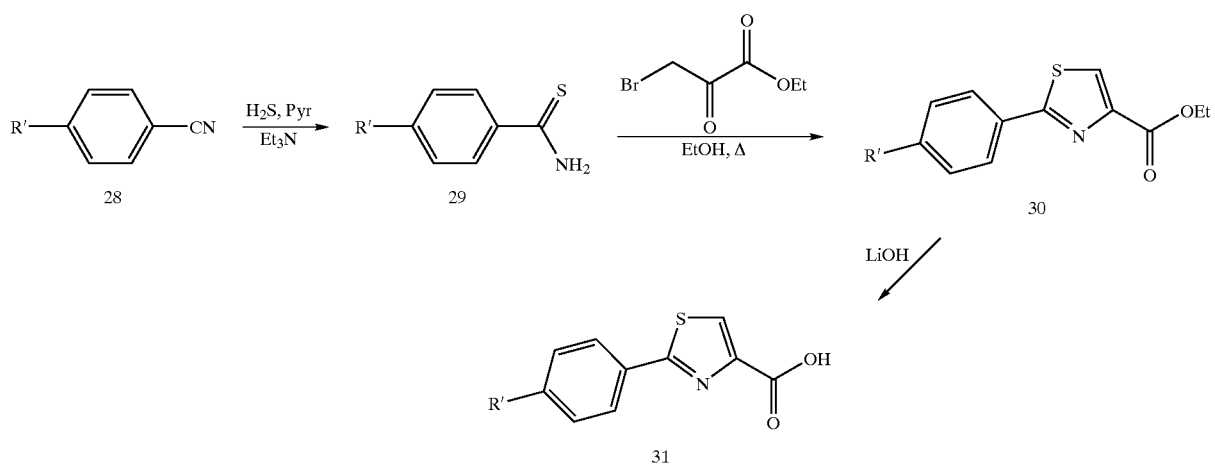

Thiazolyl carboxylic acid 31 (especially appropriate where R' is a sulfonamide or amine) are prepared from the corresponding benzonitriles 28 as described in Scheme 9. H$_2$S is added to the substituted 4-cyanobenzene 28 in the presence of base, such as Et$_3$N to afford the thiobenzamide 29. The thiobenzamide 29 is reacted with ethyl bromopyruvate, such as in an alcohol solvent like EtOH, at a temperature greater than about 50° C., and preferably at about 75° C. to give the thiazolyl ester 30. The thiazolyl ester 30 is hydrolyzed, such as with LiOH monohydrate in an alcohol like aqueous MeOH, at a temperature greater than about 50° C., and preferably at about 75° C., to provide the acid 31. The acid can be used similar to that described in Scheme 8.

Scheme 10

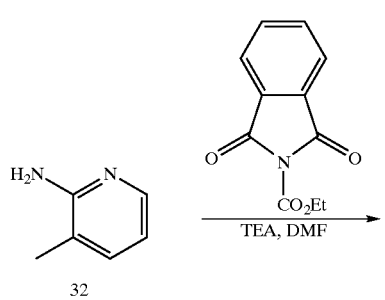

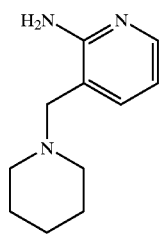

Substituted anilines 35 are prepared from the corresponding methyl compounds 32 as described in Scheme 10. 2-Amino-3-picoline is protected such as with solid carboethoxyphthalimide and base like TEA to provide the phthalimide (Phth) protected aniline 32. The protected 3-methylaniline is brominated, such as with NBS and AIBN at a temperature above 50 C. and preferably at about reflux. Additional AIBN and NBS may be needed to push the reaction to completeness. The dibromomethyl aniline 34 is reacted with an amine, preferably a secondary amine such as substituted or unsubstituted nitrogen containing heterocyclics like piperidines and piperazines, in the presence of acid like glacial AcOH and halocarbon solvent such as CH$_2$Cl$_2$. Treatment with NaBH(OAc)$_3$ provided the protected substituted methyl compound which is deported, such as by treatment with hydrazine monohydrate at a temperature greater than about 50° C., and preferably at reflux to provide the substituted aniline 35.

Scheme 11

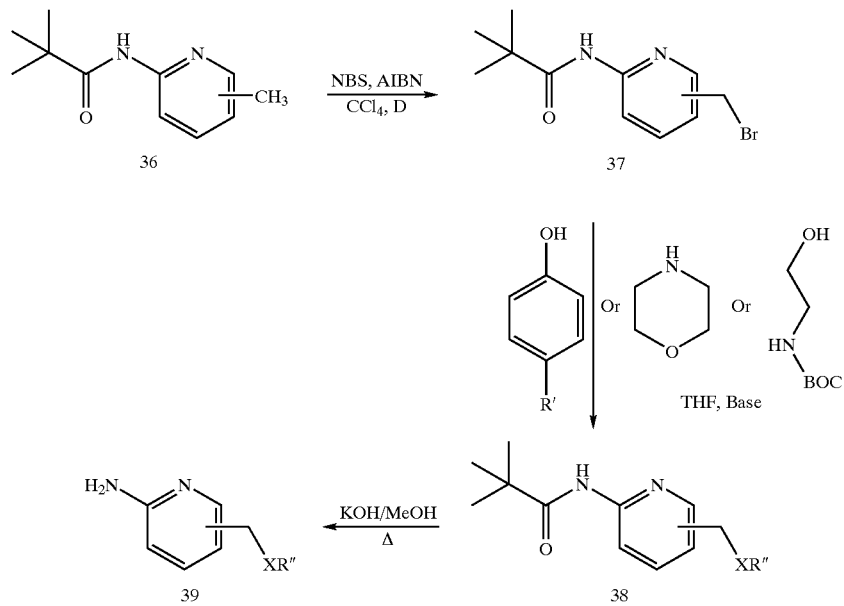

Substituted anilines 39 are prepared from the corresponding methyl compounds 36 as described in Scheme 11. N-Pivaloyl-2-amino-6-bromomethylpyridine 37 is prepared by the method of M. V. Papadopoulou, et al. (*J. Heterocyclic Chem.*, 1995, 32, 675–681). The protected bromomethyl compound is treated with an alcohol or amine in the presence of base, such as NaH to yield the corresponding ether or amino alkyl compounds 38 (where X is O or N). The protected ether or amino alkyl compounds 38 is treated with base, such as in methanolic KOH and warmed to a temperature greater than about RT, and preferably at about 55° C., to provide the substituted anilines 39.

Thiazolylcarbonylazides 43 are prepared as described in Scheme 12. Bromothiazole is coupled with an aryl alcohol, such as phenol, at a temperature greater than about 100° C., and preferably at about 180° C., to provide the phenoxy compound 41. The thiazolyl ester 41 is hydrolyzed, such as with LiOH monohydrate in an alcohol like aqueous MeOH, at a temperature greater than about 50° C., and preferably at about 75° C., to provide the acid 42. Acid 42 is added to ethyl chloroformate and $NaN_3$, in the presence of base such as TEA, to provide the azide 43, which can be used as described in Scheme 8.

Scheme 12

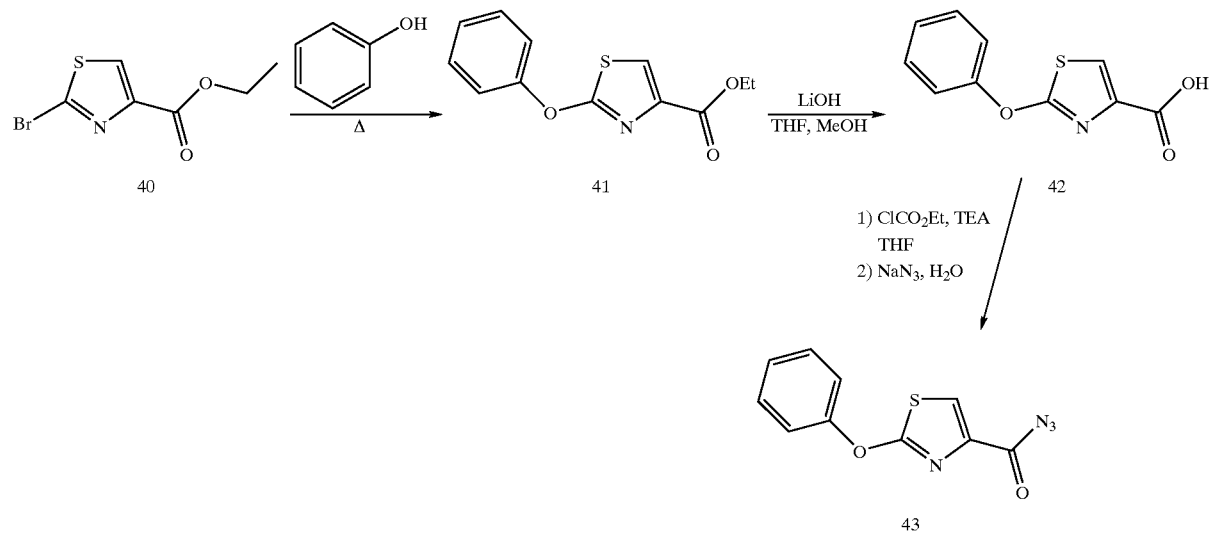

Scheme 13

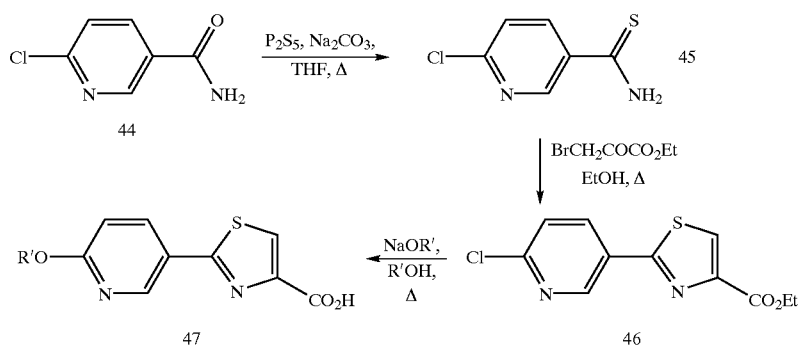

Pyridyl-2-thiazoles 47 are prepared as described in Scheme 13. 4-Chloronicotinamide 44 is converted to the thioamide 45 such as be treatment with $P_2S_5$, in the presence of base, such as $Na_2CO_3$, at a temperature greater than about 50° C., and preferably at about reflux. The thioamide 45 is converted to the thiazole ester 46 by treatment with bromo-ethylpyruvate and heating at a temperature greater than about 50° C., and preferably at about reflux. The ethyl ester is transesterified to the methyl ester with treatment with base, such as NaOMe. Further addition of base and heating at a temperature greater than about 50° C., and preferably at about reflux, hydrolyzed the ester to the acid. Additional NaOMe, in the presence of MeOH, and heating at a temperature greater than about 50° C., and preferably at about reflux, provided the methoxy substituted pyridine compound 47. Use of other bases and alcohols provide alternative alkoxy substituted compounds.

Scheme 14

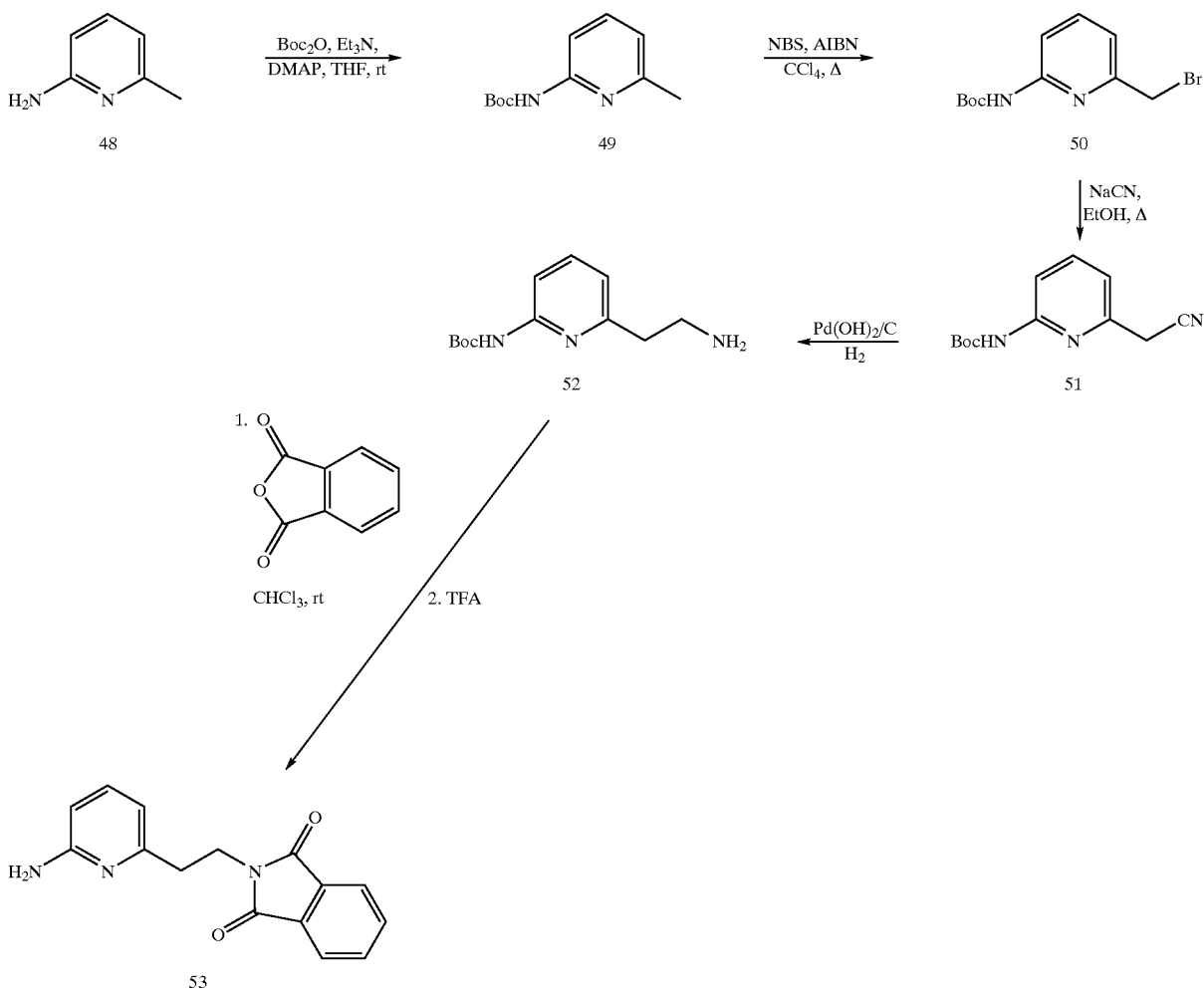

Protected aminoalkyl pyridines 53 are prepared from the 2-amino-6-methylpyridine 48 as described in Scheme 14. The amino group of 2-amino-6-methylpyridine 48 is protected, such as with BOC and normal coupling chemistry, such as with Boc$_2$O and base, like TEA, and DMAP. The protected compound 49 is brominated such as with NBS and AIBN and heating at a temperature greater than about 50° C., and preferably at reflux to provide the bromomethyl derivative 50. The bromomethyl derivative 50 is converted to the cyanomethyl compound 51 such as with treatment with NaCN in the presence of alcohol solvent such as EtOH, and heating at a temperature greater than about 50° C., and preferably at reflux. The cyanomethyl compound 51 is hydrogenated to the aminoethyl derivative 52 such as with hydrogen in the presence of Pd(OH)$_2$/C at a temperature about RT. The aminoethyl derivative 52 is converted to the di-protected compound such as with phthalic anhydride and heating at a temperature between RT and about 70° C. Upon on treatment with strong acid, such as TFA, provides the 2-aminopyridyl compound 53.

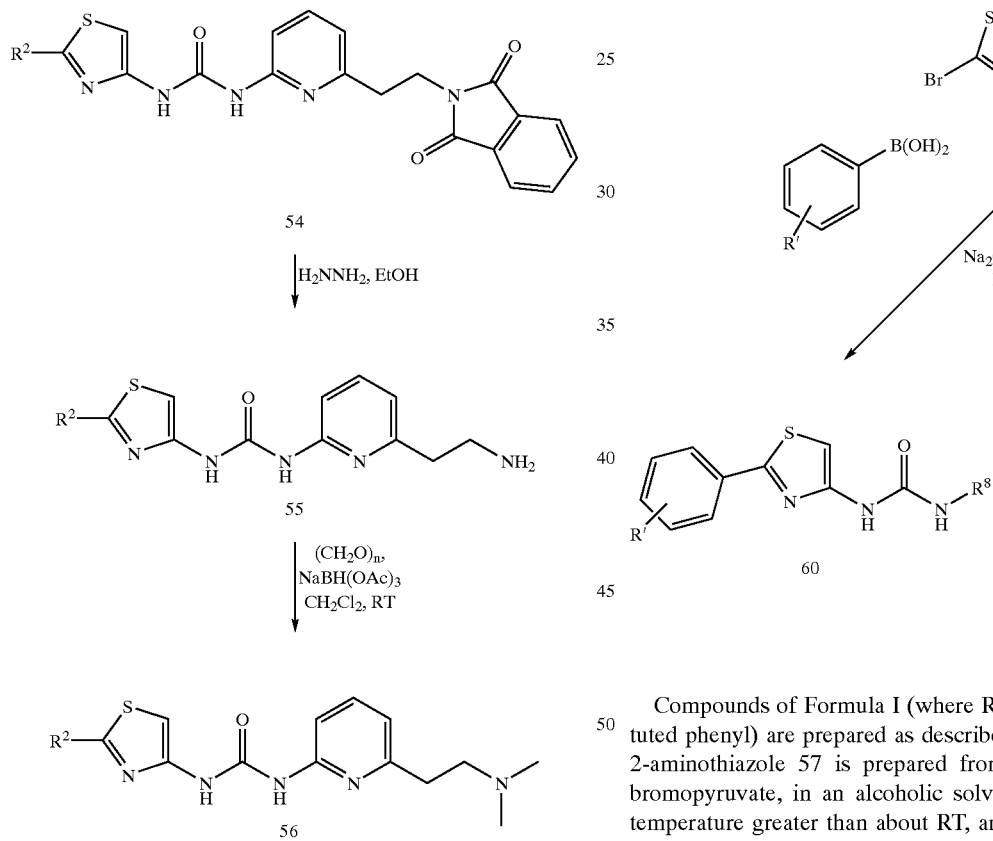

Compounds of Formula I are prepared as described in Scheme 15. Phthalimidylethyl compounds 54 are prepared from the coupling of compounds prepared similar to those described in Scheme 14 and thiazolyl acylazides as described in Scheme 8. Treatment of 54 with hydrazine hydrate and heating at a temperature greater than about 50° C., and preferably at ref lux, provides the aminoethyl derivatives 55. Alkylation of the amine 55, such as with paraformaldehyde and NaBH(OAc)$_3$ in a haloalkyl solvent, such as CH$_2$Cl$_2$ provides the dimethylamine 56.

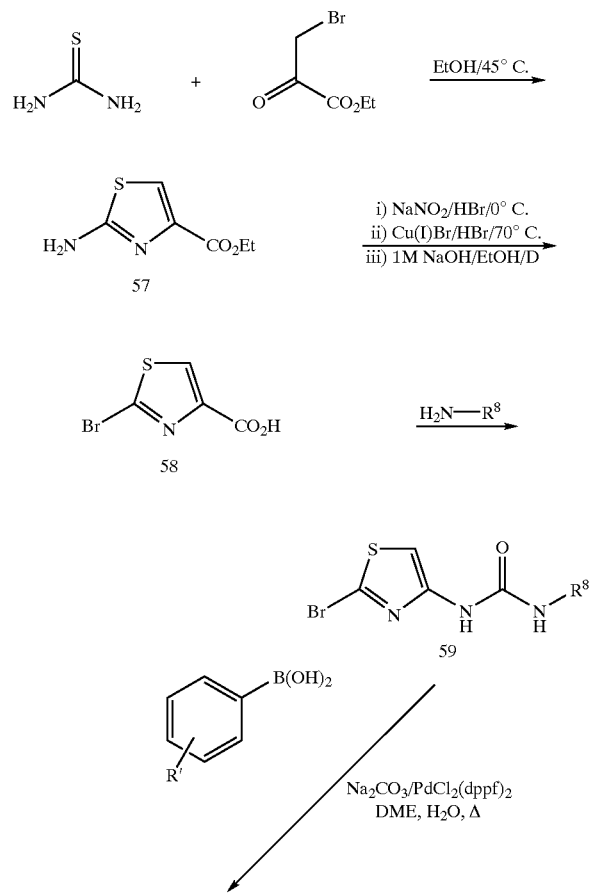

Compounds of Formula I (where R$^7$ is optionally substituted phenyl) are prepared as described in Scheme 16. The 2-aminothiazole 57 is prepared from thiourea and ethyl bromopyruvate, in an alcoholic solvent like ethanol, at a temperature greater than about RT, and preferably at about 45° C. Treatment of the ethyl 2-aminothiazole-4-carboxylate with HBr, NaNO$_2$, CuBr and heating at a temperature greater than about 50° C., and preferably at about 70° C., provides the bromo thiazole ester. Hydrolysis of the ester, such as with aqueous NaOH and alcohol, such as EtOH and heating at a temperature greater than about 50° C., and preferably at reflux provides the bromothiazole acid 58. Coupling with substituted amines, similar to that described in Scheme 8, provides the 2-bromothiazolyl urea 59. Suzuki coupling of 2-bromothiazolyl urea 59 with phenyl boronic acids provides the compounds where R$^7$ is optionally substituted phenyl 60.

Scheme 17

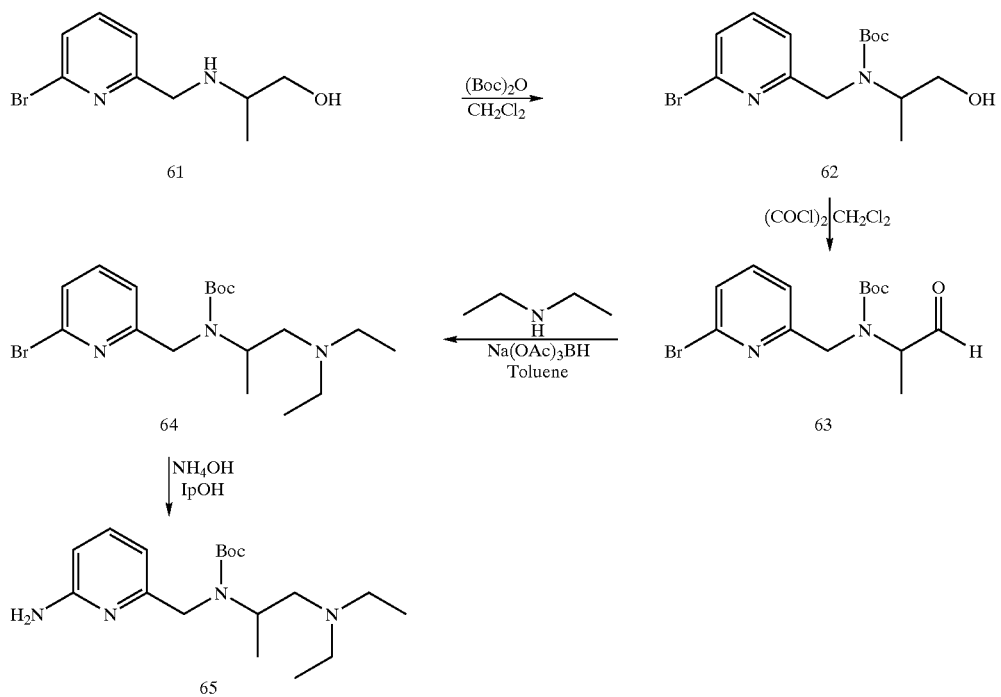

Substituted aminopyridines 65 are prepared by the method described in Scheme 17. 2-[(6-Bromo-2-pyridyl)methyl]aminopropan-1-ol 61 is protected such as with Boc with di-tert-butyldicarbonate in dry $CH_2Cl_2$. Conversion to the aldehyde 63 is accomplished by treatment with oxalyl chloride (in $CH_2Cl_2$), and DMSO at a temperature below RT, preferably below about −23° C. and more preferably at about −63° C. Addition of bas,e such as DEA, to the aldehyde 63, and heating to reflux in a Dean-Stark trap, followed by the addition of a solution of $NaBH(OAc)_3$ in acid such as AcOH at RT provided the aminoalkyl—aminoalkyl derivative 64. The aminopyridine 65 is prepared as described above.

Scheme 18

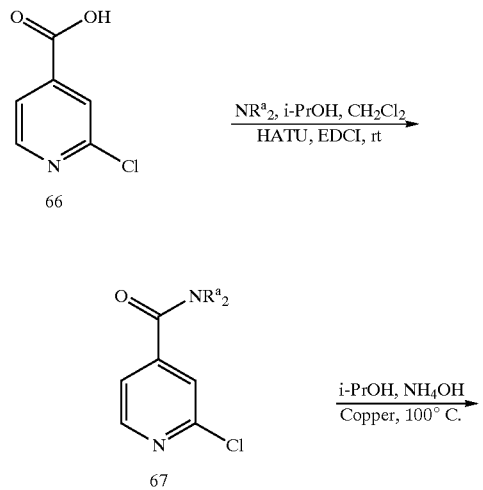

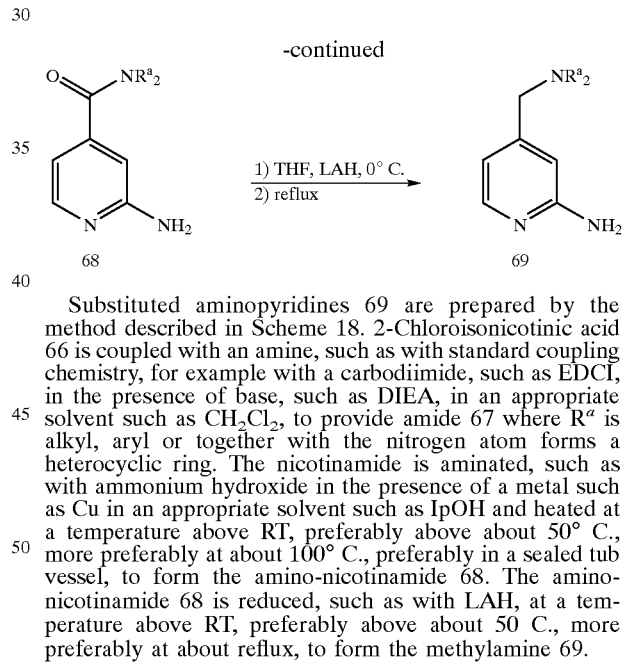

Substituted aminopyridines 69 are prepared by the method described in Scheme 18. 2-Chloroisonicotinic acid 66 is coupled with an amine, such as with standard coupling chemistry, for example with a carbodiimide, such as EDCI, in the presence of base, such as DIEA, in an appropriate solvent such as $CH_2Cl_2$, to provide amide 67 where $R^a$ is alkyl, aryl or together with the nitrogen atom forms a heterocyclic ring. The nicotinamide is aminated, such as with ammonium hydroxide in the presence of a metal such as Cu in an appropriate solvent such as IpOH and heated at a temperature above RT, preferably above about 50° C., more preferably at about 100° C., preferably in a sealed tub vessel, to form the amino-nicotinamide 68. The amino-nicotinamide 68 is reduced, such as with LAH, at a temperature above RT, preferably above about 50 C., more preferably at about reflux, to form the methylamine 69.

Scheme 19

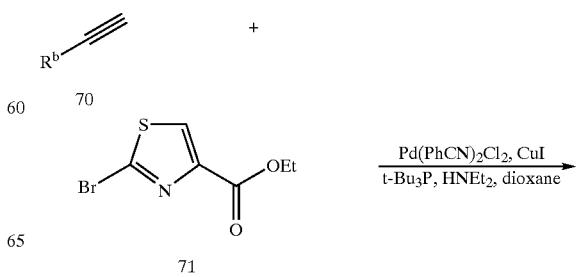

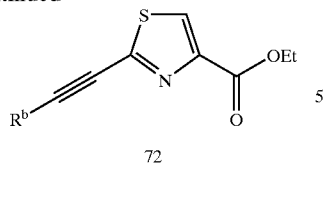

72

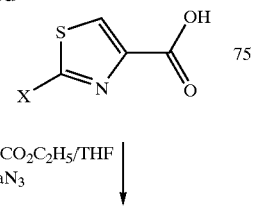

75 i) ClCO$_2$C$_2$H$_5$/THF
ii) NaN$_3$

76

X = Br or Cl

Substituted alkynyl thiazoles 72 are prepared by the method outlined in Scheme 19 where R$^b$ is cycloalkyl, alkyl and the like. Bromothiazole 71 is substituted with the alkyne 70, such as in the presence of Pd(PhCN)$_2$Cl$_2$, CuI$_2$ and t-Bu$_3$P, and base such as DEA, in an appropriate solvent such as dioxane. The reaction temperature is maintained at about RT, to form the alkynyl thiazoles 72.

Scheme 20

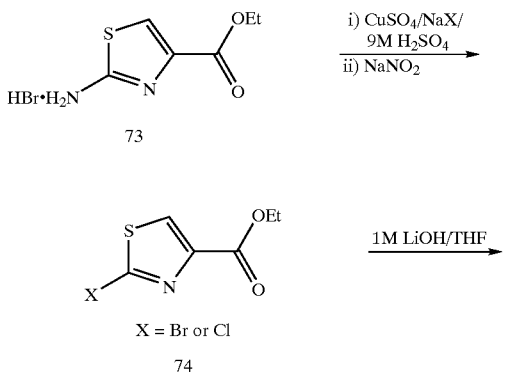

Thiazolylazides 76 are prepared by the method shown in Scheme 20. 2-Amino-thiazole-4-carboxylic acid ester hydrobromide is basified, such as with a saturated solution of NaHCO$_3$ to provide the free base. The free base is subsequently halogenated, such as with a metal halide, preferably NaCl or NaBr, in the presence of acid, preferably H$_2$SO$_4$, more preferably 9M H$_2$SO$_4$, and CuSO$_4$ and NaNO$_2$ at a temperature of about RT to form the halothiazole. The 2-halothiazole-4-carboxylic acid ester is hydrolyzed with a base, such as LIOH, at a temperature above RT, preferably above about 50° C., more preferably about 65° C., to form acid 75. The azido-thiazole 76 is prepared from the 2-halo-thiazole-4-carboxylic acid 75 in the presence of base, such as TEA, ethyl chloroformate and sodium azide at a temperature about RT.

Scheme 21

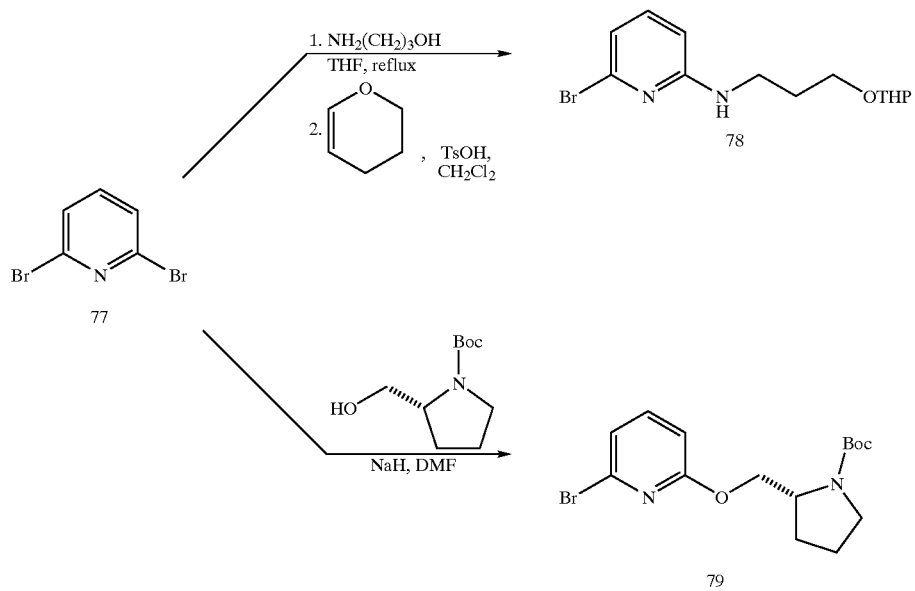

Substituted bromo-pyridines 78 and 79 are prepared from dibromo-pyridine 77 as described in Scheme 21. 2,6-Dibromopyridine 77 is reacted with an aminoalcohol in an appropriate solvent, such as THF, at a temperature above RT, preferably at a temperature above about 50° C., more preferably at reflux, to form the amino pyridine. The alcoholamino-pyridine is coupled with 3,4-dihydro-2H-pyran such as with TsOH in the presence of an appropriate solvent, such as $CH_2Cl_2$ at a temperature of about RT, to form the pyran substituted pyridine 78.

D-2-Hydroxymethyl-pyrrolidine-1-carboxylic acid tert-butyl ester is treated with a strong base, preferably NaH, at a temperature about RT, then 2,6-dibromopyridine 77 is added and reacted at a temperature above RT, preferably at a temperature above about 50° C., more preferably at about 90° C. to form the pyrrolidinyl ether 79.

2-(Piperidinyl)pyridines 83 are prepared as described in Scheme 22. Strong base, such as n-BuLi, in a solvent such as dry THF, is added to dibromopyridine 77 at a temperature less than RT, preferably below about −50° C., more preferably at about −70° C. 4-Methylpiperidone is added to form the 4-hydroxy-piperidine 80 at a temperature less than RT, preferably below about −50° C., more preferably at about −70° C. The 4-hydroxy piperidine 80 is hydrated, such as with strong acid, preferably $H_2SO_4$, at a temperature above RT, preferably above 750C, more preferably at about 100 C., to form the tetrahydro-bipyridine 81. The 2-bromo-pyridine 81 is aminated, such as with $NH_4OH$, in the presence of Cu powder at a temperature above RT, preferably above about 75° C., more preferably at about 100° C., to form the amino-pyridine 82. Preferably the reaction is run in a sealed tube. The 1',2,3',6'-tetrahdyro-[2,4']bipyridinyl-6-ylamine is hydrogenated, such as with $H_2$ in the presence of $Pd(OH)_2/C$, at a temperature of about RT, to form the piperidinyl pyridine 83.

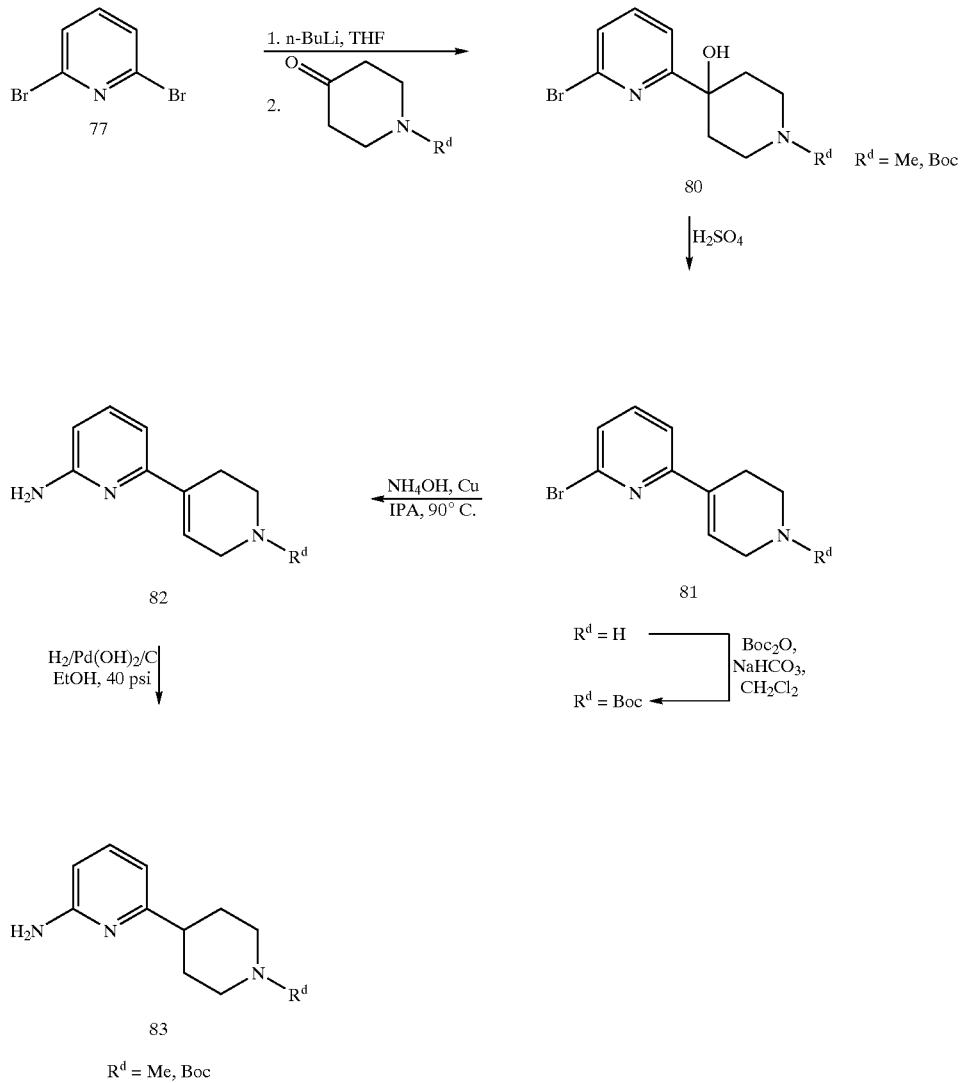

Scheme 22

Scheme 23

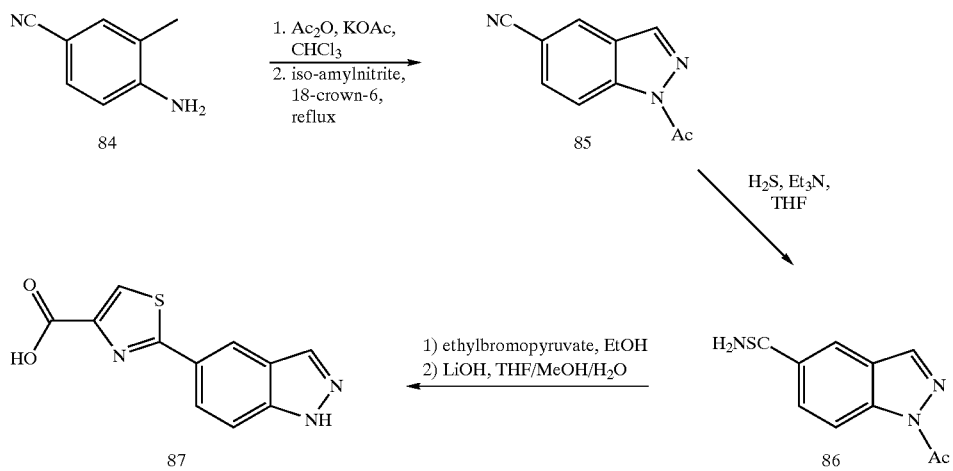

Thiazolyl indazoles 87 can be prepared from anilines as outlined in Scheme 23. Similar to the method of J. Sun, et al, J. Org. Chem., 1997, p. 5627, protected 1H-indazole-5-carbonitrile 85 is prepared from 4-amino-3-methylbenzonitrile 84 in the presence of acetic anhydride, and KOAc in an appropriate solvent such as $CHCl_3$. The protected 1H-indazole-5-carbothioic acid amide 85 is prepared from the carbonitrile 84 by treatment with $H_2S$ gas in the presence of base, such as $Et_3N$ and solvent, such as THF, at a temperature below RT, preferably at about 0° C. The amide 86 is added to a diketo compound, such as ethylbromopyruvate at a temperature above RT, preferably above about 50° C., more preferably at reflux, in an appropriate solvent such as EtOH, to form the thiazolyl indazole ester. The ester is hydrolyzed with base, such as with LiOH at a temperature of about RT to yield the free acid 87. Additionally, the indazole may be acylated, such as with $Ac_2O$.

Scheme 24

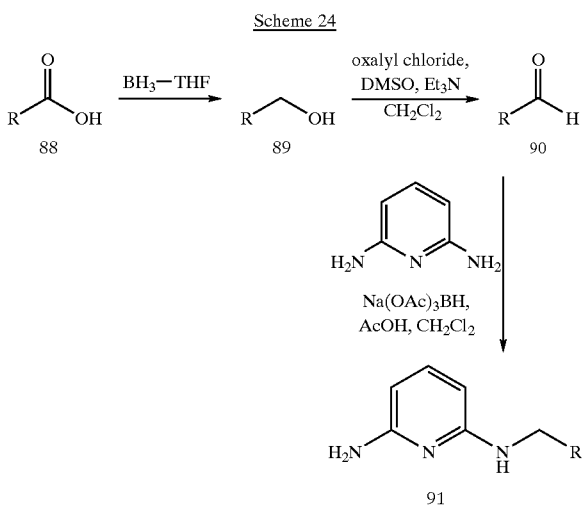

Disubstituted aminopyridines 91 can be prepared from the corresponding acids 88, where $R^c$ is heterocyclyl, as described in Scheme 24. Carboxylic acid or the corresponding ester is reduced, such as with $BH_3$-THF solution in a solvent, such as in dry THF, at a temperature of about RT, to form the alcohols 89. Oxalyl chloride and DMSO in a solvent such as dry $CH_2Cl_2$, is treated with the alcohol 89 in the presence of base, such as TEA at a temperature of about RT, to form the aldehyde 90. The aldehyde 90 is coupled with an heteroaryl group, such as diaminopyridine in a solvent such as dry $CH_2Cl_2$, via reductive amination for example in the presence of $NaBH(OAc)_3$, piperidine and HOAc, at a temperature above RT, preferably at about 40° C., to form the substituted amino pyridine 91.

N-Oxides can be obtained in a known matter by reacting a compound of Formula I–VI with hydrogen peroxide or a peracid, e.g. 3-chloroperoxy-benzoic acid, in an inert solvent, e.g. $CH_2Cl_2$, at a temperature between about –10 to about 35° C., such as about 0° C. to about RT.

In the preparation of starting materials, existing functional groups, for example carboxy, hydroxy, amino, or mercapto, which do not participate in the reaction should, if necessary, be protected. Such protecting groups are those or similar to those usually used in the synthesis of peptide compounds, cephalosporins, penicillins, nucleic acid derivatives or sugars. Preferred protecting groups, their introduction and their removal are described above or in the examples.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves ready removal, i.e. without undesired secondary reactions, typically by solvolysis, reduction, photolysis or also by enzyme activity, for example under conditions analogous to physiological conditions, and that they are not present in the end-products. One skilled in the art knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/1, Georg Thieme Verlag, Stuttgart 1974, in H. -D. Jakubke and H. Jescheit, "Aminosauren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide und Derivate" (Chemistry of carbohydrates: monosaccharides and derivatives), Georg Thieme Verlag, Stuttgart 1974.

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

In certain cases, typically in hydrogenation processes, it is possible to achieve stereoselective reactions, allowing for example easier recovery of individual isomers.

The solvents from which those can be selected which are suitable for the reaction in question include, for example, water, esters, typically lower alkyl-lower alkanoates, e.g EtOAc, ethers, typically aliphatic ethers, e.g. $Et_2O$, or cyclic ethers, e.g. THF, liquid aromatic hydrocarbons, typically benzene or toluene, alcohols, typically MeOH, EtOH or 1-propanol or iPrOH, nitrites, typically $CH_3CN$, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g. AcOH, carboxylic acid anhydrides, typically lower alkane acid anhydrides, e.g. $Ac_2O$, cyclic, linear, or branched hydrocarbons, typically cyclohexane, hexane, or isopentane, or mixtures of these solvents, e.g. aqueous solutions, unless otherwise stated in the description of the process.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of Formula I–VI, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

All remaining starting materials are known, capable of being prepared according to known processes, or commercially obtainable; in particular, they can be prepared using processes as described above or as in the examples.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds of this invention may also be represented in multiple tautomeric forms, for example, as illustrated below:

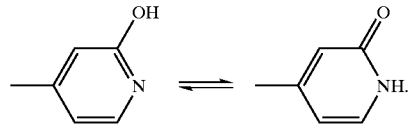

The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thiazolyl, etc.) may be attached to specific atoms, whereby they a re intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

A compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, simulated moving bed ("SMB")), extraction, distillation, trituration, reverse phase HPLC and the like. Reactions conditions such as temperature, duration, pressure, and atmosphere (inert gas, ambient) are known in the art and may be adjusted as appropriate for the reaction. Additionally, the compounds can be produced metabolically.

As can be appreciated by one skilled in the art, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. Greene and P. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995); P. Lopez et al., Synthesis 2, 186 (1998); A. Mikhalev, et al., Khim. Geterotsikl Soedin, 5, 697 (1997); M. Fernandez, et al., Synthesis, 11, 1362 (1995); P. Desos, et al., J. Med. Chem, 39, 197 (1996); G. Timari, et al., Synlett, 9, 1067 (1997); Y. Tagawa, et al., J. Heterocycl. Chem., 34, 1677 (1997); A. Fuerstner, et al., Chem. Sci. 50, 326 (1995); A. Katritzky and A. Pozharski, Handbook of Heterocyclic Chemistry, 2$^{nd}$ Ed. (2001); and WO01/132658.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The following examples contain detailed descriptions of the methods of preparation of compounds of Formulas I–VI. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures.

The following abbreviations are used:

| | |
|---|---|
| AcOH, HOAc | acetic acid |
| Ac$_2$O | acetic anhydride |
| AcCN, CH$_3$CN | acetonitrile |
| ATP | adenosine triphosphate |
| NH$_3$ | ammonia |
| NH$_4$OH | ammonium hydroxide |
| NH$_4$Cl | ammonium chloride |
| AIBN | 2,2'-azobis-isobutyrlnitrile |
| HATU | O-(7-azabenzotriazol-l-yl)-N,N,N',N'-tetramethyluronium hexafluorophosphate |
| BOP-Cl | bis(2-oxo-3-oxazolidinyl)phosphinic chloride |
| PdCl$_2$ (dppf) | 1,1-bis (diphenylphosphino) ferrocene palladium chloride |
| BH$_3$-THF | borane-tetrahydrofuran |
| BSA | bovine serum albumin |
| BOC | tert-butyloxycarbonyl |
| BuLi | n-butyllithium |
| Boc$_2$O | di-tert-butyl dicarbonate, BOC anhydride |
| CCl$_4$ | carbon tetrachloride |
| CHCl$_3$ | chloroform |
| Cu | copper |
| CuBr- | copper (I) bromide |
| CuI$_2$ | copper (II) iodide |
| CuSO$_4$ | copper (II) sulfate |
| CH$_2$Cl$_2$ | dichloromethane, methylene chloride |
| Pd(PhCN)$_2$Cl$_2$ | dichlorobis(benzonitrile)palladium |
| DEA, Et$_2$NH | diethylamine |
| Et$_2$O | diethyl ether |
| DIEA | diisopropylethylamine |
| DIBAL-H | diisobutylaluminum hydride |
| DME | 1,2-dimetoxyethane |
| EDC, EDCI | 1-(3-dimethylaminopropyl)-3-ethylcarbodiimide hydrochloride |
| DMAP | 4-(dimethylamino)pyridine |
| DMF | dimethylformamide |
| DMSO | dimethylsulfoxide |
| DPPA, (PhO)$_2$PON$_3$ | diphenylphosphoryl azide |
| DTT | dithiothreitol |
| EtOH | ethanol |
| EtOAc | ethyl acetate |
| EGTA | ethylene glycol-bis(β-aminoethyl ether)-N,N,N',N'-tetraacetic acid |
| EDTA | ethylenediaminetetraacetic acid |
| g | gram |
| h | hour |
| HCl | hydrochloric acid |
| HBr | hydrobromic acid |

-continued

| | |
|---|---|
| H$_2$S | hydrogen sulfide |
| HOBt | hydroxybenzotriazole |
| IpOH | isopropanol |
| LAH, LiAlH$_4$ | lithium aluminum hydride |
| LiOH | lithium hydroxide |
| MgCl$_2$ | magnesium chloride |
| MgSO$_4$ | magnesium sulfate |
| MnCl$_2$ | manganese chloride |
| MeOH | methanol |
| MeMgI | methyl magnesium iodide |
| mg | milligram |
| ml, mL | milliliter |
| min | minutes |
| NBS | N-bromosuccinimide |
| N$_2$ | nitrogen |
| Pd(OH)$_2$/C | palladium hydroxide on carbon |
| H$_3$PO$_4$ | phosphoric acid |
| P$_2$S$_5$ | phosphorous pentasulfide |
| PtO$_2$ | platinum oxide |
| KOAc | potassium acetate |
| KOH | potassium hydroxide |
| pyr | pyridine |
| RT | room temperature |
| Na$_2$SO$_4$ | sodium sulfate |
| Na$_2$CO$_3$ | sodium carbonate |
| NaCNBH$_3$ | sodium cyanoborohydride |
| NaBH$_4$ | sodium borohydride |
| NaOH | sodium hydroxide |
| NaOEt | sodium ethoxide |
| NaOMe | sodium methoxide |
| NaBr | sodium bromide |
| NaCl | sodium chloride |
| NaCN | sodium cyanide |
| NaNO$_2$ | sodium nitrite |
| NaN$_3$ | sodium azide |
| SOV | sodium orthovanadate |
| NaBH(OAc)$_3$ | sodium trisacetoxy borohydride |
| NaH | sodium hydride |
| NaHCO$_3$ | sodium bicarbonate |
| H$_2$SO$_4$ | sulfuric acid |
| THF | tetrahydrofuran |
| TsOH | Toluenesulfonic acid |
| t-Bu$_3$P | tri-tert-butylphosphine |
| TEA, Et$_3$N | triethylamine |
| TFA | trifluoroacetic acid |
| Tris-HCl | Tris (hydroxymethyl) aminomethane hydrochloride salt |
| H$_2$O | water |

Preparation A: 2-Amino-6-morpholinopyridine:

A mixture of 2-chloro-6-aminopyridine (200 mg, 1.49 mmol), morpholine (326 mg, 3.75 mmol) and phenol (2 g) was heated at 150° C. for 20 h. After cooling to RT, 3N NaOH (10 mL) was added and the mixture was extracted with EtOAc (3×50 mL). The combined organic layers were washed with brine, dried over Na$_2$SO$_4$, filtered and concentrated in vacuo. The crude was purified by chromatography on silica gel (1:10 MeOH/CH$_2$Cl$_2$) to afford the morpholino derivative as an amber oil. MS m/z: 180 (M+1).

Preparation B: 2-Bromo-6-N,N-diethylamidopyridine:

Ethyl chloroformate (1.76 g, 16.3 mmol) was added dropwise to a mixture of 6-bromopicolinic acid (3 g, 14.8 mmol) and Et$_3$N (1.8 g, 17.8 mmol) in THF (150 mL) at 0° C. After the mixture was stirred for 1 h, DEA (1.3 g, 17.8 mmol) was added slowly to the mixture at 0° C. The resulting mixture was stirred at RT for 5 h. H$_2$O (200 mL) was added and the mixture was extracted with EtOAc (3×120 mL). The combined organic layers were washed with 1N NaOH and brine, dried over Na$_2$SO$_4$, and filtered. The filtrate was concentrated in vacuo to afford 2-bromo-6-N,N-diethylamidopyridine as an amber oil. MS m/z: 259 (M+1).

Preparation C: 2-Amino-6-N,N-diethylamidopyridine:

A mixture of 2-bromo-6-N,N-diethylamidopyridine (3.5 g), 50 mL of 37% NH$_4$OH and 0.8 g of Cu powder in 40 mL of IpOH was heated at 100° C. in sealed tube for 20 h. After cooling to RT, brine was added and the mixture was extracted with EtOAc (3×120 mL). The combined organic layers were washed with brine, dried over $Na_2SO_4$, filtered and concentrated in vacuo to afford the amino derivative as a light amber solid. MS m/z: 194 (M+1).

Preparation D: 2-Amino-6-N,N-diethylaminomethylpyridine:

To a solution of 2-amino-6-N,N-diethylamidopyridine (2.2 g, 11.4 mmol) in 200 mL of THF was added slowly 34.2 mL of $LiAlH_4$ (1.3 g, 34.2 mmol) solution in $Et_2O$ at 0° C. The resulting mixture was heated at reflux for 6 h. After cooling to 0° C., 2 mL of $H_2O$, 1.3 mL of 15% NaOH and 7.5 mL of $H_2O$ was added to the mixture sequentially. After stirring for 2 h at RT, the mixture was filtered through Celite®. The filtrate was concentrated and purified by chromatography on silica gel (1:10 $MeOH(NH_3)/CH_2Cl_2$) to afford the aminomethyl compound as an amber oil. MS m/z: 180 (M+1).

Preparation E: 2-Amino-6-(N-methylpiperazinyl)pyridine:

A mixture of 2-bromo-6-aminopyridine (3 g, 17.34 mmol), 1-methylpiperizine (2.3 g, 22.54 mmol) and Cu powder (0.5 g, 7.87 mmol) in 5 mL of 2,4-diethylphenol was heated at 150° C. for 20 h. After cooling to RT, 3N HCl (30 mL) was added and the mixture was extracted with $Et_2O$ (2×100 mL). The aqueous layer was basified with concentrated $NH_4OH$ to pH>10 and then extracted with EtOAc (3×100 mL). The combined organic layers were washed with brine, dried over $Na_2SO_4$, filtered and concentrated in vacuo. The crude was purified by chromatography on silica gel (1:10 $MeOH(NH_3)/CH_2Cl_2$) to afford the piperazinyl compound as a light amber solid. MS m/z: 193 (M+1).

Preparation F: 2-Amino-6-(4-morpholino)propylaminopyridine:

A mixture of 2-bromo-6-aminopyridine (0.5 g, 2.92 mmol), 4-(3-aminopropyl)morpholine (1.5 g 10.42 mmol) and Cu powder (0.6 g, 9.52 mmol) in 15 mL of IpOH and 5 mL of $H_2O$ was heated at 100° C. in a sealed tube for 24 h. After cooling to RT, water was added and the mixture was extracted with EtOAc (3×50 mL). The combined organic layers were washed with brine, dried over $Na_2SO_4$, filtered and concentrated in vacuo. The crude was purified by chromatography on silica gel (1:10 $MeOH(NH_3)/CH_2Cl_2$) to afford the morpholino compound as an amber oil. MS m/z: 237 (M+1).

Preparation G: 2-Amino-6-(2-N,N-dimethylamino) ethylaminopyridine:

A mixture of 2-bromo-6-aminopyridine (0.3 g, 1.17 mmol), N,N-dimethylethylenediamine (1 g, 11.36 mmol) and Cu powder (0.74 g, 11.7 mmol) in 30 mL of IpOH was heated at 100° C. in sealed tube for 20 h. After cooling to RT, $H_2O$ was added and the mixture was extracted with EtOAc (3×50 mL). The combined organic layers were washed with brine, dried over $Na_2SO_4$, filtered and concentrated in vacuo. The crude was purified by chromatography on silica gel (1:10 MeOH ($NH_3$)/$CH_2Cl_2$) to afford the compound as an oil. MS m/z: 181 (M+1)

Preparation H: Amino-2-pyridylmethane-1-thione:

2-Cyanopyridine (2.6 g, 0.025 mol) was added to a solution of TEA (5.5 mL) and dry pyridine (50 mL) at RT. $H_2S$ was bubbled through the solution for 1 h. Afterwards, $H_2O$ (150 mL) was added and the mixture was extracted with EtOAc (3×50 mL). The EtOAc extracts were dried over $Na_2SO_4$, filtered, and the solvent was removed under vacuum. The resulting residue was purified by column chromatography eluting with hexanes:EtOAc (4:1) to give amino-2-pyridylmethane-1-thione as a light yellow solid. GC/MS m/z: 139 (M+H); GC Retention time: 7.93 min.

Preparation I: 2-(2-Pyridinyl)thiazole-4-carboxylic acid:

Amino-2-pyridylmethane-1-thione (1.88 g, 0.0136 mol), ethyl bromopyruvate (1.80 mL, 0.0143 mol) and EtOH (30 mL) were combined and heated to reflux. GC/MS of reaction mixture after 3 h showed total consumption of the starting materials. After cooling to RT, the solvent was removed under vacuum resulting in a dark brown oil (GC/MS m/z: 235 (M+H); GC Retention time: 10.69 min). The material was taken up in MeOH (20 mL), 1.0M $LiOH-H_2O$ (20 mL) was added and the mixture was heated to 100° C. for 14 h. After cooling to RT, the excess MeOH was evaporated and the resulting brown solid filtered. The material was washed with a minimum of $H_2O$ and dried in vacuo to give the thiazole as a brown solid.

Preparation J: 2-(4-Pyridinyl)-4-thiazolylcarbonylazide:

To a suspension of 2-(4-pyridinyl)-4-thiazolyl carboxylic acid (Maybridge Chem., 6.0 g, 29.1 mmol) in 150 mL MeOH at RT was added NaOH (1.28 g, 32.0 mmol) and the mixture was stirred at RT for 45 min. The reaction mixture was concentrated in vacuo then dried under high vacuum for 60 h (overnight drying is a minimum). The crude salt was suspended in 150 mL of $CH_2Cl_2$ and cooled in an ice bath. Oxalyl chloride (2.8 mL) was added slowly to the suspension followed by a catalytic amount of DMF (0.2 mL). The mixture was stirred for 2 h and warmed to RT. The reaction was cooled in an ice bath and a solution of $NaN_3$ (2.27 g) in water (90 mL) was added and stirring was continued for 3 h. The reaction mixture was diluted with water (90 mL) and extracted with $CH_2Cl_2$ (3×75 mL). The combined organic layers were filtered through Celite® (~12 g) washed with 90 mL brine, dried with $MgSO_4$ and concentrated in vacuo. Drying the crude compound on the vacuum line afforded the azido derivative as a light brown solid. MS m/z: 204.5 ($M-N_2+H$).

Preparation K: 2-(3-Pyridinyl)-4-thiazolylcarbonylazide:

In a manner similar to that described for the preparation of 2-(4-pyridinyl)-4-thiazolylcarbonylazide, 6.0 g of 2-(3-pyridinyl)-4-thiazolylcarboxylic acid was treated successively with NaOH, oxalyl chloride and a solution of $NaN_3$ in water to give the 3-pyridinylazide as a pale brown solid. MS m/z: 204.5 ($M-N_2+H$)

Preparation L: 2-(2-Pyridinyl)-4-thiazolylcarbonylazide:

In a manner similar to that described for the preparation of 2-(4-pyridinyl)-4-thiazolyl-carbonylazide, 2-(2-pyridinyl)-4-thiazolylcarboxylic acid (1.0 g)was treated successively with NaOH, oxalyl chloride and a solution of $NaN_3$ in water to give the 2-pyridinyl azide as a pale brown solid: m.p. 112–114° C. MS m/z: 232 (M+H).

Preparation M: 2-Phenyl-4-thiazolylcarbonylazide:

In a manner similar to that described for the preparation of 2-(4-pyridinyl)-4-thiazolylcarbonyl-azide, 1.0 g of 2-phenyl-4-thiazolylcarboxylic acid was treated successively with NaOH, oxalyl chloride and a solution of $NaN_3$ in water to give the phenylazide as an off white solid. MS m/z: 203.5 ($M-N_2+H$).

Preparation N: 4-(6-Bromo-pyridin-2-ylmethyl)-morpholine

To a stirred solution of 6-bromo-2-pyridine-carboxaldehyde (200 mg, 1.08 mmol) in dichloroethane (10 mL) was added morpholine (0.14 mL, 1.62 mmol) followed by $NaBH(OAc)_3$ (458 mg, 2.16 mmol) and AcOH (0.25 mL, 4.32 mmol). The resulting mixture was stirred at RT for 12 h. The reaction was quenched with 2M $Na_2CO_3$ solution and stirred 1 h. The mixture was poured into $Et_2O$ and washed with 2 M $Na_2CO_3$ solution. The organic layer was collected, dried over $Na_2SO_4$ and concentrated in vacuo to give 2-bromo-6-morpholinyl-methylpyridine as a white solid. MS m/z: 256.9 (M+H).

The following compounds were prepared in a manner similar to that described above:

1] 1-(6-Bromopyridin-2-ylmethyl)-piperidine-4-carboxylic acid ethyl ester, as a pale yellow solid, was prepared in a manner similar to that described in General Preparation N [6-bromo-2-pyridinecarboxaldehyde (400 mg, 2.16 mmol) was added to ethyl isonipecotate (0.5 mL, 3.24 mmol) in dry $CH_2Cl_2$ (10 mL)]. MS m/z: 327.0 (M+H). Calc'd for $C_{14}H_{19}BrN_2O_2$: 326.90.

2] To 6-bromo-2-pyridinecarboxaldehyde (400 mg, 2.16 mmol) was added L-leucinol (0.42 mL, 3.24 mmol) in dry $CH_2Cl_2$ (10 mL) to give 2-[(6-bromo-pyridin-2-ylmethyl)-amino]-4-methyl-pentan-1-ol as brown solid. MS m/z: 287.6 (M+H). Calc'd for $Cl_2H_{19}BrN_2O$: 287.2.

3] To 6-bromo-2-pyridinecarboxaldehyde (500 mg, 2.69 mmol) was added 1,4-dioxa-8-azaspiro-[4,5]-decane (0.5 mL, 4.03 mmol) in dry $CH_2Cl_2$ (10 mL) to give 2-bromo-6-(4-ethoxyacetal)-piperidinylmethylpyridine as white solid. MS m/z: 313 (M+H). Calc'd for $C_{13}H_{17}BrN_2O2$: 313.2.

4] To 6-bromo-2-pyridinecarboxaldehyde (400 mg, 2.15 mmol) was added 3,5-dimethylpiperidine (0.4 mL, 3.22 mmol) in dry $CH_2Cl_2$ (10 mL) to give 2-bromo-6-(3,5-dimethyl)piperidinylmethyl pyridine as white solid. MS m/z: 283.2 (M+H). Calc'd for $C_{13}H_{19}BrN_2$: 283.2

5] To 6-bromo-2-pyridinecarboxaldehyde (400 mg, 2.15 mmol) was added 4-methylpiperidine (0.4 mL, 3.22 mmol) in dry $CH_2Cl_2$ (10 mL) to give 2-bromo-6-[(4-methyl)piperidinylmethyl]pyridine as a white solid. MS m/z: 269.4 (M+H). Calc'd for $C_{12}H_{17}BrN_2$: 269.18.

6] To 6-bromo-2-pyridinecarboxaldehyde (400 mg, 2.15 mmol) was added 2-methylpiperidine (0.4 mL, 3.22 mmol) in dry $CH_2Cl_2$ (10 mL) to give 2-bromo-6-[(2-methylpiperidinyl)methyl]pyridine as a pale yellow solid. MS m/z: 269.1(M+H). Calc'd for $C_{12}H_{17}BrN_2$: 269.18.

7] To 6-bromo-2-pyridinecarboxaldehyde (400 mg, 2.15 mmol) was added 4-(1-pyrrolidinyl)-piperidine (500 mg, 3.22 mmol) in dry $CH_2Cl_2$ (15 mL) to give 2-bromo-6-[4-(1-pyrrolidinyl)-piperidinylmethyl] pyridine as a pale yellow solid. MS m/z: 326.1(M+2H). Calc'd for $C_{15}H_{22}BrN_3$: 324.26.

8] To 6-bromo-2-pyridinecarboxaldehyde (400 mg, 2.15 mmol) was added 3-hydroxypiperidine (326 mg, 3.22 mmol) in dry $CH_2Cl_2$ (15 mL) to give 2-bromo-6-(3-hydroxypiperidinyl)methyl pyridine as pale yellow solid. MS m/z: 271.2 (M+H). Calc'd for $C_{11}H_{15}BrN_2O$: 271.15.

9] To 6-bromo-2-pyridinecarboxaldehyde (300 mg, 1.62 mmol) was added hexamethyleneimine (0.27 mL, 2.43 mmol) in dry $CH_2Cl_2$ (10 mL) to give 2-bromo-6-(azaperhydroepinylmethyl)pyridine as a white solid. MS m/z: 270.3(M+H). Calc'd for $C_{12}H_{17}BrN_2$: 269.18.

10] To 4-hydroxypiperidine (143 mg, 1.41 mmol) was added a solution of 6-bromo-2-pyridine-carboxaldehyde (200 mg, 1.08 mmol) to give 2-bromo-6-[(4-hydroxypiperidyl)methyl]-pyridine as a white -solid. MS m/z: 271.0 (M+H). Calc'd for $C_{11}H_{15}BrN_2O$—271.15.

11] 3-Hydroxypropylamine (0.15 mL, 2.02 mmol) was added to a solution of 6-bromo-2-pyridine-carboxaldehyde (250 mg, 1.35 mmol) to give 2-bromo-6-[(3-hydroxypropyl)amino]-methylpyridine as a white solid. MS m/z: 245.1 (M+H). Calc'd for $C_{11}H_{13}BrN_2O$—245.19.

12] Ethyl(piperidyl-3-carboxylate (0.92 mL, 5.92 mmol) was added to a solution of 6-bromo-2-pyridinecarboxaldehyde (1.0 g, 5.38 mmol) to give ethyl 1-[(6-bromopyridin-2-yl)methyl]-piperidine-3-carboxylate as a colorless oil. MS m/z: 327.1 (M+H). Calc'd for $C_{14}H_{19}BrN_2O_2$—327.22.

13] Ethyl (2-piperidyl)carboxylate (0.92 mL, 5.92 mmol) was added to a solution of 6-bromo-2-pyridinecarboxaldehyde (1.0 g, 5.38 mmol) to give ethyl 1-[(6-bromopyridin-2-yl)methyl]-piperidine-2-carboxylate as a colorless oil). MS m/z: 327.1 (M+H). Calc'd for $C_{14}H_{1}gBrN_2O_2$—327.22.

14] N,N-Diethylcarbamoyl-piperidine-3-carboxamide (0.92 mL, 5.92 mmol) was added to a solution of 6-bromo-2-pyridinecarboxaldehyde (1.0 g, 5.38 mmol) to give N,N-diethyl 1-(6-bromopyridin-2-ylmethyl) piperidine-3-carboxamide as a colorless oil. MS m/z: 354.1 (M+H). Calc'd for $C_{16}H_{24}BrN_3O$—354.29.

15] 2-Pyrrolidine carboxylic acid (0.68 g, 5.92 mmol) was added to a solution of 6-bromo-2-pyridine-carboxaldehyde (1.0 g, 5.38 mmol) to give 1-(6-bromopyridin-2-ylmethyl)-pyrrolidine-2-carboxylic acid as a white solid. MS m/z: 285.1 (M+H). Calc'd for $C_{11}H_{13}BrN_2O_2$—285.14.

16] 3-Methylpiperidine (0.33 mL, 2.8 mmol) was added to a solution of 6-bromo-2-pyridine-carboxaldehyde (350 mg, 1.88 mmol) to give 2-bromo-6-[(3-methylpiperidyl)methyl]pyridine as a white solid. MS m/z: 269.1 (M+H). Calc'd for $C_{12}H_{17}BrN_2$— 269.18.

Preparation O: 6-Morpholin-4-ylmethyl-pyridin-2-ylamine $NH_4OH$ (2 mL) and Cu powder (10 mg, 0.15 mmol) were added to a solution of 2-bromo-6-morpholinylpyridine (231 mg, 0.90 mmol) in IpOH (5 mL) and the resulting mixture was heated at 100° C. for 36 h in a sealed tube. After cooling to RT, the mixture was partitioned between $H_2O$ and EtOAc. The organic layer was collected, washed with brine, and dried over $Na_2SO_4$. Concentration in vacuo gave the tilted compound as a pale yellow solid. MS m/z: 194.1 (M+H).

The following amines were prepared from the corresponding bromo compounds (prepared by Preparation N) in a manner similar to that described in General Preparation O:

1] 1-(6-amino-pyridin-2-ylmethyl)-piperidine-4-carboxylic acid ethyl ester as brown liquid. MS m/z: 264.2 (M+H). Calc'd for $C_{14}H_{21}N_3O_2$: 263.34.

2] 2-amino-6-[N'-tert-butoxycarbonyl-N'-2-(1-hydroxy-4-methyl)pentylamino]methylpyridine as a brown -liquid. MS m/z: 324.3 (M+H). Calc'd for $C_{17}H_{29}N_3O_3$: 323.2.

3] 2-amino-6-(4-ethoxyacetalpiperidinyl)-methylpyridine as a white solid. MS m/z: 250 (M+2H). Calc'd for $C_{13}H_{19}N_3O_2$: 249.1.

4] 2-Amino-6-(3,5-dimethylpiperidinyl)methyl-pyridine as a yellow solid. MS m/z: 220.3 (M+H). Calc'd for $C_{13}H_{21}N_3$: 219.

5] 2-Amino-6-(4-methylpiperidinyl)methylpyridine as a yellow solid. MS m/z: 206.3 (M+H). Calc'd for $C_{12}H_{19}N_3$: 205.28.

6] 2-Amino-6-(2-methylpiperidinyl)methylpyridine as a yellow liquid. MS m/z: 206.3 (M+H). Calc'd for $C_{12}H_{19}N_3$: 205.28.

7] 2-Amino-6-[[4-(1-pyrrolidinyl)piperidinyl]methyl]-pyridine as a brown liquid. MS m/z: 261.1 (M+2H). Calc'd for $C_{12}H_{19}N_3$: 260.

8] 2-Amino-6-(3-hydroxypiperidinyl)methylpyridine as a yellow liquid. MS m/z: 410.9 (M+H). Calc'd for $C_{11}H_{17}N_3O$: 410.5.

9] 2-Amino-6-(azaperhydroepinylmethyl)pyridine as a white solid. MS m/z: 206.1 (M+H). Calc'd for $C_{12}H_{19}N_3$: 205.32.

10] 2-Amino-6-[(4-hydroxypiperidyl)methyl]pyridine as a pale yellow oil. MS m/z: 208.1 (M+H). Calc'd for $C_{11}H_{17}N_3O$—207.27.

11] 2-Amino-6-[(N-tert-butoxycarbonyl-N-(3-hydroxypropyl)amino]methylpyridine as a pale yellow oil. MS m/z: 282.3 (M+H). Calc'd for $C_{14}H_{23}N_3O_3$—281.35.

12] Ethyl 1-[(6-aminopyridin-2-yl)methyl]-piperidine-3-carboxylate as a pale yellow oil. MS m/z: 264.1 (M+H). Calc'd for $C_{14}H_{21}N_3O_2$—263.34.

13] Ethyl 1-[(6-aminopyridin-2-yl)methyl]-piperidine-2-carboxylate as a pale yellow oil. MS m/z: 264.1 (M+H). Calc'd for $C_{14}H_{21}N_3O_2$—263.34.

14] N,N-Diethyl 1-(6-aminopyridin-2-ylmethyl)-piperidine-3-carboxamide as a pale yellow oil. MS m/z: 291.5 (M+H). Calc'd for $C_{16}H_{26}N_4O$-290.40.

15] 1-(6-Aminopyridin-2-ylmethyl)-pyrrolidine-2-carboxylic acid as a white solid. MS m/z: 220.3 (M–H). Calc'd for $C_{11}H_{15}N_3O_2$-221.26.

16] 2-Amino-6-[(3-methylpiperidyl)methyl]pyridine as a pale yellow solid. MS m/z: 206.5 (M+H). Calc'd for $C_{12}H_{19}N_3$—205.30.

17] 1-(6-Aminopyridin-2-ylmethyl)-piperidine-3-carboxylic acid as a pale yellow oil. MS m/z: 235.0 (M+H). Calc'd for $C_{12}H_{17}N_3O_2$—235.28.

Preparation P: 4-(6-Aminopyridin-2-yloxy)-benzonitrile

To a stirred solution of 4-cyanophenol (1.7 g, 14.3 mmol) in 45 mL dry DMF was added NaH (0.71 g, 17.7 mmol). After stirring at RT for 15 min, 2,6-dibromopyridine (3.2 g, 13.4 mmol) was added and the mixture was heated at 95° C. for 24 h. After cooling to RT, 100 mL of $H_2O$ was added and the mixture was extracted with EtOAc (2×100 mL). The combined organic layers were washed with 40 mL brine, dried over $MgSO_4$ and concentrated in vacuo. The crude intermediate was dissolved in 20 mL IpOH, transferred to a Teflon lined pressure vessel and 20 mL of conc. $NH_4OH$ was added. Powdered Cu (1 g) was added and the vessel was sealed and heated at 140° C. for 24 h. After cooling to RT, the Cu was removed by filtration and the filtrate was diluted with 75 mL of $H_2O$ and extracted with EtOAc (2×75 mL). The organic layers were washed with brine, dried over $MgSO_4$ and concentrated in vacuo. The compound was purified by chromatography on silica gel using 10:1 $CHCl_3$/ (~2M $NH_3$/MeOH) as eluent to afford the title compound as a dark oil. MS m/z: 212.2 (M+H).

The following compounds were prepared from 2,6-dibromopyridine in a manner similar to that described in General Preparation P:

1] 6-Phenoxy-pyridin-2-ylamine: MS m/z: 187.2 (M+H). Calc'd for $C_{11}H_{10}N_2O$: 186.08.

2] 6-(4-Methylphenyloxy)pyridin-2-ylamine: MS m/z: 201.3 (M+H). Calc'd for $C_{12}H_{12}N_2O$: 200.09.

3] 6-(2,4-Dimethylphenyloxy)pyridin-2-ylamine: MS m/z: 215.3 (M+H). Calc'd for $C_{13}H_{14}N_2O$: 214.11.

4] 6-[4-(1-Imidazolyl)phenyloxy]pyridin-2-ylamine: MS m/z: 253.3 (M+H). Calc'd for $C_{14}H_{12}N_4O$: 252.10.

5] 6-[4-[1,3]Dioxolan-2-yl-phenoxy)pyridin-2-ylamine: MS m/z: 259.3 (M+H). Calc'd for $C_{14}H_{14}N_2O_3$: 258.10.

6] 6-(4-Fluorophenyloxy)pyridin-2-ylamine: MS m/z: 205.2 (M+H). Calc'd for $C_{11}H_9FN_2O$: 204.07.

7] 6-(4-Difluorophenyloxy)pyridin-2-ylamine: MS m/z: 223.2 (M+H). Calc'd for $C_{11}H_8F_2N_2O$: 222.06.

8] tert-Butyl {2-[4-(6-aminopyridin-2-yloxy)phenyl]ethyl}carbamate: MS m/z: 330.4 (M+H). Calc'd for $C_{18}H_{23}N_3O_3$: 329.17.

9] 6-(2-Dimethylaminoethoxy)pyridin-2-ylamine: MS m/z: 182.2 (M+H). Calc'd for $C_9H_{15}N_3O$: 181.12.

10] 6-[(1-Methylpyrrolidin-2-yl)methoxy]pyridin-2-ylamine: MS m/z: 208.3 (M+H). Calc'd for $C_{11}H_{17}N_3O$: 207.14.

11] 6-(1-Aza-bicyclo[2.2.2]oct-3-yloxy)pyridin-2-ylamine: MS m/z: 220.3 (M+H). Calc'd for $C_{12}H_{17}N_3O$: 219.14.

12] tert-Butyl 3-[(6-aminopyridin-2-yl)oxymethyl]-azetidine-1-carboxylate: MS m/z: 280 (M+H). Calc'd for $C_{14}H_{21}N_3O_3$: 279.16.

13] tert-Butyl 4-[2-(6-Aminopyridin-2-yloxy)ethyl]-piperidine-1-carboxylate: MS m/z: 322 (M+H). Calc'd for $C_{17}H_{27}N_3O_3$: 321.21.

Preparation Q: 2-Bromo-6-[N'-tert-butoxycarbonyl-N'-2-(1-hydroxy-4-methyl)pentylamino]methylpyridine To 2-bromo-6-[2-N-(1-hydroxy-4-methyl)-pentylamino]methylpyridine (550 mg, 1.91 mmol) in dry $CH_2Cl_2$ (10 mL) was added $(Boc)_2O$ (460 mg, 2.106 mmol). The resulting mixture was stirred under $N_2$ at RT for 15 h. The solvent was removed and the residue was extracted with $CHCl_3$. The organic layer was wash with $H_2O$, brine, and dried over $MgSO_4$ and removed to give a yellow liquid. MS m/z:387.6 (M+H). Calc'd for $C_{17}H_{27}BrN_2O_3$: 387.32.

The following BOC protected compounds were prepared from the corresponding amines (prepared by Preparation N) in a manner similar to that described in General Preparation Q:

1] 2-Bromo-6-[(N-tert-butoxycarbonyl-N-(3-hydroxypropyl)amino]methylpyridine was prepared from 2-bromo-6-[(3-hydroxypropyl)-amino]-methylpyridine (300 mg, 1.22 mmol) [purified by chromatography on silica gel (hexane/acetone, 80/20]) as a colorless oil. MS m/z: 345.1 (M+H).

Calc'd for $C_{14}H_{21}BrN_2O_3$—345.23.

Preparation R: 2,2-Dimethyl-N-[6-(2-methylimidazol-1-ylmethyl)pyridin-2-yl]propionamide A solution of 2-methylimidazole (68 mg, 0.83 mmol) in dry THF (8 mL) was treated under $N_2$ with NaH (33 mg, 0.83 mmol, 60% in mineral oil) at 0° C. After the addition, the mixture was warmed to RT and stirred for 0.5 h. It was then treated dropwise with a solution of N-pivaloyl-2-amino-6-bromomethylpyridine (150 mg, 0.55 mmol; M. V. Papadopoulou, et al., J. Heterocyclic Chem., 1995, 32, 675–681) in dry THF (10 mL) over period of 15 min. After the addition, it was stirred for 1 h. The resulting mixture was quenched with saturated $NH_4Cl$ (3 mL). Solvent was removed and the residue was extracted with $CHCl_3$. The organic layer was washed with $H_2O$, brine, dried over $MgSO_4$, and concentrated in vacuo to yield the title compound as light brownish solid. MS m/z: 272.2 (M+H). Calc'd. for $C_{16}H_{21}N_3O$—271.37.

The following amines were prepared from the corresponding bromomethylpyridine in a manner similar to that described in Preparation R:

1] 2,2-Dimethyl-N-[6-(4-(N,N-dimethylamino-methyl)phenyloxymethyl)pyridin-2-yl]propionamide. MS m/z: 342 (M+H).

Preparation S: N-(6-Azidomethylpyridin-2-yl)-2,2-dimethylpropionamide

N-Pivaloyl-2-amino-6-bromomethylpyridine (1.1 g, 4.05 mmol; M. V. Papadopoulou, et al., J. Heterocyclic Chem., 1995, 32, 675–681) was dissolved in dry THF (15 mL).

NaN$_3$ (530 mg, 8.1 mmol) and dry DMF (5 mL) was added and the resulting mixture was heated to reflux under N$_2$ for 2 h. After cooling to RT, solvent was removed and the residue was partitioned between H$_2$O and CHCl$_3$. The organic layer was washed with H$_2$O, brine, dried over MgSO$_4$, and concentrated in vacuo to give the title compound as a pale yellow solid. MS m/z: 234.1 (M+H). Calc'd. for C$_{11}$H$_{15}$N$_5$O—233.28.

Preparation T: 6-Azidomethyl-pyridin-2-ylamine 2-(N'-Pivaloyl)amino-6-azidomethylpyridine (680 mg, 2.91 mmol) was dissolved in MeOH (20 mL) and KOH was added (3.4 g, 60.6 mmol). The resulting mixture was heated to reflux under N$_2$ for 2 h. After cooling to RT, pH was adjusted to 7 followed by removing the solvent. The residue was partitioned between H$_2$O and CHCl$_3$ and the aqueous layer was extracted more with CHCl$_3$. The combined organic layers was washed with H$_2$O, brine, dried over MgSO$_4$, and concentrated in vacuo to yield the title compound as brown solid. MS m/z: 150.3 (M+H). Calc'd. for C$_6$H$_7$N$_5$: 149.15.

The following amines were prepared from the corresponding bromo compounds (prepared by Preparations R–S, and AA) in a manner similar to that described in Preparation T:

1] 3-(2-Methylimidazol-1-ylmethyl)phenylamine. MS m/z: 189.3 (M+H). Calc'd. for C$_{10}$H$_{12}$N$_4$-188.23.

2] 2-Amino-6-[4-(dimethylamino)methyl]phenoxymethyl-pyridine. MS m/z: 258 (M+H).

3] 2-Amino-6-[1-(N-tert-butoxycarbonyl) amino]-ethoxymethyl-pyridine. MS m/z: 268 (M+H).

4] 2-Amino-6-[4-(methylphenyl)oxymethyl]pyridine. MS m/z: 215 (M+H).

5] 2-Amino-6-[1-(N-tert-butoxycarbonyl)amino]-ethoxymethyl-pyridine. MS m/z: 267 (M+H)

6] 2-Amino-5-[1-morpholinylmethyl]pyridine. MS m/z: 194 (M+H).

7] 5-Methoxymethyl-pyridin-2-ylamine.

Preparation U: Methyl 1-(6-aminopyridin-2-ylmethyl)-pyrrolidine-2-carboxylate

Concentrated H$_2$SO$_4$ (1.0 mL) was added to a solution of 1-(6-aminopyridin-2-ylmethyl)-pyrrolidine-2-carboxylic acid (620 mg, 2.80 mmol) in MeOH (15 mL) and the resulting mixture was heated at 80° C. for 10 h. After cooling to RT, the mixture was quenched with saturated 2 M Na$_2$CO$_3$ solution and concentrated in vacuo. CHCl$_3$ (15 mL) was added and the solution washed with 1.0 N NaOH solution (15 mL). The organics were collected and the aqueous layer was extracted with CHCl$_3$/IpOH (3/1, 3×10 mL). The combined organics were dried over MgSO$_4$ and concentrated in vacuo. The crude compound was purified by chromatography on silica gel (CH$_2$Cl$_2$/MeOH, 95/5) to give a pale yellow oil. MS m/z: 236.1 (M+H). Calc'd for C$_{12}$H$_{17}$N$_3$O$_2$—235.28.

Preparation V: 3-Methyl-2-(phthalimidyl)pyridine

2-Amino-3-picoline (1.00 mL, 8.62 mmol) was dissolved in DMF (30 mL) at 230C, and treated with solid carboethoxy-phthalimide (1.89 g, 8.64 mmol), followed by TEA (1.44 mL, 10.3 mmol). The resulting solution was stirred at 230C for 15 h. After 15 h, the mixture was diluted with EtOAc (50 mL), and washed with saturated NaCl (1×50 mL), H$_2$O (1×50 mL), dried (MgSO$_4$), and concentrated in vacuo to a yellow solid. Purification over silica gel (0 to 50% EtOAc/Hexanes) provided the title compound as a white solid.

Preparation W: 3-(Dibromomethyl)-2-(phthalimidyl)pyridine

3-Methyl-2-(phthalimidyl)pyridine (360 mg, 1.51 mmol) was dissolved in CCl$_4$ (5 mL), and treated with NBS (267 mg, 1.50 mmol), followed by AIBN (46.9 mg, 0.29 mmol). The resulting suspension was warmed to reflux for 2 h, treated again with AIBN (55.4 mg, 0.34 mmol), and heated at reflux an additional 12 h. After 12 h, AIBN was again added (96.7 mg, 0.59 mmol) and reflux was continued. After 2 h, more AIBN was added (59.6 mg, 0.36 mmol), and reflux continued. After 2 h, additional NBS was added (253 mg, 1.42 mmol) and the mixture was treated with additional AIBN (49.6 mg, 0.30 mmol), and heated at reflux an additional 12 h. The mixture was cooled to RT, diluted with EtOAc (50 mL), washed with saturated NaCl (1×50 mL), then dried (MgSO$_4$) and concentrated in vacuo. The resulting white solid was purified over silica gel (0 to 40% EtOAc/Hexanes) to provide the title compound. MS m/z: 397 (M+H).

Preparation X: 2-(phthalimidyl)-3-(1-piperidinylmethyl)-pyridine 3-(Dibromomethyl)-2-(phthalimidyl)pyridine (185 mg, 0.47 mmol) was dissolved in CH$_2$Cl$_2$ (2 mL) and treated with piperidine (0.460 mL, 4.66 mmol), and glacial AcOH (0.160 mL, 2.80 mmol) in a dropwise fashion. The resulting yellow solution was stirred at 23° C. for 2 h, then treated with solid NaBH(OAc)$_3$ (393 mg, 1.86 mmol) in one portion, and stirring was continued for 14 h. After stirring 14 h at 23° C., the mixture was treated with 2M K$_2$CO$_3$ (6 mL), and stirred for 1 h. After 1 h, the mixture was diluted with EtOAc (50 mL) and washed with H$_2$O (1×50 mL), and saturated NaCl (1×50 mL). The organic phase was then dried (MgSO$_4$) and concentrated in vacuo to provide the title compound as a yellow residue. The crude material was used in subsequent transformations without further purification. MS m/z: 323 (M+H).

Preparation Y: 2-Amino-3-(1-piperidinylmethyl)-pyridine 2-(Phthalimidyl)-3-(1-piperidinylmethyl)-pyridine (196 mg, 0.609 mmol) was dissolved in EtOH (95%, 2 mL) at 23° C., and treated with hydrazine monohydrate (0.0320 mL, 0.670 mmol) in a dropwise fashion. The resulting mixture was warmed to reflux and stirred for 3 h at reflux. The solution was treated with additional hydrazine monohydrate (0.150 mL, 3.050 mmol), and reflux continued. After 14 h at reflux, the mixture was cooled to RT, and concentrated using a rotary evaporator to a white paste. The resulting white paste was dissolved in CHCl$_3$:IpOH (3:1, 75 mL), and washed with saturated NaHCO$_3$ (3×50 mL), and H$_2$O (1×50 mL). The organic layer was dried over MgSO$_4$ and concentrated in vacuo to provide the title compound as a white solid. MS m/z: 192 (M+H).

Preparation Z: N-Pivaloyl 2-amino-5-(bromomethyl) pyridine

N-Pivaloyl-2-amino-5-methylpyridine (5.12 g, 26.6 mmol) was dissolved in CCl$_4$ (75 mL) at 23° C., and treated with NBS (9.69 g, 54.4 mmol), followed by AIBN (937 mg, 5.71 mmol) with stirring. The resulting orange, biphasic suspension was then warmed to reflux for 4 h. After 4 h at reflux, the rust-colored mixture was cooled to RT, filtered through a Celite® pad, and concentrated in vacuo to a red residue. Purification over silica gel (gradient, 0 to 25% EtOAc/hexanes) provided the title compound as a light yellow solid. MS m/z: 272 (M+H).

Preparation AA: N-Pivaloyl-2-amino-5-[2-(N-tert-butoxycarbonyl)amino]ethoxymethylpyridine N-Pivaloyl-2-amino-5-bromomethylpyridine (484 mg, 1.78 mmol) was dissolved in THF (6 mL) at 23° C., and treated with 2-(N-tert-butoxycarbonyl)aminoethanol (0.551 mL, 3.56 mmol), followed by NaH (60% suspension in mineral oil, 221 mg, 5.52 mmol) with stirring. The resulting mixture was stirred at 23° C. for 14 h, then treated with additional NaH (75.6 mg, 1.89 mmol) as well as DMSO (1 mL), and stirred an additional 5 h at 230C. After 5 h at 230C, the solution was warmed to 55° C. for 3 h, then cooled to RT. The mixture was treated with saturated $NaHCO_3$ (10 mL), diluted with EtOAc (50 mL), and washed with saturated $NaHCO_3$ (2×50 mL). The mixture was dried over $MgSO_4$ and purified over silica gel to provide the title compound as a pale yellow oil. MS m/z: 352 (M+H).

The following amines were prepared from the corresponding bromomethylpyridine in a manner similar to that described in General Preparation AA:

1] 2,2-Dimethyl-N-[6-(N-(tert-butoxycarbonyl)-amino-1-ethoxymethyl)pyridin-2-yl]propionamide. MS m/z: 352 (M+H).
2] N-Pivaloyl-2-amino-6-[(4-methylphenyl)-oxymethyl]-pyridine. MS m/z: 299 (M+H).
3] N-Pivaloyl-2-amino-5-[(4-methylphenyl)-oxymethyl]pyridine. MS m/z: 299 (M+H).

Preparation AB: N-Pivaloyl-2-amino-5-[1-morpholinylmethyl]pyridine

N-Pivaloyl-2-amino-5-bromomethylpyridine (478 mg, 1.76 mmol) was dissolved in THF at 23° C. with stirring and treated with morpholine (0.770 mL, 8.81 mmol) in a dropwise fashion. The resulting brown mixture was stirred at 23° C. for 14 h. After stirring 14 h, the mixture was treated with saturated $NaHCO_3$ (2 mL) and stirred an additional 5 h at 23° C. After 5 h, the brown mixture was warmed to 55° C. for 3 h, then cooled to RT and diluted with EtOAc (50 mL). The mixture was washed with saturated $NaHCO_3$ (2×50 mL), dried ($MgSO_4$), and concentrated to a brown residue which was immediately purified over silica gel (0 to 5% $MeOH/CHCl_3$) to provide the title compound as a yellow oil. MS m/z: 278 (M+H).

Preparation AC: 2-(Butyloxycarbonyl)amino-6-methylpyridine

To a 2-L 3-neck Miller flask charged with 2-amino-6-methylpicoline (15 g, 138.7 mmol) and dry THF (1 L) was added di-tert-butyl dicarbonate (33.3 g, 152.6 mmol) then TEA (21.2 mL, 152.6 mmol) via addition funnel at 0° C. The reaction mixture was warmed to RT and added DMAP (1.7 g, 13.9 mmol). After 3.5 h, extracted with EtOAc, washed with saturated $NH_4Cl$, $H_2O$ (3×), and brine (3×), dried ($MgSO_4$) and concentrated in vacuo to afford the crude material as a turbid yellow oil. Trituration with hexane formed a precipitate which was filtered and the filtrate was concentrated in vacuo to give the title compound as a yellow oil.

Preparation AD: 6-Bromomethyl-2-(butyloxycarbonyl)amino-pyridine

To a solution of N-Boc-2-amino-6-picoline (28.7 g, 138 mmol) and $CCl_4$ (500 mL) was added NBS (27.1 g, 151.8 mmol) and AIBN (2.3 g, 13.8 mmol) and heated to reflux. After 2 h, added 0.1 equivalent of AIBN. The reaction mixture was heated at reflux for 20 h, filtered and concentrated in vacuo to give a dark oil. Purified by silica flash chromatography (100% hexane to 5% EtOAc/Hexane) to afford the desired as a yellow oil. MS m/z: 288.0 (M+H)

Preparation AE: 2-(Butyloxycarbonyl)amino-6-cyanomethylpyridine

To a solution of N-Boc-2-amino-6-methylbromidepyridine (12 g, 41.8 mmol) and EtOH (250 mL) was added NaCN (2 g, 41.8 mmol). The reaction mixture was heated to reflux for 2 h then cooled to RT and concentrated in vacuo. Purification by silica flash chromatography (100% Hexane to 20% EtOAc/Hexane) afforded the title compound as a yellow oil. MS m/z: 234.0 (M+H).

Preparation AF: 2-Amino-6-cyanomethylpyridine

To a solution of N-Boc-2-amino-6-methylnitrilepyridine and $CH_2Cl_2$ (10 mL) was added TFA (8 mL) and stirred at RT. After 3 h, the mixture was concentrated in vacuo, diluted with EtOAc and saturated $NaHCO_3$ was carefully added. The mixture was washed with saturated $NaHCO_3$ (2×) and brine, dried ($MgSO_4$) and concentrated in vacuo to afford the title compound as a yellow solid.

Preparation AG: 6-Aminoethyl-2-(butyloxycarbonyl)amino-pyridine

A solution of N-Boc-2-amino-6-methylnitrile-pyridine (1 g, 4.3 mmol) and EtOH (25 mL) was hydrogenated over 20% $Pd(OH)_2/C$ at RT and 40 psi. After 18 h, the mixture was filtered through Celite® and eluted with EtOAc. The filtrate was concentrated in vacuo to afford the title compound as a white foamy solid.

Preparation AH: 2-Amino-6-(phthalimidyl)ethyl-pyridine

To a solution of N-Boc-2-amino-6-ethylaminopyridine (1 g, 4.3 mmol) and $CHCl_3$ (25 mL) was added phthalic anhydride (0.64 g, 4.3 mmol). Heated to 70° C. for 15 h then at RT for 5 days. The mixture was washed with $H_2O$ and brine, dried ($MgSO_4$) and concentrated in vacuo to give crude N-Boc-2-amino-6-ethylphthalamidylpyridine, which was used without further purification. To a solution of crude N-Boc-2-amino-6-ethylphthalamidylpyridine (1.6 g, 4.3 mmol) and $CH_2Cl_2$ (10 mL) was added 10 mL of TFA and the mixture was stirred at RT. After 30 min, the mixture was concentrated in vacuo. The residue was diluted with 90% $MeOH/CH_2Cl_2$ and treated with solid $NaHCO_3$, stirred for 15 min then filtered. The filtrate was concentrated in vacuo to afford the title compound as a yellow solid. MS m/z: 268.2 (M+H).

Preparation AI: 2-[(6-Bromopyridin-2-yl)methylamino]-propan-1-ol

To a stirred solution of the (6-bromo-2-pyridyl)-formaldehyde (0.52 g, 2.8 mmol) in toluene (14 mL) was added DL-2-amino-1-propanol (0.67 mL). The resulting mixture was heated to reflux with a Dean-Stark trap for 3 h under $N_2$ until complete formation of the imine was observed. The mixture was brought to RT followed by the addition of a solution of $NaBH(OAc)_3$ (2.0 g, 9.8 mmol) in ACOH (6 mL). The resulting mixture was stirred at RT and under $N_2$ for 56 h. The mixture was neutralized (pH 7.0) with a saturated solution of $NaHCO_3$ (aq) and extracted with $CH_2Cl_2$ (3×50 mL). The aqueous layer was concentrated by rotary evaporation and the residue obtained was extracted with $CH_2Cl_2$ (3×50 mL). The organic layers were combined, dried over $MgSO_4$, filtered and concentrated by rotary evaporation to afford the title compound as a pale yellow oil. EI-MS m/z 245 (M+H).

Preparation AJ: (tert-Butoxy)-N-[(6-bromo(2-pyridyl))methyl]-N-(2-hydroxy-isopropyl)carboxamide To a stirred solution of 2-[(6-bromo-2-pyridyl)-methyl]aminopropan-1-ol (0.55 g, 2.2 mmol) in dry $CH_2Cl_2$ (11 mL) was added $Boc_2O$ (0.51 g, 2.42 mmol). The resulting mixture was stirred at RT and under $N_2$ for 15 h. The mixture was concentrated by rotary evaporation and purified on silica gel (2:1 hexanes/EtOAc, 5:95 $MeOH/CH_2Cl_2$ and, 10:90 $MeOH/CH_2Cl_2$) as eluent to afford the title compound as an off-white oil. EI-MS m/z 345 (M+H).

Preparation AK: (tert-Butoxy-N-[(6-bromo(2-pyridyl))-methyl]-N-(1-methyl-2-oxoethyl)carboxamide To a dry flask was added oxalyl chloride (72 μL) followed by the addition of dry $CH_2Cl_2$ (2 mL). The resulting colorless solution was brought to −63° C. (dry ice/CHCl$_3$) and a solution of DMSO (80 μL) in 0.5 mL dry CH$_2$Cl$_2$ was slowly added dropwise. A solution of (tert-butoxy)-N-[(6-bromo(2-pyridyl))methyl]-N-(2-hydroxy-isopropyl) carboxamide (0.19 g, 0.55 mmol) in dry CH$_2$Cl$_2$ (2 mL), was added slowly drop wise. The resulting mixture was kept at −63° C. and stirred for 30 min, followed by the slow addition of a solution of TEA (0.31 mL) in dry CH$_2$Cl$_2$ (1 mL). The mixture was stirred at −63° C. until all the starting material was consumed (checked by MS). The mixture was brought to −20° C., quenched with a saturated solution of NH$_4$Cl (aq) and diluted with EtOAc. The organic phase was separated and the aqueous phase was extracted with EtOAc (3×20 mL). The organic layers were combined, dried over MgSO$_4$, filtered and concentrated by rotary evaporation to afford the title compound as a pale yellow semi-solid. EI-MS m/z 343 (M+H).

Preparation AL: N-[2-(diethylamino)-isopropyl](tert-butoxy)-N-[(6-bromo(2-pyridyl))methyl]-carboxamide To a stirred solution of (tert-butoxy-N-[(6-bromo(2-pyridyl))methyl]-N-(1-methyl-2-oxoethyl)-carboxamide (0.15 g, 0.44 mmol) in toluene (3 mL) was added DEA (0.2 mL). The resulting mixture was heated to reflux in a Dean-Stark trap under N$_2$ for 3 h. The mixture was brought to RT followed by the addition of a solution of NaBH(OAc)$_3$ (0.33 g, 1.54 mmol) in AcOH (6 mL). The yellow-solution was stirred at RT and under N$_2$ for 15 h. The mixture was diluted with EtOAc (20 mL) and washed with a saturated solution of NaHCO$_3$ (aq) (50 mL). The organic phase was separated, dried (MgSO$_4$), filtered and concentrated by rotary evaporator to afford the title compound as a brown/yellow oil. EI-MS m/z 400 (M+H).

Preparation AM: N-[2-(diethylamino)isopropyl](tert-butoxy)-N-[(6-amino(2-pyridyl))methyl]-carboxamide To a stirred solution of N-[2-(diethylamino)-isopropyl](tert-butoxy)-N-[(6-bromo(2-pyridyl))methyl]-carboxamide (80 mg 0.2 mmol) in IpOH (4 mL) in a sealed tube, was added NH$_4$OH (28–30%, 6 mL) followed by an excess of Cu. The resulting solution was heated under pressure at 90° C. for 24 h. The mixture was brought to RT, diluted with H$_2$O (20 mL) and extracted with CHCl$_3$ (3×20 mL). The organic layers were combined, dried over MgSO$_4$, filtered and concentrated by rotary evaporation to afford the title compound as a pale-yellow oil. EI-MS m/z 337 (M+H).

Preparation AN: Methyl 2-[(6-bromo-2-pyridylmethyl)amino]-3-methyl-butyrate

To a stirred solution of L-valine methyl ester hydrochloride (0.54 g, 3.24 mmol) in dry toluene (15 mL) at 80° C. was added DIEA (2.0 mL 11 mmol) followed by (6-bromo-2-pyridyl)formaldehyde (0.50 g, 2.70 mmol). The resulting mixture was heated at 80° C. for 3 h. The reaction was brought to RT and a solution of NaBH(OAc)$_3$ (1.4 g, 6.75 mmol) in glacial AcOH (4 mL) was added. The resulting mixture was stirred for 15 h and concentrated by rotary evaporation. The resulting yellow oil was dissolved in CH$_2$Cl$_2$ (100 mL), washed with a saturated solution of NaHCO$_3$ (aq) (50 mL), brine (50 mL), dried over Na$_2$SO$_4$, filtered and concentrated by rotary evaporation and purified by flash chromatography (2:1 hexanes/EtOAc) to afford the title compound as a pale-yellow oil. EI-MS m/z 301 (M+H).

Preparation AO: 2-[(6-Bromo-2-pyridylmethyl)amino]-3-methyl-butanol

To a stirred solution of (tert-butoxy)-N-[(6-bromo(2-pyridyl))methyl]-N-[2-oxomethoxide-1-(methylethyl)-ethyl]carboxamide (0.47 g, 1.57 mmol) in dry toluene (25 mL) at −78° C. was added dropwise DIBAL-H (1.0 M solution in hexane, 4.7 mL). The resulting brown-solution was stirred at −78° C. for 3 h, brought to RT and stirred until starting material was consumed. The organic layer was separated, dried over Na$_2$SO$_4$, filtered, concentrated by rotary evaporation and purified on silica gel (10:90 MeOH/CH$_2$Cl$_2$) to afford the title compound as a yellow oil. EI-MS m/z 273 (M+H).

Preparation AP: Tert Butyl(6-bromopyridin-2-ylmethyl)-(1-hydroxymethyl-2-methyl-propyl)-carbamate To a stirred solution of 2-[(6-bromo-2-pyridylmethyl)amino]-3-methyl-butanol (0.30 g, 1.10 mmol) in CH$_2$Cl$_2$ (5 mL) was added Boc$_2$O (0.26 g, 1.21 mmol). The resulting solution was stirred for 15 h, concentrated by rotary evaporation and purified on silica gel (5:95 MeOH/CH$_2$Cl$_2$ and 10:90 MeOH/CH$_2$Cl$_2$) to afford the title compound as a pale yellow solid. EI-MS m/z 373 (M+H).

Preparation AQ: Tert Butyl (6-bromopyridin-2-ylmethyl)-(1-formyl-2-methyl-propyl)carbamate To a flame-dried flask was added oxalyl chloride (70 μL) followed by the addition of dry CH$_2$Cl$_2$ (2 mL). The resulting colorless solution was brought to −63° C. (dry ice/CHCl$_3$) and a solution of DMSO (70 μL) in 0.5 mL dry CH$_2$Cl$_2$ was slowly added drop wise. The (tert-butoxy)-N-[(6-bromo(2-pyridyl))methyl]-N-[2-hydroxy-1-(methylethyl)ethyl]carboxamide (0.19 g, 0.51 mmol), previously dissolved in dry CH$_2$Cl$_2$ (2 mL), was added slowly dropwise. The resulting mixture was kept at −63° C. and stirred for 30 min followed by the slowly addition of a solution of TEA (0.3 mL) in dry CH$_2$Cl$_2$ (1 mL). The mixture was stirred at −63° C. until all the starting material was consumed (checked by MS) (1.5 h). The mixture was brought to −20° C., quenched with a saturated solution of NH$_4$Cl (15 mL) and diluted with EtOAc (35 mL). The organic phase was separated and the aqueous phase was extracted with EtOAc (3×30 mL). The organic layers were combined, dried over MgSO$_4$, filtered and concentrated by rotary evaporation without further purification to afford the title compound as a yellow-semi solid. EI-MS m/z 371 (M+H).

Preparation AR: tert-Butyl(6-bromopyridin-2-ylmethyl)-(1-diethylaminomethyl-2-methyl-propyl)carbamate To a stirred solution of (tert-butoxy)-N-[(6-bromo(2-pyridyl))methyl]-N-[1-(methylethyl)-2-oxoethyl] carboxamide (0.17 g, 0.46 mmol) in toluene (5 mL) was added DEA (0.14 mL). The resulting mixture was heated to reflux in a Dean-Stark trap under N$_2$ for 3 h. The mixture was brought to RT followed by the addition of a solution of NaBH(OAc)$_3$ (0.34 g, 1.61 mmol) in glacial AcOH (6 mL). The yellow-solution was stirred at RT and under N$_2$ for 15 h. The mixture was diluted with EtOAc (20 mL) and washed with a saturated solution of NaHCO$_3$ (aq) (15 mL). The aqueous layer was separated and concentrated under reduced pressure. The solid obtained was extracted with CH$_2$Cl$_2$. The extracts were combined, dried over MgSO$_4$, filtered and, concentrated by rotary evaporation to afford the title compound as a pale yellow oil. EI-MS m/z 428 (M+H).

Preparation AS: tert-Butyl(6-aminopyridin-2-ylmethyl)-(1-diethylaminomethyl-2-methyl-propyl)carbamate To a stirred solution of N-{1-[(diethylamino)-methyl]-2-methylpropyl}(tert-butoxy)-N-[(6-bromo(2-pyridyl))methyl]carboxamide (5 mg, 0.012 mmol) in IpOH (5 mL) in a sealed tube, was added NH$_4$OH (28–30% 6 mL) followed by excess Cu. The resulting solution was heated under pressure at 90° C. for 24 h. The mixture was brought to RT, diluted with H$_2$O (10 mL) and extracted with CHCl$_3$ (3×20 mL). The organic layers were combined, dried over MgSO$_4$, filtered and concentrated by rotary evaporation to afford the title compound as a green oil. No purification was required. EI-MS m/z 365 (M+H).

Preparation AT: 2-Bromo-6-(piperidin-1-ylmethyl)pyridine

To a stirred solution of 6-bromo-2-pyridine carboxaldehyde (5.05 g, 27 mmol) in anhydrous $CH_2Cl_2$ (200 mL) at RT, under $N_2$, piperidine (2.95 mL, 29 mmol) was added, followed by $NaBH(OAc)_3$ (11.51 g, 54 mmol) and AcOH (6.2 mL, 108 mmol) 30 min later. After 20 h, a 2M solution of $Na_2CO_3$(aq) (20 mL) was added. The mixture was vigorously stirred for an additional 30 min, washed successively with a saturated solution of $NaHCO_3$(aq) until the pH of the aqueous layer reached 7 (2×100 mL), $H_2O$ (100 mL) and brine (100 mL) The organic layer was separated, dried over $MgSO_4$, filtered and concentrated under reduced pressure to yield the title compound as a yellow oil. This was used crude in the next step. MS m/z: 255 (M+H), 257 (M+3).

Preparation AU: 2-Amino-6-(piperidin-1-ylmethyl)pyridine

To a solution of 2-bromo-6-(piperidylmethyl)pyridine (5.21 g, 20 mmol) in IpOH (30 mL) in a sealed tube at RT, a catalytic amount of Cu (100 mg) and 28–30% $NH_4OH$ (35 mL) were added. The stirred suspension was heated to 95° C. for 40 h. After cooling to RT, the reaction mixture was diluted with $H_2O$ (100 mL) and extracted with EtOAc (4×80 mL). The organic layers were combined, then washed with $H_2O$ (50 mL) followed by brine (50 mL). The organic layer was separated, dried over $Na_2SO_4$, filtered and concentrated under reduced pressure to yield the title compound as a dark yellow oil. This was used as crude. MS m/z: 193 $(M+H)^+$.

Preparation AV: Ethyl 2-(4-aminosulfonylphenyl) thiazole-4-carboxylate

In an oven-dried, 100-mL, round-bottomed flask were placed 4-cyanobenzenesulphonamide (4.1 g, 22.50 mmol), TEA (5 mL) in pyridine (40 mL). $H_2S$ was bubbled through this mixture for 1 h at RT. The reaction was diluted with EtOAc (125 mL) and $H_2O$ (50 mL). The phases were separated, and the organic layer was washed with $H_2O$ (4×25 mL) and brine (15 mL), dried over $MgSO_4$, and concentrated in vacuo to afford the crude thiobenzamide as an oily solid; MS m/z: 217 (M+H). In an oven-dried, 100-mL, round-bottomed flask were placed the crude thiobenzamide, ethyl bromopyruvate (3.0 mL, 23.66 mmol) in EtOH (40 mL). The reaction was heated to 75° C. for 12 h, then cooled to RT. The mixture was concentrated in vacuo to give the crude sulfonamide as a yellow solid which was filtered, washed with $H_2O$ (1×10 mL) and $Et_2O$ (4×10 mL) to afford the title compound as a yellow solid. MS m/z: 313 (M+H).

Preparation AW: 2-(4-Aminosulfonylphenyl)thiazole-4-carboxylic Acid

In an oven-dried, 100-mL, round-bottomed flask was placed ethyl 2-(4-aminosulfonylphenyl)thiazole-4-carboxylate (1300 mg, 4.2 mmol), LiOH monohydrate (350 mg, 8.3 mmol) in MeOH (40 mL) and $H_2O$ (4 mL). The solution was heated to 75° C. for 3 h, cooled to RT, and concentrated. The resulted yellow solid was dissolved in $H_2O$ (10 mL), extracted with EtOAc (1×15 mL). The aqueous layer was acidified with 2N aqueous HCl (4.15 mL). The precipitate was filtered, and washed with $H_2O$ (10 mL) to afford the title compound as a light-yellow solid. MS m/z: 285 (M+H).

Preparation AX: 2-(4-(4-morpholinyl)sulfonylphenyl)-thiazole-4-carboxylic Acid

In a manner similar to that described for the preparation of 2-(4-aminosulfonylphenyl)thiazole-4-carboxylic acid, 460 mg of 4-(morpholinosulfonyl)-benzonitrile was treated with $H_2S$, ethyl bromopyruvate, and LIOH successively to give the title compound. MS m/z: 355 (M+H).

Preparation AY: 2-(4-Boc-aminophenyl)-thiazole-4-carboxylic acid

In a manner similar to that described for the preparation of 2-(4-aminosulfonylphenyl)thiazole-4-carboxylic acid, 4-[(1,1-dimethylethoxy)carbonyl]-aminobenzonitrile was treated with $H_2S$, ethyl bromopyruvate, and LiOH successively to give the title compound. MS m/z: 321 (M+H).

Preparation AZ: Ethyl 2-(phenoxy)thiazole-4-carboxylate

A mixture of the bromothiazole (1.03 g, 4.36 mmol) and phenol (10.0 g, 106 mmol) was stirred at 180° C. for 1 h, cooled to RT, diluted with 100 mL of EtOAc, washed with 1N NaOH (40×3), $H_2O$, and brine, then dried over $MgSO_4$, and concentrated in vacuo to yield a light yellow residue. Purification over silica gel (gradient, 5% to 10% EtOAc/hexanes) provided the title compound. MS m/z: 250 $(M+H)^{+}$.

Preparation BA: 2-(Phenoxy)thiazol-4-ylcarbonylazide

TEA (0.17 mL, 1.20 mmol) was added to a solution of the thiazole carboxylic acid (0.13 g, 0.59 mmol) in 10 mL of THF at 0° C. The mixture was stirred at 0° C. for 20 min whereupon ethyl chloroformate (0.065 mL, 0.65 mmol) was added. After the mixture was stirred for 30 min, a solution of $NaN_3$ (0.043 g, 0.65 mmol) in 3 mL of $H_2O$ was added, the reaction was stirred for 30 min, then warmed to RT, diluted with 25 mL of $H_2O$, and extracted with EtOAc. The combined organic portions were washed with brine, dried over $MgSO_4$, filtered, and removal of the solvents in vacuo yielded the title compound as a light brownish solid. MS m/z: 247 (M+H).

Preparation BB: 6-Chloro-thionicotinamide

To a solution of the 4-chloronicotinamide (5 g, 31.9 mmol) and dry THF (200 mL) was added $P_2S5$ (15.6 g, 35.1 mmol) and $Na_2CO_3$ (3.7 g, 35.1 mmol). The mixture was heated at reflux for 1.5 h, cooled and filtered off a yellow solid. The filtrate was extracted with EtOAc, washed with $H_2O$ and brine; dried ($MgSO_4$) then concentrated in vacuo to give the title compound as a yellow solid. MS m/z: 173.0 (M+H).

Preparation BC: Ethyl 2-(6-chloro-3-pyridyl)thiazole-4-carboxylate

To a mixture of the 4-chloro-thionicotinamide (5.5 g, 31.9 mmol) and EtOH (300 mL) was added bromo-ethyl-pyruvate (4.4 mL, 35.1 mmol). The mixture was heated at reflux for 15 h, cooled and concentrated in vacuo to afford a yellow solid/orange oil. The oil was diluted with EtOAc and filtered off yellow solid. The filtrate was filtered through Celite® and concentrated in vacuo to give a dark yellow oil. The oil was diluted with 2% $MeOH/CH_2Cl_2$ and filtered through a pad of silica gel (150 mL). Elution with 2% $MeOH/CH_2Cl_2$ (500 mL), followed by concentration in vacuo afforded the title compound as a yellow crystalline solid. MS m/z: 269.1 (M+H).

Preparation BD: 2-(6-Methoxy-3-pyridyl)thiazole-4-carboxylic Acid

To a solution of the ethyl 2-(6-chloro-3-pyridyl)thiazole-4-carboxylate (0.61 g, 2.3 mmol) and MeOH (50 mL) was added solid NaOMe (135 mg, 2.5 mmol) and stirred at RT. After 3 h the ethyl ester transesterified to the methyl ester. NaOMe (1 eq, 135 mg) was added and the mixture was heated to reflux. After 15 h, the ester hydrolyzed to the 2-(6-chloro-3-pyridyl)thiazole carboxylic acid. NaOMe (2 eq) was added and the reaction was heated at reflux for 18 h. The mixture was acidified to pH 5 with concentrated HCl, extracted with EtOAc, washed with $H_2O$ and brine; dried ($MgSO_4$) and concentrated in vacuo to give the desired carboxylic acid as a yellow solid. MS m/z: 237.1 (M+H).

Preparation BE: 2-(2-Chloropyridin-4-yl)thiazole-4-carbonyl Azide

A mixture of 3-(3-chloro-4-pyridyl)-4-thiazole carboxylic acid (0.6 g, 2.5 mmol) and dry THF (20 mL) was cooled to 0° C. with stirring. TEA (0.7 mL, 5.0 mmol) was added and the reaction mixture was stirred for 20 min. Ethyl chloroformate (0.24 mL, 2.5 mmol) was added and the solution was stirred for 30 min. A solution of $NaN_3$ (174 mg, 2.7 mmol) in 3 mL of $H_2O$ was added and the reaction mixture was warmed to RT. After 30 min, 10 mL of $H_2O$ was added and the mixture was extracted with EtOAc (3×), dried ($MgSO_4$) and concentrated in vacuo to give the title compound as a pink solid. MS m/z: 266.0 (M+H)+.

Preparation BF: Ethyl 2-(3-methoxyphenyl)-thiazole-4-carboxylate

A suspension of 3-methoxyphenyl boronic acid (0.25 g, 1.65 mmol), ethyl 2-bromothiazole-4-carboxylate (0.33 g, 1.4 mmol), $PdCl_2(dppf)_2$ (0.11 g) and 2M $Na_2CO_3$ (aq) (2 mL) in DME (10 mL) was heated to reflux for 20 h. The mixture was cooled to RT, filtered, concentrated by rotary evaporation and purified on silica gel (6:1 hexanes/EtOAc and 4:1 hexanes/EtOAc) to afford the title compound as a light-brown oil. EI-MS m/z 264 (M+H).

Preparation BG: 2-(3-Methoxyphenyl)thiazole-4-carboxylic Acid

To a stirred solution of the ethyl 2-(3-methoxy-phenyl) thiazole-4-carboxylate (0.23 g, 0.87 mmol) in EtOH (10 mL) was added 1N NaOH (aq) (5 mL). The resulting mixture was heated to reflux until the starting material was consumed (2 h). The mixture was cooled to RT, acidified with 1N HCl (aq) and concentrated by rotary evaporation. The residue was extracted with $CH_2Cl_2$ (3×15 mL). The extracts were combined, dried over $MgSO_4$, filtered and concentrated by rotary evaporation to afford the title compound as an off-white solid. EI-MS m/z 236 (M+H).

Preparation BH: Ethyl 2-(2-methoxyphenyl)-thiazole-4-carboxylate

A suspension of 2-methoxyphenyl boronic acid (0.25 g, 1.65 mmol), ethyl 2-bromothiazole-4-carboxylate (0.33 g, 1.4 mmol), $PdCl_{12}(dppf)_2$ (0.11 g, 0.14 mmol) and 2M $Na_2CO_3$(aq) (2 mL) in DME (10 mL) was heated at reflux for 20 h, cooled to RT, filtered, concentrated by rotary evaporation and purified on silica gel (6:1 hexanes/EtOAc and 4:1 hexanes/EtOAc) to afford the title compound as a light-brown oil. EI-MS m/z 264 (M+H).

Preparation BI: 2-(2-Methoxyphenyl)thiazole-4-carboxylic Acid

To a stirred solution of ethyl 2-(2-methoxy-phenyl) thiazole-4-carboxylate (0.27 g, 1.03 mmol) in EtOH (10 mL) was added 1N NaOH (aq) (5 mL). The resulting mixture was heated to reflux for 2 h. The mixture was cooled to RT, acidified with 1N HCl (aq) and concentrated by rotary evaporation. The residue was extracted with $CH_2Cl_2$ (3×5 mL). The extracts were combined, dried over $MgSO_4$, filtered and concentrated by rotary evaporation to afford the title compound as an off-white solid. EI-MS m/z 236 (M+H).

Preparation BJ: 2-[(4-Methoxyphenoxy)methyl]thiazole-4-carboxylic Acid

To a stirred solution of ethyl 2-(4-methoxyphenoxy) methyl]thiazole4-carboxylate (0.10 g, 0.34 mmol) in EtOH (5 mL) was added 1N NaOH (2.0 mL) and was heated to reflux until the starting material was consumed (2 h). The mixture was brought to RT, acidified with 1N HCl (pH 4.0) and concentrated by rotary evaporation. The residue obtained was partitioned between EtOAc (50 mL) and $H_2O$ (30 mL). The organic phase was separated, dried over $MgSO_4$, filtered and concentrated by rotary evaporation to afford the title compound as a white solid. EI-MS m/z 266 (M+H).

Preparation BK: 2-Amino-thiazole-4-carboxylic Acid Ethyl Ester Hydrobromide

To a stirred suspension of thiourea (24.26 g, 0.319 mol) in 200 proof EtOH (350 mL) at RT, under $N_2$, ethyl bromopyruvate (62.16 g, 0.319 mol) was added dropwise. Upon completion the yellow solution was heated to 45° C. for 15 h, then placed in a fridge overnight. The precipitate was filtered off and washed with cold EtOH (3×100 mL) to yield the title compound as a pale yellow amorphous solid. MS m/z: 173.1 (M+H), 195.1 (M+Na). Calc'd. for $C_6H_9BrN_2O_2S$-253.12.

Preparation BL: 2-Bromothiazole-4-carboxylic Acid

To a well stirred suspension of ethyl 2-aminothiazole-4-carboxylate hydrobromide (29.99 g, 0.17 mol) in 16% HBr(aq) (400 mL) at 0° C., a solution of $NaNO_2$ (12.49 g, 0.18 mol) in $H_2O$ (22 mL) was added dropwise. The mixture was maintained at 0° C. for an additional 35 min then CuBr (28.23 g, 0.20 mol) and an additional volume of 16% HBr(aq) (150 mL) were added. The ice bath was removed and the suspension heated to 70° C. for 1 hr. The mixture was filtered hot. The filtrate was saturated with NaCl then extracted with EtOAc (2×400 mL). The combined organic layers were dried over $MgSO_4$, filtered and concentrated under reduced pressure. The crude brown oil/solid residue was used directly in the next step. A solution of the brown residue in EtOH (100 mL) and 1M NaOH (aq) (367 mL, 0.36 mol) was stirred and heated at reflux for 1 h. The reaction mixture was filtered then extracted with EtOAc (100 mL). The aqueous layer was separated and concentrated under reduced pressure to remove the remaining EtOH. The aqueous solution was acidified to pH 1 with 2N HCl(aq). The solid was filtered off and air dried to yield the title compound as a beige amorphous solid. MS m/z: 208 (M+H) 210 (M+3).

Preparation BM: Ethyl 2-(2,6-dichloro-4-pyridyl)thiazole-4-carboxylate 2,6-Dichloropyridine-4-thiocarboxamide (1.0 g, 4.83 mmol) was dissolved in dry 1,4-dioxane followed by adding ethyl bromopyruvate (0.9 mL, 7.24 mmol) and pyridine (0.4 mL, 4.83 mmol). The resulting mixture was heated to reflux under $N_2$ for 5 h. After cooling to RT, solvent was removed. The residue was extracted with $CHCl_3$. The organic layer was washed with $H_2O$ and brine, dried over $MgSO_4$, and concentrated to give a brownish solid. This crude was purified by chromatography on silica gel. Elution with hexane:acetone (90:10) gave a title compound as yellow solid. MS m/z: 303 (M+H). Calc'd. for $C_{11}H_8Cl_2N_2O_2S$—303.16.

Preparation BN: 2-(2,6-Dichloro-4-pyridyl)thiazole-4-carboxylic Acid 2-(2,6-Dichloropyridin-4-yl)-ethylthiazolo-4-carboxylate (500 mg, 1.65 mmol) was dissolved in MeOH (10 mL) followed by adding 1N NaOH (2.5 mL, 2.47 mmol). The resulting mixture was stirred at RT for 4 h. The pH was adjusted to 5 using 1N HCl. The solvent was removed in vacuo and the residue was partitioned between EtOAc and $H_2O$. The aqueous layer was extracted more with EtOAc. The combined organic layers was dried over $MgSO_4$ and concentrated to give a white solid. MS m/z: 275.1 (M+H). Calc'd. for $C_9H_4Cl_2N_2O_2S$-275.11.

Preparation BO: Ethyl 6-[2-(2,2,2-trifluoroethoxy)-3-pyridyl]thiazole-4-carboxylate 6-(2,2,2-Trifluoroethoxy)pyridine-3-thiocarboxamide (800 mg, 3.4 mmol), ethyl bromopyruvate (0.9 mL, 6.8 mmol), and pyridine (0.3 mL, 3.4 mmol) were heated at reflux in dry 1,4-dioxane (20 mL) to yield title compound as pale yellow solid. MS m/z: 333.1 (M+H). Calc'd. for $C_{13}H_{11}F_3N_2O_3S$—332.3.

Preparation BP: 6-[2-(2,2,2-trifluoroethoxy)-3-pyridyl]thiazole-4-carboxylic Acid Ethyl 6-[2-(2,2,2-trifluoroethoxy)-3-pyridyl]thiazole-4-carboxylate (750 mg, 2.25 mmol) and 1N NaOH (3.4 mL, 3.4 mmol) were dissolved in MeOH (10 mL) to afford the title compound as a white solid. MS m/z: 305.1 (M+H). Calc'd. for $C_{11}H_7F_3N_2O_3S$-304.25.

Preparation BQ: 2-(Phenoxy)thiazole-4-carboxylic acid

A mixture of ethyl 2-phenoxythiazole-4-carboxylate (0.17 g, 0.68 mmol) and LiOH monohydrate (0.14 g, 3.40 mmol) in 2 mL of MeOH, 2 mL of $H_2O$, and 2 mL of THF was stirred at RT overnight, the solvents were removed in vacuo and the residue was diluted with water. The aqueous mixture was acidified with 1N HCl (aq) to pH=1–2, then extracted with EtOAc, the combined organic portions were washed with brine, dried over $MgSO_4$, filtered, removal of the solvents in vacuo yielded the title compound as a white solid. EI-MS=222.4 (M+H)+. Calc'd for $C_{10}H_7NO_3S$: 221.01.

Preparation BR: 3-(3-Nitrophenyl)pyridine

To a 1-iodo-3-nitrobenzene (1.0 g, 4.01 mmol) in dry DME (20 mL) was added pyridine-3-boronic acid (641 mg, 5.22 mmol), $PdCl_2$ dppf (327 mg, 0.40 mmol), and 2M $Na_2CO_3$ (3.0 mL). The resulting mixture was heated to reflux under $N_2$ for 15 h. Solvent was separated from inorganic solid by filtration. The solvent was removed and the residue was extracted with $CHCl_3$. The organic layer was washed with water, brine, and dried over $MgSO_4$. The solvent was removed to give dark brown solid which was purified by chromatography on silica gel. Elution with Hexane:acetone mixture (80:20) gave the final compound as a tan solid. MS m/z: 201.3 (M+H). Calc'd. for $C_{11}H_8N_2O_2$-200.23.

Preparation BS: 3-(3-Aminophenyl)pyridine

To a pre-hydrogenated solution of $Pd(OH)_2$ (298 mg, 2.12 mmol) in EtOH (10 mL) was added 3-(3-pyrid-1-yl)-1-nitrobenzene (440 mg, 2.12 mmol) in EtOH (10 mL). The resulting mixture was stirred at RT under $H_2$ for 2 h. Solvent was separated from $Pd(OH)_2$ by filtration through Celite®. Solvent was then removed to give final compound as pale yellow solid. MS m/z: 171.3 (M+H). Calc'd. for $C_{11}H_{10}N_2$— 170.22.

Preparation BT: 2,2-Dimethyl-N-[6-(2,2,6,6-tetramethyl-piperidin-1-ylmethyl)-pyridin-2-yl]-propionamide:

2,2,6,6-Tetramethylpiperidine (0.17 mL, 1.0 mmol) was added to a solution of N-pivaloyl-2-amino-6-bromomethylpyridine (180 mg, 0.66 mmol; M. Papadopoulou, et al., *J. Het. Chem.*, 1995, 32, 675–681) in DMF (10 mL) at 25° C. and the resulting mixture was stirred for 12 h. The reaction mixture was partitioned between $H_2O$ (15 mL) and EtOAc (20 mL) and the organics collected. The organics were washed with $H_2O$ (20 mL) followed by brine (20 mL) and dried over $MgSO_4$. Concentration in vacuo gave a colorless oil. MS m/z: 330.1 (M–H). Calc'd for $C_{20}H_{33}N_3O$—331.50.

Preparation BU: 6-(2,2,6,6-Tetramethyl-piperidin-1-ylmethyl)-pyridin-2-ylamine:

KOH (1.68 g, 33.5 mmol) in MeOH (100 mL) was added to 2,2-dimethyl-N-[6-(2,2,6,6-tetramethyl-piperidin-1-ylmethyl)-pyridin-2-yl]-propionamide (150 mg, 0.45 mmol) and the resulting mixture was heated at reflux for 12 h. After cooling to 25° C., the mixture was neutralized to pH 7–8 with concentrated HCl and extracted with $CHCl_3$ (3×75 mL). The organics were combined and dried over $MgSO_4$. Concentration in vacuo gave a pale yellow solid. MS m/z: 247.7 (M+). Calc'd for $C_{15}H_{25}N_3$—247.38.

Preparation BV: (2-Chloro-pyridin-4-yl)-piperidin-1-yl-methanone

To 2-chloroisonicotinic acid (1.0 g, 6.35 mmol) in dry $CH_2Cl_2$ (50 mL) was added piperidine (1.3 mL, 12.69 mmol), DIEA (2.2 mL, 12.69 mmol), HATU (1.2 g, 3.17 mmol), and EDCI (1.3 g, 6.98 mmol). The mixture was stirred under $N_2$ at RT for 15 h. Solvent was removed and the crude compound was purified by chromatography on silica gel. Elution with hexane:acetone mixture (80:20) gave a white solid. MS m/z: 225.1 (M+H). Calc'd. for $C_{11}H_{13}ClN_2O$—224.07.

Preparation BW: (2-Amino-pyridin-4-yl)-piperidin-1-yl-methanone $NH_4OH$ (25 mL) and Cu powder (100 mg) were added to a solution of (2-amino-pyridin-4-yl)-piperidin-1-yl-methanone (1.0 g, 4.45 mmol) in IpOH (15 mL) and the mixture was heated at 100° C. for 48 h in a sealed tube. After cooling to RT, the mixture was partitioned between $H_2O$ and $CHCl_3$. The aqueous layer was extracted with more $CHCl_3$ (3×20 mL). The combined organic layers was washed with brine, and dried over $MgSO_4$. Concentration in vacuo gave a light brown solid. MS m/z: 206.3 (M+H). Calc'd. for $C_{11}H_{15}N_3O$—205.12.

Preparation BX: 4-Piperidin-1-ylmethyl-pyridin-2-ylamine

To a stirred solution of (2-amino-pyridin-4-yl)-piperidin-1-yl-methanone (100 mg, 0.487 mmol) in dry THF (10 mL) at 0° C. was added LAH (1.5 mL, 1.46 mmol) dropwise. The mixture was heated to reflux for 20 h. The resulting mixture was cooled to 0° C. and quenched with $H_2O$ (1.5 mL) dropwise followed by 10% NaOH (1.5 mL). Solvent was removed and the residue was partitioned between $H_2O$ and $CHCl_3$. The organic layer was washed with $H_2O$, brine, dried over $MgSO_4$. Concentration in vacuo gave a light brown liquid. MS m/z: 192.2 (M+H). Calc'd. for $C_{11}H_{17}N_3$-191.14.

Preparation BY: 4-Diethylaminomethyl-pyridin-2-ylamine

Prepared in a manner similar to that described for 4-piperidin-1-ylmethyl-pyridin-2-ylamine. MS m/z: 180.2 (M+H). Calc'd. for $CloH_{17}N_3$—179.14.

Preparation BZ: [6-(2,6-Dimethyl-piperidin-1-ylmethyl)-pyridin-2-yl]-carbamic Acid Tert-Butyl Ester 2,6-Dimethylpiperidine (0.24 mL, 1.74 mmol) was added to a solution of (6-bromomethyl-pyridin-2-yl)-carbamic acid tert-butyl ester (250 mg, 0.87 mmol) in DMF (10 mL) followed by heating at 50° C. and the resulting mixture was stirred for 18 h. The resulting mixture was partitioned between water (10 mL) and $CHCl_3$ (20 mL). The organic layer was washed with $H_3O$, brine, and dried over $MgSO_4$. Concentration in vacuo gave a pale yellow solid. MS m/z: 320.3 (M+H). Calc'd. for $C_{18}H_{29}N_3O_2$—319.23.

Preparation CA: 6-(2,6-Dimethyl-piperidin-1-ylmethyl)-pyridin-2-ylamine

HCl (1.25 mL, 1.25 mmol) in MeOH (15 mL) was added to [6-(2,6-dimethyl-piperidin-1-ylmethyl)-pyridin-2-yl]-carbamic acid tert-butyl ester (200 mg, 0.63 mmol) followed by heating at 40° C. for 18 h. The resulting mixture was cooled to RT and basified to pH 9 with 2 N NaOH. The mixture was extracted with $CHCl_3$ (3×20 mL). The combined organic layers was dried over $MgSO_4$ and concentrated in vacuo to give a yellow oil. MS m/z: 220.2 (M+H). Calc'd. for $C_{13}H_{21}N_3$—219.17.

Preparation CB: 1-(6-Bromo-pyridin-2-yl)-ethanol

6-Bromo-2-pyridine carboxaldehyde (1.0 g, 5.37 mmol) in dry THF (20 mL) was cooled to −78° C. followed by adding MeMgI (2.0 mL, 5.91 mmol) dropwise via the addition funnel. The cooling bath was removed. The resulting mixture was stirred for 1 h then quenched with sat. $NH_4Cl$. Solvent was removed. The residue was partitioned between water and $CHCl_3$. The organic layer was washed with $H_2O$, brine, dried over $MgSO_4$. Solvent was removed and crude compound was purified by chromatography on silica gel. Elution with hexane:acetone mixture (70:30) gave a white solid. MS m/z: 201.9(M+H). Calc'd. for $C_7H_8BrNO$—200.98.

Preparation CC: 1-(6-Bromo-pyridin-2-yl)-ethanone

Oxalyl chloride (2.1 mL, 3.81 mmol) in dry $CH_2Cl_2$ was cooled to −70° C. followed by adding DMSO (0.6 mL, 8.39 mmol) dropwise. After stirred for 5 min under −60° C., 1-(6-bromo-pyridin-2-yl)-ethanol (770 mg, 3.81 mmol) in dry $CH_2Cl_2$ (10 mL) was added dropwise. After stirred for 30 min, TEA (2.7 mL, 19.83 mmol) was added and the resulting mixture was warmed to RT and stirred for 1 h. The reaction mixture was quenched with $H_2O$. The organic layer was washed with $H_2O$, brine, and dried over $MgSO_4$. Solvent was removed and the crude compound was purified by chromatography on silica gel. Elution with hexane:acetone mixture (90:10) gave a white solid. MS m/z: 200.3 (M+H). Calc'd. for $C_7H_8BrNO$—198.96.

Preparation CD: 2-Bromo-6-(1-piperidin-1-yl-ethyl)-pyridine

To a stirred solution of 1-(6-bromo-pyridin-2-yl)-ethanone (600 mg, 3.01 mmol) in dry $CH_2Cl_2$ (20 mL) was added piperidine (0.5 mL) followed by $NaBH(OAc)_3$ (1.3 g, 12.06 mmol) and HOAc (0.7 mL, 6.03 mmol). The mixture was heated at 40° C. for 72 h. The reaction was quenched with 2M $Na_2CO_3$ and stirred 1 h. The organic layer was collected, dried over $MgSO_4$ and concentrated in vacuo. This crude compound was purified by chromatography on silica gel. Elution with hexane:acetone mixture (90:10) gave a light yellow solid. MS m/z: 269.2 (M+H). Calc'd. for $C_{12}H_{17}BrN_2$—268.06.

Preparation CE: 2-Hydroxymethyl-piperidine-1-carboxylic Acid Tert-Butyl Ester

Piperidine-1,2-dicarboxylic acid 1-tert-butyl ester (50 g, 218.1 mmol) in dry THF (300 mL) was cooled to −78° C. followed by adding $BH_3$-THF solution (261.7 mL, 260.0 mmol) dropwise over 1 h. The resulting mixture was warmed to RT and stirred for 48 h. The reaction was quenched with $HOAc/H_2O$ (1:1 ratio, 100 mL). The resulting mixture was partitioned between EtOAc and sat. $NaHCO_3$. The organic layer was washed with more sat. $NaHCO_3$, $H_2O$, brine, and dried over $MgSO_4$. Concentration in vacuo gave a white solid. MS m/z: 216.2 (M+H). Calc'd. for $C_{11}H_{21}NO_3$—215.15.

Preparation CF: 2-Formyl-piperidine-1-carboxylic Acid Tert-Butyl Ester

In a manner similar to that described in Preparation CC, 2-hydroxymethyl-piperidine-1-carboxylic acid tert-butyl ester (500 mg, 2.32 mmol) was added to a mixture of oxalyl chloride (1.3 mL, 2.55 mmol) and DMSO (0.36 mL, 5.11 mmol) followed by adding TEA (1.7 mL, 12.07 mmol) to give a white solid. MS m/z: 214.2 (M+H). Calc'd. for $C_{11}H_{19}NO_3$—213.14.

Preparation CG: 2-[(6-Amino-pyridin-2-ylamino)-methyl]-piperidine-1-carboxylic Acid Tert-Butyl Ester In a manner similar to that described in Preparation CD, 2-formyl-piperidine-1-carboxylic acid tert-butyl ester (360 mg, 1.69 mmol) was treated with 2,6-diaminopyridine (184 mg, 1.69 mmol) and stirred at RT to give a light brown oil. MS m/z: 307.3(M+H). Calc'd. for $C_{16}H_{26}N_4O_2$—306.21.

Preparation CH: 5-Cyano-indole-1-carboxylic Acid Tert-Butyl Ester

To a solution of 5-cyanoindole (9.76 g, 68.7 mmol), 100 mL of anhydrous $CH_3CN$, and DMAP (423 mg, 3.5 mmol) was added di-tert-butyl dicarbonate (15.78 g, 72.3 mmol). The resulting solution was stirred for 18 h then concentrated in vacuo. The resulting solid was redissolved in EtOAc (350 mL) and washed with 1N HCl (aq) (2×25 mL). The acidic aqueous solution was extracted with EtOAc (2×). The combined EtOAc layers were washed with brine, dried over MgSO4, and concentrated in vacuo to give a light yellow solid. MS m/z: 243 (M+1). Calc'd for $C_{14}H_{14}N_2O_2$—242.47.

Preparation CI: 5-Thiocarbamoyl-indole-1-carboxylic Acid Tert-Butyl Ester $H_2S$ (g) was bubbled through a solution of 5-cyano-indole-1-carboxylic acid tert-butyl ester (15.71 g, 64.8 mmol), 120 mL of pyridine, and TEA (27.5 mL, 197.3 mmol). The reaction was followed by LC-MS and concentrated in vacuo upon completion to give a black solid. MS m/z: 277 (M+1). Calc'd for $C_{14}H_{16}N_2O_2S$-276.36.

Preparation CJ: 5-(4-Ethoxycarbonyl-thiazol-2-yl)-indole-1-carboxylic Acid Tert-Butyl Ester To a solution of 5-thiocarbamoyl-indole-1-carboxylic acid tert-butyl ester (13.16 g, 47.6 mmol) and 250 mL of EtOH was added ethyl bromopyruvate (6.05 mL, 48.2 mmol). The resulting solution was stirred at 60° C. for 1.5 h, then concentrated in vacuo. The resulting solid was purified by flash chromatography on silica gel using 5% EtOAc/hexane→80% EtOAc/hexane→$CH_2Cl_2$ as the eluant to give a white solid. MS m/z: 373 (M+1). Calc'd for $C_{19}H_{20}N_2O_4S$-372.44.

Preparation CK: 5-(4-Carboxy-thiazol-2-yl)-indole-1-carboxylic Acid Tert-Butyl Ester To a solution of 5-(4-ethoxycarbonyl-thiazol-2-yl)-indole-1-carboxylic acid tert-butyl ester (3.34 g, 9.0 mmol) and 125 mL of THF was added 1N NaOH (aq) (30.0 mL, 30.0 mmol). The solution was stirred for 24 h then concentrated in vacuo. The crude solid was redissolved in $H_2O$ and acidified with 5% $KHSO_4$. The solid was filtered and dried in vacuo at 60° C. to give a pinkish-white solid. MS m/z: 345 (M+1). Calc'd for $C_{17}H_{16}N_2O_4S$-344.39.

Preparation CL: 2-Bromo-thiazole-4-carboxylic Acid Ethyl Ester

To a stirred mixture of 2-amino-thiazole-4-carboxylic acid ethyl ester hydrobromide (10 g, 58 mmol), $CuSO_4$ (26.9 g, 168 mmol) and NaBr (22.7 g, 221 mmol) in 9M $H_4SO_4$ (aq) (120 mL) at −5° C. −0° C., a pre-cooled solution of $NaNO_2$ (4.4 g, 64 mmol) in $H_2O$ (40 mL) was added at such a rate to maintain the temperature at or below 0° C. After complete addition the mixture was maintained at 0° C. for another 30 min then warmed to RT over 2.5 h. The reaction mixture was diluted with $H_2O$ (120 mL) and extracted with $Et_2O$ (3×100 mL). The aqueous layer was separated, basified to pH 12 with 5N NaOH (aq), then extracted with $Et_2O$ (2×100 mL). The organic layers were combined, dried over $Na_2SO_4$, filtered and the solvent evaporated in vacuo. The residue was purified by flash chromatography on silica gel (1:9, EtOAc:hexane) to yield the title compound as a white amorphous solid. MS m/z: 235.8, 237.8 (M+H). Calc'd. for $C_6H_6BrNO_2S$-234.93.

Preparation CM: 2-Chloro-thiazole-4-carboxylic Acid Ethyl Ester

2-Amino-thiazole-4-carboxylic acid ethyl ester hydrobromide (34.46 g, 0.137 mol) was basified with a saturated solution of $NaHCO_3$ (aq) (300 mL) and extracted with EtOAc (8×300 mL). The combined organic layers were dried over $Na_2SO_4$, filtered and the solvent evaporated in vacuo to liberate the free base. To a well stirred suspension of the free base in 9M $H_2SO_4$ (aq) (500 mL) at 00C to −5° C., $CUSO_4$ (63.34 g, 0.397 mol) and NaCl (30.39 g, 0.520 mol) were added, followed by the dropwise addition of a solution of $NaNO_2$ (10.39 g, 0.151 mol) in $H_2O$ (150 mL), over 45 min. The mixture was maintained at 0° C. for 1 h then warmed to RT. After 1 h at RT the reaction mixture was diluted with $H_2O$ (2 L) and extracted with $Et_2O$ (3×300 mL).

The combined organic layers were dried over $Na_2SO_4$, filtered and the solvent was evaporated in vacuo to yield the title compound as a pale yellow amorphous solid (sufficiently pure to be used directly in the next step). MS m/z: 192.0 (M+H). Calc'd. for $C_6H_6ClNO_2S$-191.64.

Preparation CN: 2-Chloro-thiazole-4-carboxylic Acid

To a stirred solution of 2-chlorothiazole-4-carboxylic acid ethyl ester (20.49 g, 0.107 mol) in THF (180 mL) at RT, a 1M solution of LiOH (aq) (160 mL, 0.160 mol) was added. The resulting solution was heated to 65° C. for 1 h. The solvent was evaporated in vacuo. The residue was treated with brine (100 mL) and acidified to pH 1 with 1M HCl (aq). The precipitate was filtered off, washed with $H_2O$ (2×50 mL) and $Et_2O$ (2×50 mL) and dried in a vacuum oven at 60° C. for 62 h to yield the title compound as a pale yellow solid. MS m/z: 164.1 (M+H). Calc'd. for $C_4H_2ClNO_2S$-163.58.

Preparation CO: 2-Chloro-thiazole-4-carbonyl Azide

To a stirred solution of 2-chlorothiazole-4-carboxylic acid (15.30 g, 94 mmol) in anhydrous THF (200 mL) at 0° C., under nitrogen, TEA (26.1 mL, 187 mmol) was added. After 30 min ethyl chloroformate (9.39 mL, 98 mmol) was added dropwise over 10 min. After 25 min a solution of $NaN_3$ (6.38 g, 98 mmol) in $H_2O$ (110 mL) was added. The mixture was warmed to RT over 1 h then diluted with $H_2O$ (500 mL). The precipitate was filtered off and air dried to yield the title compound as a white amorphous solid. MS m/z: 189.3 (M+H). Calc'd. for $C_4HClN_4OS$-188.60.

Preparation CP: 2-Bromo-thiazole-4-carbonyl Azide

To a stirred solution of 2-bromo-thiazole-4-carboxylic acid (5.33 g, 25.7 mmol) in anhydrous THF (40 mL) at 0° C., under $N_2$, TEA (7.18 mL, 51.5 mmol) was added. After 30 min ethyl chloroformate (2.59 mL, 27.0 mmol) was added dropwise over 10 min. After 25 min a solution of $NaN_3$ (1.76 g, 27.0 mmol) in $H_2O$ (12 mL) was added. The mixture was warmed to RT over 1 h then diluted with $H_2O$ (100 mL). The precipitate was filtered off and air dried to yield the title compound as a white amorphous solid. MS m/z: 233.2, 235.2 (M+H). Calc'd. for $C_4HBrN_4OS$-233.05.

Preparation CQ: 3-(Benzyloxycarbonylamino-methyl)-piperidine-1-carboxylic Acid Tert-Butyl Ester To a stirred solution of 3-(aminomethyl)-1-N-Boc-piperidine (1.64 g, 7.65 mmol) and TEA (1.6 mL, 11 mmol) in THF (5 mL) at 0° C., benzyl chloroformate (1.15 mL, 8.04 mmol) was added dropwise. The reaction was maintained at 0° C. for 1 h, then warmed to RT overnight. The solvent was evaporated in vacuo. The residue was taken up in a saturated solution of $NH_4Cl$ (aq) (15 mL) and extracted with EtOAc (10 mL). The organic layer was separated, dried over $MgSO_4$, filtered and the solvent was evaporated in vacuo. The residue was purified by flash chromatography on silica gel (1:4, EtOAc:hexane) to yield the title compound as a colorless oil. MS m/z: 349.3 (M+H). Calc'd. for $C_{19}H_{28}N_2O_4$— 348.44.

Preparation CR: Piperidin-3-ylmethyl-carbamic Acid Benzyl Ester

To a stirred solution of 3-(benxyloxycarbonylamino-methyl)-piperidine-1-carboxylic acid tert-butyl ester (983 mg, 2.82 mmol) in anhydrous $CH_2Cl_2$ (10 mL) at RT, under $N_2$, TFA (3 mL) was added. After 2.5 h the solvent was evaporated in vacuo and the residue was dissolved in EtOAc (20 mL). The organic layer was washed with a saturated solution of $NaHCO_3$ (aq) (30 mL), separated, dried over $Na_2SO_4$, filtered and the solvent evaporated in vacuo to yield the title compound as a pale yellow oil. MS m/z: 249.0 (M+H). Calc'd. for $C_{19}H_{28}N_2O_4$—248.32.

Preparation CS: 2-[3-(Benzyloxycarbonylamino-methyl)-piperidin-1-yl]-thiazole-4-carboxylic Acid Ethyl Ester To a stirred solution of piperidin-3-ylmethyl-carbamic acid benzyl ester (43 mg, 0.17 mmol) in $CH_3CN$ (5 mL), at RT under $N_2$, $K_2CO_3$ (26 mg, 0.19 mmol) and 2-bromo-thiazole-4-carboxylic acid ethyl ester (41 mg, 0.17 mmol) were added. The resulting mixture was heated at reflux for 29 h. The solvent was evaporated in vacuo. The residue was treated with a saturated solution of $NH_4Cl$ (aq) (10 mL) and extracted with EtOAc (10 mL). The organic layer was separated, dried over $Na_2SO_4$, filtered and the solvent evaporated in vacuo. The residue was purified by flash chromatography on silica gel (1:2, EtOAc:hexane) to yield the title compound as a colorless oil. MS m/z: 404.2 (M+H). Calc'd. for $C_{20}H_{25}N_3O_4S$-403.50.

Preparation CT: 2-[3-(Benzyloxycarbonylamino-methyl)-piperidin-1-yl]-thiazole-4-carboxylic Acid To a stirred solution of 2-[3-(benzyloxycarbonylamino-methyl)-piperidin-1-yl]-thiazole-4-carboxylic acid ethyl ester (439 mg, 1.15 mmol) in THF (5 mL) at RT, a 1M solution of LiOH (aq) (1.72 mL, 1.72 mmol) was added. After 16 h the solvent was evaporated in vacuo. The residue was treated with brine (25 mL) and acidified to pH 1 with 2N HCl (aq) then extracted with EtOAc (30 mL). The organic layer was separated, dried over $Na_2SO_4$, filtered and the solvent evaporated in vacuo to yield the title compound as a colorless oil. MS m/z: 355.9 (M+H). Calc'd. for $C_{16}H_{25}N_3O_4S$-355.45.

Preparation CU: Cyclopropanecarbothioamide

To a solution of cyclopropanecarboxamide (0.525 g, 6.169 mmol) and $Na_2CO_3$ (0.654 g, 6.169 mmol) in THF (100 mL) was added solid $P_2S_5$ (2.742 g, 6.169 mmol). The reaction was brought to reflux and kept at this temperature for 2 h. The reaction mixture was cooled to RT, filtered through Celite® and concentrated in vacuo to yield crude cyclopropane-carbothioamide (used for the next step without purification). MS m/z: 102.1 (M+H) Calc'd. for $C_4H_8NS$—102.0.

Preparation CV: Ethyl 2-cyclopropyl-thiazole-4-carboxylate

To a solution of cyclopropanecarbothiotic acid amide (1.18 g, 0.012 mol) in EtOH (60 mL) was added ethylbromopyruvate (1.71 mL, 0.012 mol) at RT and the mixture was brought to reflux and kept at this temperature for 3 h. The reaction mixture was cooled to RT and evaporated to dryness. Crude compound was dissolved in cold $CH_3CN$ (5 mL) and filtered. The filtrate was concentrated in vacuo and the resulting residue was purified by column chromatography eluting with hexanes:EtOAc (4:1) to give ethyl 2-cyclopropyl-thiazole-4-carboxylate. MS m/z: 197.9 (M+H) Calc'd. for $C_9H_{12}NO_2S$-198.0.

Preparation CW: 2-Cyclopropyl-thiazole-4-carboxylic Acid

To a mixture of ethyl 2-cyclopropyl-thiazole-4-carboxylate (0.443 g, 2.249 mmol) and LiOH monohydrate (0.472 g, 11.243 mmol) was added a mixture of THF/MeOH/$H_2O$ (3:1:1, 50 mL). The reaction was stirred at RT for 24 h. The solution was acidified by addition of conc. HCl (0.1 mL) and the volatiles were removed. Remaining aqueous solution was extracted with EtOAc (3×20 mL). The combined organic layers were dried over $Na_2SO_4$ and evaporated to dryness. MS m/z: 169.9 (M+H) Calc'd. for $C_7H_7NO_2S$-170.0.

Preparation CX: 2-Cyclopropyl-thiazole-4-carbonyl Azide

To a solution of 2-cyclopropyl-thiazole-4-carboxylic acid (0.360 g, 2.130 mmol) and TEA (0.59 mL, 4.260 mmol) in THF (10 mL) at 0° C., was added ethylchloroformate (0.22 mL, 2.343 mmol) and the mixture was stirred for 30 min. A solution of $NaN_3$ (0.152 g, 2.343 mmol) in $H_2O$ (10 mL) was added to this mixture and warmed to RT. After 1 h, the reaction mixture was diluted with $H_2O$ (10 mL) and extracted with EtOAc (3×20 mL). The combined organic extracts were dried over $Na2SO_4$ and evaporated to dryness. MS m/z: 195.0 (M+H) Calc'd. for $C_7H_7N_4OS$-195.0.

Preparation CY: 2-tert-Butyl-thiazole-4-carbonylazide

Synthesized from 2,2-dimethylpropionamide following preparations CU-CX. MS m/z: 211.3 (M+H) Calc'd. for $C_8H_{11}N_4OS$-211.0.

Preparation CZ: 3-Sulfamoylthiobenzamide

3-Cyanobenzenesulfonamide (12.6 g, 0.067 mol) was added to a solution of TEA (0.8 mL), dry pyridine (0.5 mL) and benzene (30 mL) at RT and cooled to 0° C. $H_2S$ was bubbled through the solution for 20 min. The reaction was stirred at RT for 20 h. The resulting solid was dissolved in MeOH (30 mL) and transferred for the next step. LC-MS m/z: 217 (M+H).

Preparation DA: 2-(3-Sulfamoyl-phenyl)-thiazole-4-carbonylazide

Synthesized from 3-sulfamoylthiobenzamide following preparations CV-CX. MS m/z: 310.2 (M+H). Calc'd. for $C_{10}H_8N_5O_3S_2$—310.0.

Preparation DB: Ethyl 2-cyclopropylethynyl-thiazole-4-carboxylate

To a solution of bromothiazole (319.5 mg, 1.353 mmol), $Pd(PhCN)_2Cl_2$ (155.7 mg, 0.406 mmol), $CuI_2$ (51.5 mg, 0.271 mmol) and tri-t-butylphosphine (0.2 M in toluene, 4.4 mL, 0.880 mmol) in dioxane (10 mL) was added DEA (0.21 mL, 2.030 mmol) and ethynylcyclopropane (107.2 mg, 1.624 mmol). The reaction mixture was stirred at RT for 12 h. Volatiles were removed in vacuo and was passed through a pad $SiO_2$ (elution with EtOAc). Chromatography (Hexanes: EtOAc, 9:1) gave pure ethyl 2-cyclopropylethynyl-thiazole-4-carboxylate. MS m/z: 222.2 (M+H) Calc'd. for $C_{11}H_{12}NO_2S$-222.0.

Preparation DC: 2-Cyclopropylethynyl-thiazole-4-carbonyl Azide

Prepared from ethyl 2-cyclopropylethynyl-thiazole-4-carboxylate following preparations CW-CX. MS m/z: 219.3 (M+H) Calc'd. for $C_9H_7N_4OS$-219.0.

Preparation DD: (6-Bromo-pyridin-2-ylmethyl)-isopropyl-amine

To a stirred solution of 6-bromo-pyridine-2-carbaldehyde (1.06 g, 5.73 nmmol) in dry $CH_2Cl_2$ (30 mL) was added isopropylamine (0.51 mL, 6.02 mmol). The mixture was stirred at RT and under $N_2$ for 30 min followed by the addition of $NaBH(OAc)_3$ (2.42 g, 11.46 mmol) and HOAc (1.3 mL, 22.92 mmol). The resulting cloudy light-yellow solution was stirred at RT and under $N_2$ for 15 h. A 10% solution of $Na_2CO_3$ (50 mL) was added to the mixture and stirred for 30 min. The organic phase was separated, washed with $H_2O$, brine, dried over $MgSO_4$ and concentrated to afford a light yellow-oil without further purification. MS m/z: 229.1 (M+H). Calc'd for $C_9H_{13}BrN_2$: 228.03.

Preparation DE: (6-Bromo-pyridin-2-ylmethyl)-isopropyl-carbamic Acid Tert-Butyl Ester To a stirred solution of (6-bromo-pyridin-2-ylmethyl)-isopropyl-amine in $CH_2Cl_2$ (100 mL) was added $(Boc)_2O$ (10.2 g, 46.7 mmol). The resulting mixture was stirred at RT for 3 days. The mixture was concentrated and purified by chromatography on silica gel using 6:1 Hex/EtOAc as eluent to afford a very pale yellow-oil which solidified once cooled to RT. MS m/z: 329.3 (M+H). Calc'd for $C_{14}H_{21}BrN_2O_2$: 328.08.

Preparation DF: 4-pyrrolidin-1-ylmethylphenol

To a stirred solution of 4-hydroxylbenzaldehyde (10 g, 81.9 mmol) in anhydrous $CH_2Cl_2$ (500 mL) at RT, under $N_2$, pyrrolidine (10.2 mL, 122.9 mmol) was added, followed by $NaBH(OAc)_3$ (34.6 g, 163.9 mmol) and AcOH (19.7 g, 327.8 mmol). After the mixture was stirred at RT for 24 h, a saturated solution of $NaHCO_3$(aq) (150 mL) was added. The mixture was vigorously stirred for an additional 1 h and then extracted with $CH_2Cl_2$ (3×200 mL). The combined organic layer was washed with brine (300 mL), dried over $MgSO_4$, filtered and concentrated under reduced pressure to yield the title compound as amber oil. This was used crude in the next step. MS m/z: 178 (M+1). Calc'd for $C_{11}H_{15}NO$—177.2.

Preparation DG: 2-Bromo-6-(4-pyrrolidin-1-ylmethylphenoxy)pyridine

To a stirred suspension of NaH (2.6 g, 108.5 mmol) in DMF (300 mL) at 0° C., under $N_2$, a solution of 4-pyrrolidin-1-ylmethylphenol (16 g, 90.4 mmol) was added slowly. After stirring at 0° C. for 30 min, 2,6-dibromopyridine (23.6 g, 99.4 mmol) was added and the resulting mixture was heated at 950C for 20 h. After cooling to RT, 200 mL of $H_2O$ was added and the mixture was extracted with EtOAc (3×300 mL). The combined organic layer was washed with brine (3×400 mL), dried over $MgSO_4$, filtered and concentrated under reduced pressure to yield the title compound as an amber solid. This was used crude in the next step. MS m/z: 333 (M+1). Calc'd for $C_{16}H_{17}BrN_2O$-333.2

Preparation DH: 2-Amino-6-(4-pyrrolidin-1-ylmethylphenoxy)pyridine

A mixture of 2-bromo-6-(4-pyrrolidin-1-ylmethylphenoxy)pyridine (20 g) and Cu powder (1 g) in concentrated $NH_4OH$ (250 mL, aq) and IpOH (60 mL) was heated at 100° C. in a sealed flask for 48 h. After cooling to RT, brine (300 mL) was added and the mixture was extracted with EtOAc (3×200 mL). The combined organic layer was washed with brine (300 mL), dried over $MgSO_4$, filtered and concentrated under reduced pressure. The residues were filtered through silica gel pad eluting with $MeOH/CH_2Cl_2$ (5%). The filtrate was concentrated to dryness, then 50 mL of MeOH was added. After stirring for a while the solid was filtered to give the title compound. MS m/z: 270 (M+1). Calc'd for $C_{16}H_{19}N_3O$—269.3.

Preparation DI: 5-tert-Butyl-oxazole-2-carboxylic Acid Ethyl Ester

The mixture of N-(3,3-dimethyl-2-oxo-butyl)-oxalamic acid ethyl ester (0.79 g, 3.67 mmol) and phosphorus oxychloride (2.0 mL, 22.0 mmol) was stirred at 105° C. under $N_2$ for 2 h, cooled to RT, quenched slowly with ice-water, extracted with EtOAc. The combined organic portions were washed with brine, dried with $Na_2SO_4$, removal of the solvents gave a dark brownish oil which was purified by flash column chromatography to yield the title compound. MS m/z: 197.9 (M+H). Calc'd for $C_{10}H_{15}NO_3$— 197.23.

Preparation DJ: 5-tert-Butyl-oxazole-2-carboxylic Acid Amide

The mixture of 5-tert-butyl-oxazole-2-carboxylic acid ethyl ester(0.52 g, 2.64 nmmol) and $NH_3$ (2.0M solution in MeOH, 6.6 mL, 13.2 mmol) was stirred at RT under $N_2$ for 20 h. The solvents were removed under reduced pressure and the residue was dissolved in EtOAc washed with brine, dried with $Na_2SO_4$ and filtered. Removal of the solvents afforded the title compound as a white solid. MS m/z: 169.2 (M+H). Calc'd for $C_8H_{12}N_2O_2$—168.19.

Preparation DK: 5-tert-Butyl-oxazole-2-carbothioic Acid Amide

In a manner similar to that described in preparation BB, the title compound was isolated as a yellow solid. MS m/z: 185.3 (M+H). Calc'd for $C_8H_{12}N_2OS$-184.26.

Preparation DL: 2-(5-tert-Butyl-oxazol-2-yl)-thiazole-4-carboxylic Acid Ethyl Ester In a manner similar to that described in preparation BC, the title compound was isolated as a white solid. MS m/z: 281.2 (M+H). Calc'd for $C_{13}H_{16}N_2O_3S$-280.34.

Preparation DM: 2-(5-tert-Butyl-oxazol-2-yl)-thiazole-4-carboxylic Acid

In a manner similar to that described in preparation BD, the title compound was isolated as a white solid. MS m/z: 253.3 (M+H). Calc'd for $C_{12}H_{12}N_2O_3S$-252.29.

Preparation DN: 2-(5-tert-Butyl-oxazol-2-yl)-thiazole-4-carbonyl Azide

In a manner similar to that described in preparation BE, the title compound was isolated as an off-white solid. MS m/z: 278.2 (M+H)$^+$. Calc'd for $C_{11}H_{11}N_5O_2S$-277.30.

Preparation DO: 2-Thiophen-2-yl-thiazole-4-carboxylic Acid Ethyl Ester

The mixture of 2-bromo-thiazole-4-carboxylic acid ethyl ester (0.965 g, 4.09 mmol), 2-thiopheneboronic acid (0.52 g, 4.09 mmol), Pd(PPh$_3$)$_4$ (0.24 g, 0.20 mmol) in 6.2 mL of 2M Na$_2$CO$_3$ (aq) and 25 mL of ethylene glycol dimethyl ether was heated at reflux for 16 h, cooled to RT, diluted with H$_2$O (25 mL), and extracted with EtOAc (30 mL×3). The combined organic portions were washed with brine, dried with Na$_2$SO$_4$, and filtered. Removal of the solvents afforded a light yellowish oil which was purified by flash column chromatography (5% to 10% of EtOAc in hexanes). The desired compound was obtained as a pale solid. MS m/z: 239.9 (M+H). Calc'd for $C_{10}H_9NO2S_2$—239.32.

Preparation DP: 2-(Thiophene-2-sulfonylmethyl)-thiazole-4-carboxylic Acid Ethyl Ester In a manner similar to that described in preparation BC, the title compound was isolated as a light yellowish viscous oil. MS m/z: 318.1 (M+H). Calc'd for $C_{11}H_{11}NO_4S_3$—317.41.

Preparation DQ: 2-(Thiophene-2-sulfonylmethyl)-thiazole-4-carboxylic Acid

In a manner similar to that described in preparation BD, the title compound was isolated as a white solid. MS m/z: 290.0 (M+H). Calc'd for $C_9H_7NO4S_3$—289.35.

Preparation DR: 2-(Thiophene-2-sulfonylmethyl)-thiazole-4-carbonyl Azide

In a manner similar to that described in preparation BE, the title compound was isolated as a tan solid. MS m/z: 315.1 (M+H). Calc'd for $C_9H_6N_4O_3S_3$—314.37.

Preparation DS: 6-(1-Methyl-piperidin-4-yloxy)-pyridin-2-ylamine

In a manner similar to that described in Preparation EM, the title compound was isolated as a white solid. MS m/z: 208.1 (M+H). Calc'd for $C_{11}H_{17}N_3O$—207.27.

Preparation DT: 4-(6-Amino-pyridin-2-yloxymethyl)-piperidine-1-carboxylic Acid Tert-Butyl Ester In a manner similar to that described in Preparation EM, the title compound was isolated as a white solid. MS m/z: 308.2 (M+H). Calc'd for $C_{16}H_{25}N_3O_3$—307.39.

Preparation DU: D-2-Hydroxymethyl-pyrrolidine-1-carboxylic Acid Tert-Butyl Ester To a solution of D-prolinol (8 g, 79.2 mmol) and CH$_2$Cl$_2$ (150 mL) was added (Boc)$_2$O (19 g, 87.1 mmol) and 150 mL of sat'd NaHCO$_3$. The reaction was stirred at RT for 15 h. Extraction with CH$_2$Cl$_2$, washing with brine, drying (MgSO$_4$) and concentration in vacuo gave D-2-hydroxymethyl-pyrrolidine-1-carboxylic acid tert-butyl ester as a white solid. MS m/z: 202.3 (M+H). Calc'd for $C_{10}H_{19}NO_3$— 201.26.

Preparation DV: 2-(6-Bromo-pyridin-2-yloxymethyl)-pyrrolidine-1-carboxylic Acid Tert-Butyl Ester To a solution of D-2-hydroxymethyl-pyrrolidine-1-carboxylic acid tert-butyl ester (15.9 g, 79.1 mmol) and dry DMF (250 mL) was added NaH (3.8 g, 94.9 mmol, 60% in mineral oil). Stirred at RT for 15 h, then added 2,6-dibromopyridine. Heated to 90° C. for 2 h. Cooled and extracted with EtOAc. Washed organic layer with H$_2$O and brine, dried (MgSO$_4$) and concentrated in vacuo to give an orange oil. Purified by silica flash chromatography (10% EtOAc/hexane) to give the desired compound as a clear-colorless oil. MS m/z: 358.2 (M+H). Calc'd for $C_{15}H_{21}BrN_2O_3$— 357.24.

Preparation DW: 2-(6-Amino-pyridin-2-yloxymethyl)-pyrrolidine-1-carboxylic Acid Tert-Butyl Ester In a manner similar to Preparation BW to give 2-(6-amino-pyridin-2-yloxymethyl)-pyrrolidine-1-carboxylic acid tert-butyl ester as a viscous green oil. MS m/z: 294.3 (M+H). Calc'd for $C_{15}H_{23}N_3O_3$-293.36.

Preparation DX: 2-Bromo-6-(tetrahydro-furan-3-yloxy)-pyridine

To a solution of (S)-(+)-3-hydroxy-tetrahydrofuran (0.34 mL, 4.2 mmol) and dry THF (20 mL) was added NaH (0.17 g, 4.2 mmol, 60%) under N$_2$ at RT. After 5 min, added 2,6-dibromopyridine. Stirred at RT for 4 h. Quenched with H$_2$O and extracted with EtOAc. Washed organic layer with saturated NH$_4$Cl, brine, dried (MgSO$_4$) and concentrated in vacuo to give 2-bromo-6-(tetrahydro-furan-3-yloxy)-pyridine as a clear, colorless oil. MS m/z: 245.2 (M+H). Calc'd for $C_9H_{10}BrNO_2$—244.09.

Preparation DY: 2-Bromo-6-(tetrahydro-furan-2-ylmethoxy)-pyridine

In a manner similar to preparation DX from tetra-hydrofurfuryl alcohol to give 2-bromo-6-(tetrahydro-furan-2-ylmethoxy)-pyridine as a white solid. MS m/z: 259.2 (M+H). Calc'd for $C_{10}H_{12}BrNO_2$ 258.11.

Preparation DZ: 2-Bromo-6-(tetrahdyro-furan-2-ylmethoxy)-pyridine

In a manner similar to preparation DX from tetrahydro-3-furan methanol to give 2-bromo-6-(tetrahydro-furan-2-ylmethoxy)-pyridine as a white solid. MS m/z: 259.2 (M+H). Calc'd for $C_{10}H_{12}BrNO_2$ 258.11.

Preparation EA: 6-(Tetrahydro-furan-3-yloxy)-pyridin-2-ylamine

In a manner similar to preparation BW and 2-bromo-6-(tetrahydrofuran-3-yloxy)-pyridine to give 6-(tetrahydrofuran-3-yloxy)-pyridin-2-ylamine as a dark-green oil. MS m/z: 181.0 (M+H). Calc'd for $C_9H_{12}N_2O_2$-180.20.

Preparation EB: 6-(Tetrahydro-furan-2-ylmethoxy)-pyridin-2-ylamine

In a manner similar to preparation BW from 2-bromo-6-(tetrahydro-furan-2-ylmethoxy)-pyridine to give 6-(tetrahydro-furan-3-yloxy)-pyridin-2-ylamine as a dark-green oil. MS m/z: 384.3 (M+H). Calc'd for $CloH_{14}N_2O_2$ 194.23.

Preparation EC: 6-(Tetrahydro-furan-3-ylmethoxy)-pyridin-2-ylamine

In a manner similar to preparation BW from 2-bromo-6-(tetrahydro-furan-2-ylmethoxy)-pyridine to give 6-(tetrahydro-furan-3-ylmethoxy)-pyridin-2-ylamine as a yellow oil. MS m/z: 195.0 (M+H). Calc'd for $C_{10}H_{14}N_2O_2$ 194.23.

Preparation ED: 6-Bromo-1'-methyl-2',3',5',6'-tetrahydro-1'H-[2,4']bipyridinyl-4'-ol To a solution of 1.07 M n-BuLi (36.4 mL) and dry THF (200 mL) chilled to −70° C. under a blanket of N$_2$ was added 2,6-dibromopyridine (10 g, 38.9 mmol)in 50 mL of dry THF slowly to maintain a temperature less than −69° C. Stirred at −70° C. for 20 min. Added 4-methylpiperidone (4.8 mL, 38.9 mmol) and stirred the mixture at −70° C. for 1 h.

Quenched with saturated $NaHCO_3$ and extracted with EtOAc. Washed the organic layer with brine, dried ($MgSO_4$) and concentrated in vacuo to give 6-bromo-1'-methyl-2',3',5',6'-tetrahydro-1'H-[2,4']bipyridinyl-4'-ol as a light-yellow solid. MS m/z: 272.3 (M+H). Calc'd for $C_{11}H_{15}BrN_2O$- 271.15.

Preparation EE: 6-Bromo-1'-methyl-1',2',3',6'-tetrahydro-[2,4%]bipyridinyl

To a 150 mL flask containing 6-bromo-1'-methyl-2',3',5',6'-tetrahydro-1'H-[2,4']bipyridinyl-4'-ol (5 g, 18.5 mmol) was added conc. $H_2SO_4$ (50 mL). Heated to 100° C. for 18 h. Cooled and poured onto ice carefully. Neutralized with 5 N NaOH and extracted with EtOAc. Washed with brine, dried ($MgSO_4$) and concentrated in vacuo. Diluted residue with EtOAc and filtered. Concentrated filtrate in vacuo to give 6-bromo-1'-methyl-1',2',3',6'-tetrahydro-[2,4']bipyridinyl as an orange oil. MS m/z: 254.2 (M+H). Calc'd for $C_{11}H_{13}BrN_2$ 253.14.

Preparation EF: 1'-Methyl-1',2,3',6'-tetrahdyro-[2,4']bipyridinyl-6-ylamine

In a manner similar to preparation xxx from 6-bromo-1'-methyl-1',2',3',6'-tetrahydro-[2,4']bipyridinyl to give 1'-methyl-1',2,3',6'-tetrahdyro-[2,4']bipyridinyl-6-ylamine as a yellow oil. MS m/z: 190.0 (M+H). Calc'd for $C_{11}H_{15}N_3$ 189.26.

Preparation EG: 1'-Methyl-1',2',3',4',5',6'-hexahydro-[2,4']bipyridinyl-6-ylamine A solution of 1'-methyl-1',2,3',6'-tetrahdyro-[2,4']bipyridinyl-6-ylamine (1.1 g, 5.8 mmol) and EtOH (30 mL) was hydrogenated over 20% $Pd(OH)_2/C$ (0.3 g)at 40 psi and RT. After 16 h, the mixture was filtered through Celite® and concentrated in vacuo to give the desired compound as a yellow solid. MS m/z: 192.1 (M+H). Calc'd for $C_{11}H_{17}N_3$- 191.27.

Preparation EH: 6-Bromo-4-hydroxy-3',4',5',6'-tetrahydro-2'H-[2,4']bipyridinyl-1'-carboxylic Acid Tert-Butyl Ester In a manner similar to Preparation ED from N-Boc-piperidone to give the desired compound as a yellow oil. MS m/z: 358.0 (M+H). Calc'd for $C_{15}H_{21}BrN_2O_3$ 357.24.

Preparation EI: 6-Bromo-1',2',3',6'-tetrahydro-[2,4']bipyridinyl

In a manner similar to Preparation EE from 6-bromo-4-hydroxy-3',4',5',6'-tetrahydro-2'H-[2,4']bipyridinyl-1'-carboxylic acid tert-butyl ester to give the desired compound as a yellow solid. MS m/z: 240.1 (M+H). Calc'd for $C_{10}H_{11}BrN_2$ 239.11.

Preparation EJ: 6-Bromo-3',6'-dihydro-2'H-[2,4']bipyridinyl-1'-carboxylic Acid Tert-Butyl Ester To a solution of 6-bromo-1',2',3',6'-tetrahydro-[2,4']bipyridinyl (4.3 g, 17.8 mmol)and $CH_2Cl_2$ (100 mL) was added saturated $NaHCO_3$ (100 mL) and $(Boc)_2O$ (3.8 g, 17.8 mol). Stirred at RT for 18 h. Washed organic layer with brine then dried ($MgSO_4$) and concentrated in vacuo to give the desired compound as a light-yellow oil. MS m/z: 338.9 (M–H). Calc'd for $C_{15}HlgBrN_2O_2$ 339.23.

Preparation EK: 6-Amino-3',4',5',6'-tetrahydro-2'H-[2,4']bipyridinyl-1'-carboxylic Acid Tert-Butyl Ester In a manner similar to Preparation EG from 6-amino-3',6'-dihydro-2'H-[2,4']bipyridinyl-1'-carboxylic acid tert-butyl ester to give the desired compound as a yellow oil. MS m/z: 278.3(M+H). Calc'd for $C_{15}H_{23}N_3O_2$ 277.36.

Preparation EL: 6-Amino-3',6'-dihydro-2'H-[2,4']bipyridinyl-1'-carboxylic Acid Tert-Butyl Ester In a manner similar to Preparation BW from 6-bromo-3',6'-dihydro-2'H-[2,4']bipyridinyl-1'-carboxylic acid tert-butyl ester to give the desired compound as a yellow oil. MS m/z: 275.6 (M+H). Calc'd for $C_{15}H_{21}N_3O_2$ 275.35.

Preparation EM: 3-(6-Bromo-pyridin-2-ylamino)-propan-1-ol

A solution of 2,6-dibromopyridine (10 g, 42 mmol) and 3-aminopropanol (3.5 mL, 46 mmol) in THF (60 mL) was stirred at reflux for 48 h. The reaction mixture was diluted with EtOAc and washed with $H_2O$ and brine, dried ($MgSO_4$) and concentrated in vacuo to give 3-(6-bromo-pyridin-2-ylamino)-propan-1-ol as a light-yellow oil which crystallized on standing at RT to a white solid. MS m/z: 232.0 (M+H). Calc'd for $C_8H_{11}BrN_2O$ 231.09.

Preparation EN: (6-Bromo-pyridin-2-yl)-[3-(tetrahydro-pyran-2-yloxy)-propyl]-amine A solution of 3-(6-bromo-pyridin-2-ylamino)-propan-1-ol (4.2 g, 18 mmol), 3,4-dihydro-2H-pyran (1.6 mL, 18 mmol), TsOH (0.34 g, 1.8 mmol) and $CH_2Cl_2$ (100 mL) were stirred at RT. After 15 h, the reaction was quenched with saturated $NaHCO_3$ and extracted with EtOAc. The organic layer was washed with brine, dried ($MgSO_4$) and concentrated in vacuo to give the desired compound as a pale-yellow oil. MS m/z: 316.0 (M+H). Calc'd for $C_{13}H_{1g}BrN_2O_2$ 315.21.

Preparation EO: N-[3-(Tetrahydro-pyran-2-yloxy)-propyl]-pyridine-2,6-diamine

In a manner similar to Preparation BW from (6-bromo-pyridin-2-yl)-[3-(tetrahydro-pyran-2-yloxy)-propyl]-amine to give the desired compound as green oil. MS m/z: 252.0 (M+H). Calc'd for $C_{13}H_{21}N_3O_2$ 251.32.

Preparation EP: 1-(2-Pyridin-4-yl-thiazol-4-yl)-3-[6-[3-(tetrahydro-pyran-2-yloxy)-propylamino]-pyridin-2-yl]-urea In a manner similar to Example 234, 2-(4-pyridinyl)-4-thiazolcarbonylazide and N-[3-(tetrahydro-pyran-2-yloxy)-propyl]-pyridine-2,6-diamine were heated together in toluene to give the desired compound as a yellow solid. MS m/z: 452.9 (M–H). Calc'd for $C_{22}H_{26}N_6O_3S$ 454.55.

Preparation EQ: 1-(2-Bromo-thiazol-4-yl)-3-(6-[3-(tetrahydro-pyran-2-yloxy)-propylamino]-pyridin-2-yl}-urea In a manner similar to Example 234, 2-bromo-thiazole-4-carbonyl azide and N-[3-(tetrahydro-pyran-2-yloxy)-propyl]-pyridine-2,6-diamine were heated together in toluene to give the desired compound as a yellow solid. MS m/z: 457.3 (M–H). Calc'd for $C_{17}H_{22}BrN_5O_3S$ 456.36.

Preparation ER: 1-Acetyl-1H-indazole-5-carbonitrile

In a manner similar to that described by J. Sun, et al, J.O.C., 1997, p. 5627 from 4-amino-3-methylbenzo-nitrile, acetic anhydride, KOAc and $CHCl_3$ to give 1-acetyl-1H-indazole-5-carbonitrile as a yellow solid. MS m/z: 186.0 (M+H). Calc'd for $C_{10}H_7N_3O$ 185.18.

Preparation ES: 1-Acetyl-1H-indazole-5-carbothioic Acid Amide

To a solution of 1-acetyl-1H-indazole-5-carbonitrile (1.1 g, 6 mmol), $Et_3N$ (2.5 mL, 17.8 mmol) and THF (20 mL) was bubbled in $H_2S$ gas over 10 min. Stirred at 0° C. for 24 h. Concentrated in vacuo to give a yellow solid which was triturated with $CH_2Cl_2$ and filtered insoluble solid to give 1-acetyl-1H-indazole-5-carbothioic acid amide as a yellow solid. MS m/z: 220.0 (M+H). Calc'd for $CloH_9N_3OS$ 219.26.

Preparation ET: 2-(1-Acetyl-1H-indazol-5-yl)-thiazole-4-carboxylic Acid Ethyl Ester In a manner similar to Preparation CV from 1-acetyl-1H-indazole-5-carbothioic acid amide to give 2-(1-acetyl-1H-indazol-5-yl)-thiazole-4-carboxylic acid ethyl ester as a white solid. MS m/z: 316.2 (M+H). Calc'd for $C_{15}H_{13}N_3O_3S$ 315.35.

Preparation EU: 2-(1-Acetyl-1H-indazol-5-yl)-thiazole-4-carboxylic Acid

In a manner similar to Preparation CW from 2-(1-acetyl-1H-indazol-5-yl)-thiazole-4-carboxylic acid ethyl ester to give 2-(1-acetyl-1H-indazol-5-yl)-thiazole-4-carboxylic acid as a yellow solid following re-protection with $Ac_2O$, $Et_3N$, and THF. MS m/z: 286.1 (M–H). Calc'd for $C_{13}H_9N_3O_3S$ 287.29.

Preparation EV: 2-(1-Acetyl-1H-indazol-5-yl)-thiazole-4-carbonyl azide

In a manner similar to Preparation CX from 2-(1-acetyl-1H-indazol-5-yl)-thiazole-4-carboxylic acid to give 2-(1-acetyl-1H-indazol-5-yl)-thiazole-4-carbonyl azide as a white solid. MS m/z: (M+H). Calc'd for $C_{13}H_8N_6O_2S$ 312.31.

Preparation EW: 6-(1-Piperidin-1-yl-ethyl)-pyridin-2-ylamine

In a manner similar to that described in Preparation BW, 2-bromo-6-(1-piperidin-1-yl-ethyl)-pyridine (370 mg, 1.37 mmol) was heated with $NH_4OH$ (18 mL), IpOH (10 mL) and Cu (30 mg) in sealed tube to give a brown oil. MS m/z: 206.1 (M+H). Calc'd. for $C_{12}H_{19}N_3$—205.16.

Preparation EX: (6-Amino-pyridin-2-ylmethyl)-isopropyl-carbamic Acid Tert-Butyl Ester Prepared in a manner similar to preparation BW to give a pale yellow solid. EI-MS m/z 266.3 (M+H). Calc'd for $C_{14}H_{23}N_3O_2$: 265.18.

EXAMPLE 1

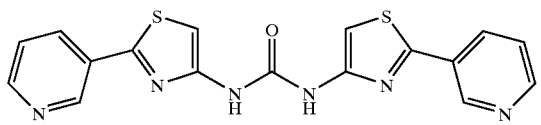

N,N'-bis [2-(3-Pyridinyl)-4-thiazolyl]urea

To a 50 mL round bottomed flask were added 0.106 g (0.458 mmol) of 2-(3-pyridinyl)-4-thiazolyl-carbonylazide, toluene (10 mL) and 5 drops of $H_2O$. The mixture was heated at 95° C. for 4 h then cooled to RT. The precipitate that formed was filtered, washed with a minimum amount of toluene and dried under high vacuum to give the product as a pale yellow solid. MS m/z: 381.5 (M+H). Calc'd. for $C_{17}H_{12}N_6OS_2$-380.453.

EXAMPLE 2

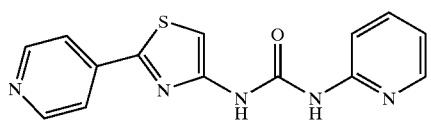

N-[2-(4-Pyridinyl)-4-thiazolyl]-N'-2-pyridinylurea

To a solution of 2-(4-pyridinyl)-4-thiazolyl-carbonylazide (60 mg, 0.260 mmol) in 10 mL toluene was added 2-aminopyridine (35 mg, 0.372 mmol). The mixture was heated at 95° C. for 18 h then cooled to RT and filtered. The precipitate was washed with toluene (3 mL) and dried under high vacuum to give the product as a pale yellow solid. MS m/z: 298.5 (M+H). Calc'd. for $C_{14}H_{11}N_5OS$-297.341.

EXAMPLE 3

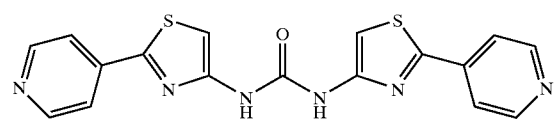

N,N'-bis [2-(4-Pyridinyl)-4-thiazolyl]urea

In a manner similar to that described in Example 2,2-(4-pyridinyl)-4-thiazolylcarbonylazide (130 mg, 0.562 mmol) was heated in toluene (10 mL) containing 4 drops of $H_2O$ to give the product as a pale yellow solid. MS m/z: 381.5 (M+H). Calc'd. for $C_{17}H_{12}N_6OS_2$-380.453.

EXAMPLE 4

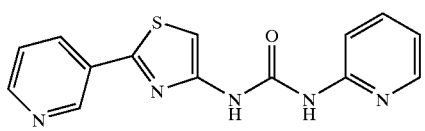

N-[2-(3-Pyridinyl)-4-thiazolyl]-N'-2-pyridinylurea

In a manner similar to that described in Example 2,2-(3-pyridinyl)-4-thiazolylcarbonylazide (48 mg, 0.208 mmol) and 2-aminopyridine (24 mg, 0.255 mmol) were heated in toluene (10 mL) to give the product as a pale yellow solid. MS m/z: 298.4 (M+H). Calc'd. for $C_{14}H_{11}N_5OS$-297.341.

EXAMPLE 5

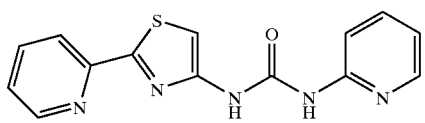

N-[2-(2-Pyridinyl)-4-thiazolyl]-N'-2-pyridinylurea 2-(2-Pyridinyl)-4-thiazolylcarbonylazide (200 mg, 0.87 mmol) and 2-aminopyridine (318 mg, 2.6 mmol) were heated in toluene (10 mL) at 100° C. for 14 h. After cooling to RT, the solids were collected by filtration and washed first with toluene (2×20 mL) followed by $Et_2O$ (2×10 mL) and cold EtOAc (3×5 mL). The solid was recrystallized from EtOAc to afford the product as an off-white solid: m.p. 233–235° C. MS m/z: 298 (M+H). Calc'd for $C_{14}H_{11}N_5OS$ 297.341.

EXAMPLE 6

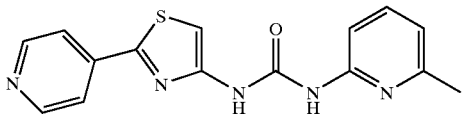

N-[2-(4-Pyridinyl)-4-thiazolyl]-N'-2-(6-methylpyridinyl)urea

In a manner similar to that described in Example 2,2-(4-pyridinyl)-4-thiazolylcarbonylazide (69 mg, 0.298 mmol) and 2-amino-6-methylpyridine (101 mg, 0.934 mmol) were heated in toluene (10 mL) to give the product as a pale yellow solid. MS m/z: 312.5 (M+H). Calc'd. for $C_{15}H_{13}N_5OS$-311.368.

EXAMPLE 7

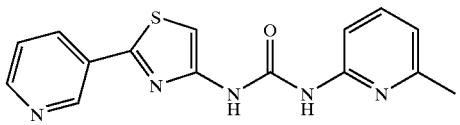

N-[2-(3-Pyridinyl)-4-thiazolyl]-N'-2-(6-methylpyridinyl)urea

In a manner similar to that described in Example 2,2-(3-pyridinyl)-4-thiazolylcarbonylazide (78 mg, 0.337 mmol) and 2-amino-6-methylpyridine (101 mg, 0.934 mmol) were heated in toluene (10 mL) to give the product as a pale yellow solid. MS m/z: 312.2 (M+H). Calc'd. for $C_{15}H_{13}N_5OS$-311.368.

EXAMPLE 8

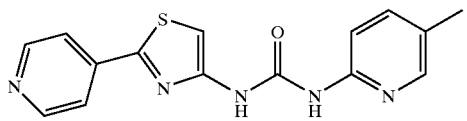

N-[2-(4-Pyridinyl)-4-thiazolyl]-N'-2-(5-methylpyridinyl)urea

In a manner similar to that described in Example 2,2-(4-pyridinyl)-4-thiazolylcarbonylazide (72 mg, 0.311 mmol) and 2-amino-5-methylpyridine (106 mg, 0.981 mmol) were heated in toluene (10 mL) to give the product as a pale yellow solid. MS m/z: 312.5 (M+H). Calc'd. for $C_{15}H_{13}N_5OS$-311.368.

EXAMPLE 9

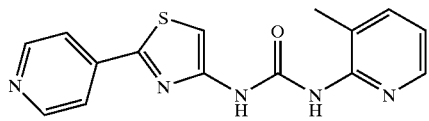

N-[2-(4-Pyridinyl)-4-thiazolyl]-N'-2-(3-methylpyridinyl)urea

In a manner similar to that described in Example 2,2-(4-pyridinyl)-4-thiazolylcarbonylazide (135 mg, 0.584 mmol) and 2-amino-3-methylpyridine (200 mg, 1.98 mmol) were heated in toluene (10 mL) to give the product as a pale yellow solid. MS m/z: 312.4 (M+H). Calc'd. for $C_{15}H_{13}N_5OS$-311.368.

EXAMPLE 10

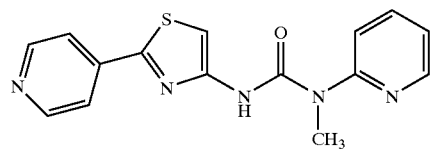

N-[2-(4-Pyridinyl)-4-thiazolyl]-N'-2-pyridinyl-N'-methylurea

In a manner similar to that described in Example 2,2-(4-pyridinyl)-4-thiazolylcarbonylazide (71 mg, 0.310 mmol) and 2-methylaminopyridine (210 mg, 1.94 mmol) were heated in toluene (7 mL) to give the product as pale yellow crystals. MS m/z: 312.5 (M+H). Calc'd. for $C_{15}H_{13}N_5OS$-311.368.

EXAMPLE 11

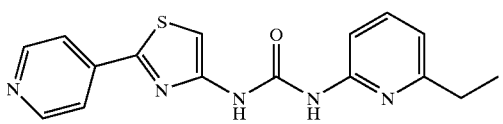

N-[2-(4-Pyridinyl)-4-thiazolyl]-N'-2-(6-ethylpyridinyl)urea

In a manner similar to that described in Example 2,2-(4-pyridinyl)-4-thiazolylcarbonylazide (75 mg, 0.324 mmol) and 2-amino-6-ethylpyridine (200 mg, 1.63 mmol) were heated in toluene (8 mL) to give the product as a pale yellow solid. MS m/z: 326.5 (M+H). Calc'd. for $C_{16}H_{15}N_5OS$-325.395.

EXAMPLE 12

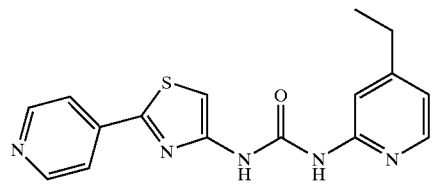

N-[2-(4-Pyridinyl)-4-thiazolyl]-N'-2-(4-ethylpyridinyl)urea

In a manner similar to that described in Example 2,2-(4-pyridinyl)-4-thiazolylcarbonylazide (82 mg, 0.355 mmol) and 2-amino-4-ethylpyridine (106 mg, 0.867 mmol) were heated in toluene (10 mL) to give the product as a pale yellow solid. MS m/z: 326.5 (M+H). Calc'd. for $C_{16}H_{15}N_5OS$-325.395.

EXAMPLE 13

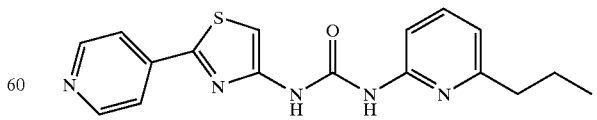

N-[2-(4-Pyridinyl)-4-thiazolyl]-N'-2-(6-propylpyridinyl)urea

In a manner similar to that described in Example 3,2-(4-pyridinyl)-4-thiazolylcarbonylazide (89 mg, 0.385 mmol)

and 2-amino-6-(n-propyl)pyridine (171 mg, 1.25 mmol) were heated in toluene (10 mL) to give the product as a pale yellow solid. MS m/z: 339.4 (M+H). Calc'd. for $C_{17}H_{17}N_5OS$-339.422.

EXAMPLE 14

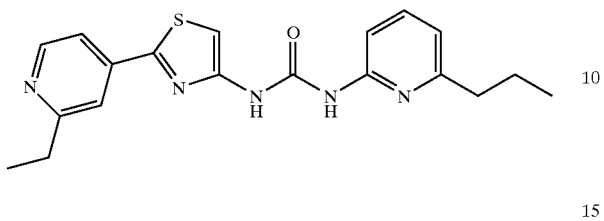

N-[2-(2-Ethyl-4-pyridinyl)-4-thiazolyl]-N'-2-(6-propylpyridinyl)urea

In a manner similar to that described in Example 6,2-(4-(2-ethyl)-pyridinyl)-4-thiazolylcarbonylazide (460 mg, 1.77 mmol) and 2-amino-6-(n-propyl)pyridine (483 mg, 3.55 mmol) were heated in toluene (20 mL) at 100° C. for 14 h. After cooling to RT, the solids were collected by filtration and washed first with toluene (2×20 mL) followed by EtOAc:Et$_2$O (4:1) (4×20 mL) to give the product as an off-white solid: m.p. 204–206° C. MS m/z: 368 (M+H). Calc'd. for $C_{19}H_{21}N_5OS$-367.476.

EXAMPLE 15

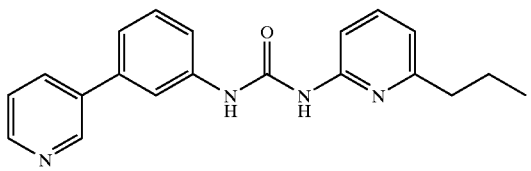

N-[3-(3-Pyridinyl)phenyl]-N'-2-(6-propylpyridinyl)urea

To a suspended anhydrous solution of 3-pyridylaniline (90 mg, 0.53 mmol) in dry toluene (4 mL) was added phosgene (0.36 mL, 0.69 mmol, 20% in toluene) followed by DIEA (0.20 mL, 1.05 mmol) under an atmosphere of argon. After stirring for 0.5 h at RT, 2-amino-6-n-propylpyridine (72 mg, 0.53 mmol) in dry toluene (4 mL) was added dropwise into the mixture. The resulting mixture was stirred at RT for 18 h. The organic solvent was removed under vacuum. The residue was purified by chromatography on flash silica gel using 2% MeOH/CH$_2$Cl$_2$ as eluant to obtain the final urea as an off-white solid. MS m/z:333.4 (M+H). Calc'd. for $C_{20}H_{20}N_4O$-332.405.

EXAMPLE 16

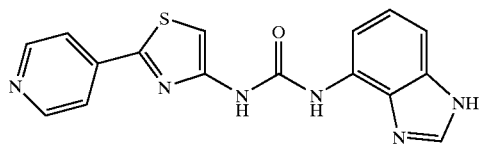

N-[2-(4-Pyridinyl)-4-thiazolyl]-N'-4-benzimidazolylurea

In a manner similar to that described in Example 2,2-(4-pyridinyl)-4-thiazolylcarbonylazide (32 mg, 0.138 mmol) and 4-aminobenzimidazole (32 mg, 0.240 mmol) were heated in toluene (8 mL). The crude product was recrystallized with CH$_3$CN:MeOH (~10:1) to give the product as a pale brown solid. MS m/z: 337.5 (M+H). Calc'd. for $C_{16}H_{12}N_6OS$-336.378.

EXAMPLE 17

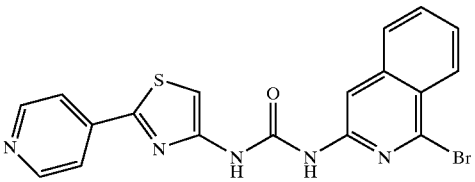

N-[2-(4-Pyridinyl)-4-thiazolyl]-N'-3-(1-bromoisoquinolinyl)urea

In a manner similar to that described in Example 2,2-(4-pyridinyl)-4-thiazolylcarbonylazide (61 mg, 0.264 mmol) and 3-amino-1-bromo-isoquinoline (120 mg, 0.538 mmol) were heated in toluene (10 mL) to give the product as a pale yellow solid. MS m/z: 427.2 (M+H). Calc'd. for $C_{18}H_{12}BrN_5OS$-426.297.

EXAMPLE 18

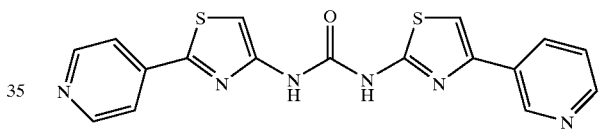

N-[2-(4-Pyridinyl)-4-thiazolyl]-N'-[4-(3-pyridinyl)-2-thiazolyl] urea

In a manner similar to that described in Example 2,2-(4-pyridinyl)-4-thiazolylcarbonylazide (36 mg, 0.298 mmol) and 2-amino-4-(3-pyridyl)-thiazole (29 mg, 163 mmol) were heated in toluene (10 mL) to give the product as a pale yellow solid. MS m/z: 381.5 (M+H). Calc. for $C_{17}H_{12}N_6OS_2$-380.453.

EXAMPLE 19

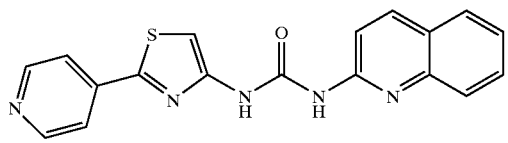

N-[2-(4-Pyridinyl)-4-thiazolyl]-N'-2-quinolinylurea

In a manner similar to that described in Example 2,2-(4-pyridinyl)-4-thiazolylcarbonylazide (38 mg, 0.164 mmol) and 2-aminoquinoline (53 mg, 0.370 mmol) were heated in toluene (10 mL) to give the product as a pale yellow solid. MS m/z: 348.4 (M+H). Calc. for $C_{18}H_{13}N_5OS$-347.401.

EXAMPLE 20

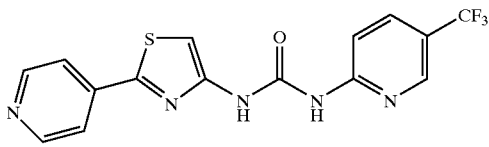

N-[2-(4-Pyridinyl)-4-thiazolyl]-N'-2-(5-trifluoromethylpyridinyl)urea

In a manner similar to that described in Example 2,2-(4-pyridinyl)-4-thiazolylcarbonylazide (40 mg, 0.173 mmol) and 2-amino-5-trifluoromethylpyridine (165 mg, 1.02 mmol) were heated in 10 mL toluene to give the product as a pale yellow solid. MS m/z: 366.3 (M+H). Calc'd. for $C_{15}H_{10}F_3N_5OS$-365.339.

EXAMPLE 21

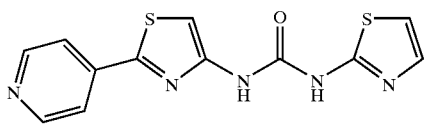

N-[2-(4-Pyridinyl)-4-thiazolyl]-N'-2-thiazolylurea

In a manner similar to that described in Example 2,2-(4-pyridinyl)-4-thiazolylcarbonylazide (70 mg, 0.303 mmol) and 2-aminothiazole (38 mg, 0.38 mmol) were heated in toluene (12 mL) to give the product as a pale yellow solid. MS m/z: 304.4 (M+H). Calc'd. for $C_{12}H_9N_5OS_2$-303.366.

EXAMPLE 22

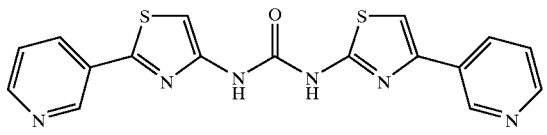

N-[2-(3-Pyridinyl)-4-thiazolyl]-N'-[4-(3-pyridinyl)-2-thiazolyl] urea

In a manner similar to that described in Example 2,2-(3-pyridinyl)-4-thiazolylcarbonylazide (36 mg, 0.156 mmol) and 2-amino-4-(3-pyridinyl)thiazole(30 mg, 0.169 mmol) were heated in toluene (8 mL) to give the product as a pale yellow solid. MS m/z: 381.5 (M+H). Calc'd. for $C_{17}H_{12}N_6OS_2$-380.453.

EXAMPLE 23

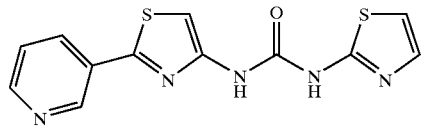

N-[2-(3-Pyridinyl)-4-thiazolyl]-N'-2-thiazolylurea

In a manner similar to that described in Example 2,2-(3-pyridinyl)-4-thiazolylcarbonylazide (59 mg, 0.255 mmol) and 2-aminothiazole (27 mg, 268 mmol) were heated in toluene (10 mL) to give the product as a pale yellow solid. MS m/z: 304.3 (M+H). Calc'd. for $C_{12}H_9N_5OS_2$-303.366.

EXAMPLE 24

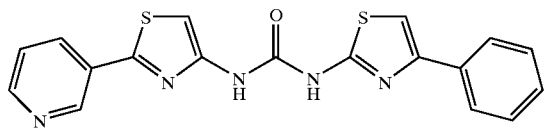

N-[2-(3-Pyridinyl)-4-thiazolyl]-N'-[4-phenyl-2-thiazolyl]urea

In a manner similar to that described in Example 2,2-(3-pyridinyl)-4-thiazolylcarbonylazide (49 mg, 0.211 mmol) and 2-amino-4-phenylthiazole (39 mg, 0.218 mmol) were heated in toluene (10 mL) to give the product as a pale yellow solid. MS m/z: 380.5 (M+H). Calc'd. for $C_{18}H_{13}N_5OS_2$-379.465.

EXAMPLE 25

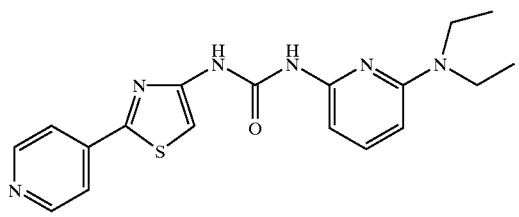

N-[2-(4-Pyridinyl)-4-thiazolyl]-N'-2-[6-(N'',N''-diethylamino)pyridinyl]urea

A mixture of 2-(4-pyridinyl)-4-thiazolyl-carbonylazide (100 mg, 0.43 mmol) and 2-amino-6-(N,N-diethylamino) pyridine (150 mg, 0.91 mmol) in toluene (3 mL) was heated at 70° C. for 1 h, and then at 80° C. for 5 h. After the mixture was cooled to RT the solvent was removed in vacuo and the crude product was purified by chromatography on silica gel (1:10 MeOH(NH$_3$)/CH$_2$Cl$_2$) to give N-[2-(4-pyridinyl)-4-thiazolyl]-N'-2-[6-(N'',N''-diethylamino)pyridinyl]urea. MS m/z: 369 (M+1). Calc'd. for $C_{18}H_{20}N_6OS$-368.463.

EXAMPLE 26

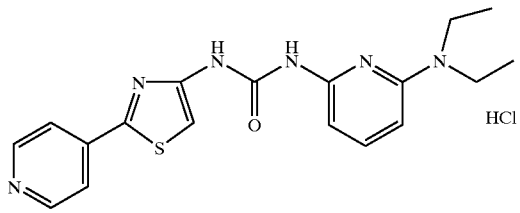

N-[2-(4-Pyridinyl)-4-thiazolyl]-N'-2-[6-(N'',N''-diethylamino)pyridinyl]urea Hydrochloride N-[2-(4-Pyridinyl)-4-thiazolyl]-N'-2-[6-(N'',N''-diethylamino)pyridinyl]urea (Example 25) was dissolved in 5 ml of MeOH/CH$_2$Cl$_2$ (1:1) and (1M) HCl (8 mL) in Et$_2$O solution was added. The solvents were removed in vacuo to afford the title salt as a yellow solid.

EXAMPLE 27

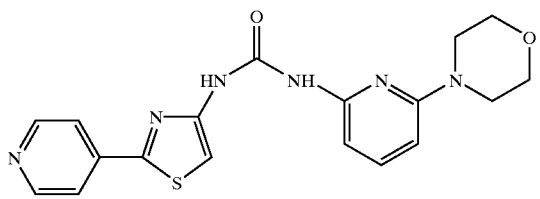

N-[2-(4-Pyridinyl)-4-thiazolyl]-N'-2-[6-(4-morpholinyl)pyridinyl]urea

A mixture of 2-(4-pyridinyl)-4-thiazolyl-carbonylazide (100 mg, 0.43 mmol) and 2-amino-6-(4-morpholinyl)pyridine (150 mg, 0.84 mmol) in toluene (5 mL) was heated at 80° C. for 5 h. After the mixture was cooled to RT the solvent was removed in vacuo and the crude product was purified by chromatography on silica gel (1:10 MeOH (NH$_3$)/CH$_2$Cl$_2$) to afford the title compound as a light yellow solid. MS m/z: 383 (M+1). Calc'd. for C$_{18}$H$_{18}$N$_6$O$_2$S-382.446.

EXAMPLE 28

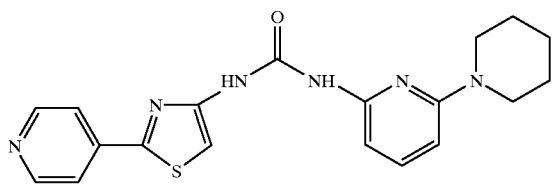

N-[2-(4-Pyridinyl)-4-thiazolyl]-N'-2-[6-(1-piperdinyl)pyridinyl]urea

A mixture of 2-(4-pyridinyl)-4-thiazolyl-carbonylazide (100 mg, 0.43 mmol) and 2-amino-6-(1-piperidinyl)pyridine (100 mg, 0.56 mmol) in toluene (3 mL) was heated at 80° C. for 4 h. After cooling to RT, H$_2$O was added and the mixture was extracted with EtOAc (3×80 mL). The combined organic layers were washed with brine, dried over Na$_2$SO$_4$, filtered and concentrated in vacuo. The crude product was purified by chromatography on silica gel (1:20 MeOH/CH$_2$Cl$_2$) to afford the title compound as a light yellow solid. MS m/z: 381 (M+1). Calc'd for C$_{19}$H$_{20}$N$_6$OS-380.475.

EXAMPLE 29

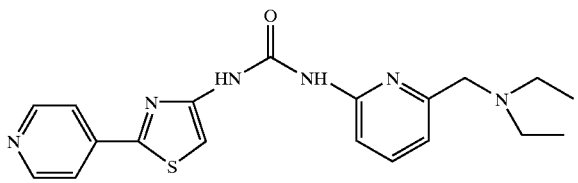

N-[2-(4-Pyridinyl)-4-thiazolyl]-N'-2-[6-(N'',N''-diethylaminomethylamino)pyridinyl]urea A mixture of 2-(4-pyridinyl)-4-thiazolyl-carbonylazide (100 mg, 0.43 mmol) and 2-amino-6-(N,N-diethylaminomethyl)pyridine (150 mg, 0.84 mmol) in toluene (5 mL) was heated at 80° C. for 5 h. After the mixture was cooled to RT the solvent was removed in vacuo and the crude product was purified by chromatography on silica gel (1:10 MeOH(NH$_3$)/CH$_2$Cl$_2$) to give the base. MS m/z: 383 (M+1). Calc'd. for C$_{19}$H$_{22}$N$_6$OS-382.49.

EXAMPLE 30

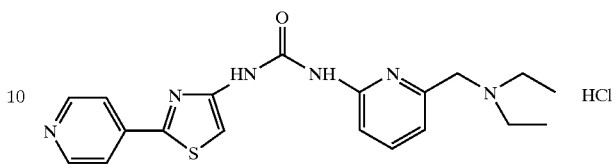

N-[2-(4-Pyridinyl)-4-thiazolyl]-N'-2-[6-(N'',N''-diethylaminomethylamino)pyridinyl]urea Hydrochloride N-[2-(4-Pyridinyl)-4-thiazolyl]-N'-2-[6-(N'',N''-diethylaminomethylamino)pyridinyl]urea (Example 29) was dissolved in 5 ml of MeOH/CH$_2$Cl$_2$ (1:1) and 1N HCl (8 mL) in Et$_2$O solution was added. The solvents were removed in vacuo to afford the title salt as a yellow solid.

EXAMPLE 31

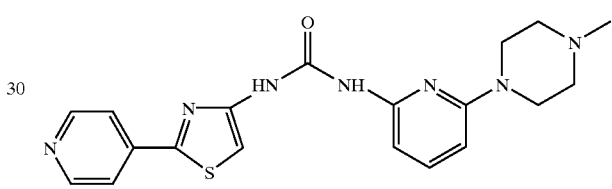

N-[2-(4-Pyridinyl)-4-thiazolyl]-N'-2-[6-(1-methyl-4-piperazinyl)pyridinyl]urea

A mixture of 2-(4-pyridinyl)-4-thiazolyl-carbonylazide (100 mg, 0.43 mmol) and 2-amino-6-(1-(4-methyl)piperazinyl)pyridine (100 mg, 5.21 mmol) in toluene (5 mL) was heated at 80° C. for 5 h. After the mixture was cooled to RT the solvent was removed in vacuo. The crude product was purified by chromatography on silica gel (1:10 MeOH (NH$_3$)/CH$_2$Cl$_2$) to give N-[2-(4-pyridinyl)-4-thiazolyl]-N'-2-[6-(1-methyl-4-piperazinyl)pyridinyl]urea. m.p. 251–253° C. MS m/z: 396 (M+1). Calc'd. for C$_{19}$H$_{22}$N$_6$OS-395.489.

EXAMPLE 32

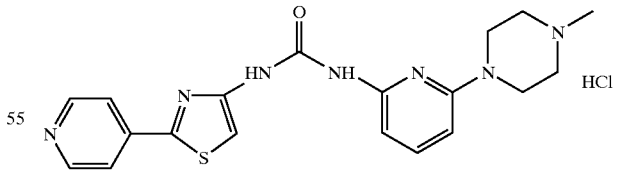

N-[2-(4-Pyridinyl)-4-thiazolyl]-N'-2-[6-(1-methyl-4-piperazinyl)pyridinyl]urea Hydrochloride N-[2-(4-Pyridinyl)-4-thiazolyl]-N'-2-[6-(1-methyl-4-piperazinyl)pyridinyl]urea (Example 31) was dissolved in 5 ml of MeOH/CH$_2$Cl$_2$ (1:1) and 1M HCl (8 mL) in Et$_2$O solution was added. The solvents were removed in vacuo to afford the title salt as a yellow solid.

EXAMPLE 33

N-[2-(4-Pyridinyl)-4-thiazolyl]-N'-2-[6-[3-(1-morpholinyl)propyl]amino]pyridinyl]urea A mixture of 2-(4-pyridinyl)-4-thiazolyl-carbonylazide (200 mg, 0.86 mmol) and 2-amino-6-(3-(N-morpholinyl)propylamino)pyridine (300 mg, 1.27 mmol) in toluene (8 mL) was heated at 70° C. for 1 h, and then at 80° C. for 5 h. After the mixture was cooled to RT the solvent was removed in vacuo and the product was purified by chromatography on silica gel (1:10 MeOH(NH$_3$)/CH$_2$Cl$_2$) to afford the title compound as a light yellow solid: m.p. 215–217° C. MS m/z: 440 (M+1). Calc'd. for $C_{21}H_{25}N_7O_2S$-439.541.

EXAMPLE 34

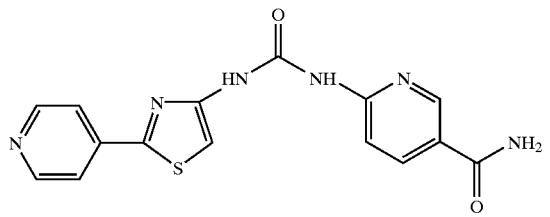

[[(2-(4-Pyridinyl)-4-thiazolylamino)carbonyl]amino]-2-pyridinyl-5-carboxamide

A mixture of 2-(4-pyridinyl)-4-thiazolyl-carbonylazide (100 mg, 0.43 mmol) and 6-aminonicotinamide (200 mg, 1.45 mmol) in toluene (5 mL) was heated at 80° C. for 6 h. After the mixture was cooled to RT the solvent was removed in vacuo and the crude product was purified by chromatography on silica gel (1:10 MeOH(NH$_3$)/CH$_2$Cl$_2$) to afford the title compound as a light yellow solid: m.p. 255–257° C. MS m/z: 341 (M+1). Calc'd for $C_{15}H_{12}N_6O_2S$-340.37.

EXAMPLE 35

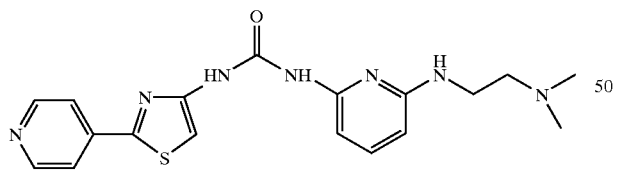

N-[2-(4-Pyridinyl)-4-thiazolyl]-N'-2-[6-(N'',N''-aminoethylamino)pyridinyl]urea

A mixture of 2-(4-pyridinyl)-4-thiazolyl-carbonylazide (200 mg, 0.86 mmol) and 2-amino-6-(N,N-dimethylethylenediamino)pyridine (234 mg, 1.30 mmol) in toluene (10 mL) was heated at 70° C. for 1 h, and then at 80° C. for 5 h. After the mixture was cooled to RT the solvent was removed in vacuo and the crude product was purified by chromatography on silica gel (1:10 MeOH(NH$_3$)/CH$_2$Cl$_2$) to afford the title compound as a light yellow solid: m.p. 210–212° C. MS m/z: 384 (M+1). Calc'd. for $C_{18}H_{21}N_7OS$-383.48.

EXAMPLE 36

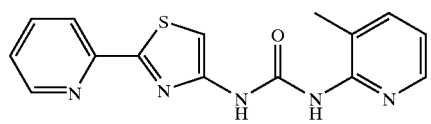

N-[2-(2-Pyridinyl)-4-thiazolyl]-N'-2-(3-methylpyridinyl)urea 2-(2-Pyridinyl)-4-thiazolylcarbonylazide (500 mg, 2.2 mmol) and 2-amino-3-methylpyridine (183 mg, 6.6 mmol) were heated in toluene (20 mL) at 100° C. for 12 h. After cooling to RT, the solids were collected by filtration and washed first with toluene (2×20 mL) followed by Et$_2$O (3×10 mL) Recrystallization of the product from MeOH afforded the desired material: m.p. 235–237° C. MS m/z: 312 (M+H) Calc'd. for $C_{15}H_{13}N_5OS$-311.368.

EXAMPLE 37

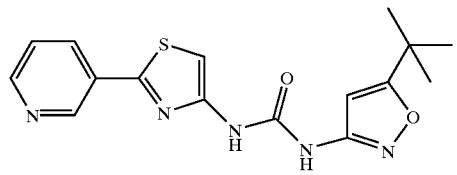

N-[2-(3-Pyridinyl)-4-thiazolyl]-N'-[5-(1,1-dimethylethyl)-3-isoxazolyl]urea 2-(3-Pyridinyl)-4-thiazolylcarbonylazide (300 mg, 1.30 mmol) and 3-amino-5-(tert-butyl)isoxazole (491 mg, 3.50 =mol) were heated in toluene (10 mL) at 95° C. for 24 h. After cooling to RT, the solids were collected by filtration and washed first with toluene (2×20 mL) followed by cold EtOAc (3×10 mL) to give the product as an off-white solid: m.p. 230–232° C. MS m/z: 344 (M+H). Calc'd. for $C_{16}H_{17}N_5O_2S$-343.410.

EXAMPLE 38

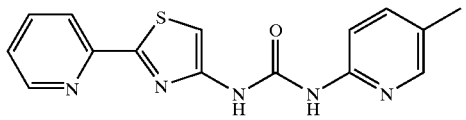

N-[2-(2-Pyridinyl)-4-thiazolyl]-N'-2-(5-methylpyridinyl)urea 2-(2-Pyridinyl)-4-thiazolylcarbonylazide (200 mg, 0.87 mmol) and 2-amino-5-methylpyridine (183 mg, 1.7 mmol) were heated in toluene (15 mL) at 100° C. for 12 h. After cooling to RT, the solids were collected by filtration and washed first with toluene (2×20mL) followed by Et$_2$O:EtOAc (3:1) (3×10 mL) to afford the product as a tan solid: m.p. 228–2300C. MS m/z: 312 (M+H). Calc'd. for $C_{15}H_{13}N_5OS$-311.368.

EXAMPLE 39

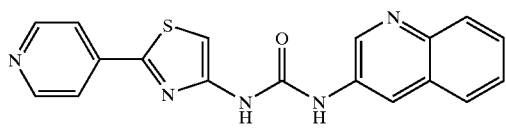

N-[2-(4-Pyridinyl)-4-thiazolyl]-N'-3-quinolinylurea

In a manner similar to that described in Example 2,2-(4-pyridinyl)-4-thiazolylcarbonylazide (53 mg, 0.229 mmol) and 3-aminoquinoline (36 mg, 260 mmol) were heated in toluene (10 mL) to give the product as a pale yellow solid. MS m/z: 348.5 (M+H). Calc. for $C_{18}H_{13}N_5OS$-347.401.

EXAMPLE 40

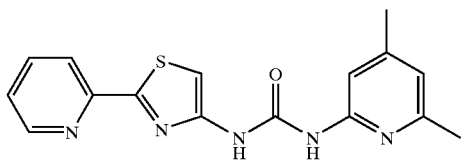

N-[2-(2-Pyridinyl)-4-thiazolyl]-N'-2-(4,6-dimethylpyridinyl)urea 2-(2-Pyridinyl)-4-thiazolylcarbonylazide (200 mg, 0.87 mmol) and 2-amino-4,6-dimethylpyridine (210 mg, 1.7 mmol) were heated in toluene (15 mL) at 100° C. for 12 h. After cooling to RT, the solids were collected by filtration and washed first with toluene (2×20 mL) followed by Et$_2$O:EtOAc (3:1) (3×10 mL) to afford the product as a tan solid: m.p. 232–234° C. MS m/z: 326 (M+H). Calc'd. for $C_{16}H_{15}N_5OS$-325.394.

EXAMPLE 41

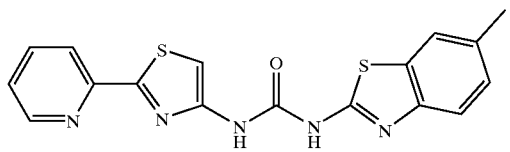

N-[2-(2-Pyridinyl)-4-thiazolyl]-N'-2-(6-methylbenzthiazolyl)urea 2-(2-Pyridinyl)-4-thiazolylcarbonylazide (200 mg, 0.87 mmol) and 2-amino-6-methylbenzothiazole (279 mg, 1.7 mmol) were heated in toluene (15 mL) at 100° C. for 12 h. After cooling to RT, the solids were collected by filtration and washed first with toluene (2×20 mL) followed by Et$_2$O:EtOAc (3:1) (3×10 mL) to afford the product as a tan solid: m.p. 263–265° C. MS m/z: 312 (M+H). Calc'd. for $C_{17}H_{13}N_5OS_2$-367.456.

EXAMPLE 42

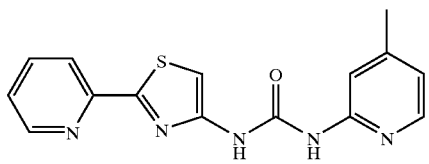

N-[2-(2-Pyridinyl)-4-thiazolyl]-N'-2-(4-methylpyridinyl)urea 2-(2-Pyridinyl)-4-thiazolylcarbonylazide (200 mg, 0.87 mmol) and 2-amino-4-methylpyridine (183 mg, 1.7 mmol) were heated in toluene (15 mL) at 100° C. for 12 h. After cooling to RT, the solids were collected by filtration and washed first with toluene (2×20 mL) followed by Et$_2$O:EtOAc (3:1) (3×10 mL) to afford the product as an off-white solid: m.p. 217–219° C. MS m/z: 312 (M+H). Calc'd. for $C_{15}H_{13}N_5OS$-311.368.

EXAMPLE 43

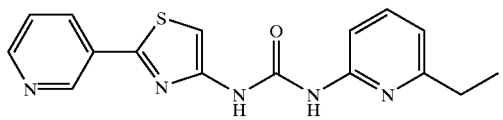

N-[2-(3-Pyridinyl)-4-thiazolyl]-N'-2-(6-ethylpyridinyl)urea

In a manner similar to that described in Example 2,2-(3-pyridinyl)-4-thiazolylcarbonylazide (186 mg, 0.804 mmol) and 2-amino-6-ethylpyridine (364 mg, 2.78 mmol) were heated in toluene (12 mL) to give the product as a pale yellow solid. MS m/z: 326.5 (M+H). Calc'd. for $C_{16}H_{15}N_5OS$-325.395.

EXAMPLE 44

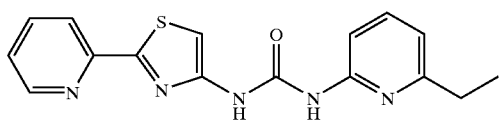

N-[2-(2-Pyridinyl)-4-thiazolyl]-N'-2-(6-ethylpyridinyl)urea 2-(2-Pyridinyl)-4-thiazolylcarbonylazide (200 mg, 0.87 mmol) and 2-amino-6-ethylpyridine (318 mg, 2.6 mmol) were heated in toluene (10 mL) at 100° C. for 14 h. After cooling to RT, the solids were collected by filtration and washed first with toluene (2×20 mL) followed by Et$_2$O (2×10 mL) and cold EtOAc (3×5 mL) to give the product as a beige solid: m.p. 213–215° C. MS m/z: 326 (M+H). Calc'd. for $C_{16}H_{15}N_5OS$-325.395.

EXAMPLE 45

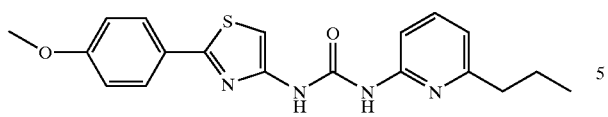

N-[2-(4-Methoxyphenyl)-4-thiazolyl]-N'-2-(6-propylpyridinyl)urea 2-(4-Methoxyphenyl)-4-thiazolylcarbonylazide (280 mg, 1.1 mmol) and 2-amino-6-n-propylpyridine (439 mg, 3.2 mmol) were heated in toluene (20 mL) at 100° C. for 14 h. After cooling to RT, the solids were collected by filtration and washed first with toluene (2×20 mL) followed by Et$_2$O (2×10 L) and cold EtOAc (3×5 mL) to afford the product as an off-white solid. m.p. 223–225° C. MS m/z: 369 (M+H). Calc'd for $C_{19}H_{20}N_4O_2S$-368.461.

EXAMPLE 46

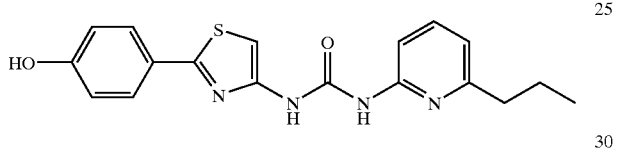

N-[2-(4-Hydroxyphenyl)-4-thiazolyl]-N'-2-(6-propylpyridinyl)urea

To a stirred solution of Example 45 (100 mg, 0.271 mmol) in CH$_2$Cl$_2$ (5 mL), boron tribromide was added dropwise at RT. The mixture was stirred for 8 h before adding H$_2$O (10 ml) and the resulting solids were collected by filtration. This material was washed several times with H$_2$O and then EtOAc followed by drying in vacuo to afford the desired product as a light yellow solid: m.p. 227–229° C. MS m/z: 355 (M+H). Calc'd for $C_{18}H_{18}N_4O_2S$-354.434.

EXAMPLE 47

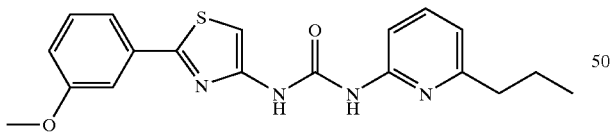

N-[2-(3-Methoxyphenyl)-4-thiazolyl]-N'-2-(6-propylpyridinyl)urea 2-(3-Methoxyphenyl)-4-thiazolylcarbonylazide (1.0 g, 3.8 mmol) and 2-amino-6-n-propylpyridine (1.05 g, 7.7 m=ol) were heated in toluene (40 mL) at 100° C. for 12 h. After cooling to RT, the solids were collected by filtration and washed first with toluene (2×40 mL) followed by cold EtOAc (3×20 mL) to afford the product as a white solid: m.p. 192–194° C. MS m/z: 369 (M+H). Calc'd for $C_{19}H_{20}N_4O_2S$-368.461.

EXAMPLE 48

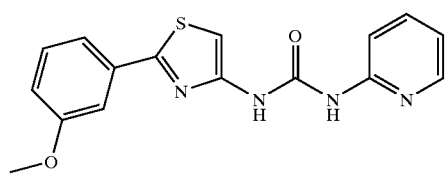

N-[2-(3-Methoxyphenyl)-4-thiazolyl]-N'-2-pyridinylurea 2-(3-Methoxyphenyl)-4-thiazolylcarbonylazide (1.0 g, 3.8 mmol) and 2-aminopyridine (0.72 g, 7.7 mmol) were heated in toluene (40 mL) at 100° C. for 12 h. After cooling to RT, the solids were collected by filtration and washed first with toluene (2×40 mL) followed by cold EtOAc (3×20 mL) to afford the product as a white solid: m.p. 201–203° C. MS m/z: 327 (M+H). Calc'd for $C_{16}H_{14}N_4O_2S$-326.380.

EXAMPLE 49

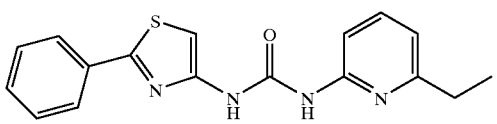

N-[2-phenyl-4-thiazolyl]-N'-2-(6-ethylpyridinyl)urea

In a manner similar to that described in Example 2,2-phenyl-4-thiazolylcarbonylazide (150 mg, 0.652 mmol) and 2-amino-6-ethylpyridine (250 mg, 2.05 mmol) were heated in toluene (10 mL) to give the product as a pale yellow solid. MS m/z: 325.4 (M+H). Calc'd for $C_{17}H_{16}N_4OS$-324.407.

EXAMPLE 50

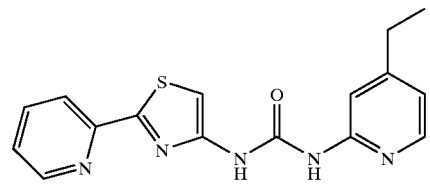

N-[2-(2-Pyridinyl)-4-thiazolyl]-N'-2-(4-ethylpyridinyl)urea 2-(2-Pyridinyl)-4-thiazolylcarbonylazide (200 mg, 0.87 mmol) and 2-amino-4-ethylpyridine (208 mg, 1.7 mmol) were heated in toluene (15 mL) at 100° C. for 12 h. After cooling to RT, the solids were collected by filtration and washed first with toluene (2×20 mL) followed by Et$_2$O:EtOAc (3:1) (3×10 mL) to afford the product as a tan solid: m.p. 196–198° C. MS m/z: 326 (M+H). Calc'd. for $C_{16}H_{15}N_5OS$-325.395.

EXAMPLE 51

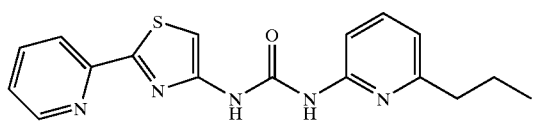

N-[2-(2-Pyridinyl)-4-thiazolyl]-N'-2-(6-propylpyridinyl)urea 2-(2-Pyridinyl)-4-thiazolylcarbonylazide (200 mg, 0.87 mmol) and 2-amino-6-(n-propyl)pyridine (350 mg, 2.6 mmol) were heated in toluene (10 mL) at 100° C. for 14 h. After cooling to RT, the solids were collected by filtration and washed first with toluene (2×20 mL) followed by $Et_2O$ (2×10 mL) and cold EtOAc (3×5 mL) to give the product as a grayish solid: m.p. 210–212° C. MS m/z: 340 (M+H). Calc'd. for $C_{17}H_{17}N_5OS$-339.422.

EXAMPLE 52

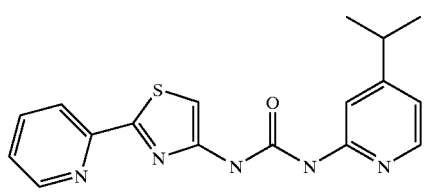

N-[2-(2-Pyridinyl)-4-thiazolyl]-N'-2-[4-(1-methylethyl)pyridinyl]urea 2-(2-Pyridinyl)-4-thiazolylcarbonylazide (300 mg, 1.3 mmol) and 2-amino-4-isopropylpyridine (500 mg, 3.6 mmol) were heated in 10 mL toluene at 100° C. for 12 h. After cooling to RT, the solvent was removed by rotary evaporation and the crude oil was purified by column chromatography with hexane:EtOAc (7:3) as eluant to give the urea as a light yellow solid. MS m/z: 340 (M+H). Calc'd for $C_{17}H_{17}N_5OS$-339.42.

EXAMPLE 53

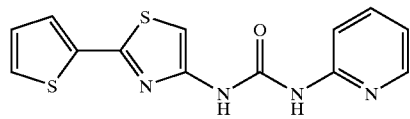

N-[2-(2-Thienyl)-4-thiazolyl]-N'-2-(pyridinyl)urea 2-(2-Thienyl)-4-thiazolylcarbonylazide (200 mg, 0.85 mmol) and 2-aminopyridine (154 mg, 1.62 mmol) were heated in 20 mL toluene at 100° C. for 16 h. After cooling to RT, the solids were collected by filtration and washed first with toluene (2×20 mL) followed by $Et_2O$:EtOAc (3:1) (3×10 mL) to afford the urea as an off-white solid. MS m/z: 303 (M+H). Calc'd for $C_{13}H_{10}N_4OS_2$-302.38.

EXAMPLE 54

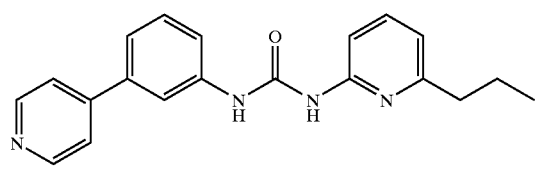

N-[3-(4-Pyridinyl)phenyl]-N'-2-(6-propylpyridinyl)urea

To a suspended anhydrous solution of 4-pyridylaniline (180 mg, 1.06 mmol) in dry toluene (8 mL) was added phosgene (0.73 mL, 1.38 mmol, 20% in toluene) followed by DIEA (0.37 mL, 2.11 mmol) under an atmosphere of argon. After stirring for 0.5 h at RT, 2-amino-6-(n-propyl)pyridine (144 mg, 1.06 mmol) in dry toluene (3 mL) was added dropwise into the reaction mixture. The resulting mixture was stirred at RT for 18 h. The organic solvent was removed under vacuum. The residue was purified by flash chromatography on silica gel using 5% $MeOH/CH_2Cl_2$ as eluant to obtain the final urea as white solid: m.p. 195–198° C. MS m/z: 333.4 (M+H). Calc'd. for $C_{20}H_{20}N_4O$-332.405.

EXAMPLE 55

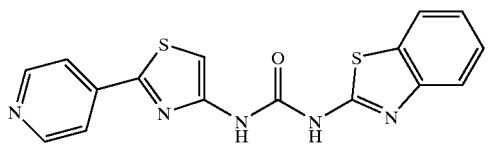

N-[2-(4-Pyridinyl)-4-thiazolyl]-N'-2-benzthiazolylurea

In a manner similar to that described in Example 2,2-(4-pyridinyl)-4-thiazolylcarbonylazide (52 mg, 0.225 mmol) and 2-aminobenzothiazole (41 mg, 0.273 mmol) were heated in toluene (10 mL) to give the product as a pale yellow solid. MS m/z: 354.4 (M+H). Calc'd. for $C_{16}H_{11}N_5OS_2$-353.427.

EXAMPLE 56

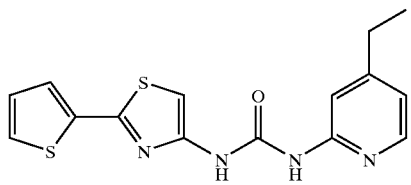

N-[2-(2-Thienyl)-4-thiazolyl]-N'-2-(4-ethylpyridinyl)urea 2-(2-Thienyl)-4-thiazolylcarbonylazide (500 mg, 2.1 mmol) and 2-amino-4-ethylpyridine (512 mg, 4.2 mmol) were heated in 15 mL toluene at 100° C. for 16 h. After cooling to RT, the solids were collected by filtration and washed first with toluene (2×20 mL) followed by $Et_2O$:EtOAc (3:1) (3×10 mL) to afford the urea as an off-white solid. MS m/z: 331 (M+H). Calc'd for $C_{15}H_{14}N_4OS_2$-330.435.

EXAMPLE 57

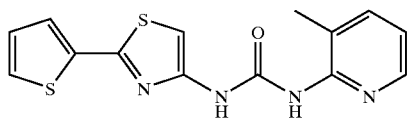

N-[2-(2-Thienyl)-4-thiazolyl]-N'-2-(3-methylpyridinyl)urea 2-(2-Thienyl)-4-thiazolylcarbonylazide (500 mg, 2.1 mmol) and 2-amino-3-methylpyridine (449 mg, 4.2 mmol) were heated in 15 mL toluene at 100° C. for 16 h. After cooling to RT, the solids were collected by filtration and washed first with toluene (2×20 mL) followed by Et$_2$O:EtOAc (3:1) (3×10 mL) to afford the urea as an off-white solid. MS m/z: 317 (M+H). Calc'd for $C_{14}H_{12}N_4OS_2$-316.408.

EXAMPLE 58

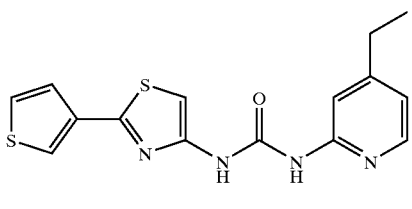

N-[2-(3-Thienyl)-4-thiazolyl]-N'-2-(4-ethylpyridinyl)urea 2-(3-Thienyl)-4-thiazolylcarbonylazide (200 mg, 0.85 mmol) and 2-amino-4-ethylpyridine (310 mg, 2.54 mmol) were heated in 10 mL toluene at 100° C. for 16 h. After cooling to RT, the solids were collected by filtration and washed first with toluene (2×20 mL) followed by Et$_2$O:EtOAc (3:1; (3×10 mL) to afford the product as an off-white solid. MS m/z: 331 (M+H). Calc'd for $C_{15}H_{14}N_4OS_2$-330.435.

EXAMPLE 59

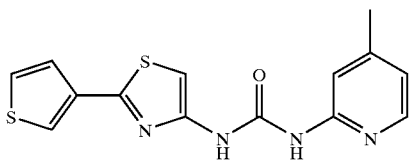

N-[2-(3-Thienyl)-4-thiazolyl]-N'-2-(4-methylpyridinyl)urea 2-(3-Thienyl)-4-thiazolylcarbonylazide (200 mg, 0.85 mmol) and 2-amino-4-methylpyridine (272 mg, 2.54 mmol) were heated in 10 mL toluene at 100° C. for 16 h. After cooling to RT, the solids were collected by filtration and washed first with toluene (2×20 mL) followed by Et$_2$O:EtOAc (3:1) (3×10 mL) to afford the product as an off-white solid. MS m/z: 317 (M+H). Calc'd for $C_{14}H_{12}N_4OS_2$-316.408.

EXAMPLE 60

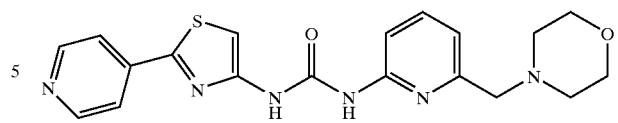

N-[2-(4-Pyridinyl)-4-thiazolyl]-N'-2-[6-(1-morpholinylmethyl)pyridinyl]urea 2-(4-Pyridinyl)-4-thiazolcarbonylazide (100 mg, 0.43 mmol) in dry toluene (10 mL) was heated to 85° C. under N$_2$ and maintained at for 5 min. A solution of 6-morpholin-4-ylmethyl-pyridin-2-ylamine (101 mg, 0.52 mmol) in dry toluene (2 mL) was added dropwise via syringe and the resulting mixture was heated at 100° C. for 12 h. After cooling to RT, a precipitate formed and was collected, rinsing with hexane to give a white solid. MS m/z: 397.3 (M+H). Calc'd for $C_{19}H_{20}N_6O_2S$: 396.14.

The following compounds were prepared from the corresponding amines in a manner similar to that described above for Example 60.

EXAMPLE 61

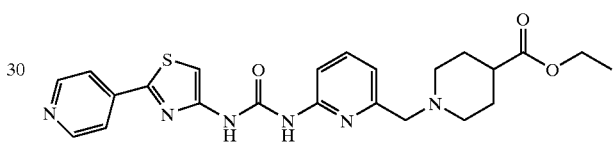

Ethyl 1-{6-[3-(2-(pyridin-4-yl)thiazol-4-yl)ureido]-pyridin-2-ylmethyl}-piperidine-4-carboxylate 2-(4-Pridinyl)-4-thiazolcarbonylazide (182 mg, 0.87 mmol) heated with ethyl 1-(6-aminopyridin-2-ylmethyl)-piperidine-4-carboxylate (230 mg, 0.87 mmol) in dry toluene (15 mL) gave the final urea. MS m/z: 466.9 (M+H). Calc'd. for $C_{23}H_{26}N_6O_3S$-466.50.

EXAMPLE 62

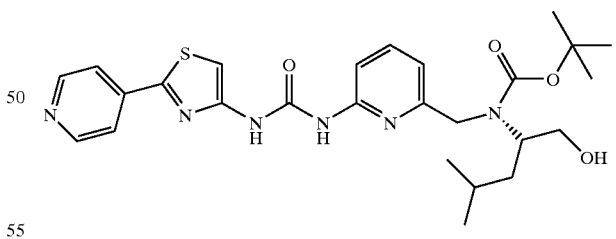

Tert-Butyl (1-hydroxymethyl-3-methyl-butyl)-{6-[3-(2-pyridin-4-yl-thiazol-4-yl)-ureidol-pyridin-2-ylmethyl}-carbamate 2-(4-Pyridinyl)-4-thiazolcarbonylazide (343 mg, 1.48 mmol) was heated with 2-amino-6-[N'-tert-butoxycarbonyl-N'-2-(1-hydroxy-4-methyl)pentylamino]methylpyridine (480 mg, 1.48 mmol) in dry toluene (20 mL) to yield the final compound as pale yellow solid. MS m/z: 527.6 (M+H). Calc'd. for $C_{26}H_{34}N_6O_4S$-526.66.

EXAMPLE 63

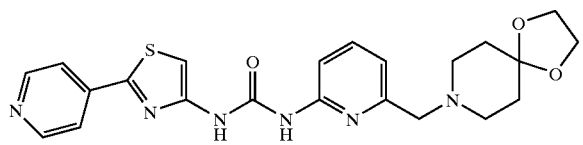

1-[6-(1,4-Dioxa-8-aza-spiro[4.5]dec-8-ylmethyl)-pyridin-2-yl]-3-(2-pyridin-4-yl-thiazol-4-yl)-urea 2-(4-Pyridinyl)-4-thiazolcarbonylazide (420 mg, 2.01 mmol) was heated with 2-amino-6-(4-ethoxyacetal)-piperidinylmethyl pyridine (500 mg, 2.01 mmol) in dry toluene (30 mL) to yield the final compound as yellow solid. MS m/z: 452.9 (M+H). Calc'd. for $C_{22}H_{24}N_6O_3S$-452.23.

EXAMPLE 64

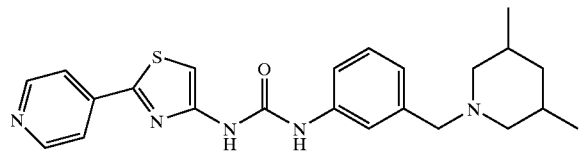

1-[6-(3,5-Dimethylpiperidin-1-ylmethyl)pyridin-2-yl]-3-(2-pyridin-4-ylthiazol-4-yl)urea 2-(4-Pyridinyl)-4-thiazolcarbonylazide (200 mg, 0.867 mmol) was heated with 2-amino-6-(3,5-dimethyl)piperidinyl-methylpyridine (190 mg, 0.867 mmol) in dry toluene (20 mL) to yield the final compound as yellow solid. MS m/z: 423.2 (M+H). Calc'd. for $C_{22}H_{26}N_6OS$-422.0.

EXAMPLE 65

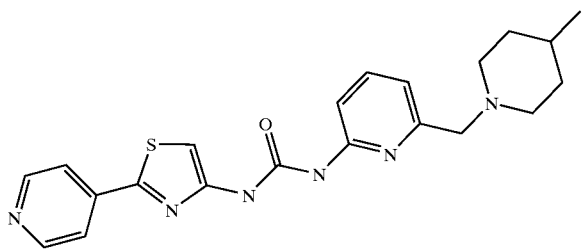

1-[6-(4-Methylpiperidin-1-ylmethyl)pyridin-2-yl]-3-(2-pyridin-4-yl-thiazol-4-yl)urea 2-(4-Pyridinyl)-4-thiazolcarbonylazide (348 mg, 1.51 mmol) was heated with 2-amino-6-(4-methyl)piperidinyl-methylpyridine (310 mg, 1.51 mmol) in dry toluene (20 mL) to yield the final compound as pale yellow solid. MS m/z: 409.5(M+H). Calc'd. for $C_{21}H_{24}N_6OS$-408.52.

EXAMPLE 66

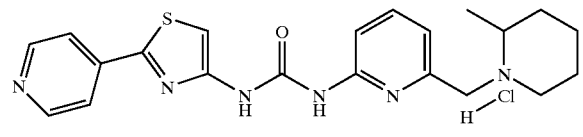

1-[6-(2-Methylpiperidin-1-ylmethyl)pyridin-2-yl]-3-(2-pyridin-4-yl-thiazol-4-yl)urea 2-(4-Pyridinyl)-4-thiazolcarbonylazide (101 mg, 0.44 mmol) was heated with 2-amino-6-(2-methyl)piperidinylmethyl pyridine (90 mg, 0.44 mmol) in dry toluene (15 mL) to yield the final compound as pale yellow solid. MS m/z: 409.6 (M+H). Calc'd. for $C_{21}H_{24}N_6OS$-408.52.

EXAMPLE 67

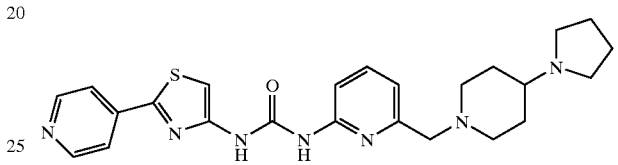

1-(2-Pyridin-4-yl-thiazol-4-yl)-3-[6-(4-pyrrolidin-1-yl-piperidin-1-ylmethyl)-pyridin-2-yl]-urea 2-(4-pyridinyl)-4-thiazolcarbonylazide (293 mg, 1.43 mmol) was heated with 2-amino-6-[4-(1-pyrrolidinyl)-piperidinylmethyl]pyridine (330 mg, 1.43 mmol) in dry toluene (20 mL) to yield the final compound as pale yellow solid. MS m/z: 464.2 (M+H). Calc'd. for $C_{24}H_{29}N_7OS$-463.

EXAMPLE 68

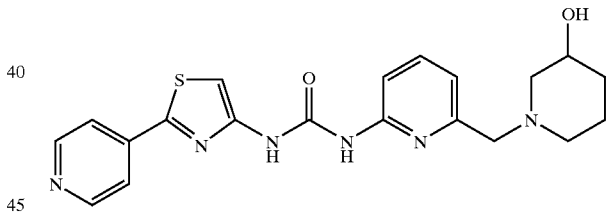

1-[6-(3-Hydroxy-piperidin-1-ylmethyl)-pyridin-2-yl]-3-(2-pyridin-4-yl-thiazol-4-yl)-urea 2-(4-Pyridinyl)-4-thiazolcarbonylazide (312 mg, 1.35 mmol) was heated with 2-amino-6-(3-hydroxy)-piperidinylmethyl pyridine (280 mg, 1.35 mmol) in dry toluene (20 mL) to yield the final compound as yellow solid. MS m/z: 410.9 (M+H). Calc'd. for $C_{20}H_{22}N_6O_2S$-410.5.

EXAMPLE 69

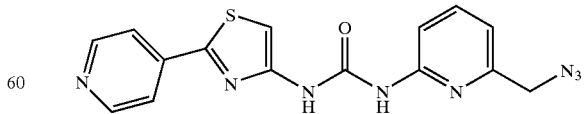

N-(6-azidomethyl-2-pyridyl)-N'-[2-(4-pyridinyl)-4-thiazolyl]urea 2-(4-Pyridinyl)-4-thiazolcarbonylazide (400 mg, 1.73 mmol) was heated with 2-amino-6-azidomethyl-pyridine (258 mg, 1.73 mmol) in dry toluene (15 mL) to yield the final compound as yellow solid. MS m/z: 353.4(M+H). Calc'd. for $C_{15}H_{12}N_8OS$-352.38.

EXAMPLE 70

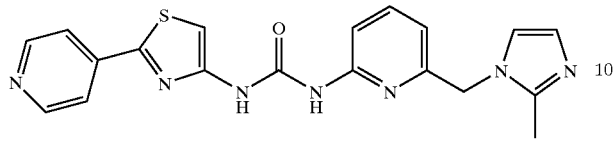

1-[6-(2-Methyl-imidazol-1-ylmethyl)-pyridin-2-yl]-3-(2-pyridin-4-yl-thiazol-4-yl)-urea 2-(4-Pyridinyl)-4-thiazolcarbonylazide (110 mg, 0.48 mmol) was heated with 2-amino-6-[2-methylimidazol-1-yl] methyl-pyridine (90 mg, 0.48 mmol) in dry toluene (15 mL) to yield the final compound as white solid. MS m/z: 392.4 (M+H). Calc'd. for $C_{19}H_{17}N_7O$-391.45.

EXAMPLE 71

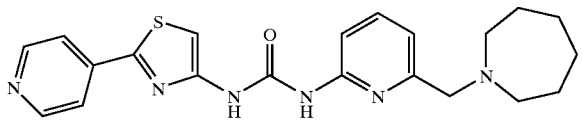

1-(6-Azepan-1-ylmethyl-pyridin-2-yl)-3-(2-pyridin-4-yl-thiazol-4-yl)urea 2-(4-Pyridinyl)-4-thiazolcarbonylazide (150 mg, 0.65 mmol) and 2-amino-6-azaperhydroepinylmethylpyridine (147 mg, 0.71 mmol) in dry toluene (15 mL) were heated at 100° C. for 12 h to give a pale yellow solid. MS m/z: 409.1 (M+H). Calc'd for $C_{21}H_{24}N_6OS$-408.52.

EXAMPLE 72

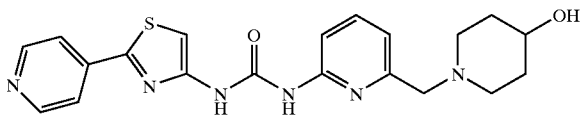

1-[6-(4-Hydroxy-piperidin-1-ylmethyl)-pyridin-2-yl]-3-(2-pyridin-4-yl-thiazol-4-yl)-urea 2-(4-Pyridinyl)-4-thiazolcarbonylazide (265 mg, 1.27 mmol) and 2-amino-6-(4-hydroxy)piperidyl-methylpyridine (220 mg, 1.06 mmol) in dry toluene (15 mL) were heated at 100° C. for 12 h to give a pale yellow solid which was recrystallized from $CHCl_3$/MeOH/hexane (94:2:1) to give a white solid. MS m/z: 410.9 (M+H). Calc'd for $C_{20}H_{22}N_6O_2S$-410.50.

EXAMPLE 73

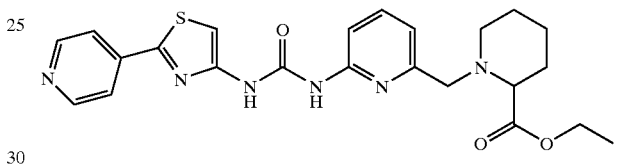

Ethyl 1-{6-[3-(2-pyridin-4-yl-thiazol-4-yl)ureido]-pyridin-2-ylmethyl}piperidine-3-carboxylate 2-(4-Pyridinyl)-4-thiazolcarbonylazide (150 mg, 0.65 mmol) and 2-amino-ethyl(6-piperidylmethyl-pyridinyl)-3-carboxylate (170 mg, 0.65 mmol) in dry toluene (15 mL) were heated at 100° C. for 12 h to give a pale yellow solid which was purified by chromatography on silica gel ($CH_2Cl_2$/MeOH, 95:5) to give a white solid. MS m/z: 467.1 (M+H). Calc'd for $C_{23}H_{26}N_6O_3S$-466.56.

EXAMPLE 74

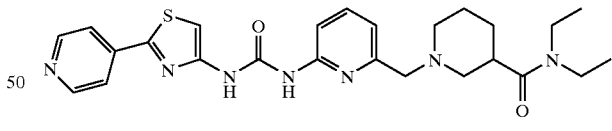

Ethyl 1-[6-[3-(2-(pyridin-4-yl)thiazol-4-yl)ureido]-pyridin-2-ylmethyl]piperidine-2-carboxylate 2-(4-Pyridinyl)-4-thiazolcarbonylazide (483 mg, 2.09 mmol) and ethyl 2-amino-(6-piperidylmethyl-pyridinyl)-2-carboxylate (550 mg, 2.09 mmol) in dry toluene (20 mL) were heated at 100° C. for 8 h to give a pale yellow solid which was purified by chromatography on silica gel ($CH_2Cl_2$/MeOH, 95:5) to give a white solid. MS m/z: 466.9 (M+H). Calc'd for $C_{23}H_{26}N_6O_3S$-466.56.

EXAMPLE 75

N,N-Diethyl 1-{6-[3-(2-pyridin-4-yl-thiazol-4-yl)-ureido]pyridin-2-ylmethyl}piperidine-3-carboxamide 2-(4-Pyridinyl)-4-thiazolcarbonylazide (320 mg, 1.38 mmol) and 2-amino-6-[(N'',N'''-diethylcarbamoyl)-piperidylmethyl]-3-carboxamide (400 mg, 1.38 mmol) in dry toluene (25 mL) were heated at 100° C. for 12 h to give a pale yellow solid which was purified by chromatography on silica gel ($CH_2Cl_2$/MeOH, 95:5) to give the urea as a white solid.

MS m/z: 494.1 (M+H). Calc'd for $C_{25}H_{31}N_7O_2S$-493.63.

EXAMPLE 76

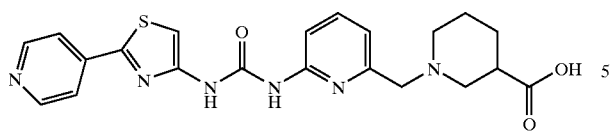

1-{6-[3-(2-Pyridin-4-yl-thiazol-4-yl)-ureido]-pyridin-2-ylmethyl}-piperidine-3-carboxylic Acid 2-(4-Pyridinyl)-4-thiazolcarbonylazide (196 mg, 0.85 mmol) and 2-amino-6-(piperidylmethylpyridinyl)-3-carboxylate (200 mg, 0.85 mmol) in dry toluene (10 mL) were heated at 100 C. for 8 h to give a pale yellow solid which was purified by chromatography on silica gel (CH$_2$Cl$_2$/MeOH, 95:5) to give a white solid. MS m/z: 437.9 (M+H). Calc'd for C$_{21}$H$_{22}$N$_6$O$_3$S-438.51.

EXAMPLE 77

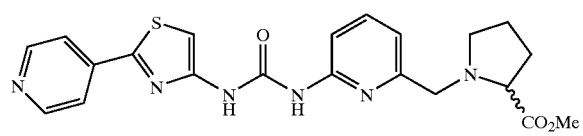

Methyl 1-{6-[3-(2-pyridin-4-yl-thiazol-4-yl)ureido]-pyridin-2-ylmethyl}-pyrrolidine-2-carboxylate 2-(4-Pyridinyl)-4-thiazolcarbonylazide (104 mg, 0.45 mmol) and 2-amino-6-(2-methoxycarbonyl)-pyrrolidinyl-methylpyridine (105 mg, 0.45 mmol) in dry toluene (10 mL) were heated at 100° C. for 12 h to give a pale yellow solid which was purified by chromatography on silica gel (CHCl$_3$/MeOH, 99:5) to give a white solid. MS m/z: 438.7 (M+H). Calc'd for C$_{21}$H$_{22}$N$_6$O$_3$S-438.51.

EXAMPLE 78

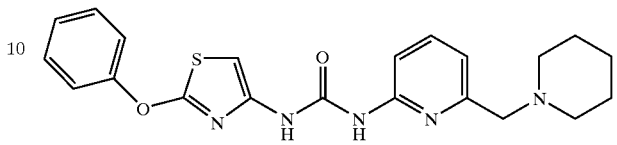

1-[6-(3-Methyl-piperidin-1-ylmethyl)-pyridin-2-yl]-3-(2-pyridin-4-yl-thiazol-4-yl)-urea 2-(4-Pyridinyl)-4-thiazolcarbonylazide (259 mg, 1.12 mmol) and 2-amino-6-(3-methyl)piperidinylmethyl-pyridine (230 mg, 1.12 mmol) in dry toluene (15 mL) were heated at 100° C. for 12 h to give a pale yellow solid which was purified by chromatography on silica gel (CHCl$_3$/MeOH, 99:5) to give a white solid. MS m/z: 408.8 (M+H). Calc'd for C$_{21}$H$_{24}$N$_6$OS-408.53.

EXAMPLE 79

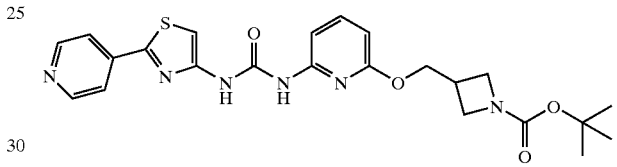

1-(2-Phenoxy-thiazol-4-yl)-3-(6-piperidin-1-ylmethyl-pyridin-2-yl)-urea

MS m/z: 410 (M+H). Calc'd for C$_{21}$H$_{23}$N$_5$O$_2$S: 409.16.

EXAMPLE 80

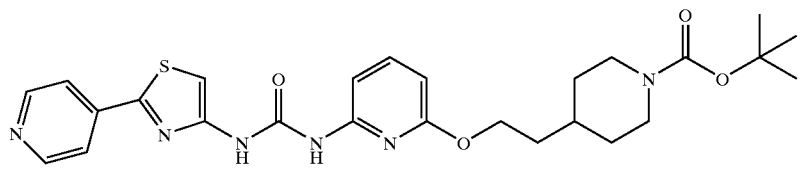

Tert Butyl 3-{6-[3-(2-pyridin-4-yl-thiazol-4-yl)-ureido]-pyridin-2-yloxymethyl}-azetidine-1-carboxylate MS m/z: 483 (M+H). Calc'd for C$_{23}$H$_{26}$N$_6$O$_4$S: 482.17.

EXAMPLE 81

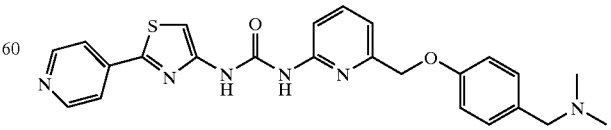

Tert Butyl 4-(2-{6-[3-(2-pyridin-4-yl-thiazol-4-yl)-ureido]pyridin-2-yloxy}ethyl)piperidine-1-carboxylate MS m/z: 525 (M+H). Calc'd for C$_{26}$H$_{32}$N$_6$O$_4$S: 524.22.

EXAMPLE 82

1-[6-(4-Dimethylaminomethyl-phenoxymethyl)-pyridin-2-yl]-3-(2-pyridin-4-yl-thiazol-4-yl)-urea MS m/z: 461 (M+H) Calc'd for C$_{24}$H$_{24}$N$_6$O$_2$S: 460.17.

EXAMPLE 83

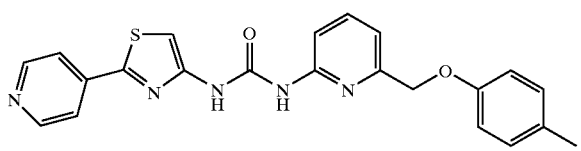

1-(2-Pyridin-4-yl-thiazol-4-yl)-3-(6-(4-methylphenyl)oxymethylpyridin-2-yl)urea

MS m/z: 416 (M−H). Calc'd for $C_{22}H_{19}N_5O_2S$: 417.13.

EXAMPLE 84

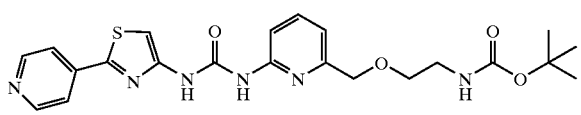

Tert Butyl (2-{6-[3-(2-pyridin-4-yl-thiazol-4-yl)-ureido]pyridin-2-ylmethoxy}ethyl)carbamate MS m/z: 471 (M+H). Calc'd for $C_{22}H_{26}N_6O_4S$: 470.17.

EXAMPLE 85

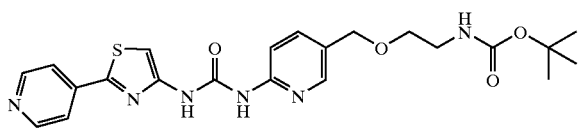

Tert Butyl (2-{6-[3-(2-pyridin-4-yl-thiazol-4-yl)-ureido]pyridin-3-ylmethoxy}ethyl)carbamate MS m/z: 471 (M+H). Calc'd for $C_{22}H_{26}N_6O_4S$: 470.17.

EXAMPLE 86

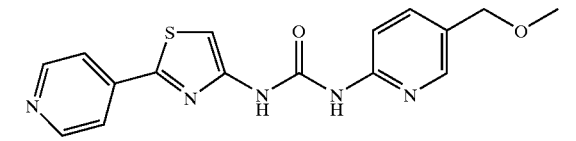

1-(5-Methoxymethyl-pyridin-2-yl)-3-(2-pyridin-4-yl-thiazol-4-yl)-urea

MS m/z: 342 (M+H). Calc'd for $C_{16}H_{15}N_5O_2S$: 341.09.

EXAMPLE 87

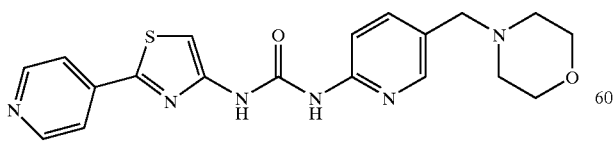

1-(5-Morpholin-4-ylmethyl-pyridin-2-yl)-3-(2-pyridin-4-yl-thiazol-4-yl)urea

MS m/z: 397 (M+H). Calc'd for $C_{19}H_{20}N_6O_2S$: 396.14.

EXAMPLE 88

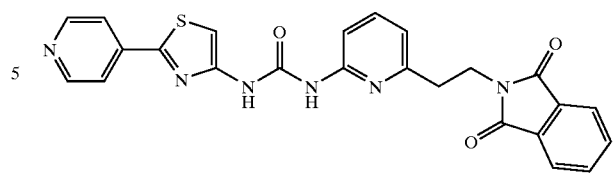

1-{6-[2-phthalimidylethyl]pyridin-2-yl}-3-(2-pyridin-4-yl-thiazol-4-yl)urea

Prepared in a manner similar to that described in Example 60 from 3-(4-pyridyl)-thiazole acyl-azide (103 mg, 0.56 mmol) and 2-amino-6-ethylphthalamidylpyridine (150 mg, 0.56 mmol) in toluene (10 mL). Concentrated in vacuo to afford a yellow solid which was treated with EtOH (10 mL) and filtered to give the title compound as a yellow solid. MS m/z: 470.9 (M+H). Calc'd for $C_{24}H_{18}N_6O_3S$: 470.12.

EXAMPLE 89

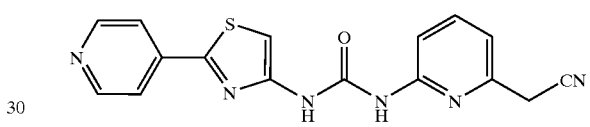

1-(6-Cyanomethylpyridin-2-yl)-3-(2-pyridin-4-yl-thiazol-4-yl)urea

Prepared in a manner similar to that described in Example 60 from 2-amino-6-methylnitrile-pyridine (0.32 g, 2.4 mmol) and 3-(4-pyridyl)-4-thiazole acylazide (0.51 g, 2.2 mmol). After 1.5 h, yellow solid precipitated out of toluene solution. The mixture was cooled to RT and the solid filtered. Purified by silica flash chromatography (3% MeOH/CH$_2$Cl$_2$) to afford the title compound as a white solid. MS m/z: 337.1 (M+H). Calc'd for $C_{16}H_{12}N_6OS$: 336.08.

EXAMPLE 90

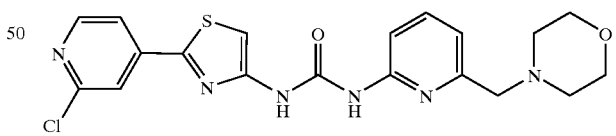

1-[2-(2-Chloropyridin-4-yl)thiazol-4-yl]-3-(6-morpholin-4-ylmethyl-pyridin-2-yl)urea Prepared in a manner similar to that described in Example 60 from 3-(4-pyridyl)-4-thiazole acyl azide (0.51 g, 1.9 mmol) and 2-amino-6-methylmorpholino-pyridine (0.42 g, 2.2 mmol) in toluene (50 mL). After 3 h, the reaction mixture was cooled to RT and filtered to afford the title compound as a light purple solid. MS m/z: 431.0 (M+H). Calc'd for $C_{19}H_{19}ClN_6O_2S$: 430.10.

EXAMPLE 91

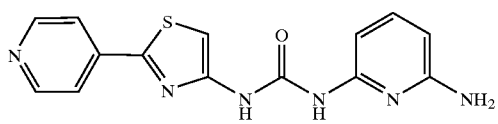

1-(6-Aminopyridin-2-yl)-3-(2-pyridin-4-yl-thiazol-4-yl)urea

Prepared in a manner similar to that described in Example 60 from 3-(4-pyridyl)-4-thiazole-acyl azide (148 mg, 0.64 mmol) and 2,6-diaminopyridine (77 mg, 0.70 mmol, Aldrich) in toluene (10 mL). After 2 h, a yellow precipitate formed. The reaction mixture was cooled and filtered to afford the title compound as a yellow solid. MS m/z: 180 (M+H). Calc'd for $C_{14}H_{12}N_6OS$: 312.08.

EXAMPLE 92

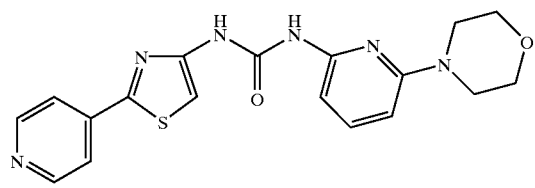

1-(6-Morpholin-4-yl-pyridin-2-yl)-3-(2-pyridin-4-yl-thiazol-4-yl)urea

EI-MS m/z 383.4 (M+H). Calc'd for $C_{18}H_{18}N_6O_2S$: 382.12.

EXAMPLE 93

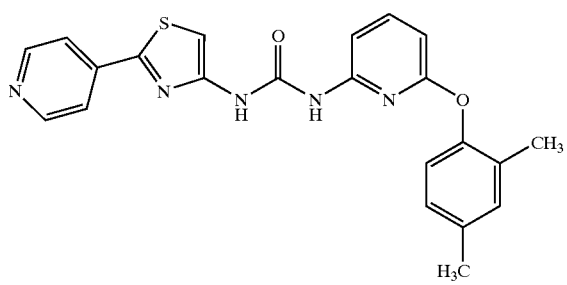

1-[6-(2,4-Dimethylphenoxy)pyridin-2-yl]-3-(2-pyridin-4-yl-thiazol-4-yl)urea

EI-MS m/z 418.5 (M+H). Calc'd for $C_{22}H_{19}N_5O_2S$: 417.13.

EXAMPLE 94

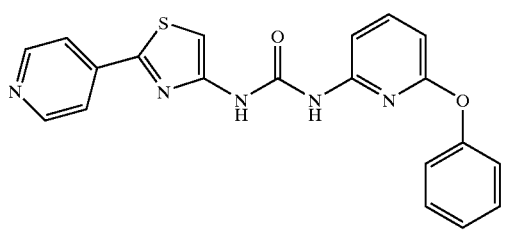

1-(6-Phenoxypyridin-2-yl)-3-(2-pyridin-4-yl-thiazol-4-yl)urea

EI-MS m/z 390.4 (M+H). Calc'd for $C_{20}H_{15}N_5O_2S$: 389.09.3.

EXAMPLE 95

1-E6-(1,4-Dioxa-8-aza-spiro[4.5]dec-8-yl)-pyridin-2-yl]-3-(2-pyridin-4-yl-thiazol-4-yl)urea Prepared in a manner similar to that described in Example 60 using 2-(4-pyridinyl)-4-thiazolcarbonylazide and the requisite 2-aminopyridine. EI-MS m/z 439.5 (M+H). Calc'd for $C_{21}H_{22}N_6O_3S$: 438.15.

EXAMPLE 96

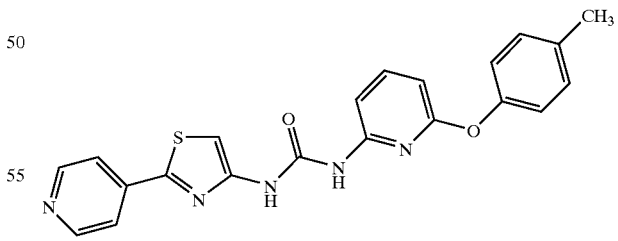

1-(2-Pyridin-4-yl-thiazol-4-yl)-3-(6-p-tolyloxy-pyridin-2-yl)-urea

EI-MS m/z 404.4 (M+H). Calc'd for $C_{21}H_{17}N_5O_2S$: 403.11.

EXAMPLE 97

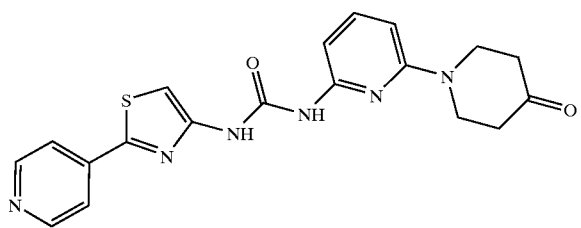

1-(4-Oxo-3,4,5,6-tetrahydro-2H-[1,2']bipyridinyl-6'-yl)-3-(2-pyridin-4-yl-thiazol-4-yl)-urea EI-MS m/z 395.4 (M+H) Calc'd for $C_{19}H_{18}N_6O_2S$: 394.12.

EXAMPLE 98

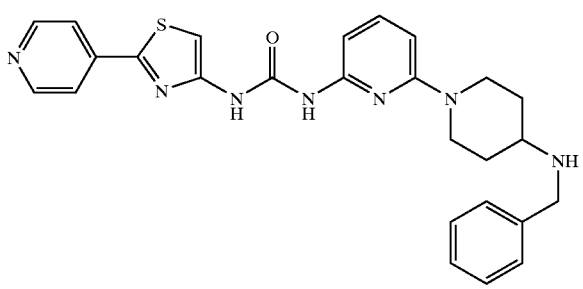

1-(4-Benzylamino-3,4,5,6-tetrahydro-2H-[1,2']bipyridinyl-6'-yl)-3-(2-pyridin-4-yl-thiazol-4-yl)-urea EI-MS m/z 486.7 (M+H). Calc'd for $C_{26}H_{27}N_7OS$: 485.20.

EXAMPLE 99

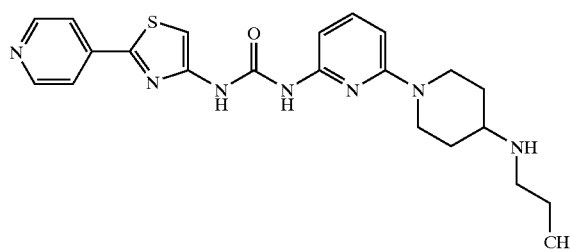

1-(4-Propylamino-3,4,5,6-tetrahydro-2H-[1,2']bipyridinyl-6'-yl)-3-(2-pyridin-4-yl-thiazol-4-yl)-urea EI-MS m/z 438.6 (M+H). Calc'd for $C_{22}H_{27}N_7OS$: 437.20.

EXAMPLE 100

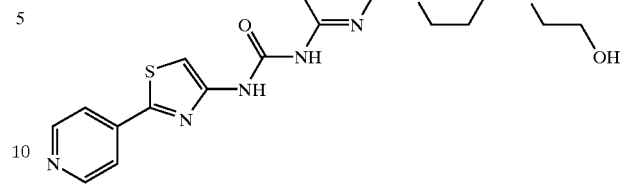

1-[4-(2-Hydroxy-ethylamino)-3,4,5,6-tetrahydro-2H-[1,2']bipyridinyl-6'-yl]-3-(2-pyridin-4-yl-thiazol-4-yl)-urea EI-MS m/z 440.5 (M+H). Calc'd for $C_{21}H_{25}N_7O_2S$: 439.18.

EXAMPLE 101

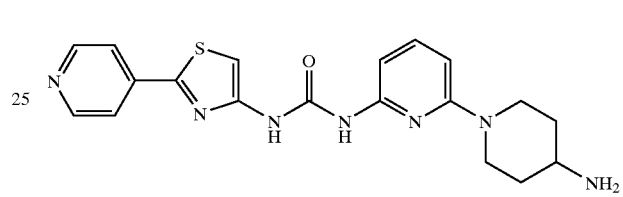

1-(4-Amino-3,4,5,6-tetrahydro-2H-[1,2']bipyridinyl-6'-yl)-3-(2-pyridin-4-yl-thiazol-4-yl)-urea EI-MS m/z 396.6 (M+H). Calc'd for $C_{19}H_{21}N_7OS$: 395.15.

EXAMPLE 102

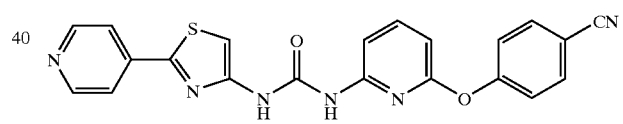

1-[6-(4-Cyanophenoxy)-pyridin-2-yl]-3-(2-pyridin-4-yl-thiazol-4-yl)urea

EI-MS m/z 415.5 (M+H). Calc'd for $C_{21}H_{14}N_6O_2S$: 414.09.

EXAMPLE 103

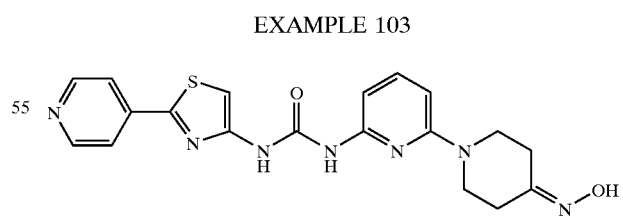

1-(4-Hydroxyimino-3,4,5,6-tetrahydro-2H-[1,2']bipyridinyl-6'-yl)-3-(2-pyridin-4-yl-thiazol-4-yl)-urea EI-MS m/z 410.4 (M+H). Calc'd for $C_{19}H_{19}N_7O_2S$: 409.13.

EXAMPLE 104

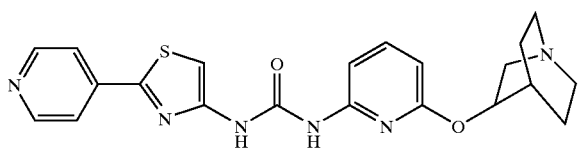

1-[6-(1-Aza-bicyclo[2.2.2]oct-3-yloxy)-pyridin-2-yl]-3-(2-pyridin-4-yl-thiazol-4-yl)-urea EI-MS m/z 423.6 (M+H). Calc'd for $C_{21}H_{22}N_6O_2S$: 422.15.

EXAMPLE 105

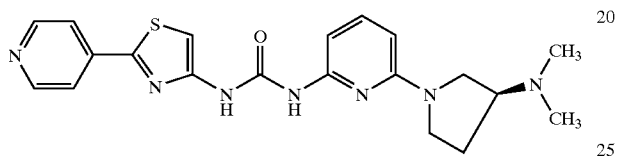

1-[6-(3-Dimethylamino-pyrrolidin-1-yl)-pyridin-2-yl]-3-(2-pyridin-4-yl-thiazol-4-yl)-urea EI-MS m/z 410.5 (M+H). Calc'd for $C_{20}H_{23}N_7OS$: 409.17.

EXAMPLE 106

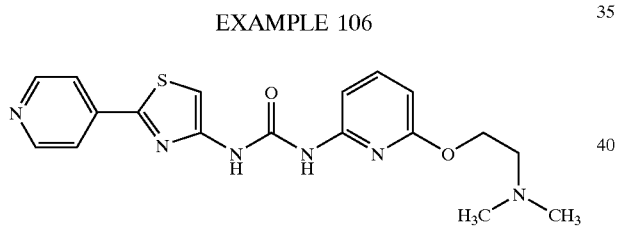

1-[6-(2-Dimethylamino-ethoxy)-pyridin-2-yl]-3-(2-pyridin-4-yl-thiazol-4-yl)-urea EI-MS m/z 385.5 (M+H). Calc'd for $C_{18}H_{20}N_6O_2S$: 384.14.

EXAMPLE 107

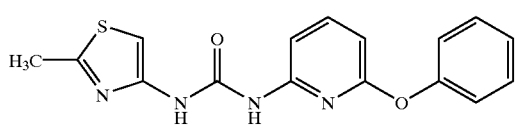

1-(2-Methylthiazol-4-yl)-3-{6-phenoxy-pyridin-2-yl}urea

EI-MS m/z 327.4 (M+H). Calc'd for $C_{16}H_{14}N_4O_2S$: 326.08.

EXAMPLE 108

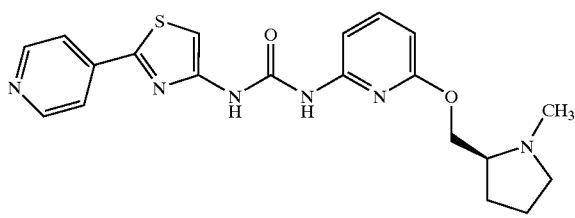

1-[6-(1-Methylpyrrolidin-2-ylmethoxy)pyridin-2-yl]-3-(2-pyridin-4-yl-thiazol-4-yl)urea EI-MS m/z 411.4 (M+H). Calc'd for $C_{20}H_{22}N_6O_2S$: 410.15.

EXAMPLE 109

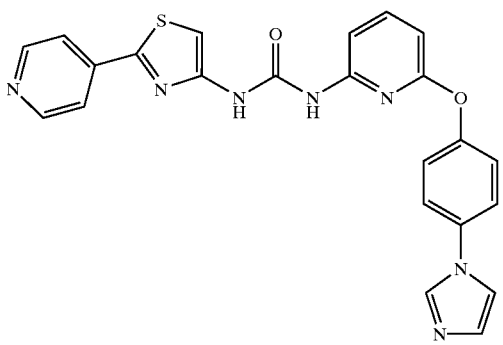

1-[6-(4-Imidazol-1-yl-phenoxy)-pyridin-2-yl]-3-(2-pyridin-4-yl-thiazol-4-yl)-urea EI-MS m/z 456.6 (M+H). Calc'd for $C_{23}H_{17}N_7O_2S$: 455.12.

EXAMPLE 110

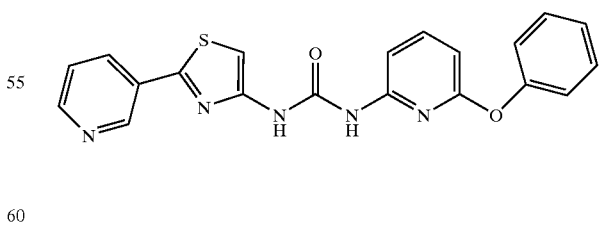

1-(6-Phenoxypyridin-2-yl)-3-(2-pyridin-3-yl-thiazol-4-yl)urea

EI-MS m/z 390.5 (M+H). Calc'd for $C_{20}H_{15}N_5O_2S$: 389.09.

EXAMPLE 111

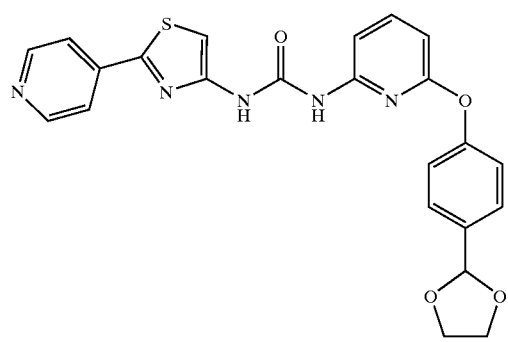

1-[6-(4-[1,3]Dioxolan-2-yl-phenoxy)pyridin-2-yl]-3-(2-pyridin-4-yl-thiazol-4-yl)urea EI-MS m/z 462.5 (M+H). Calc'd for $C_{23}H_{19}N_5O_4S$: 461.12.

EXAMPLE 112

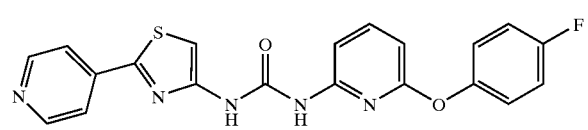

1-[6-(4-Fluorophenoxy)pyridin-2-yl]-3-(2-pyridin-4-yl-thiazol-4-yl)urea

EI-MS m/z 408.5 (M+H). Calc'd for $C_{20}H_{14}FN_5O_2S$: 407.09.

EXAMPLE 113

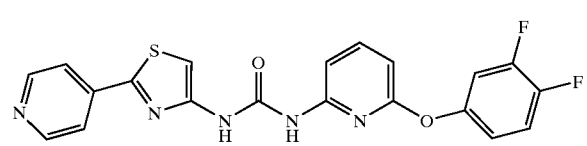

1-[6-(3,4-Difluorophenoxy)pyridin-2-yl]-3-(2-pyridin-4-yl-thiazol-4-yl)urea

EI-MS m/z 426.5 (M+H). Calc'd for $C_{20}H_{13}F_2N_5O_2S$: 425.08.

EXAMPLE 114

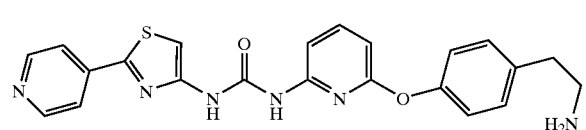

1-{6-[4-(2-Aminoethyl)phenoxy]pyridin-2-yl}-3-(2-pyridin-4-yl-thiazol-4-yl)urea

EI-MS m/z 433.5 (M+H). Calc'd for $C_{22}H_{20}N_6O_2S$: 432.14.

EXAMPLE 115

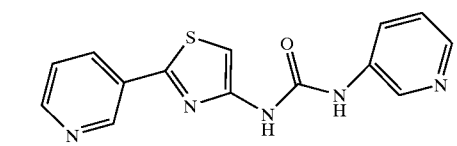

1-Pyridin-3-yl-3-(2-pyridin-3-yl-thiazol-4-yl)-urea

EI-MS m/z 396.6 (M+H). Calc'd for $C_{14}H_{11}N_5OS$: 297.07.

EXAMPLE 116

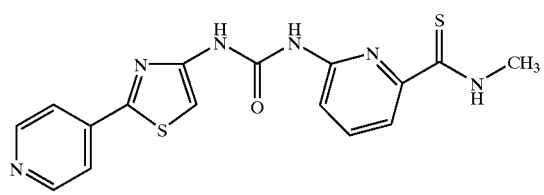

6-[3-(2-Pyridin-4-yl-thiazol-4-yl)-ureido]-pyridine-2-carbothioic acid methylamide EI-MS m/z 371.5 (M+H). Calc'd for $C_{16}H_{14}N_6OS_2$: 370.07.

EXAMPLE 117

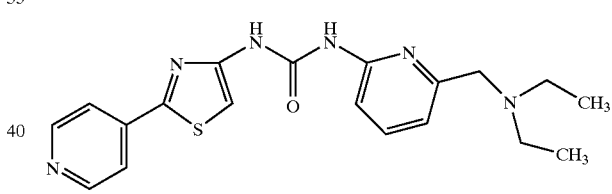

1-(6-Diethylaminomethyl-pyridin-2-yl)-3-(2-pyridin-4-yl-thiazol-4-yl)urea

EI-MS m/z 383.5 (M+H). Calc'd for $C_{19}H_{22}N_6OS$: 382.16.

EXAMPLE 118

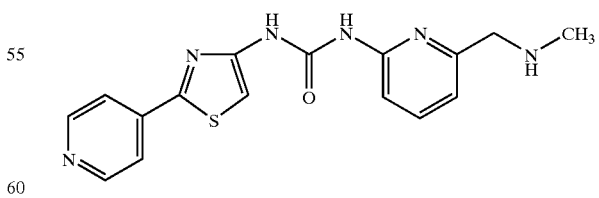

1-(6-Methylaminomethyl-pyridin-2-yl)-3-(2-pyridin-4-yl-thiazol-4-yl)urea

EI-MS m/z 341.4 (M+H). Calc'd for $C_{16}H_{16}N_6OS$: 340.11.

EXAMPLE 119

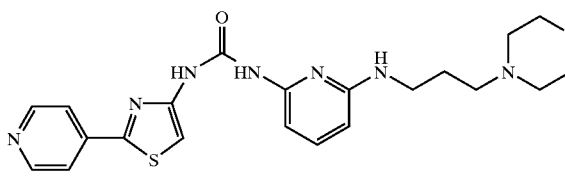

1-[6-(3-Morpholin-4-yl-propylamino)-pyridin-2-yl]-3-(2-pyridin-4-yl-thiazol-4-yl)-urea EI-MS m/z 440.4 (M+H). Calc'd for $C_{21}H_{25}N_7O_2S$: 439.18.

EXAMPLE 120

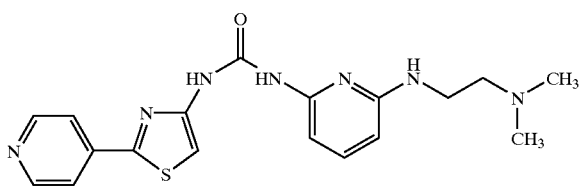

1-[6-(2-Dimethylamino-ethylamino)-pyridin-2-yl]-3-(2-pyridin-4-yl-thiazol-4-yl)-urea EI-MS m/z 384.5 (M+H). Calc'd for $C_{18}H_{21}N_7OS$: 383.15.

EXAMPLE 121

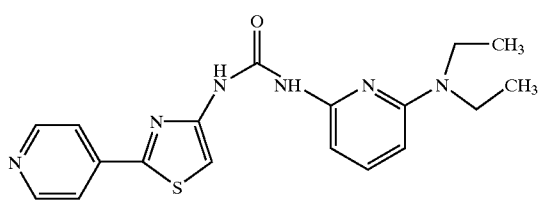

1-(6-Diethylamino-pyridin-2-yl)-3-(2-pyridin-4-yl-thiazol-4-yl)-urea

EI-MS m/z 369.3 (M+H). Calc'd for $C_{18}H_{20}N_6OS$: 368.14.

EXAMPLE 122

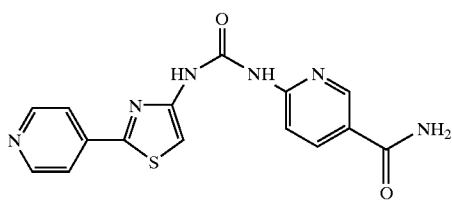

6-[3-(2-Pyridin-4-yl-thiazol-4-yl)-ureido]nicotinamide

EI-MS m/z 341.3 (M+H). Calc'd for $C_{15}H_{12}N_6O_2S$: 340.07.

EXAMPLE 123

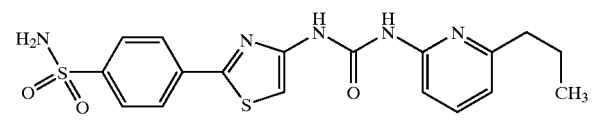

4-{4-[3-(6-Propylpyridin-2-yl)ureido]thiazol-2-yl}-benzenesulfonamide

EI-MS m/z 418.5 (M+H). Calc'd for $C_{18}H_{19}N_5O_3S_2$: 417.09.

EXAMPLE 124

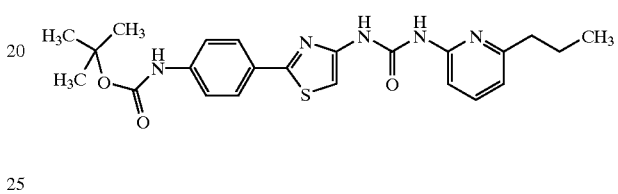

Tert Butyl (4-{4-[3-(6-Propylpyridin-2-yl)ureido]-thiazol-2-yl}phenyl)carbamate

EI-MS m/z 454.6 (M+H). Calc'd for $C_{23}H_{27}N_5O_3S$: 453.18.

EXAMPLE 125

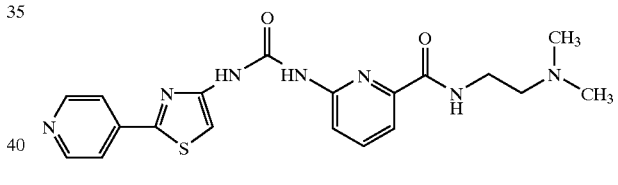

2-Dimethylaminoethyl 6-[3-(2-pyridin-4-yl-thiazol-4-yl)ureido]pyridine-2-carboxamide EI-MS m/z 412.5 (M+H). Calc'd for $C_{19}H_{21}N_7O_2S$: 411.15.

EXAMPLE 126

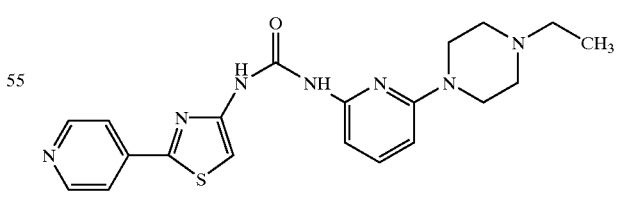

1-[6-(4-Ethylpiperazin-1-yl)-pyridin-2-yl]-3-(2-pyridin-4-yl-thiazol-4-yl)urea

EI-MS m/z 410.6 (M+H). Calc'd for $C_{20}H_{23}N_7OS$: 409.17.

EXAMPLE 127

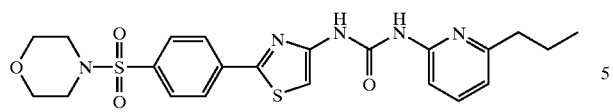

1-{2-[4-(4-Morpholinylsulfonyl)phenyl]thiazol-4-yl}-3-(6-propyl-pyridin-2-yl)urea EI-MS m/z 488.7 (M+H). Calc'd for $C_{22}H_{25}N_5O_4S_2$: 487.13.

EXAMPLE 128

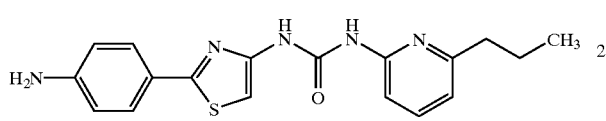

1-[2-(4-Aminophenyl)thiazol-4-yl]-3-(6-propylpyridin-2-yl)urea

EI-MS m/z 354.4 (M+H). Calc'd for $C_{18}H_{19}N_5OS$: 353.13.

EXAMPLE 129

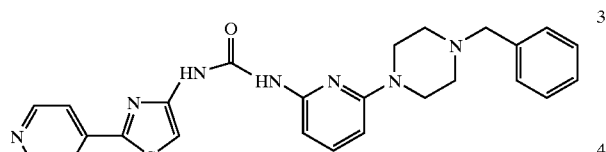

1-[6-(4-Benzylpiperazin-1-yl)pyridin-2-yl]-3-(2-pyridin-4-yl-thiazol-4-yl)urea

EI-MS m/z 472.5 (M+H). Calc'd for $C_{25}H_{25}N_7OS$: 471.18.

EXAMPLE 130

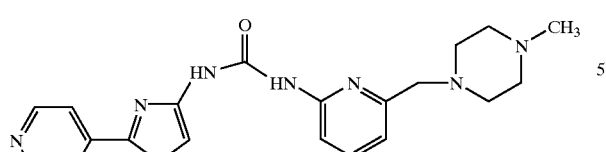

1-[6-(4-Methyl-piperazin-1-ylmethyl)-pyridin-2-yl]-3-(2-pyridin-4-yl-thiazol-4-yl)-urea EI-MS m/z 410.5 (M+H). Calc'd for $C_{20}H_{23}N_7OS$: 409.17.

EXAMPLE 131

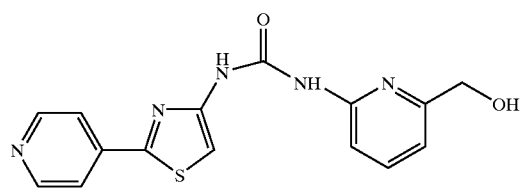

1-(6-Hydroxymethyl-pyridin-2-yl)-3-(2-pyridin-4-yl-thiazol-4-yl)-urea

EI-MS m/z 328.4 (M+H). Calc'd for $C_{15}H_{13}NSO_2S$: 327.08.

EXAMPLE 132

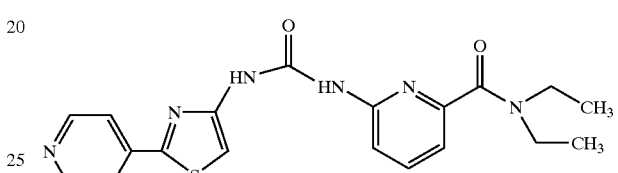

Diethyl 6-[3-(2-pyridin-4-yl-thiazol-4-yl)ureido]-pyridine-2-carboxamide

EI-MS m/z 397.6 (M+H). Calc'd for $C_{19}H_{20}N_6O_2S$: 396.14.

EXAMPLE 133

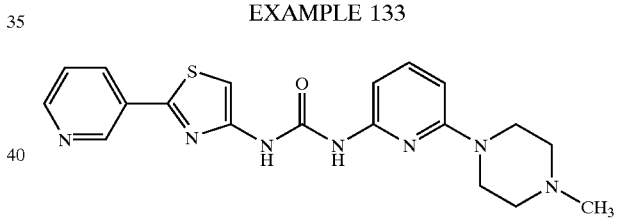

1-[6-(4-Methylpiperazin-1-yl)pyridin-2-yl]-3-(2-pyridin-3-yl-thiazol-4-yl)urea

EI-MS m/z 396.5 (M+H). Calc'd for $C_{19}H_{21}N_7OS$: 395.15.

EXAMPLE 134

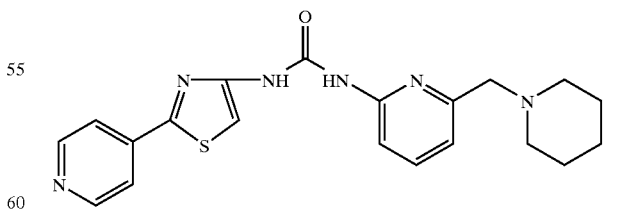

1-(6-Piperidin-1-ylmethyl-pyridin-2-yl)-3-(2-pyridin-4-yl-thiazol-4-yl)-urea

EI-MS m/z 395.6 (M+H). Calc'd for $C_{20}H_{22}N_6OS$: 394.16.

EXAMPLE 135

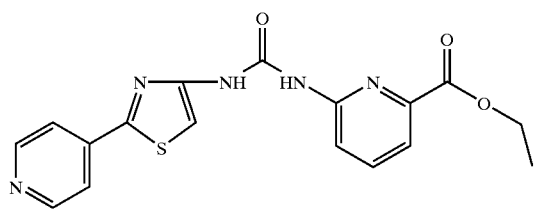

6-[3-(2-Pyridin-4-yl-thiazol-4-yl)-ureido]-pyridine-2-carboxylic Acid Ethyl Ester EI-MS m/z 370.4 (M+H). Calc'd for $C_{17}H_{15}N_5O_3S$: 369.09.

EXAMPLE 136

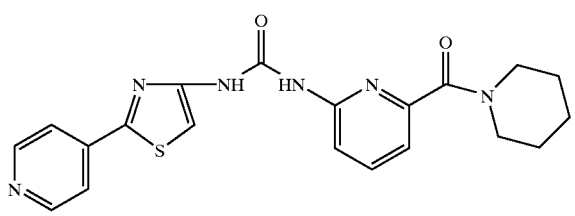

1-[6-(Piperidine-1-carbonyl)pyridin-2-yl]-3-(2-pyridin-4-yl-thiazol-4-yl)urea

EI-MS m/z 409.5 (M+H). Calc'd for $C_{20}H_{20}N_6O_2S$: 408.14.

EXAMPLE 137

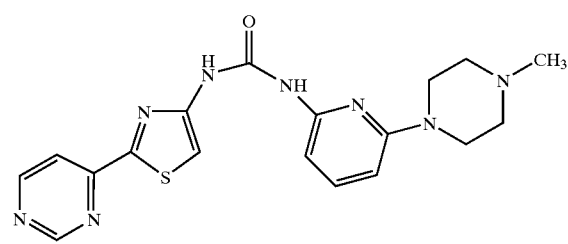

1-[6-(4-Methylpiperazin-1-yl)pyridin-2-yl]-3-(2-pyrimidin-4-yl-thiazol-4-yl)urea EI-MS m/z 397.5 (M+H). Calc'd for $C_{18}H_{20}N_{80}S$: 396.15.

EXAMPLE 138

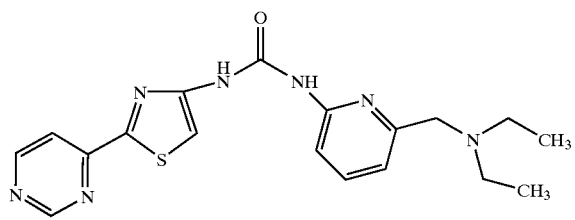

1-(6-Diethylaminomethyl-pyridin-2-yl)-3-(2-pyrimidin-4-yl-thiazol-4-yl)urea

EI-MS m/z 384.6 (M+H). Calc'd for $C_{18}H_{21}N_7OS$: 383.15.

EXAMPLE 139

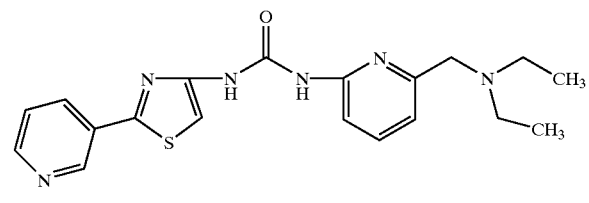

1-(6-Diethylaminomethyl-pyridin-2-yl)-3-(2-pyridin-3-yl-thiazol-4-yl)urea

EI-MS m/z 383.5 (M+H). Calc'd for $C_{19}H_{22}N_6OS$: 382.16.

EXAMPLE 140

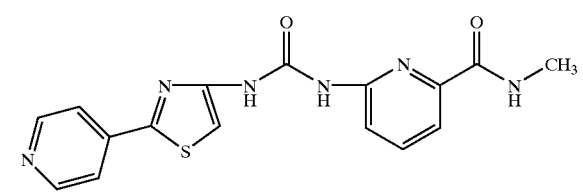

Methyl 6-[3-(2-pyridin-4-yl-thiazol-4-yl)ureido]pyridine-2-carboxamide

EI-MS m/z 355.3 (M+H). Calc'd for $C_{16}H_{14}N_6O_2S$: 354.09.

EXAMPLE 141

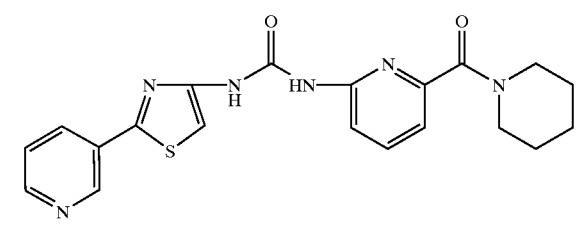

1-[6-(Piperidine-1-carbonyl)pyridin-2-yl]-3-(2-pyridin-3-yl-thiazol-4-yl)urea

EI-MS m/z 409.5 (M+H). Calc'd for $C_{20}H_{20}N_6O_2S$: 408.14.

EXAMPLE 142

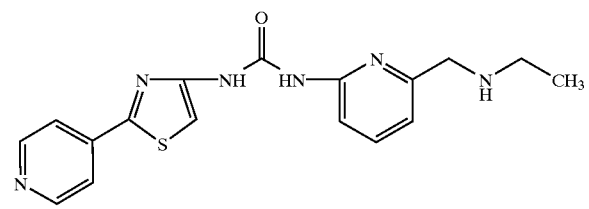

1-(6-Ethylaminomethylpyridin-2-yl)-3-(2-pyridin-4-yl-thiazol-4-yl) urea

EI-MS m/z 355.5 (M+H). Calc'd for $C_{17}H_{18}N_6OS$: 354.13.

EXAMPLE 143

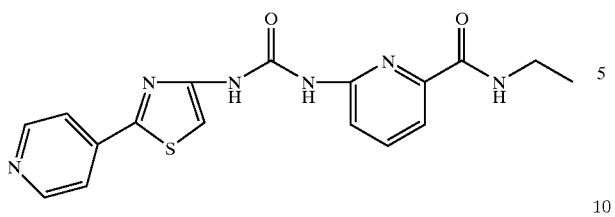

Ethyl 6-[3-(2-Pyridin-4-yl-thiazol-4-yl)ureido]
pyridine-2-carboxamide

EI-MS m/z 369.4 (M+H). Calc'd for $C_{17}H_{16}N_6O_2S$: 368.11.

EXAMPLE 144

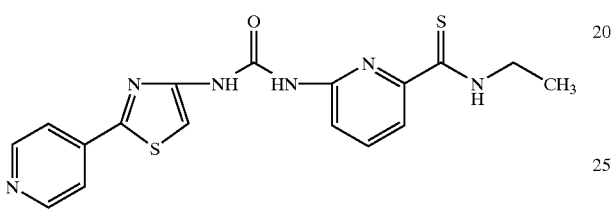

Ethyl 6-[3-(2-pyridin-4-yl-thiazol-4-yl)ureido]-
pyridine-2-thiocarboxamide

EI-MS m/z 385.5 (M+H). Calc'd for $C_{17}H_{16}N_6OS_2$: 384.08.

EXAMPLE 145

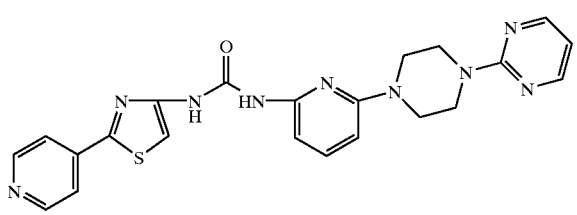

1-(2-Pyridin-4-yl-thiazol-4-yl)-3-[6-(4-pyrimidin-2-
yl-piperazin-1-yl)pyridin-2-yl]urea EI-MS m/z 460.5 (M+H). Calc'd for $C_{22}H_{21}N_9OS$: 459.16.

EXAMPLE 146

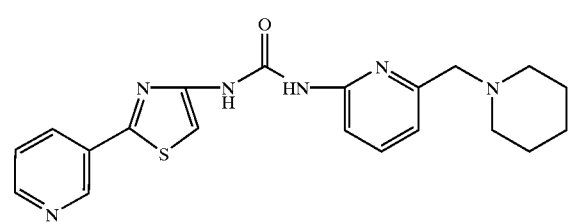

1-(6-Piperidin-1-ylmethyl-pyridin-2-yl)-3-(2-
pyridin-3-yl-thiazol-4-yl)-urea

EI-MS m/z 395.5 (M+H). Calc'd for $C_{20}H_{22}N_6OS$: 394.16.

EXAMPLE 147

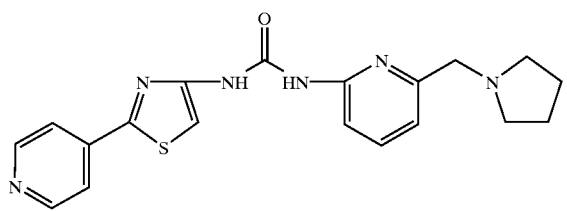

1-(2-Pyridin-4-yl-thiazol-4-yl)-3-(6-pyrrolidin-1-
ylmethyl-pyridin-2-yl)-urea

EI-MS m/z 381.5 (M+H). Calc'd for $C_{19}H_{20}N_6OS$: 380.14.

EXAMPLE 148

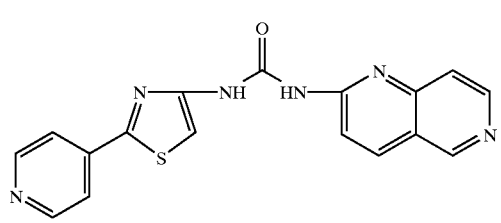

1-[1,6]Naphthyridin-2-yl-3-(2-pyridin-4-yl-thiazol-
4-yl)-urea

EI-MS m/z 349.5 (M+H). Calc'd for $C_{17}H_{12}N_6OS$: 348.08.

EXAMPLE 149

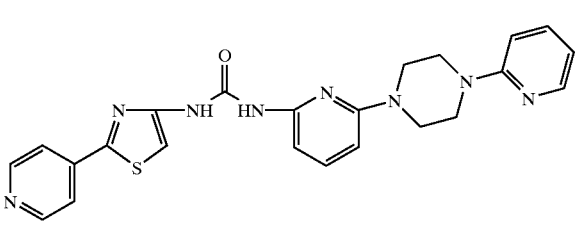

1-[6-(4-Pyridin-2-yl-piperazin-1-yl)pyridin-2-yl]-3-
(2-pyridin-4-yl-thiazol-4-yl)urea EI-MS m/z 459.5 (M+H). Calc'd for $C_{23}H_{22}N_8OS$: 458.16.

EXAMPLE 150

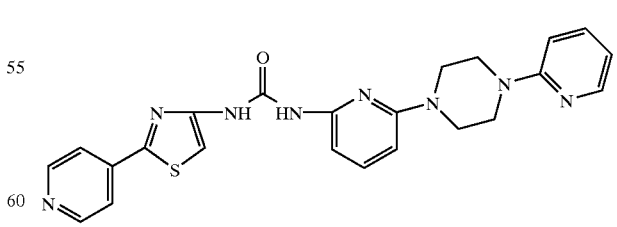

1-[6-(4-Pyridin-2-yl-piperazin-1-yl)-pyridin-2-yl]-3-
(2-pyridin-4-yl-thiazol-4-yl)-urea EI-MS m/z 459.5 (M+H). Calc'd for $C_{23}H_{22}N_8OS$: 458.16.

EXAMPLE 151

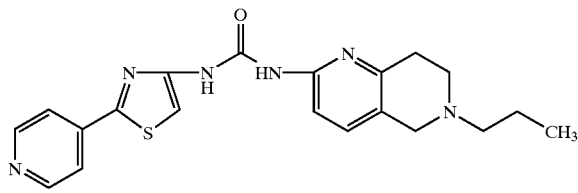

1-(6-Propyl-5,6,7,8-tetrahydro-[1,6]naphthyridin-2-yl)-3-(2-pyridin-4-yl-thiazol-4-yl)-urea EI-MS m/z 395.6 (M+H). Calc'd for $C_{20}H_{22}N_6OS$: 394.16.

EXAMPLE 152

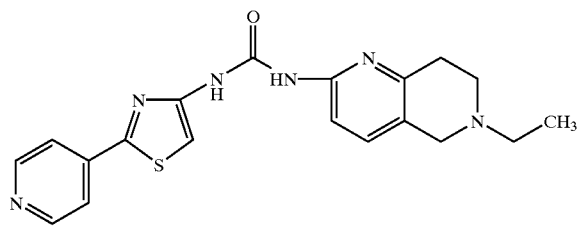

1-(6-Ethyl-5,6,7,8-tetrahydro-[1,6]naphthyridin-2-yl)-3-(2-pyridin-4-yl-thiazol-4-yl)-urea EI-MS m/z 381.5(M+H). Calc'd for $C_{19}H_{20}N_6OS$: 380.14.

EXAMPLE 153

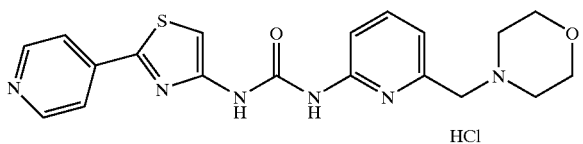

N-[2-(4-Pyridinyl)-4-thiazolyl]-N'-2-[6-(1-morpholinylmethyl)pyridinyl]urea Hydrochloride To a solution of N-[2-(pyridin-4-yl)-4-thiazolyl]-N'-2-(6-morpholinylmethylpyridinyl)urea (90 mg, 0.23 mmol, Example 60) in MeOH (3 mL) was added HCl (0.25 mL, 0.25 mmol, 1.0 M in Et₂O). The resulting mixture was stirred at RT for 2 h then concentrated in vacuo to give a pale yellow solid.

The following Examples 154–165 were prepared from the corresponding amines in a manner similar to that described above for Example 153.

EXAMPLE 154

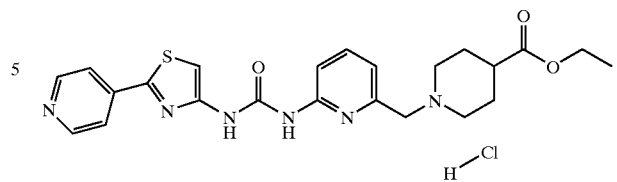

Ethyl 1-{6-[3-(2-pyridin-4-yl-thiazol-4-yl)ureido]-pyridin-2-ylmethyl}-piperidine-4-carboxylate Hydrochloride Ethyl 1-{6-[3-(2-pyridin-4-yl-thiazol-4-yl)-ureido]-pyridin-2-ylmethyl}-piperidine-4-carboxylate (50 mg, 0.05 mmol, Example 61) in MeOH (5 mL) was treated with HCl (0.12 mL, 0.06 mmol, 1M in Et₂O) to afford the title salt as a yellow solid.

EXAMPLE 155

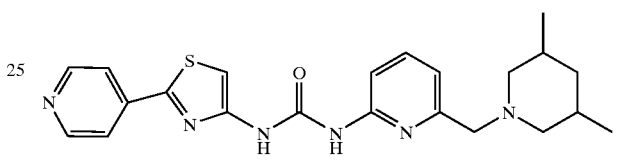

1-[6-(3,5-Dimethylpiperidin-1-ylmethyl)pyridin-2-yl]-3-(2-pyridin-4-ylthiazol-4-yl)urea Hydrochloride 1-[6-(3,5-Dimethylpiperidin-1-ylmethyl)pyridin-2-yl]-3-(2-pyridin-4-ylthiazol-4-yl)urea (52 mg, 0.123 mmol, Example 64) was treated with HCl (0.08 mL, 0.135 mmol, 1 M in Et₂O) to afford the title salt as a yellow solid.

EXAMPLE 156

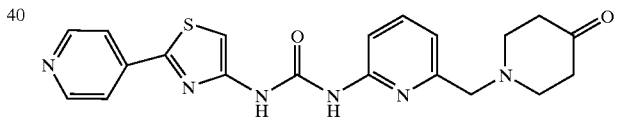

1-[6-(4-Oxo-piperidin-1-ylmethyl)pyridin-2-yl]-3-(2-pyridin-4-yl-thiazol-4-yl)urea hydrochloride 1-[6-(4-Oxo-piperidin-1-ylmethyl)pyridin-2-yl]-3-(2-pyridin-4-yl-thiazol-4-yl)urea (30 mg, 0.073 mmol, Example 175) was treated with HCl (0.08 mL, 0.081 mmol, 1M in Et₂O) to afford the title salt as a yellow solid.

EXAMPLE 157

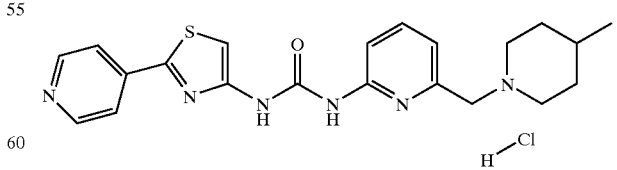

1-[6-(4-Methylpiperidin-1-ylmethyl)pyridin-2-yl]-3-(2-pyridin-4-yl-thiazol-4-yl)urea hydrochloride 1-[6-(4-Methylpiperidin-1-ylmethyl)pyridin-2-yl]-3-(2-pyridin-4-yl-thiazol-4-yl)urea (70 mg, 0.171 mmol, Example 65) was treated with HCl (0.19 mL., 0.188 mmol, 1M in Et₂O) to afford the title salt as a yellow solid.

EXAMPLE 158

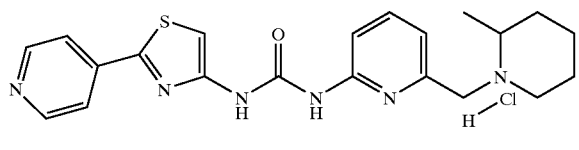

1-[6-(2-Methylpiperidin-1-ylmethyl)pyridin-2-yl]-3-(2-pyridin-4-yl-thiazol-4-yl)urea Hydrochloride 1-[6-(2-Methylpiperidin-1-ylmethyl)pyridin-2-yl]-3-(2-pyridin-4-yl-thiazol-4-yl)urea (70 mg, 0.171 mmol, Example 66) was treated with HCl (0.19 mL, 0.188 mmol, 1M in Et₂O) to afford the title salt as a yellow solid.

EXAMPLE 159

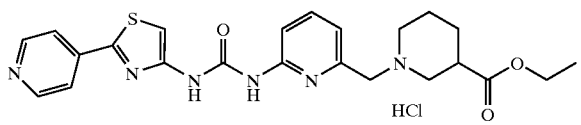

Ethyl 1-{6-[3-(2-pyridin-4-yl-thiazol-4-yl)ureido]-pyridin-2-ylmethyl}piperidine-3-carboxylate Hydrochloride HCl (0.21 mL, 0.212 mmol, 1.0 M soln in Et₂O) was added to ethyl 1-{6-[3-(2-pyridin-4-yl-thiazol-4-yl)ureido]-pyridin-2-ylmethyl}piperidine-3-carboxylate (90 mg, 0.193 mmol, Example 73) in a solution of MeOH (2 mL) to give a pale yellow solid.

EXAMPLE 160

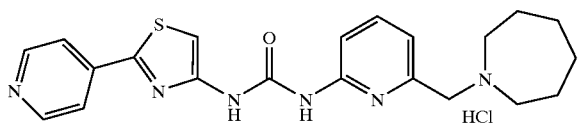

1-(6-Azepan-1-ylmethyl-pyridin-2-yl)-3-(2-pyridin-4-yl-thiazol-4-yl)urea Hydrochloride HCl (0.29 mL, 0.28 mmol, 1.0 M soln in Et₂O) was added to 1-(6-azepan-1-ylmethyl-pyridin-2-yl)-3-(2-pyridin-4-yl-thiazol-4-yl)urea (106 mg, 0.26 mmol, Example 71) in a solution of MeOH (4 mL) and the resulting mixture stirred 6 h. Concentration in vacuo gave a yellow solid.

EXAMPLE 161

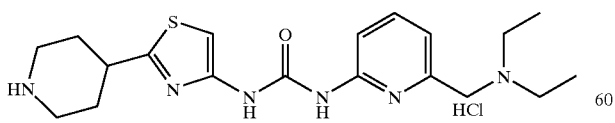

1-(6-Diethylaminomethyl-pyridin-2-yl)-3-(2-piperidin-4-yl-thiazol-4-yl)urea Hydrochloride HCl (27 µL, 0.026 mmol, 1.0 M soln in Et₂O) was added to 1-(6-diethylaminomethyl-pyridin-2-yl)-3-(2-piperidin-4-yl-thiazol-4-yl)urea (11 mg, 0.026 mmol, Example 179) in a solution of MeOH (1 mL) and the resulting mixture stirred 3 h. Concentration in vacuo gave a yellow solid.

EXAMPLE 162

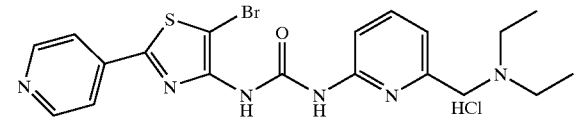

1-[5-Bromo-2-(pyridin-4-yl)thiazol-4-yl)-3-(6-diethylaminomethyl-pyridin-2-yl)urea Hydrochloride HCl (54 µL, 0.054 mmol, 1.0 M soln in Et₂O) was added to 1-[5-bromo-2-(pyridin-4-yl)thiazol-4-yl)-3-(6-diethylaminomethyl-pyridin-2-yl)urea (25 mg, 0.054 mmol, Example 180) in a solution of MeOH (0.5 mL) to give a yellow solid.

EXAMPLE 163

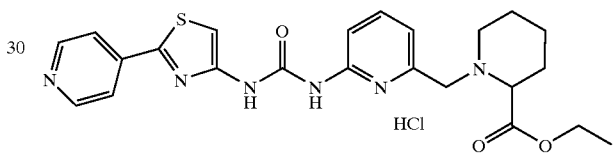

Ethyl 1-{6-[3-(2-pyridin-4-yl-thiazol-4-yl)-ureido]-pyridin-2-ylmethyl}-piperidine-2-carboxylate hydrochloride HCl (0.12 mL, 0.12 mmol, 1.0 M soln in Et₂O) was added to ethyl 1-[6-[3-(2-(pyridin-4-yl)thiazol-4-yl)ureido]-pyridin-2-ylmethyl]piperidine-2-carboxylate (50 mg, 0.11 mmol, Example 74) in a solution of MeOH (2 mL) to give a pale yellow solid.

EXAMPLE 164

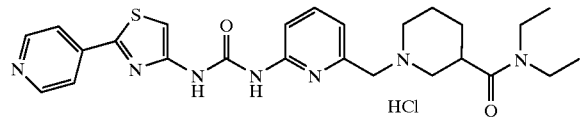

N,N-Diethyl 1-{6-[3-(2-pyridin-4-yl-thiazol-4-yl)-ureido]pyridin-2-ylmethyl}piperidine-3-carboxamide Hydrochloride HCl (0.15 mL, 0.156 mmol, 1.0 M soln in Et₂O) was added to N,N-diethyl 1-{6-[3-(2-pyridin-4-yl-thiazol-4-yl)-ureido]pyridin-2-ylmethyl}piperidine-3-carboxamide (70 mg, 0.142 mmol, Example 75) in a solution of MeOH (3 mL) to give a pale yellow solid.

EXAMPLE 165

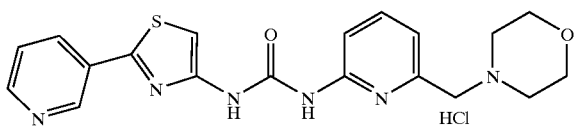

1-[6-(Morpholin-4-ylmethyl)-pyridin-2-yl]-3-[(2-pyridin-3-yl)thiazol-4-yl]urea Hydrochloride HCl (55 'L, 0.05 mmol, 1.0 M in Et$_2$O) was added to 1-[6-(morpholin-4-ylmethyl)-pyridin-2-yl]-3-[(2-pyridin-3-yl)thiazol-4-yl]urea (20 mg, 0.05 mmol, Example 180) in a solution of MeOH (1 mL) and the resulting mixture stirred 3 h. Concentration in vacuo gave a yellow solid.

The following Examples 166–167 were prepared from the corresponding protected amines in a manner similar to that described above for Example 157:

EXAMPLE 166

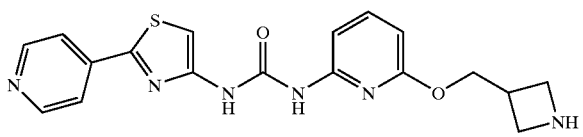

1-[6-(Azetidin-3-ylmethoxy)pyridin-2-yl]-3-[2-(pyridin-4-yl)thiazol-4-yl]urea

From tert butyl 3-{6-[3-(2-pyridin-4-yl-thiazol-4-yl)-ureido]-pyridin-2-yloxymethyl)-azetidine-1-carboxylate (Example 80) EI-MS m/z 382.2 (M+H). Calc'd for C$_{18}$H$_{18}$N$_6$O$_2$S: 382.12.

EXAMPLE 167

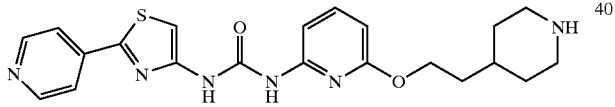

1-[6-(2-Piperidin-4-yl-ethoxy)pyridin-2-yl]-3-[2-(pyridin-4-yl)thiazol-4-yl]urea From tert-butyl 4-(2-{6-[3-(2-pyridin-4-yl-thiazol-4-yl)ureido]pyridin-2-yloxy}ethyl)piperidine-1-carboxylate (Example 81) MS m/z: 425 (M+1)+. Calc'd for C$_{21}$H$_{24}$N$_6$O$_2$S: 424.17.

EXAMPLE 168

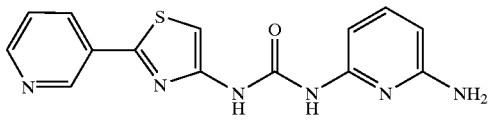

N-[2-(3-Pyridinyl)-4-thiazolyl]-N'-2-[6-aminopyridin-2-yl]urea

TEA (0.27 mL, 1.94 mmol) was added to a solution of 2-(pyridin-3-yl)thiazole-4-carboxylic acid (200 mg, 0.97 mmol) and 4A molecular sieves in THF (25 mL) under N$_2$ at RT. (PhO)$_2$PON$_3$ (0.33 mL, 1.55 mmol) followed by 2,6-diaminopyridine (265 mg, 2.43 mmol) was added and the resulting mixture was heated at reflux for 12 h. After cooling to RT, the heterogeneous mixture was decanted to remove the molecular sieves. The precipitate was collected, rinsing with EtOAc to give a light tan solid. MS m/z: 313.0 (M+H). Calc'd for C$_{14}$H$_{12}$N$_6$OS: 312.08.

The following compounds were prepared from the corresponding amines in a manner similar to that described above for Example 168:

EXAMPLE 169

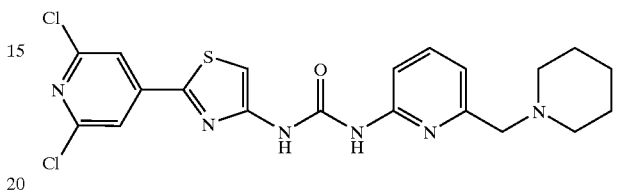

1-[2-(2,6-Dichloropyridin-4-yl)thiazol-4-yl]-3-[6-(piperidin-1-ylmethyl)pyridin-2-yl]urea 2-(2,6-Dichloropyridin-4-yl)thiazol-4-carboxylic acid (100 mg, 0.36 mmol), 2-amino-6-piperidinylmethyl-pyridine (76 mg, 0.39 mmol), (PhO)$_2$PON$_3$ (0.1 mL, 0.55 mmol), and TEA (0.08 mL, 0.55 mmol) were heated in toluene (15 mL) to yield the title compound as white solid. MS m/z: 464.3 (M+H). Calc'd. for C$_{20}$H$_{20}$Cl$_2$N$_6$OS-463.39.

EXAMPLE 170

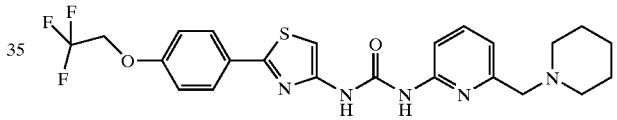

1-[6-(Piperidin-1-ylmethyl)pyridin-2-yl]-3-[2-[6-(2,2,2-trifluoroethoxy)pyridin-3-yl]thiazol-4-yl]urea 2-(4-Trifluoroethoxypyridin-4-yl)thiazolyl-4-carboxylic acid (150 mg, 0.49 mmol), 2-amino-6-piperidinylmethyl-pyridine (104 mg, 0.54 mmol), (PhO)$_2$PON$_3$ (0.16 mL, 0.74 mmol), and TEA (0.1 mL, 0.74 mmol) were heated in toluene (15 mL) to yield the title compound as white solid. MS m/z: 493.6 (M+H). Calc'd. for C$_{22}$H$_{23}$F$_3$N$_6$O$_2$S-492.52.

EXAMPLE 171

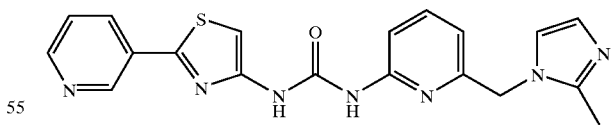

1-[6-(2-Methylimidazol-1-ylmethyl)pyridin-2-yl]-3-[2-(pyridin-3-yl)thiazol-4-yl]urea 2-(Pyridin-3-yl)-4-thiazole-4-carboxylic acid (75 mg, 0.36 mmol), 2-amino-6-[2-methylimidazol-1-yl]methyl-pyridine (75 mg, 0.40 mmol), (PhO)$_2$PON$_3$ (0.12 mL, 0.54 mmol), and TEA (0.1 mL, 0.54 mmol) were heated in toluene (15 mL) to yield the title compound as light brown solid. MS m/z: 392.3 (M+H). Calc'd. for C$_{19}$H$_{17}$N$_7$OS-391.45.

EXAMPLE 172

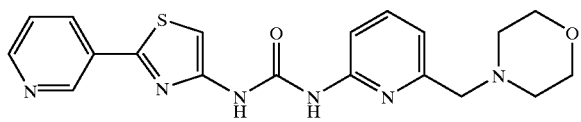

1-[6-(Morpholin-4-ylmethyl)-pyridin-2-yl]-3-[(2-pyridin-3-yl)thiazol-4-yl]urea

TEA (0.27 mL, 1.94 mmol) was added to a solution of 2-(pyridin-3-yl)thiazole-4-carboxylic acid (200 mg, 0.97 mmol) and 4A molecular sieves in THF (25 mL) under $N_2$ at RT. $(PhO)_2PON_3$ (0.33 mL, 1.55 mmol) followed by 2-amino, 6-morpholinylmethylpyridine (280 mg, 1.45 mmol) was added and the resulting mixture was heated at reflux for 12 h. After cooling to RT, the heterogeneous mixture was decanted to remove the molecular sieves. The precipitate was collected, rinsed with EtOAc and purified by chromatography on silica gel ($CH_2Cl_2$/MeOH, 95:5) to give a white solid. MS m/z: 397.1 (M+H). Calc'd. for $C_{19}H_{20}N_6O_2S$-396.47.

EXAMPLE 173

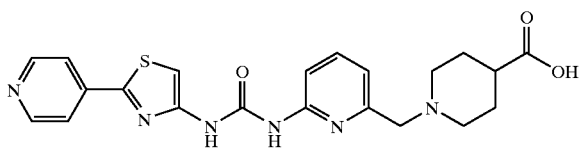

1-{6-[3-(2-(4-Pyridinyl)-4-thiazolyl)ureido]-pyridin-2-ylmethyl}-piperidine-4-carboxylic acid Ethyl 1-{6-[3-(2-(pyridin-4-yl)thiazol-4-yl)ureido]-pyridin-2-ylmethyl}-piperidine-4-carboxylate (55 mg, 0.12 mmol, Example 61) was suspended in MeOH (10 ml) followed by adding LiOH (50 mg, 1.18 mmol) in $H_2O$ (1 ml). The resulting mixture was heated at 45° C. for 15 h. After cooling to RT, the solvent was removed. The residue was suspended in $H_2O$ (20 mL). The pH was adjusted to 7 using HCl (1N). The resulting mixture was extracted with $CHCl_3$:IpOH (3:1). The organic layer was washed with $H_2O$ and brine. After being dried over anhydrous $MgSO_4$, the solvent was removed in vacuo to yield the final compound as light yellow solid. MS m/z: 438.7 (M+H). Calc'd. for $C_{21}H_{22}N_6O_3S$-438.51.

EXAMPLE 174

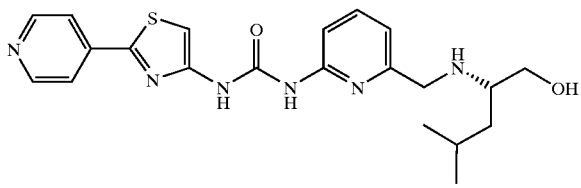

1-(6-[(1-Hydroxymethyl-3-methylbutylamino)methyl]-pyridin-2-yl}-3-(2-pyridin-4-yl-thiazol-4-yl)urea tert-Butyl (1-hydroxymethyl-3-methyl-butyl)-(6-[3-(2-pyridin-4-yl-thiazol-4-yl)-ureido]-pyridin-2-ylmethyl}- carbamate (165 mg, 0.313 mmol, Example 62) in MeOH (5 mL) was treated with HCl (0.16 mL, 0.627 mmol, 4M in dioxane). The resulting stirred solution was heated at 40° C. in a closed system for 15 h. After cooling to RT, the pH was adjusted to 7 using 1 N NaOH. Solvent was removed and the residue was extracted with $CHCl_3$. The organic layer was washed with $H_2O$, brine, dried over $MgSO_4$, and concentrated to yield a brown liquid crude product. This crude product was purified by chromatography on silica gel. Elution with $CH_2Cl_2$:MeOH mixture (95:5) gave the final compound as a tan solid. MS m/z: 427.2 (M+H). Calc'd. for $C_{21}H_{26}N_6O_2S$-426.54.

EXAMPLE 175

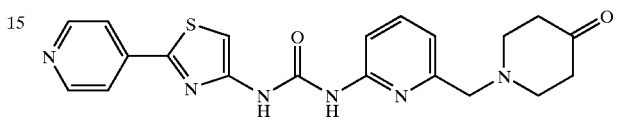

1-[6-(4-Oxo-piperidin-1-ylmethyl)pyridin-2-yl]-3-(2-pyridin-4-yl-thiazol-4-yl)urea N-[2-(4-Pyridinyl)-4-thiazolyl]-N'-2-[6-(4-ethoxyacetal)piperidylmethyl]urea (300 mg, 0.66 mmol) in THF (15 mL) was treated with 5N HCl (5 mL). The resulting mixture was heated to reflux under $N_2$ for 5 h. After cooling to RT, the mixture was basified using 5 N NaOH. Solvent was removed and the residue was extracted with $CHCl_3$. The organic layer was washed with $H_2O$, brine, dried over $MgSO_4$, and concentrated to yield a pale yellow solid. MS m/z: 409.3 (M+H). Calc'd. for $C_{20}H_{20}N_6O_2S$-408.32.

EXAMPLE 176

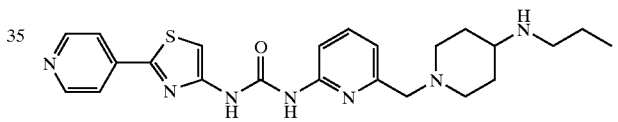

1-[6-[4-(Propylamino)piperidin-1-ylmethyl]pyridin-2-yl]-3-(2-pyridin-4-yl-thiazol-4-yl)urea To a suspension of N-[2-(4-pyridinyl)-4-thiazolyl]-N'-2-[6-(piperidon-4-yl)methyl]urea (50 mg, 0.12 mmol, Example 175) in MeOH (10 mL) was added propylamine (0.1 mL, 1.22 mmol). The resulting mixture was heated at 50° C. for 4 h under $N_2$. After the mixture was cooled to RT, $NaBH_4$ (83 mg, 2.20 mmol) was added. The mixture was stirred at RT under $N_2$ for 3 h. Solvent was removed in vacuo and the crude product was purified by chromatography on silica gel. Elution with $CH_2Cl_2$:MeOH (90:10) gave the title compound as a white solid. MS m/z: 451.7 (M+H). Calc'd. for $C_{23}H_{29}N_7OS$-451.6.

EXAMPLE 177

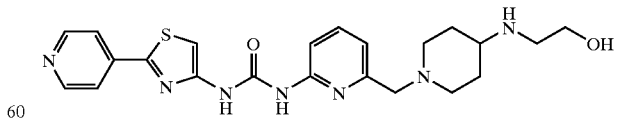

1-{6-[4-(2-Hydroxyethylamino)piperidin-1-ylmethyl]-pyridin-2-yl}-3-(2-pyridin-4-yl-thiazol-4-yl)urea N-[2-(4-Pyridinyl)-4-thiazolyl]-N'-2-[6-(piperidon-4-yl)methyl]urea (60 mg, 0.147 mmol, Example 175) and ethanolamine (0.09 mL, 1.47 mmol) were heated in MeOH (10 mL) yielded the title compound as pale yellow solid. MS m/z: 454.6 (M+H). Calc'd. for C$_{22}$H$_{27}$N$_{7}$O$_{2}$S-453.57.

EXAMPLE 178

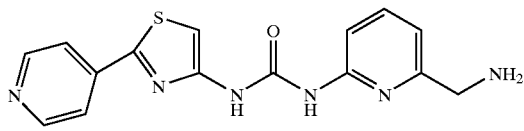

N-(6-Aminomethyl-2-pyridyl)-N'-[2-(4-pyridinyl)-4-thiazolyl]urea

Pd(OH)$_2$ (70 mg, 0.5 mmol) was suspended in EtOH (5 mL) followed by adding N-(6-azidomethyl-2-pyridyl)-N'-[2-(4-pyridinyl)-4-thiazolyl]urea (70 mg, 0.198 mmol, Example 69) in EtOH (8 mL). The resulting mixture was heated at 45° C. under H$_2$ balloon for 3 h. After cooling to RT, the mixture was filtered by passing through 2 layers of pleated filtered papers. Solvent was removed in vacuo to yield the final compound as a yellow solid. MS m/z: 327.3 (M+H). Calc'd. for C$_{15}$H$_{14}$N$_{6}$OS-326.38.

EXAMPLE 179

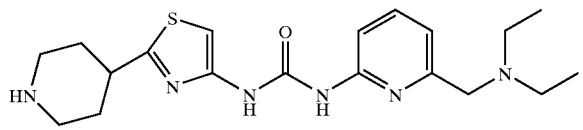

1-(6-Diethylaminomethyl-pyridin-2-yl)-3-(2-piperidin-4-yl-thiazol-4-yl)urea

Lithium triethylborohydride (0.84 mL, 0.84 mmol, 1.0 M in THF) was added to a solution of 1-(6-diethylaminomethyl-pyridin-2-yl)-3-(2-pyridin-4-yl-thiazol-4-yl)urea (100 mg, 0.24 mmol, Example 117) and DIEA (63 µL, 0.36 mmol) in THF (5 mL) and the resulting mixture was stirred 6 h at RT. The reaction was quenched via dropwise addition of MeOH and concentrated in vacuo. Purification by preparative HPLC (5–60% CH$_3$CN/H$_2$O) gave a white solid. MS m/z: 389.2 (M+H). Calc'd for C$_{19}$H$_{28}$N$_{6}$OS-388.53.

EXAMPLE 180

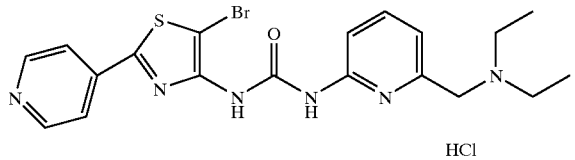

1-[5-Bromo-2-(pyridin-4-yl)thiazol-4-yl)-3-(6-diethylaminomethyl-pyridin-2-yl)urea Bromine (46 µL, 0.90 mmol) was added to a solution of 1-(6-diethylaminomethyl-pyridin-2-yl)-3-(2-pyridin-4-yl-thiazol-4-yl)urea (190 mg, 0.45 mmol, Example 117) in MeOH (8 mL) and the resulting solution was stirred at RT for 1 h. The reaction was quenched with saturated sodium bisulfite solution and concentrated in vacuo. The residue was dissolved in CHCl$_3$/IpOH (3/1, 10 mL) and washed with H$_2$O (3×10 mL) followed by 1N NaOH solution (10 mL). The organics were combined, dried over Na$_2$SO$_4$, and concentrated in vacuo to give a yellow solid. MS m/z: 461.1 (M+H). Calc'd for C$_{19}$H$_{21}$BrN$_{6}$OS-461.39.

EXAMPLE 181

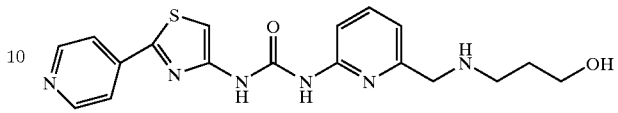

1-{6-[(3-Hydroxypropylamino)methyl]-pyridin-2-yl}-3-(2-pyridin-4-yl-thiazol-4-yl)urea Step A 2-(4-Pyridinyl)-4-thiazolcarbonylazide (220 mg, 0.78 mmol) and 2-amino-6-[(N'''-tert-butoxycarbonyl-N''-3-hydroxypropyl)amino]methylpyridine (196 mg, 0.94 mmol) in dry toluene (10 mL) were heated at 100° C. for 12 h to give a pale yellow solid which was purified by chromatography on silica gel (CH$_2$Cl$_2$/MeOH, 95:5) to give N-[2-(pyridin-4-yl)-4-thiazolyl]-N'-2-[6-(N'''-tert-butoxycarbonyl-N''-(3-hydroxypropyl)-amino]methyl-pyridinyl urea as a white solid. MS m/z: 485.2 (M+H). Calc'd for C$_{23}$H$_{28}$N$_{6}$O$_{4}$S-484.58.

Step B

HCl (112 µL, 0.112 mmol, 1.0 M in Et$_2$O) was added to a solution of N-[2-(pyridin-4-yl)-4-thiazolyl]-N'-2-[6-(N'-tert-butoxycarbonyl-N''-(3-hydroxypropyl)-amino] methylpyridinyl urea (25 mg, 0.051 mmol, Step A) in MeOH (1 mL) and the resulting mixture was heated at 45° C. for 12 h. A yellow precipitate formed and was filtered off, rinsing with hexane. The precipitate was added to CH$_2$Cl$_2$ (15 mL) and washed with 1N NaOH solution (5 mL). The organics were collected, dried over Na$_2$SO$_4$ and concentrated in vacuo to give a pale yellow solid. MS m/z: 385.0 (M+H). Calc'd for C$_{18}$H$_{20}$N$_{6}$O$_{2}$S-384.62.

EXAMPLE 182

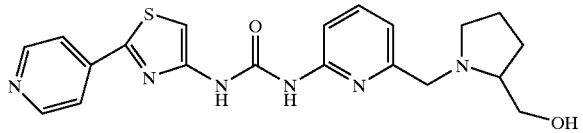

1-[6-(2-Hydroxymethylpyrrolidin-1-ylmethyl)-pyridin-2-yl]-3-(2-pyridin-4-yl-thiazol-4-yl)urea LiAlH$_4$ (3 mg, 0.079 mmol) was added to a solution of methyl 1-{6-[3-(2-pyridin-4-yl-thiazol-4-yl)ureido]-pyridin-2-ylmethyl}-pyrrolidine-2-carboxylate (15 mg, 0.034 mmol, Example 77) in THF (5 mL) at RT and the resulting mixture was stirred for 8 h. A precipitate formed and was collected. The solid was dissolved in CHCl$_3$ (5 mL) and washed with saturated NaHCO$_3$ solution (5 mL). The aqueous layer was adjusted to pH 7 with 1N HCl and extracted with CHCl$_3$. The organics were combined, dried over MgSO$_4$ and concentrated in vacuo to give a pale yellow solid. MS m/z: 411.1 (M+H). Calc'd for C$_{20}$H$_{22}$N$_{6}$O$_{2}$S-410.50.

EXAMPLE 183

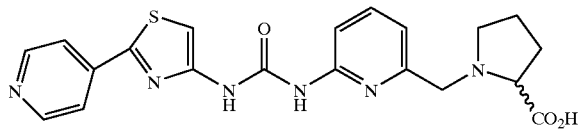

1-{6-[3-(2-Pyridin-4-yl-thiazol-4-yl)ureido]-pyridin-2-ylmethyl}-pyrrolidine-2-carboxylic Acid A 1.0 N NaOH solution (0.40 mL) was added to a solution of methyl 1-{6-[3-(2-pyridin-4-yl-thiazol-4-yl)ureido]-pyridin-2-ylmethyl}pyrrolidine-2-carboxylate (3 mg, 6.84 µM, Example 77) in MeOH (1 mL) and the resulting mixture was stirred at RT for 12 h. The mixture was adjusted to pH 7 with 1N HCl solution and concentrated in vacuo. The residue was dissolved in $CH_2Cl_2$ and a few drops of MeOH. A precipitate formed and was collected to give a white solid. MS m/z: 423.5 (M−H) Calc'd for $C_{20}H_{20}N_6O_3S$-424.48.

EXAMPLE 184

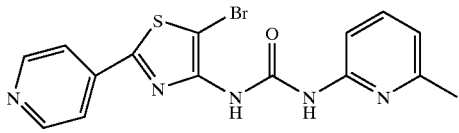

1-(5-Bromo-(2-pyridin-4-yl)thiazol-4-yl)-3-(6-methylpyridin-2-yl)urea

NBS (686 mg, 3.85 mmol) and AIBN (158 mg, 0.96 mmol) were added to a heterogeneous solution of 1-((2-pyridin-4-yl)thiazol-4-yl)-3-(6-methylpyridin-2-yl)urea (600 mg, 1.93 mmol, Example 6) in $CCl_4$ (25 mL) and the resulting mixture was heated at reflux for 2 h. After cooling to RT, a precipitate formed and was collected, rinsing with hexane to give a white solid. MS m/z: 392.0 (M+2H). Calc'd for $C_{15}H_{12}BrN_5OS$-390.26.

EXAMPLE 185

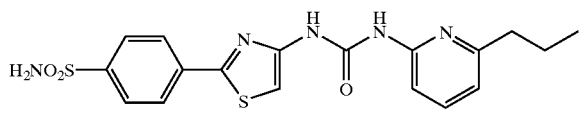

4-{4-[3-(6-Propyl-pyridin-2-yl)-ureido]-thiazol-2-yl}-benzenesulfonamide

In an oven-dried, 50-mL, round-bottomed flask were placed 2-(p-sulfamoylphenyl) thiazole-4-carboxylic acid (250 Mg/0.82 mmol), molecular sieves (800 mg) in THF (20 mL). To this mixture was added $Et_3N$ (0. 23 mL, 1. 64 mmol), followed by DPPA (0.28 mL, 1.28 mmol). The reaction was stirred for 5 min, then 6-propylpyridine-2-amine (280 mg, 2.06 mmol) was added. The suspension was heated to 75° C. for 14 h, cooled to RT, diluted with $H_2O$ (10 mL) and EtOAc (150 mL), and filtered to remove molecular sieves. The filtrate was concentrated in vacuo to give the crude product as a yellow solid which was filtered, washed with $H_2O$ (3×10 mL), EtOAc (1×10 mL) and $Et_2O$ (3×10 mL) to afford the title compound as a yellow solid. MS m/z: 418 (M+H). Calc'd for $C_{18}H_{19}N_5O_3S_2$: 417.09.

EXAMPLE 186

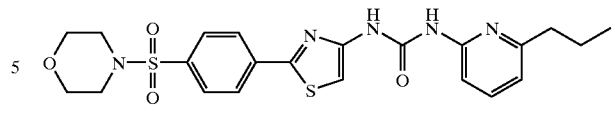

1-{2-[4-(4-Morpholinylsulfonyl)phenyl]thiazol-4-yl}-3-(6-propylpyridin-2-yl)urea In a manner similar to that described for the preparation of Example 185, 2-[(4-morpholinylsulfonyl)-phenyl] thiazole-4-carboxylic acid (354 mg) was treated with DPPA and 6-propylpyridine-2-amine to give the title compound. MS m/z: 488 (M+H). Calc'd for $C_{22}H_{25}N_5O_4S_2$: 487.13.

EXAMPLE 187

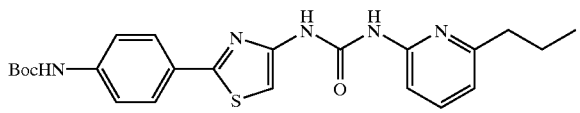

Tert-Butyl (4-{4-[3-(6-propylpyridin-2-yl)ureido]-thiazol-2-yl}phenyl)carbamate

In a manner similar to that described for the preparation of Example 185, 2-[4-[N-Boc-amino]-phenyl]-thiazole-4-carboxylic acid (130 mg) was treated with DPPA and 6-propylpyridine-2-amine to give the title compound. MS m/z: 454.5 (M+H). Calc'd for $C_{23}H_{27}N_5O_3S$: 453.18.

EXAMPLE 188

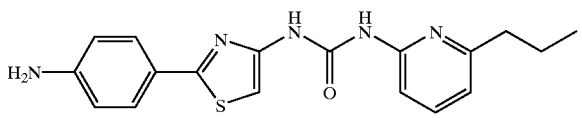

1-[2-(4-Aminophenyl)thiazol-4-yl]-3-(6-propylpyridin-2-yl)urea

In an oven-dried, 25-mL, round-bottomed flask were placed N-[6-propylpyridine]-N'-[4-[N-Bocamino]pheny]-4-thiazolyl]urea (55 mg, 0.12 mmol, Example 187), thioanisole (0.35 mL) in $CH_2Cl_2$ (10 mL). TFA (0.35 mL) was added, the mixture was stirred at RT for 6 h then concentrated in vacuo. Purification by flash chromatography on silica gel [EtOAc/hexane (extracted with aq. $NH_4OH$), 40:60] afforded the title compound. MS m/z: 354.0 (M+H). Calc'd for $C_{18}H_{19}N_5OS$: 353.13.

EXAMPLE 189

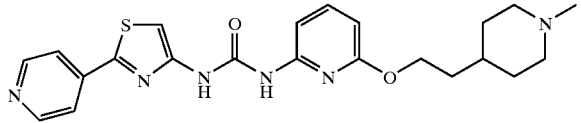

1-{6-[2-(1-Methylpiperidin-4-yl)ethoxy]pyridin-2-yl}-3-(2-pyridin-4-yl-thiazol-4-yl)urea A mixture of N-[2-(4-pyridinyl)-4-thiazolyl]-N'-2-[6-(4-piperidinylethoxy)pyridinyl]urea (0.17 g, 0.40 mmol, Example 167), paraformaldehyde (0.17 g), and NaBH(OAc)₃ (0.21 g, 1.0 mmol) in 40 mL of CH₂Cl₂ was stirred at RT under N₂ for 12 h. After 12 h, the solvent was removed in vacuo, and the residue was diluted with 20 mL of H₂O, then extracted with CHCl₃/IpOH (3:1, 3×20 mL). The combined organic portions were washed with brine, and dried over MgSO₄, and the solvents were removed in vacuo to yield a residue. Purification over silica gel (gradient, 5% to 7.5% MeOH/CH₂Cl₂ with 0.5% of TEA) provided the title compound as an off-white solid. MS m/z: 439 (M+H). Calc'd for C₂₂H₂₆N₆O₂S: 438.18.

EXAMPLE 190

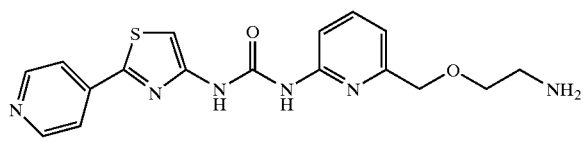

1-[6-(2-Aminoethoxymethyl)pyridin-2-yl]-3-(2-pyridin-4-yl-thiazol-4-yl)urea

Prepared in a manner similar to that described in Example 189. MS m/z: 371 (M+H). Calc'd for C₁₇H₁₈N₆O₂S: 370.12.

EXAMPLE 191

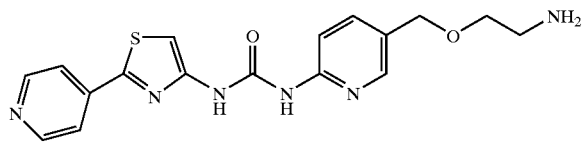

1-[5-(2-Aminoethoxymethyl)pyridin-2-yl]-3-(2-pyridin-4-yl-thiazol-4-yl)urea

Prepared in a manner similar to that described in Example 189. MS m/z: 371 (M+H). Calc'd for C₁₇H₁₈N₆O₂S: 370.12.

EXAMPLE 192

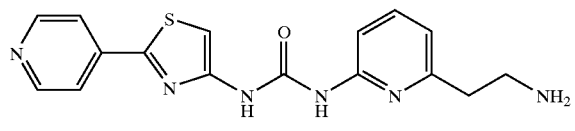

1-{6-[2-Aminoethyl]pyridin-2-yl}-3-(2-pyridin-4-yl-thiazol-4-yl)urea

To a mixture of 1-{6-[2-(phthalimidyl)ethyl]-pyridin-2-yl}-3-(2-pyridin-4-yl-thiazol-4-yl)urea (75 mg, 0.16 mmol, Example 88) and EtOH (10 mL) was added hydrazine hydrate (0.1 mL, 0.18 mmol). The mixture was heated at reflux for 2 h then cooled to RT. The residue was dissolved in 3:1 CHCl₃/IpOH, washed with saturated NaHCO₃, dried (MgSO₄) and concentrated in vacuo to afford the title compound as a yellow solid. MS m/z: 341.0 (M+H). Calc'd for C₁₆H₁₆N₆OS: 340.11.

EXAMPLE 193

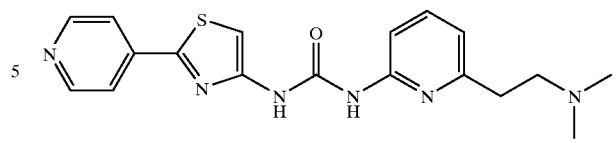

1-{6-[2-(N,N-Dimethylamino)ethyl]pyridin-2-yl}-3-(2-pyridin-4-yl-thiazol-4-yl)urea To a solution of 1-{6-[2-aminoethyl]pyridin-2-yl}-3-(2-pyridin-4-yl-thiazol-4-yl)urea (20 mg, 0.06 mmol, Example 192) and CH₂Cl₂ (5 mL) was added paraformaldehyde (20 mg) and NaBH(OAc)₃ (30 mg, 0.14 mmol). The mixture was stirred at RT for 2.5 h. Extracted with 3:1 CHCl₃/IpOH and washed with brine, dried (MgSO₄) and concentrated in vacuo to afford the desired compound as a yellow solid. MS m/z: 369.1 (M+H). Calc'd for C₁₈H₂₀N₆OS: 368.14.

EXAMPLE 194

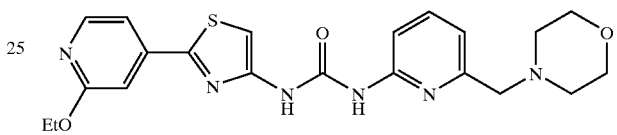

1-[2-(2-Ethoxypyridin-4-yl)thiazol-4-yl]-3-(6-morpholin-4-ylmethyl-pyridin-2-yl)urea To a mixture of 1-[2-(2-chloropyridin-4-yl)thiazol-4-yl]-3-(6-morpholin-4-ylmethyl-pyridin-2-yl)urea (100 mg, 0.23 mmol, Example 90) and EtOH (50 mL) was added a 21 wt % NaOEt/EtOH solution (0.4 mL, 1.2 mmol) and DMF (2 mL). The mixture was heated to reflux for 15 h then additional 21 wt % NaOEt/EtOH solution (10 mL) were added. After 2.5 h, the reaction was complete as judged by LC/MS. The reaction mixture was concentrated in vacuo then diluted with EtOAc and the solid was filtered off. The filtrate was concentrated in vacuo to afford an orange slushy oil which was purified by silica flash chromatography (5–10% MeOH/CH₂Cl₂) to afford the title compound as a yellow solid. MS m/z: 441.1 (M+H). Calc'd for C₂₁H₂₄N₆O₃S: 440.16.

EXAMPLE 195

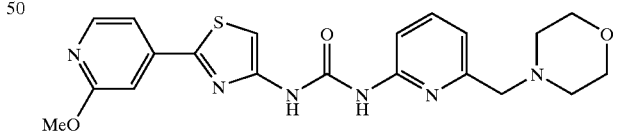

1-[2-(2-Methoxypyridin-4-yl)thiazol-4-yl]-3-(6-morpholin-4-ylmethyl-pyridin-2-yl)urea To a mixture of 1-[2-(2-chloropyridin-4-yl)thiazol-4-yl]-3-(6-morpholin-4-ylmethyl-pyridin-2-yl)urea (100 mg, 0.23 mmol, Example 90) and MeOH (50 mL) was added solid NaOMe (1.6 g, 29.6 mmol) and DMF (20 mL). The reaction mixture was heated to 130° C. After 2 h, the reaction mixture was cooled to RT and filtered. The filtrate was concentrated in vacuo and diluted with EtOAc and filtered to remove the solid. The filtrate was concentrated in vacuo to afford an orange oil which was purified by silica flash chromatography (5% MeOH/CH$_2$Cl$_2$) to afford the title compound as a white solid. MS m/z: 427.2 (M+H). Calc'd for C$_{20}$H$_{22}$N$_6$O$_3$S: 426.15.

EXAMPLE 196

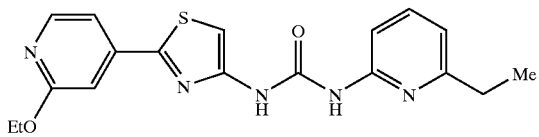

1-[2-(2-Ethoxypyridin-4-yl)thiazol-4-yl]-3-(6-ethyl-pyridin-2-yl)urea

To a 10 mL round bottom flask containing 1-[2-(2-chloropyridin-4-yl)thiazol-4-yl]-3-(6-ethylpyridin-2-yl)urea (40 mg, 0.11 mmol) (prepared similar to that described for Example 95) was charged a 21 wt % NaOEt/EtOH solution (5 mL). The reaction mixture was heated to reflux. After 2 h, the reaction mixture was cooled to RT and diluted with H$_2$O then concentrated in vacuo. The solid residue was washed with CH$_2$Cl$_2$ and EtOAc then the solid was diluted with MeOH and concentrated in vacuo. The residue was diluted with EtOAc; washed with saturated NH$_4$Cl and H$_2$O, dried (MgSO$_4$) and concentrated in vacuo to afford the title compound as a light-orange solid. MS m/z: 370.2 (M+H). Calc'd for C$_{18}$H$_{19}$N$_5$O$_2$S: 369.13.

EXAMPLE 197

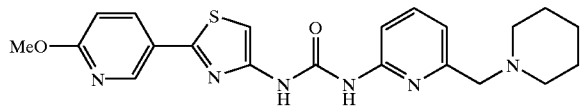

1-[2-(6-Methoxypyridin-3-yl)thiazol-4-yl]-3-(6-piperidin-1-ylmethyl-pyridin-2-yl)urea To a solution of the 3-(4-methoxy-3-pyridyl)thiazole carboxylic acid (200 mg, 0.85 mmol) and dry toluene (20 mL) was added (PhO)$_2$PON$_3$ (0.2 mL, 0.94 mmol) and TEA (0.13 mL, 0.94 mmol). The mixture was heated to 85° C. for five min then 2-amino-6-methylpiperdinylpyridine (0.16 g, 0.85 mmol) in CH$_3$CN (3 mL) was added. The reaction was heated at reflux for 15 h then concentrated in vacuo and purified by silica flash chromatography (1% to 5% MeOH/CH$_2$Cl$_2$) to give the title compound as an orange oil. Diluted with MeOH (5 mL) and added one equivalent of 1M HCl in Et$_2$O. Concentrated in vacuo to afford the HCl salt as an orange solid. MS m/z: 424.9 (M+H). Calc'd for C$_{21}$H$_{24}$N$_6$O$_2$S: 424.17.

EXAMPLE 198

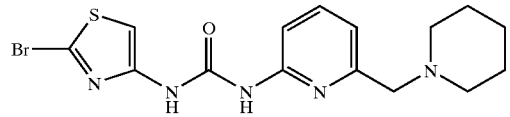

1-(2-Bromothiazol-4-yl)-3-(6-piperidin-1-ylmethyl-pyridin-2-yl)urea

To a stirred suspension of 2-bromothiazole-4-carboxylic acid (5.13 g, 2 mmol) in anhydrous CH$_3$CN (40 ml) at RT, under N$_2$, TEA (3.80 ml, 27 mmol) and (PhO)$_2$PON$_3$ (5.90 ml, 27 mmol) were added. The resulting solution was heated to 85° C. Upon reaching 85° C., a solution of 6-(piperidylmethyl)-2-pyridylamine (4.74 g, 25 mmol) in anhydrous CH$_3$CN (60 ml) was added. The reaction was maintained at this temperature for 2.25 h. After cooling to RT the mixture was diluted with CH$_2$Cl$_2$ (50 ml) then washed with a saturated solution of NH$_4$Cl(aq) (40 ml). The organic layer was separated, dried over MgSO$_4$, filtered and concentrated under reduced pressure. The residue was purified by flash chromatography on silica gel (3:1/2:1/1:1, EtOAc:acetone) to yield the title compound as a pale yellow solid. MS m/z: 396 (M+H), 398 (M+3). Calc'd for C$_{15}$H$_{18}$BrN$_5$OS: 395.04.

EXAMPLE 199

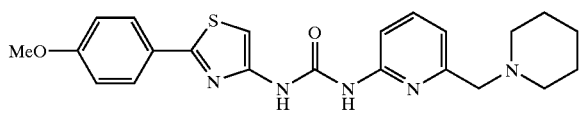

1-[2-(4-Methoxyphenyl)thiazol-4-yl]-3-(6-piperidin-1-ylmethyl-pyridin-2-yl)urea

A stirred suspension of N-(2-bromo(1,3-thiazol-4-yl)){6-(piperidylmethyl)(2-pyridyl)]amino}carboxamide (2.23 g, 5.64 mmol), 4-methoxyphenylboronic acid (0.94 g, 6.21 mmol), PdCl$_2$(dppf)$_2$ (0.46 g, 0.56 mmol) and Na$_2$CO$_3$ (2.10 g, 17.0 mmol) in ethylene glycol dimethyl ether (25 ml) and H$_2$O (8 ml) was heated at reflux for 12 h. After cooling to RT the mixture was filtered through Celite®. The filtrate was concentrated under reduced pressure. The crude product was purified by flash chromatography on silica gel (3:1, EtOAc:acetone) to yield the title compound as a pale yellow amorphous solid. MS m/z: 424 (M+H). Calc'd for C$_{22}$H$_{25}$N$_5$O$_2$S: 423.17.

The following compounds were prepared from the corresponding boronic acids in a manner similar to Example 199:

EXAMPLE 200

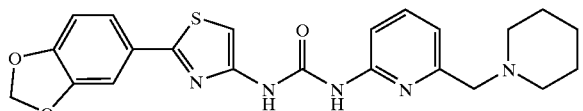

1-(2-Benzo[1,3]dioxol-5-yl-thiazol-4-yl)-3-(6-piperidin-1-ylmethyl-pyridin-2-yl)-urea MS m/z: 438 (M+H). Calc'd for C$_{22}$H$_{23}$N$_5$O$_3$S: 437.15.

EXAMPLE 201

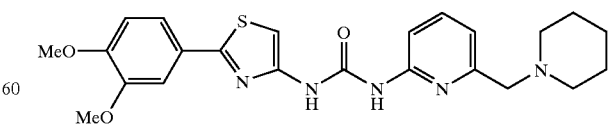

1-[2-(3,4-Dimethoxyphenyl)thiazol-4-yl]-3-(6-piperidin-1-ylmethyl-pyridin-2-yl)urea MS m/z: 454 (M+H). Calc'd for C$_{23}$H$_{27}$N$_5$O$_3$S: 453.18.

EXAMPLE 202

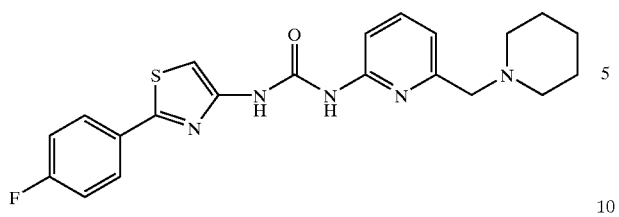

1-[2-(4-Fluorophenyl)thiazol-4-yl]-3-(6-piperidin-1-ylmethyl-pyridin-2-yl)urea

EI-MS m/z 412 (M+H). Calc'd for $C_{21}H_{22}FN_5OS$: 411.15.

EXAMPLE 203

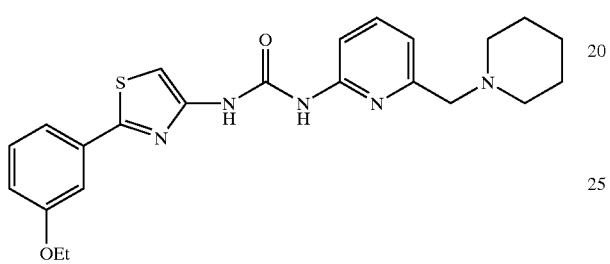

1-[2-(3-Ethoxyphenyl)thiazol-4-yl]-3-(6-piperidin-1-ylmethyl-pyridin-2-yl)urea

EI-MS m/z 438 (M+H). Calc'd for $C_{23}H_{27}N_5O_2S$: 437.19.

EXAMPLE 204

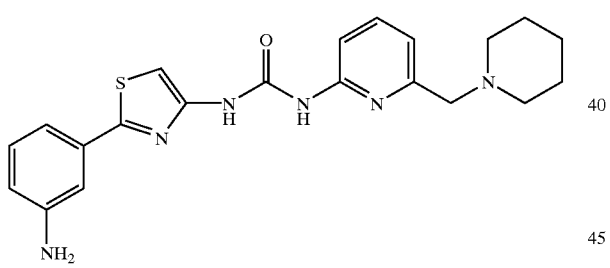

1-[2-(3-Aminophenyl)thiazol-4-yl]-3-(6-piperidin-1-ylmethyl-pyridin-2-yl)urea

EI-MS m/z 409 (M+H). Calc'd for $C_{21}H_{24}N_6OS$: 408.17.

EXAMPLE 205

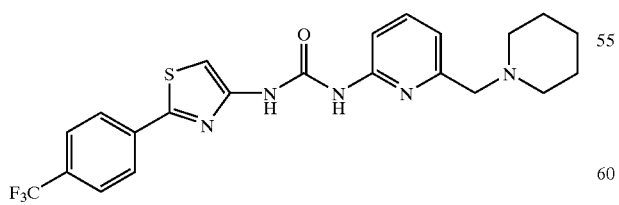

1-[2-(4-Trifluoromethylophenyl)thiazol-4-yl]-3-(6-piperidin-1-ylmethyl-pyridin-2-yl)urea EI-MS m/z 462 (M+H). Calc'd for $C_{22}H_{22}F_3N_5OS$: 461.15.

EXAMPLE 206

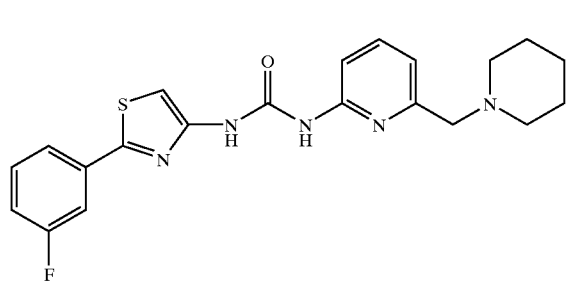

1-[2-(3-Trifluoromethylophenyl)thiazol-4-yl]-3-(6-piperidin-1-ylmethyl-pyridin-2-yl) urea EI-MS m/z 462 (M+H)$^+$. Calc'd for Calc'd for $C_{22}H_{22}F_3N_5OS$: 461.15.

EXAMPLE 207

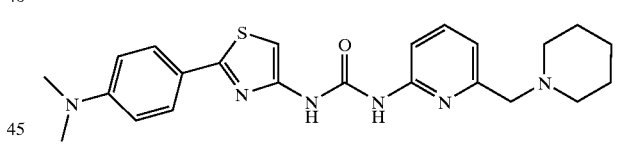

1-[2-(3-Fluorophenyl)thiazol-4-yl]-3-(6-piperidin-1-ylmethyl-pyridin-2-yl)urea

EI-MS m/z 412 (M+H). Calc'd for Calc'd for $C_{21}H_{22}FN_5OS$: 411.15.

EXAMPLE 208

1-[2-(4-Dimethylaminophenyl)thiazol-4-yl]-3-(6-piperidin-1-ylmethyl-pyridin-2-yl)urea EI-MS m/z 437 (M+H). Calc'd for $C_{23}H_{28}N_6OS$: 436.20.

EXAMPLE 209

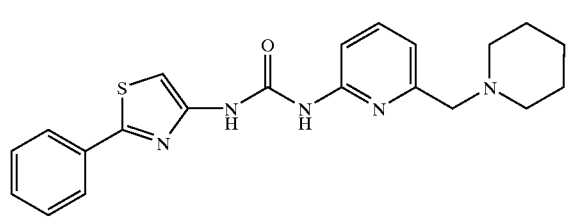

1-[2-phenylthiazol-4-yl]-3-(6-piperidin-1-ylmethyl-pyridin-2-yl)urea

EI-MS m/z 394 (M+H). Calc'd for $C_{21}H_{23}N_5OS$: 393.16.

EXAMPLE 210

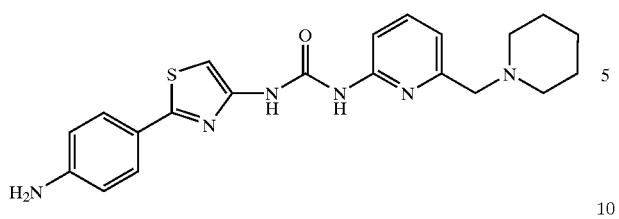

1-[2-(4-Aminophenyl)thiazol-4-yl]-3-(6-piperidin-1-ylmethyl-pyridin-2-yl)urea

EI-MS m/z 409 (M+H). Calc'd for $C_{21}H_{24}N_5OS$: 408.17.

EXAMPLE 211

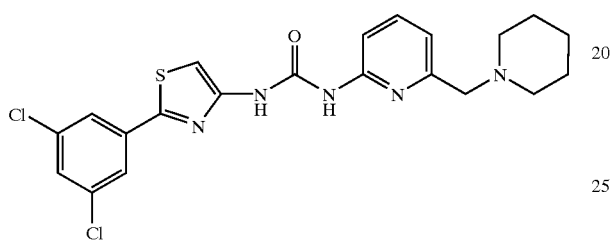

1-[2-(3,5-Dichlorophenyl)thiazol-4-yl]-3-(6-piperidin-1-ylmethyl pyridin-2-yl)urea EI-MS m/z 462 (M+H). Calc'd for $C_{21}H_{21}Cl_2N_5OS$: 461.08.

EXAMPLE 212

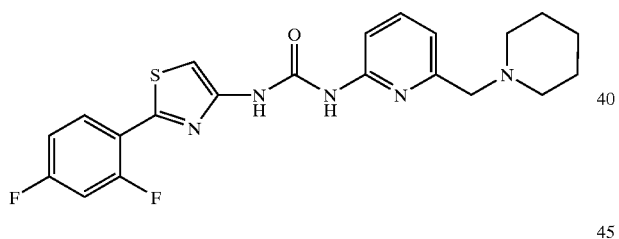

1-[2-(2,4-Difluorophenyl)thiazol-4-yl]-3-(6-piperidin-1-ylmethyl-pyridin-2-yl)urea EI-MS m/z 430 (M+H). Calc'd for $C_{21}H_{21}F_2N_5OS$: 429.14.

EXAMPLE 213

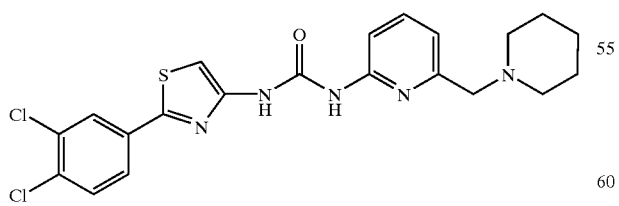

1-[2-(3,4-Dichlorophenyl)thiazol-4-yl]-3-(6-piperidin-1-ylmethyl-pyridin-2-yl)urea EI-MS m/z 462 (M+H). Calc'd for $C_{21}H_{21}Cl_2N_5OS$: 461.08.

EXAMPLE 214

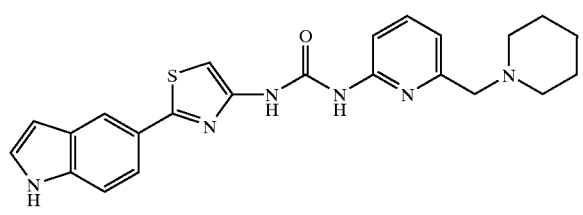

1-[2-(1H-Indol-5-yl)-thiazol-4-yl]-3-(6-piperidin-1-ylmethyl-pyridin-2-yl)-urea

EI-MS m/z 433 (M+H). Calc'd for $C_{23}H_{24}N_6OS$: 432.17.

EXAMPLE 215

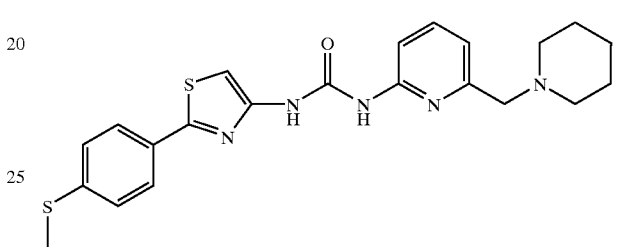

1-[2-(4-Methylthiophenyl)thiazol-4-yl]-3-(6-piperidin-1-ylmethyl-pyridin-2-yl)urea EI-MS m/z 440 (M+H). Calc'd for $C_{22}H_{25}N_5OS_2$: 439.15.

EXAMPLE 216

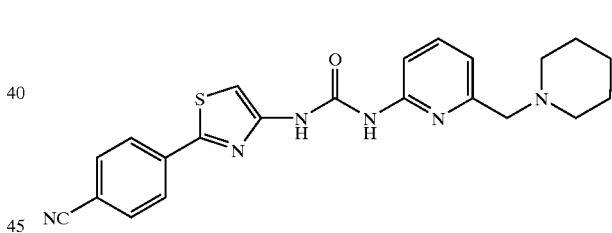

1-[2-(4-Cyanophenyl)thiazol-4-yl]-3-(6-piperidin-1-ylmethyl-pyridin-2-yl)urea

EI-MS m/z 419 (M+H). Calc'd for $C_{22}H_{22}N_6OS$: 418.16

EXAMPLE 217

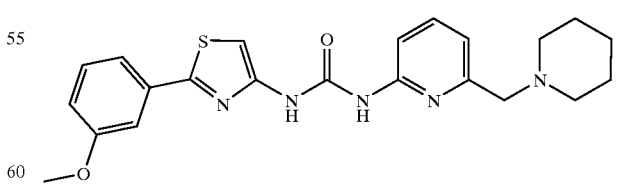

1-[2-(3-Methoxyphenyl)thiazol-4-yl]-3-(6-piperidin-1-ylmethyl-pyridin-2-yl)urea

To a stirred solution of 2-(3-methoxyphenyl)-1,3-thiazole-4-carboxylic acid (0.17 g, 0.72 mmol) in toluene (10 mL) at RT and under $N_2$ was added TEA (0.2 mL). After 5 min, $(PhO)_2PON_3$ (0.2 5 mL) was added and the reaction mixture was heated at 85° C. for 20 min followed by the addition of 6-(piperidylmethyl)-2-pyridylamine (0.21 g, 1.1 mmol). The resulting mixture was heated at reflux for 4 h using a Dean-Stark trap. The mixture was cooled to RT, concentrated by rotary evaporation and purified on silica gel (5:95 MeOH/$CH_2Cl_2$). The yellow solid obtained was dissolved in EtOAc (15 mL) and washed with a saturated solution of $NH_4Cl$ (aq). The organic phase was separated, dried over $MgSO_4$, filtered and concentrated by rotary evaporation. The product was recrystallized from hexanes to afford the title compound as a white solid. EI-MS m/z 424 (M+H). Calc'd for $C_{22}H_{25}N_5O_2S$: 423.17.

EXAMPLE 218

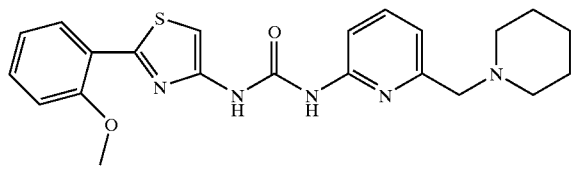

1-[2-(2-Methoxyphenyl)thiazol-4-yl]-3-(6-piperidin-1-ylmethyl-pyridin-2-yl)urea

To a stirred solution of 2-(2-methoxyphenyl)-1,3-thiazole-4-carboxylic acid (0.22 g, 0.94 mmol) in toluene (10 mL) at RT and under $N_2$ was added TEA (0.3 mL). After 5 min, $(PhO)_2PON_3$ (0.32 mL) was added and the reaction mixture was heated at 85° C. for 20 min followed by the addition of 6-(piperidylmethyl)-2-pyridylamine (0.27 g, 1.41 mmol). The resulting mixture was heated at reflux for 4 h using a Dean-Stark trap. The mixture was cooled to RT, concentrated by rotary evaporation and purified on silica gel (5:95 MeOH/$CH_2Cl_2$). The yellow solid obtained was dissolved in EtOAc (15 mL) and washed with saturated $NH_4Cl$ (10 mL). The organic phase was separated, dried over $MgSO_4$, filtered and concentrated by rotary evaporation to afford the title compound as a pale-yellow solid. EI-MS m/z 424 (M+H). Calc'd for $C_{22}H_{25}N_5O_2S$: 423.17.

EXAMPLE 219

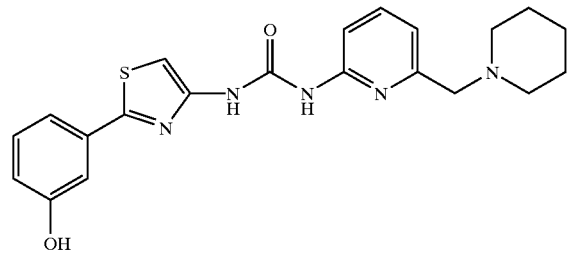

1-[2-(3-Hydroxyphenyl)thiazol-4-yl]-3-(6-piperidin-1-ylmethyl-pyridin-2-yl)urea

A mixture of 1-[2-(3-methoxyphenyl)thiazol-4-yl]-3-(6-piperidin-1-ylmethyl-pyridin-2-yl)urea (Example 218) and beryllium chloride (5.0 eq) in dry toluene (0.2 M) and 4A molecular sieves was heated at reflux for 10 h. The starting material was not totally soluble in toluene. The mixture was brought to RT, diluted with EtOAc and washed with saturated $NH_4Cl$. The organic phase was separated, dried over $MgSO_4$, filtered, concentrated by rotary evaporation and purified by prep HPLC (Column Phenomenex type Prodigy 50 ODS3 100A size 250×21.20 mm 5u, Gradient 10% to 90% $CH_3CN$:$H_2O$ containing 1% TFA over 20 min, Detector 254 nm, 4 nm Band) to afford the title compound as an off white solid. EI-MS m/z 410 (M+H). Calc'd for $C_{21}H_{23}N_5O_2S$: 409.16.

EXAMPLE 220

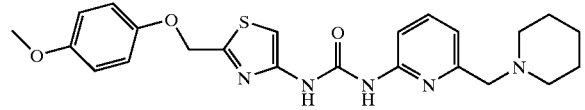

1-[2-(4-Methoxyphenoxymethyl)thiazol-4-yl]-3-(6-piperidin-1-ylmethyl-pyridin-2-yl)urea To a stirred solution of 2-[(4-methoxyphenoxy)-methyl]-1,3-thiazole-4-carboxylic acid (0.10 g, 0.38 mmol) and TEA (0.06 mL, 0.46 mmol) in dry toluene (15 mL) and 4A° molecular sieves was added $(PhO)_2PON_3$ (0.10 mL, 0.46 mmol). The resulting mixture was heated at 85° C. for 25 min followed by the addition of 6-(piperidyl-methyl)-2-pyridylamine (0.09 g, 0.46 mmol). The resulting mixture was heated to reflux for 15 h, cooled to RT, filtered, concentrated by rotary evaporation and purified on silica gel (5:95 MeOH/$CH_2Cl_2$) to afford the title compound as a yellow oil. EI-MS m/z 454 (M+H). Calc'd for $C_{23}H_{27}N_5O_3S$: 453.18.

EXAMPLE 221

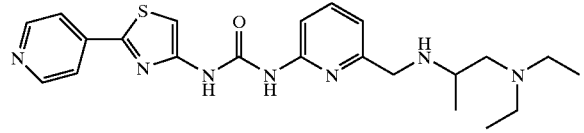

1-{6-[(2-Diethylamino-1-methylethylamino)methyl]-pyridin-2-yl}-3-(2-pyridin-4-yl-thiazol-4-yl)urea Step A To a stirred solution of N-[(6-amino(2-pyridyl))methyl]-N-[2-(diethylamino)-isopropyl](tert-butoxy)-carboxamide (30 mg, 0.09 mmol) in toluene (5 mL) was added 2-aza-2-diazo-1-(2-(4-pyridyl)(1,3-thiazol-4-yl))ethen-1-one (0.02 g, 0.09 mmol). The resulting green solution was heated to reflux in a Dean-Stark trap for 1.5 h until the starting materials were consumed. The mixture was brought to RT, concentrated by rotary evaporation and the residue obtained was partitioned between $H_2O$ (10 mL) and $CHCl_3$ (10 ml). The organic phase was separated and the aqueous phase was extracted (3×10 ml) with $CHCl_3$. The organic layers were combined, dried over $MgSO_4$, filtered, concentrated by rotary evaporation and purified by prep TLC (10:90 MeOH/$CH_2Cl_2$) to afford tert butyl (2-dimethylamino-1-methyl-ethyl)-(6-[3-(2-pyridin-4-yl-thiazol-4-yl)ureido]pyridin-2-yl}carbamate as a white solid. EI-MS m/z 540 (M+H). Calc'd for $C_{27}H_{37}N_7O_3S$: 539.27.

Step B

To a stirred solution of N-[2-diethylamino)-ethyl](tert-butoxy)-N-[(6-{[N-(2-(4-pyridyl)(1,3-thiazol-4-yl))carbamoyl]amino}(2-pyridyl))methyl]-carboxamide (4 mg, 0.007 mmol) in dry $CH_2Cl_2$ (1 mL) was added TFA (1 mL).

The resulting solution was stirred at RT and under N₂ atmosphere for 2 h, concentrated by rotary evaporation and the residue was diluted with EtOAc (5 mL) and washed with a saturated solution of NaHCO₃ (aq) (15 mL). The organic phase was separated, dried over MgSO₄, filtered, concentrated by rotary evaporation and purified by prep TLC (1:1 MeOH/CH₂Cl₂) to yield 1-{6-[(2-diethylamino-1-methylethylamino)methyl]-pyridin-2-yl}-3-(2-pyridin-4-yl-thiazol-4-yl)urea. EI-MS m/z 540 (M+H). Calc'd for $C_{22}H_{29}N_7OS$: 439.22.

EXAMPLE 222

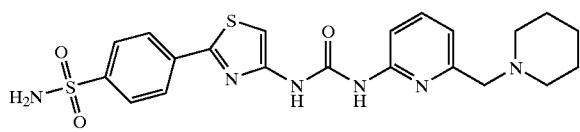

4-{4-[3-(6-Piperidin-1-ylmethyl-pyridin-2-yl)-ureido]-thiazol-2-yl)-benzenesulfonamide To a stirred solution of ethyl 2-(4-sulfamoyl-phenyl)-1,3-thiazole-4-carboxylic acid (90 mg, 0.32 mmol) in dry TFA (3 mL) and 4A molecular sieves at RT and under N₂ was added TEA (0.1 mL). After 5 min, (PhO)₂PON₃ (0.11 mL) and 6-(piperidylmethyl)-2-pyridylamine (0.10 g, 0.51 mmol) were added and the reaction mixture was heated to reflux for 4 h and then cooled to RT. The mixture was washed with 10% HCl (aq) and extracted with EtOAc (3×10 mL). The aqueous layer was brought to a pH 8.0 and extracted with CH₂Cl₂ (3×20 mL) The extracts were combined, dried over MgSO₄, concentrated by rotary evaporation and purified on silica gel (2:1 hexanes/EtOAc and 1:1 MeOH/CH₂Cl₂) to afford the title compound as a pale yellow solid. EI-MS m/z 473 (M+H). Calc'd for $C_{21}H_{24}N_6O_3S_2$: 472.14.

EXAMPLE 223

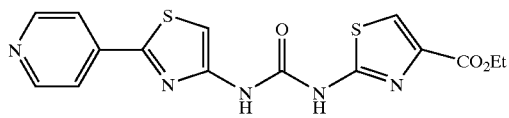

Ethyl 2-[3-[2-(pyridin-4-yl)-thiazol-4-yl]ureido]-thiazole-4-carboxylate 2-(4-Pyridinyl)-4-thiazolcarbonylazide (420 mg, 1.8 mmol) in dry toluene (20 mL) was heated to 85° C. under N₂ and maintained at this temperature for 5 min. A solution of 2-amino-4-thiazolcarboxylic acid ethyl ester (350 mg, 2.0 mmol) was added and the resulting mixture was heated at 85° C. for 15 h. After cooling to RT, a precipitate formed and was filtered to give the desired compound as a yellow solid. MS m/z: 376.0 (M+H). Calc'd for $C_{15}H_{13}N_5O_3S_2$: 375.05.

EXAMPLE 224

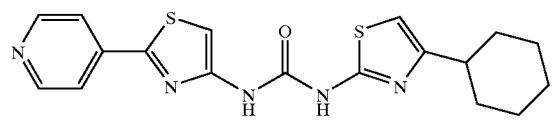

1-(4-Cyclohexylthiazol-2-yl)-3-[2-(pyridin-4-yl)-thiazol-4-yl]urea 2-(4-Pyridinyl)-4-thiazolcarbonylazide (200 mg, 0.87 mmol) in dry toluene (10 mL) was heated to 85° C. under N₂ and maintained at this temperature for 5 min. A solution of 2-amino-4-cyclohexylthiazole (158 mg, 0.87 mmol) was added and the resulting mixture was heated at 85° C. for 15 h. After cooling to RT, a precipitate formed and was filtered to give the desired compound as a yellow solid. MS m/z: 386.0 (M+H). Calc'd for $C_{18}H_{19}N_5OS_2$: 385.10.

EXAMPLE 225

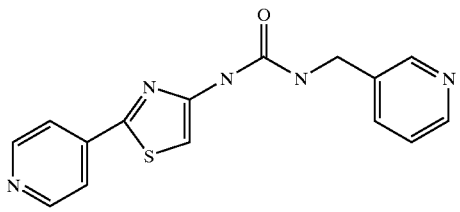

1-(Pyridin-3-ylmethyl)-3-(2-pyridin-4-yl-thiazol-4-yl)urea 2-(4-Pyridinyl)-4-thiazolcarbonylazide (100 mg, 0.43 mmol) in dry toluene (3 mL) was heated to 105° C. under N₂ and maintained at this temperature for 5 min. A solution of 3-(aminomethyl)pyridine (47 mg, 0.43 mmol) in dry toluene (1 mL) was added dropwise via syringe and the resulting mixture heated at 105° C. for 2 h. After cooling to RT, solvent was removed under vacuum and the product was purified by silica gel chromatograpy eluting with MeOH/CH₂Cl₂ (10%) to give the desired compound as a light yellow solid. MS m/z: 312.1 (M+H). Calcd for $C_{15}H_{13}N_5OS$: 311.08.

EXAMPLE 226

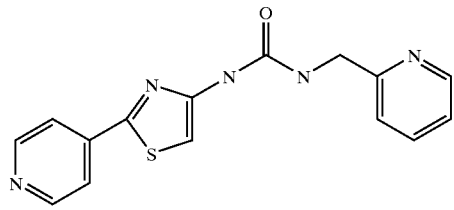

1-(Pyridin-2-ylmethyl)-3-(2-pyridin-4-yl-thiazol-4-yl)urea 2-(4-Pyridinyl)-4-thiazolcarbonylazide (100 mg, 0.43 mmol) in dry toluene (3 mL) was heated to 105° C. under N₂ and maintained at this temperature for 5 min. A solution of 2-(aminomethyl)pyridine (47 mg, 0.43 mmol) in dry toluene (1 mL) was then added dropwise via syringe and the resulting mixture heated at 105° C. for 3 h. After cooling to RT, solvent was removed under vacuum and the product was purified by silica gel chromatograpy eluting with MeOH/CH$_2$Cl$_2$ (10%) to give a light yellow solid. MS m/z: 312.1 (M+H). Calc'd for C$_{15}$H$_{13}$N$_5$OS: 311.08.

EXAMPLE 227

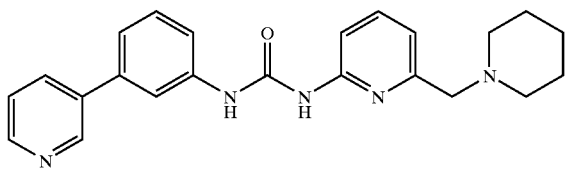

1-[6-(Piperidin-1-ylmethyl)pyridin-2-yl]-3-(3-pyridin-3-yl-phenyl)urea

To a stirred solution of phosgene (0.35 mL, 0.65 mmol, 20% in toluene) in dry THF (5 mL) was added 3-(3-pyrid-1-yl)-1-aminobenzene (85 mg, 0.5 mmol) dropwise via the addition funnel. After stirring for 10 min, isopropylethylamine (0.26 mL, 2.0 mmol) was added. The resulting mixture was stirred at RT under N$_2$ for 30 min. 2-Amino-6-piperidinylmethylpyridine (96 mg, 0.5 mmol) in dry THF (5 mL) was added dropwise into the reaction mixture via the addition funnel. The resulting mixture was stirred at RT for 15 h. Solvent was removed to give a dark brown liquid which was purified by chromatography on silica gel. Elution with CH$_2$Cl$_2$:MeOH mixture (95:5) gave the final compound as a pale yellow solid. MS m/z: 387.9 (M+). Calc'd for C$_{23}$H$_{25}$N$_5$O-387.49.

EXAMPLE 228

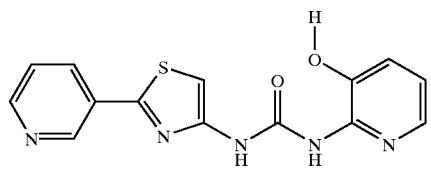

1-(3-Hydroxy-pyridin-2-yl)-3-(2-pyridin-3-yl-thiazol-4-yl)-urea

TEA (0.27 mL, 1.94 mmol) was added to a solution of 2-(pyridin-3-yl)thiazole-4-carboxylic acid (200 mg, 0.97 mmol) and 4A molecular sieves in THF (25 mL) under N$_2$ at RT. (PhO)$_2$PON$_3$ (0.33 mL, 1.55 mmol) followed by 2-amino-6-hydroxypyridine (268 mg, 2.43 mmol) was added and the resulting mixture heated at reflux for 12 h. After cooling to RT, the heterogeneous mixture was decanted to remove the molecular sieves. The precipitate was collected, rinsing with EtOAc to give a white solid. MS m/z: 313.0 (M+H). Calc'd for C$_{14}$H$_{11}$N$_5$O$_2$S-313.34.

EXAMPLE 229

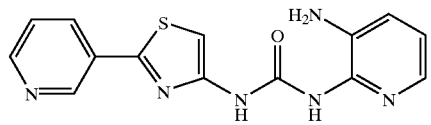

1-(3-Amino-pyridin-2-yl)-3-(2-pyridin-3-yl-thiazol-4-yl)-urea

TEA (0.27 mL, 1.94 mmol) was added to a solution of 2-(pyridin-3-yl)thiazole-4-carboxylic acid (200 mg, 0.97 mmol) and 4A molecular sieves in THF (25 mL) under N$_2$ at RT. (PhO)$_2$PON$_3$ (0.33 mL, 1.55 mmol) followed by 2-amino-3-aminomethylpyridine (265 mg, 2.43 mmol) was added and the resulting mixture was heated at reflux for 12 h. After cooling to RT, the heterogeneous mixture was decanted to remove the molecular sieves. The precipitate was collected and discarded. The filtrate was purified by chromatography on silica gel (CH$_2$Cl$_2$/MeOH, 95:5) to give a white solid. MS m/z: 313.8 (M+H). Calc'd for C$_{14}$H$_{12}$N$_6$OS-312.36.

EXAMPLE 230

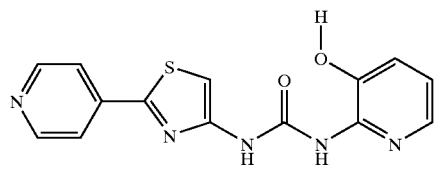

1-(3-Hydroxy-pyridin-2-yl)-3-(2-pyridin-4-yl-thiazol-4-yl)-urea 2-(4-Pyridinyl)-4-thiazolcarbonylazide (200 mg, 0.86 mmol) and 2-amino-3-hydroxymethylpyridine (95 mg, 0.86 mmol) in dry toluene (10 mL) were heated at 100° C. for 12 h to give a pale yellow solid which was recrystallized from CHCl$_3$/MeOH (99:5) to give a pale yellow solid. MS m/z: 314.0 (M+H). Calc'd for C$_{14}$H$_{11}$N$_5$O$_2$S-313.34.

EXAMPLE 231

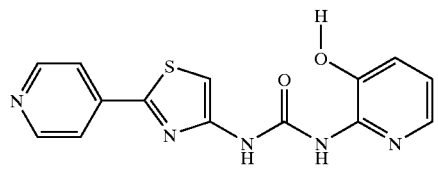

1-(3-Amino-pyridin-2-yl)-3-(2-pyridin-4-yl-thiazol-4-yl)-urea 2-(4-Pyridinyl)-4-thiazolcarbonylazide (200 mg, 0.86 mmol) and 2-amino-3-aminomethylpyridine (94 mg, 0.86 mmol) in dry toluene (10 mL) were heated at 100° C. for 12 h to give a pale yellow solid which was recrystallized from CHCl$_3$/MeOH (99:5) to give a pale yellow solid. MS m/z: 313.0 (M+H). Calc'd for C$_{14}$H$_{12}$N$_6$OS-312.36.

EXAMPLE 232

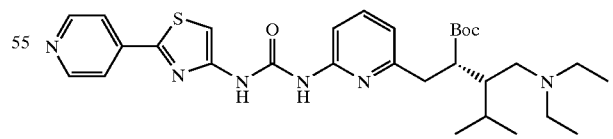

(1-Diethylaminomethyl-2-methyl-propyl)-{6-[3-(2-pyridin-4-yl-thiazol-4-yl)-ureido]-pyridin-2-ylmethyl}-carbamic Acid Tert-Butyl Ester To a stirred solution of N-[(6-amino-(2-pyridyl))-methyl]-N-{1-[(diethylamino)methyl]-2-methylpropyl}-(tert-butoxy)carboxamide (6 mg, 0.016 mmol) in toluene (5 mL)

was added 6-(piperidylmethyl)-2-pyridylamine (0.004 g, 0.016 mmol). The resulting green solution was heated at reflux in a Dean-Stark trap for 1.5 h until the starting materials were consumed. The mixture was brought to RT, concentrated by rotary evaporation and the residue obtained was partitioned between H$_2$O (10 mL) and CHCl$_3$ (35 mL). The organic phase was separated and the aqueous phase was extracted with CHCl$_3$ (3×10 mL). The organic layers were combined, dried over MgSO$_4$, filtered, concentrated by rotary evaporation and purified by prep TLC (5:95 MeOH/CH$_2$Cl$_2$) to afford (1-diethylaminomethyl-2-methyl-propyl)-{6-[3-(2pyridin-4-yl-thiazol-4-yl)-ureido]-pyridin-2-ylmethyl}-carbamic acid tert-butyl ester as an off-white solid. EI-MS m/z 568 (M+H). Calc'd for C$_{29}$H$_{41}$N$_7$O$_3$S: 567.30.

EXAMPLE 233

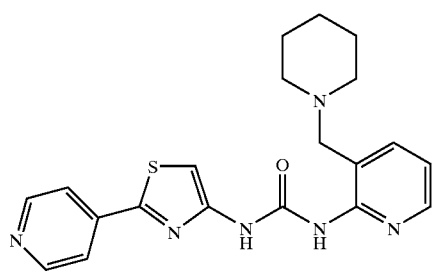

1-(3-Piperidin-1-ylmethyl-pyridin-2-yl)-3-(2-pyridin-4-yl-thiazol-4-yl)-urea

MS m/z: 395 (M+H). Calc'd MS C$_{20}$H$_{22}$N$_6$OS-394.49.

EXAMPLE 234

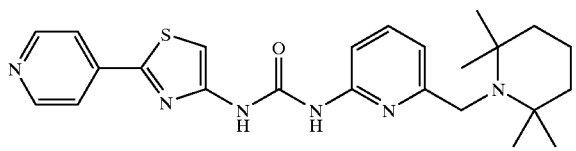

1-(2-Pyridin-4-yl-thiazol-4-yl)-3-[6-(2,2,6,6-tetramethyl-piperidin-1-ylmethyl)-pyridin-2-yl]-urea 2-(4-Pyridinyl)-4-thiazolcarbonylazide (35 mg, 0.15 mmol) in dry toluene (10 mL) was heated to 80° C. under N$_2$ and maintained at this temperature for 10 min. A solution of 6-(2,2,6,6-tetramethyl-piperidin-1-ylmethyl)-pyridin-2-ylamine (30 mg, 0.12 mmol) in dry toluene (2 mL) was added dropwise via syringe and the resulting mixture heated at 85° C. for 3 h. After cooling to RT, the crude mixture was purified by chromatography on silica gel (MeOH/CHCl$_3$, 3:97) to give a pale yellow solid. MS m/z: 449.3 (M–H). Calc'd for C$_{24}$H$_{30}$N$_6$OS-450.60.

EXAMPLE 235

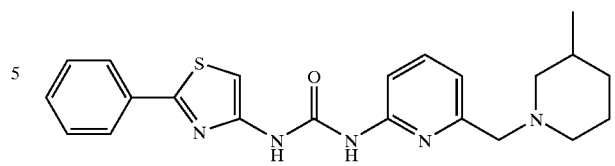

1-[6-(3-Methyl-piperidin-1-ylmethyl)-pyridin-2-yl]-3-(2-phenyl-thiazol-4-yl)-urea In a manner similar to that described in Example 234, 2-(4-pyridinyl)-4-thiazolcarbonylazide (100 mg, 0.43 mmol) in dry toluene (10 mL) was heated with 6-(3-methyl-piperidin-1-ylmethyl)-pyridin-2-ylamine (106 mg, 0.52 mmol) to give an off-white solid. MS m/z: 408.3 (M+H). Calc'd for C$_{22}$H$_{25}$N$_5$OS-407.53.

EXAMPLE 236

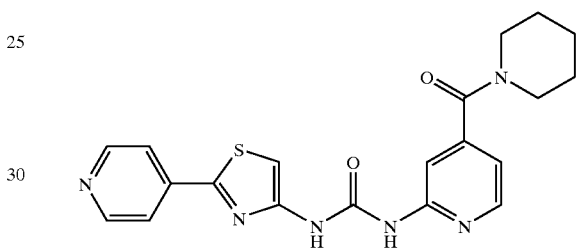

1-[4-(Piperidine-1-carbonyl)-pyridin-2-yl]-3-(2-pyridin-4-yl-thiazol-4-yl)-urea

In a manner similar to that described in Example 234, 2-(4-pyridinyl)-4-thiazolcarbonylazide (100 mg, 0.43 mmol) was heated with (2-amino-pyridin-4-yl)-piperidin-1-yl-methanone (88 mg, 0.43 mmol) in dry toluene (10 mL) to give a white solid. MS m/z: 409.3 (M+H). Calc'd. for C$_{20}$H$_{20}$N$_6$O$_2$S-408.14.

EXAMPLE 237

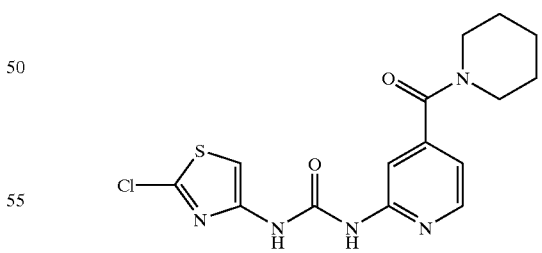

1-(2-Chloro-thiazol-4-yl)-3-[4-(piperidine-1-carbonyl)-pyridin-2-yl]-urea

In a manner similar to that described in Example 234, 2-chloro-4-thiazolcarbonylazide (74 mg, 0.39 mmol) was heated with 4-piperidin-1-ylmethyl-pyridin-2-ylamine (80 mg, 0.39 mmol) in dry toluene (10 mL) to give a white solid. MS m/z: 366.2 (M+H). Calc'd. for C$_{15}$H$_{16}$ClN$_5$O$_2$S-365.07.

EXAMPLE 238

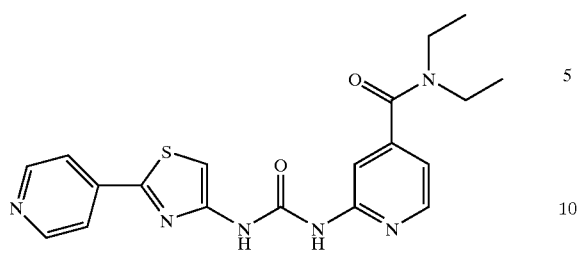

N,N-Diethyl-2-[3-(2-pyridin-4-yl-thiazol-4-yl)-ureido]-isonicotinamide

In a manner similar to that described in Example 234, 2-(4-pyridinyl)-4-thiazolcarbonylazide (95 mg, 0.41 mmol) was heated with 2-amino-N,N-diethyl-isonicotinamide (80 mg, 0.41 mmol) in dry toluene (10 mL) to give a white solid. MS m/z: 397.2 (M+H). Calc'd. for $C_{19}H_{20}N_6O_2S$-396.14.

EXAMPLE 239

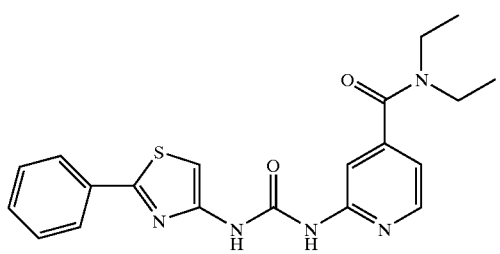

N,N-Diethyl-2-[3-(2-phenyl-thiazol-4-yl)-ureido]-isonicotinamide

In a manner similar to that described in Example 234, 2-phenyl-4-thiazolcarbonylazide (83 mg, 0.36 mmol) was heated with 2-amino-N,N-diethyl-isonicotinamide (70 mg, 0.36 mmol) in dry toluene (10 mL) to give a white solid. MS m/z: 396.3 (M+H). Calc'd. for $C_{19}H_{20}N_6O_2S$-395.14.

EXAMPLE 240

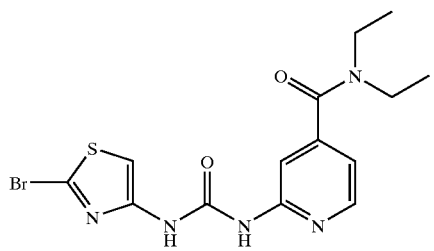

2-[3-(2-Bromo-thiazol-4-yl)-ureido]-N,N-diethyl-isonicotinamide

In a manner similar to that described in Example 234, 2-bromo-4-thiazolcarbonylazide (85 mg, 0.36 mmol) was heated with 2-amino-N,N-diethyl-isonicotinamide (70 mg, 0.36 mmol) in dry toluene (10 mL) to give a white solid. MS m/z: 398.1 (M+H). Calc'd. for $C_{14}H_{16}BrN_5O_2S$-397.02.

EXAMPLE 241

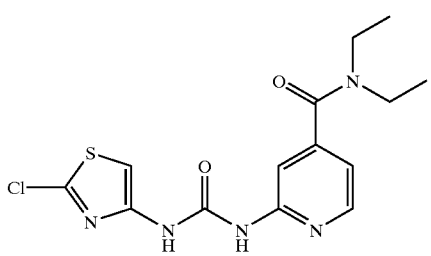

2-[3-(2-Chloro-thiazol-4-yl)-ureido]-N,N-diethyl-isonicotinamide

In a manner similar to that described in Example 234, 2-chloro-4-thiazolcarbonylazide (50 mg, 0.26 mmol) was heated with 2-amino-N,N-diethyl-isonicotinamide (50 mg, 0.26 mmol) in dry toluene (10 mL) to give a white solid. MS m/z: 354.2 (M+H). Calc'd. for $C_{14}H_{16}ClN_5O_2S$-353.07.

EXAMPLE 242

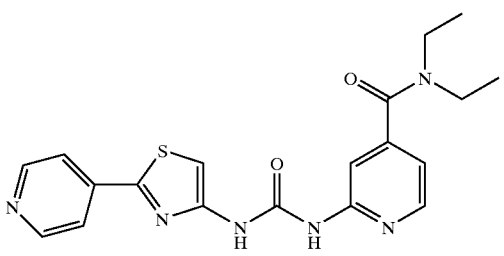

1-(4-Diethylaminomethyl-pyridin-2-yl)-3-(2-pyridin-4-yl-thiazol-4-yl)-urea

In a manner similar to that described in Example 234, 2-(4-pyridinyl)-4-thiazolcarbonylazide (78 mg, 0.34 mmol) was heated with 4-diethylaminomethyl-pyridin-2-ylamine (60 mg, 0.34 mmol) in dry toluene (10 mL) to give a white solid. MS m/z: 383.2 (M+H). Calc'd. for $C_{19}H_{22}N_6OS$-382.16.

EXAMPLE 243

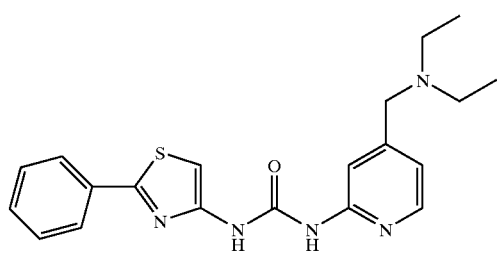

1-(4-Diethylaminomethyl-pyridin-2-yl)-3-(2-phenyl-thiazol-4-yl)-urea

In a manner similar to that described in Example 234, 2-phenyl-4-thiazolcarbonylazide (77 mg, 0.34 mmol) was heated with 4-diethylaminomethyl-pyridin-2-ylamine (60 mg, 0.34 mmol) in dry toluene (10 mL) to give a white solid. MS m/z: 382.1 (M+H). Calc'd. for $C_{19}H_{22}N_6OS$-381.16.

EXAMPLE 244

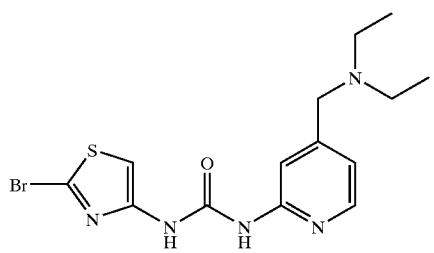

1-(2-Bromo-thiazol-4-yl)-3-(4-diethylaminomethyl-pyridin-2-yl)-urea

In a manner similar to that described in Example 234, 2-bromo-4-thiazolcarbonylazide (85 mg, 0.36 mmol) was heated with 4-diethylaminomethyl-pyridin-2-ylamine (65 mg, 0.36 mmol) in dry toluene (10 mL) to give a white solid. MS m/z: 384.1 (M+H). Calc'd. for $C_{14}H_{18}BrN_5OS$-383.04.

EXAMPLE 245

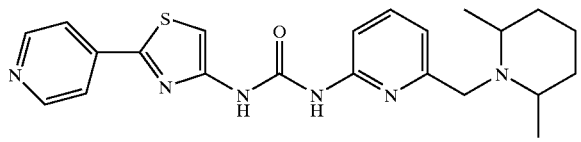

1-[6-(2,6-Dimethyl-piperidin-1-ylmethyl)-pyridin-2-yl]-3-(2-pyridin-4-yl-thiazol-4-yl)-urea In a manner similar to that described in Example 234, 2-(4-pyridinyl)-4-thiazolcarbonylazide (132 mg, 0.57 mmol) was heated with 6-(2,6-dimethyl-piperidin-1-ylmethyl)-pyridin-2-ylamine (125 mg, 0.57 mmol) in dry toluene (10 mL) to give a yellow solid. MS m/z: 423.3 (M+H). Calc'd. for $C_{22}H_{26}N_6OS$-422.19.

EXAMPLE 247

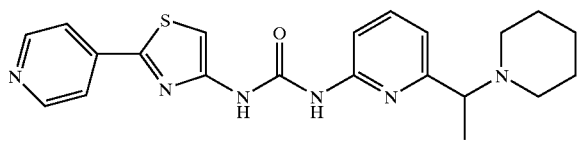

1-[6-(1-Piperidin-1-yl-ethyl)-pyridin-2-yl]-3-(2-pyridin-4-yl-thiazol-4-yl)-urea In a manner similar to that described in Example 234, 2-(4-pyridinyl)-4-thiazolcarbonylazide (180 mg, 0.78 mmol) was heated with 6-(1-piperidin-1-yl-ethyl)-pyridin-2-ylamine (160 mg, 0.78 mmol) in dry toluene (10 mL) to give a yellow solid. MS m/z: 409.2 (M+H). Calc'd. for $C_{21}H_{24}N_6OS$-408.17.

EXAMPLE 248

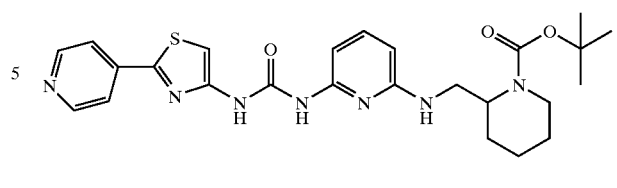

2-({6-[3-(2-Pyridin-4-yl-thiazol-4-yl)-ureido]-pyridin-2-ylamino}-methyl)-piperidine-1-carboxylic Acid Tert-Butyl Ester In a manner similar to that described in Example 234, 2-(4-pyridinyl)-4-thiazolcarbonylazide (45 mg, 0.196 mmol) was heated with 2-[(6-amino-pyridin-2-ylamino)-methyl]-piperidine-1-carboxylic acid tert-butyl ester (60 mg, 0.196 mmol) in dry toluene (10 mL) to give a yellow solid. MS m/z: 510.4 (M+H). Calc'd. for $C_{25}H_{31}N_7O_3S$-509.2.

EXAMPLE 249

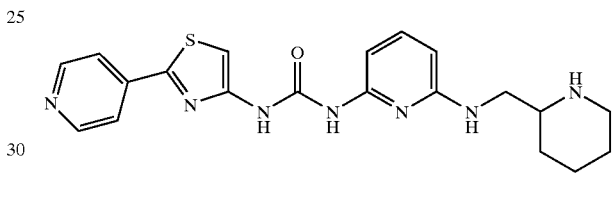

1-(6-[(Piperidin-2-ylmethyl)-amino]-pyridin-2-yl}-3-(2-pyridin-4-yl-thiazol-4-yl)-urea 2-({6-[3-(2-Pyridin-4-yl-thiazol-4-yl)-ureido]-pyridin-2-ylamino}-methyl)-piperidine-1-carboxylic acid tert-butyl ester (52 mg, 0.102 mmol) in MeOH (10 mL) was treated with TFA (0.1 mL, 1.3 mmol). The resulting mixture was heated at 50° C. for 24 h. The reaction mixture was cooled to RT and neutralized to pH between 8–9. Solvent was removed. The residue was partitioned between $H_2O$ and $CHCl_3$. The organic layer was washed with $H_2O$, brine, dried over $MgSO_4$, and concentrated to give a yellow solid. MS m/z: 410.2 (M+H). Calc'd. for $C_{20}H_{23}N_7OS$-409.17.

EXAMPLE 250

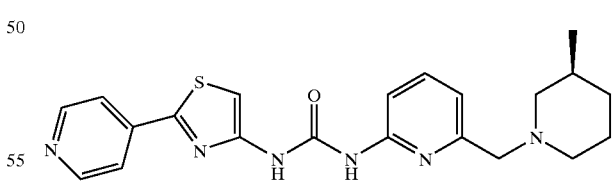

(S)-1-[6-(3-Methyl-piperidin-1-ylmethyl)-pyridin-2-yl]-3-(2-pyridin-4-yl-thiazol-4-yl)-urea 1-[6-(3-Methyl-piperidin-1-ylmethyl)-pyridin-2-yl]-3-(2-pyridin-4-yl-thiazol-4-yl)-urea (50 mg, 0.12 mmol, Example 78) was separated by chiral HPLC (Chiraltech Chiralcel OJ 50×4.6 mm i.d.) using hexane/EtOH/DEA (90:10:0.2) to give a white solid. MS m/z: 409.3 (M+H). Calc'd for $C_{21}H_{24}N_6OS$-408.52.

EXAMPLE 251

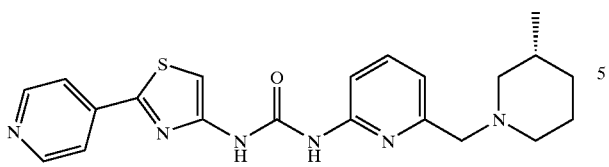

(R)-1-[6-(3-Methyl-piperidin-1-ylmethyl)-pyridin-2-yl]-3-(2-pyridin-4-yl-thiazol-4-yl)-urea 1-[6-(3-Methyl-piperidin-1-ylmethyl)-pyridin-2-yl]-3-(2-pyridin-4-yl-thiazol-4-yl)-urea (50 mg, 0.12 mmol, Example 78) was separated by chiral HPLC (Chiraltech Chiralcel OJ 50×4.6 mm i.d.) using hexane/EtOH/DEA (90:10:0.2) to give a white solid. MS m/z: 409.3 (M+H). Calc'd for $C_{21}H_{24}N_6OS$-408.52.

EXAMPLE 252

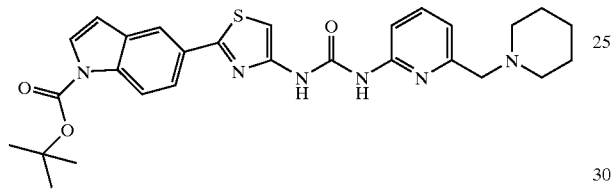

5-{4-[3-(6-Piperidin-ylmethylpyridin-2-yl)-ureido]thiazol-2-yl}-indole-1-carboxylic Acid Tert-Butyl Ester To a solution of 5-(4-carboxy-thiazol-2-yl)-indole-1-carboxylic acid tert-butyl ester (2.65 g, 7.69 mmol), molecular sieves, and 100 mL of dry toluene was added TEA (1.6 mL, 11.5 mmol). The resulting solution was stirred for 20 min then DPPA (2.5 mL, 11.6 mmol) was added and the resulting solution was stirred at 80° C. for 40 min. 6-Piperdin-1-ylmethyl-pyridin-2-ylamine (1.64 g, 8.6 mmol) and pyridine (1.0 mL, 12.4 mmol) were added and the mixture was stirred at 80° C. for another 14 h. The molecular sieves were filtered off and washed with $CH_2Cl_2$ and MeOH. The filtrate was concentrated in vacuo and the resulting residue was purified by flash chromatography on silica gel using 3% MeOH/$CH_2Cl_2$ to give a brown solid. MS m/z: 533 (M+1). Calc'd for $C_{28}H_{32}N_6O_3S$-532.66.

EXAMPLE 253

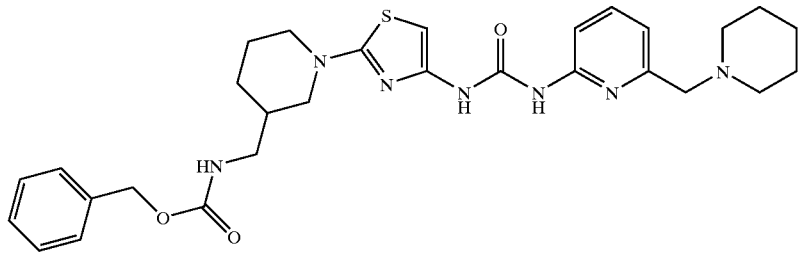

(1-{4-[3-(6-Piperidin-1-ylmethyl-pyridin-2-yl)-ureido]-thiazol-2-yl}-piperidin-3-ylmethyl)-carbamic Acid Benzyl Ester To a stirred solution of 2-[3-(benzyloxy-carbonylamino-methyl)-piperidin-1-yl]-thiazole-4-carboxylic acid (351 mg, 0.93 mmol) in anhydrous toluene (15 mL), under $N_2$, at RT, over 4A activated molecular sieves, TEA (0.16 mL, 1.12 mmol) was added. After 7 min, DPPA (0.24 mL, 1.12 mmol) was added and the solution was heated to 85° C. for 20 min. Neat 6-piperidin-1-ylmethyl-pyridin-2-ylamine (179 mg, 0.93 mmol) was added and the reaction was maintained at 85° C. for an additional 2.5 h. After cooling to RT the solution was filtered through a Celite® pad that was washed successively with $CH_2Cl_2$ (4×5 mL). The filtrate was evaporated in vacuo and the residue purified by flash chromatography on silica gel (97:3, $CHCl_3$:MeOH) to yield the title compound as a red/orange oil. MS m/z: 564.4 (M+H). Calc'd for $C_{29}H_{37}N_7O_3S$-563.72.

EXAMPLE 254

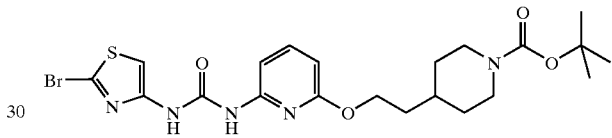

4-(2-{6-[3-(2-Bromo-thiazol-4-yl)-ureido]-pyridin-2-yloxy}-ethyl)-piperidine-1-carboxylic Acid Tert-Butyl Ester To a stirred solution of 2-bromo-thiazole-4-carbonyl azide (194 mg, 0.83 mmol) in anhydrous toluene (4 mL) under $N_2$, that had been heated to 85 C. and held there for 5 min, a solution of 4-[2-(6-amino-pyridin-2-yloxy)-ethyl] piperidine-1-carboxylic acid tert-butyl ester (268 mg, 0.83 mmol) in anhydrous toluene (3 mL) was added over 5 min. After 3 h the reaction mixture was cooled to RT. The precipitate was filtered off to yield the title compound as a white amorphous solid. MS m/z: 526.1, 528.1 (M+H). Calc'd for $C_{21}H_{28}BrN_5O_4S$-526.4.

The following Examples 255–263 were prepared from their respective amines and azides in a manner similar to example 254.

EXAMPLE 255

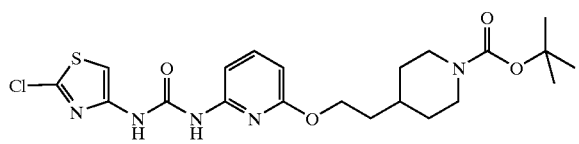

4-(2-{6-[3-(2-Chloro-thiazol-4-yl)-ureido]-pyridin-2-yloxy}-ethyl)-piperidine-1-carboxylic Acid Tert-Butyl Ester MS m/z: 482.3 (M+H). Calc'd. for $C_{21}H_{28}ClN_5O_4S$- 482.00.

EXAMPLE 256

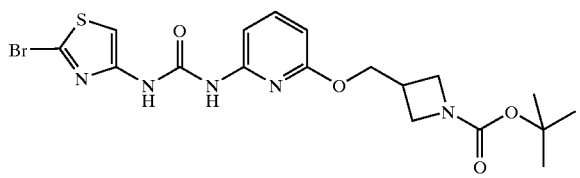

3-{6-[3-(2-Bromo-thiazol-4-yl)-ureido]-pyridin-2-yloxymethyl}-azetidine-1-carboxylic Acid Tert-Butyl Ester MS m/z: 484.1, 486.1 (M+H). Calc'd. for $C_{18}H_{22}BrN_5O_4S$-484.37.

EXAMPLE 257

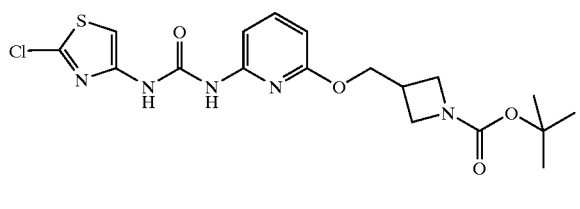

3-{6-[3-(2-Chloro-thiazol-4-yl)-ureido]-pyridin-2-yloxymethyl}-azetidine-1-carboxylic acid tert-butyl ester MS m/z: 440.1 (M+H). Calc'd. for $C_{18}H_{22}ClN_5O_4S$- 439.92.

EXAMPLE 258

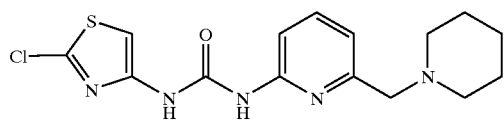

1-(2-Chloro-thiazol-4-yl)-3-(6-piperidin-1-ylmethyl-pyridin-2-yl)-urea

MS m/z: 352.3 (M+H). Calc'd. for $C_{15}H_{18}ClN_5OS$- 351.86.

EXAMPLE 259

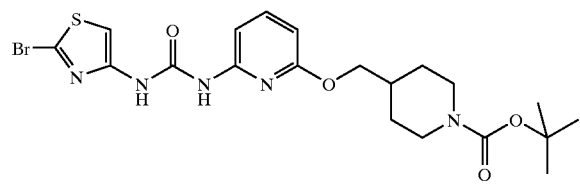

4-{6-[3-(2-Bromo-thiazol-4-yl)-ureido]-pyridin-2-yloxymethyl}-piperidine-1-carboxylic Acid Tert-Butyl Ester MS m/z: 512.3, 514.3 (M+H). Calc'd. for $C_{20}H_{26}BrN_5O_4S$—512.42.

EXAMPLE 260

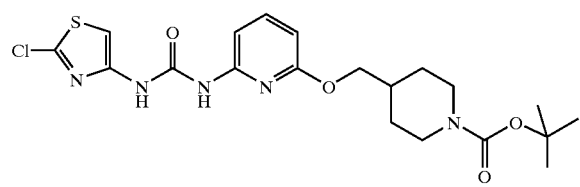

4-{6-[3-(2-Chloro-thiazol-4-yl)-ureido]-pyridin-2-yloxymethyl}-piperidine-1-carboxylic Acid Tert-Butyl Ester MS m/z: 468.1 (M+H) Calc'd. for $C_{20}H_{26}ClN_5O_4S$- 467.97.

EXAMPLE 261

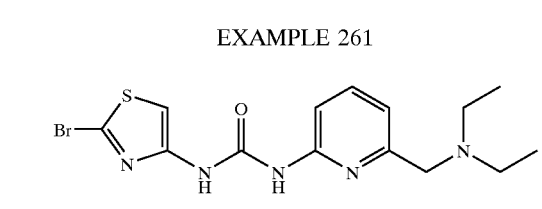

1-(2-Bromo-thiazol-4-yl)-3-(6-diethylaminomethyl-pyridin-2-yl)-urea

MS m/z: 384.1, 386.1 (M+H). Calc'd. for $C_{14}H_{18}BrN_5OS$-384.30.

EXAMPLE 262

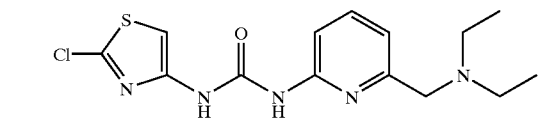

1-(2-Chloro-thiazol-4-yl)-3-(6-diethylaminomethyl-pyridin-2-yl)-urea

MS m/z: 340.2 (M+H). Calc'd. for $C_{14}H_{18}ClN_5OS$- 339.84.

EXAMPLE 263

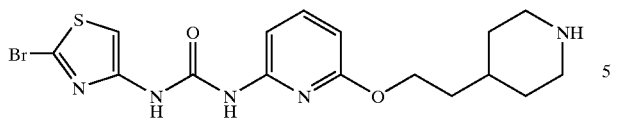

1-(2-Bromo-thiazol-4-yl)-3-[6-(2-piperidin-4-yl-ethoxy)-pyridin-2-yl]-urea

To a stirred solution of 4-(2-{6-[3-(2-bromo-thiazol-4-yl)-ureido]-pyridin-2-yloxy}-ethyl)-piperidine-1-carboxylic acid tert-butyl ester (285 mg, 0.54 mmol) in anhydrous $CH_2Cl_2$ (6 mL) at RT, under $N_2$, TFA (1.5 mL) was added. After 1.5 h the solvent was evaporated in vacuo. The residue was carefully treated with a saturated solution of $NaHCO_3$ (aq) (10 mL), the precipitate was filtered off, washed with $Et_2O$ (3×5 mL) and dried in a vacuum oven at 60° C. for 5 h to yield the title compound as a white amorphous solid. MS m/z: 426.2, 428.2 (M+H). Calc'd. for $C_{16}H_{20}BrN_5O_2S$-426.33.

The following Examples 264–268 were prepared from their respective tert-butyl esters in a manner similar to example 263.

EXAMPLE 264

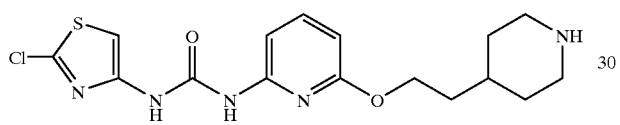

1-(2-Chloro-thiazol-4-yl)-3-[6-(2-piperidin-4-yl-ethoxy)-pyridin-2-yl]-urea

MS m/z: 382.3 (M+H). Calc'd. for $C_{16}H_{20}ClN_5O_2S$-381.88.

EXAMPLE 265

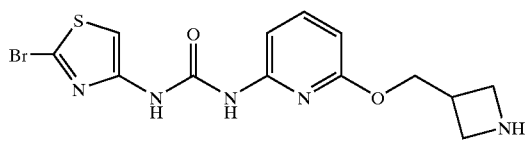

1-[6-(Azetidin-3-ylmethoxy)-pyridin-2-yl]-3-(2-bromo-thiazol-4-yl)-urea

MS m/z: 384.0, 386.0 (M+H). Calc'd. for $C_{13}H_{14}BrN_5O_2S$—384.25.

EXAMPLE 266

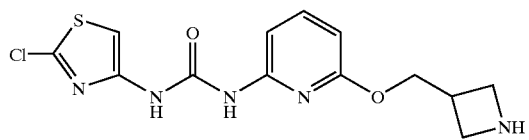

1-[6-(Azetidin-3-ylmethoxy)-pyridin-2-yl]-3-(2-chloro-thiazol-4-yl)-urea

MS m/z: 340.1 (M+H). Calc'd. for $C_{13}H_{14}ClN_5O_2S$-339.80.

EXAMPLE 267

1-(2-Bromo-thiazol-4-yl)-3-[6-(piperidin-4-ylmethoxy)-pyridin-2-yl]-urea

MS m/z: 412.0, 414.0 (M+H). Calc'd. for $C_{15}H_{18}BrN_5O_2S$-412.31.

EXAMPLE 268

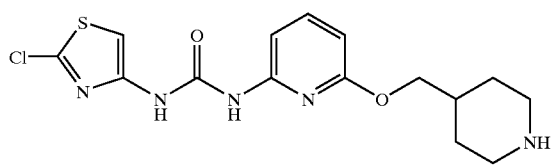

1-(2-Chloro-thiazol-4-yl)-3-[6-(piperidin-4-ylmethoxy)-pyridin-2-yl]-urea

MS m/z: 368.2 (M+H). Calc'd. for $C_{15}H_{18}ClN_5O_2S$-367.85.

EXAMPLE 269

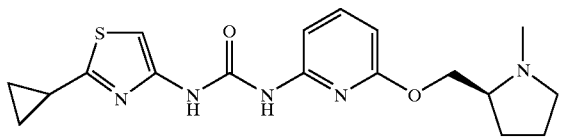

1-(2-Cyclopropyl-thiazol-4-yl)-3-[6-(1-methyl-pyrrolidin-2-ylmethoxy)-pyridin-2-yl]-urea In a manner similar to that described in Example 2,2-cyclopropylthiazole-4-carbonylazide (97.0 mg, 0.5 mmol) and 6-(1-methyl-pyrrolidin-2-ylmethoxy)-pyridin-2-ylamine (103.5 mg, 0.5 mmol) were heated in toluene (20 mL) to give the product as a yellow oil. MS m/z: 374.2 (M+H). Calc'd. for $C_{18}H_{24}N_5O_2S$-374.2.

EXAMPLE 270

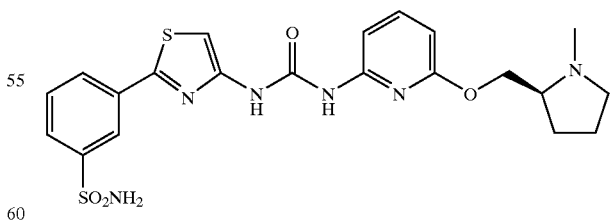

3-(4-{3-[6-(1-Methyl-pyrrolidin-2-ylmethoxy)-pyridin-2-yl]-ureido}-thiazol-2-yl)-benzenesulfonamide In a manner similar to that described in Example 2, 2-2-(3-sulfamoyl-phenyl)-thiazole-4-carbonylazide (224.0 mg, 0.725 mmol) and 6-(1-methyl-pyrrolidin-2-ylmethoxy)-pyridin-2-ylamine (150.0 mg, 0.725 mmol) were heated in toluene (70 mL) to give the product as a white solid. MS m/z: 489.2 (M+H). Calc'd. for $C_{21}H_{25}N_6O_4S_2$-489.2.

EXAMPLE 271

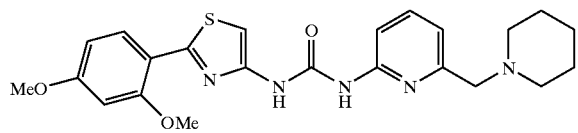

1-[2-(2,4-Dimethoxyphenyl)thiazol-4-yl]-3-(6-piperidin-1-ylmethyl-pyridin-2-yl)urea The title compound was prepared by the method of Example 199. EI-MS m/z 454 (M+H). Calc'd for $C_{23}H_{27}N_5O_3S$: 453.18.

EXAMPLE 272

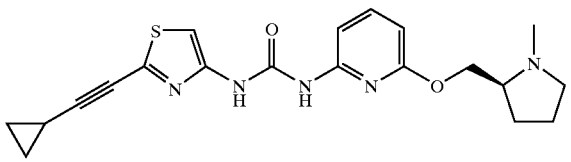

1-(2-Cyclopropylethynyl-thiazol-4-yl)-3-[6-(1-methyl-pyrrolidin-2-ylmethoxy)-pyridin-2-yl]-urea In a manner similar to that described in Example 2, 2-2-cyclopropylethynyl-thiazole-4-carbonylazide (41.4 mg, 0.190 mmol) and 6-(1-methyl-pyrrolidin-2-ylmethoxy)-pyridin-2-ylamine (47.2 mg, 0.228 mmol) were heated in toluene (1 mL) to give the product as a pale yellow solid. MS m/z: 398.3 (M+H). Calc'd. for $C_{20}H_{24}N_5O_2S$-397.16.

EXAMPLE 273

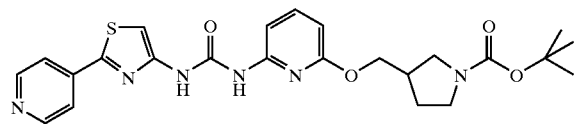

tert-Butyl 3-{6-[3-(2-pyridin-4-yl-thiazol-4-yl)-ureido]-pyridin-2-yloxymethyl)-pyrrolidine-1-carboxylate In a manner similar to that described in Example 2, 2-2-pyridin-4-yl-thiazole-4-carbonylazide (1.927 g, 8.334 mmol) and tert-butyl 3-(6-amino-pyridin-2-yloxymethyl)-pyrrolidine-1-carboxylate (2.220 g, 7.577 mmol) were heated in toluene (60 mL) to give the product as a white solid. MS m/z: 497.0 (M+H). Calc'd. for $C_{24}H_{29}N_6O_4S$-497.2.

EXAMPLE 274

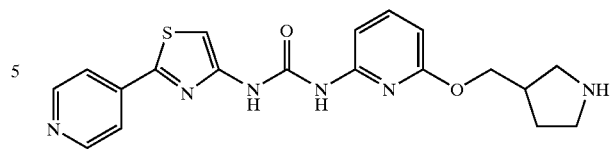

1-(2-Pyridin-4-yl-thiazol-4-yl)-3-[6-(pyrrolidin-3-ylmethoxy)-pyridin-2-yl]-urea To a slurry of tert-butyl 3-{6-[3-(2-pyridin-4-yl-thiazol-4-yl)-ureido]-pyridin-2-yloxymethyl}-pyrrolidine-1-carboxylate (1.291 g, 2.603 mmol) in $CH_2Cl_2$ (25 mL) was added TFA (5 mL) under $N_2$. The reaction mixture was heated to reflux for 3 h, then cooled to rt. Saturated $NaHCO_3$ solution (40 mL) was added and the precipitate was washed with EtOAc (3×40 mL) and $H_2O$ (2×10 mL), filtered and dried under high vacuum to give a white solid. MS m/z: 397.0 (M+H). Calc'd. for $C_{19}H_{21}N_6O_2S$-397.1.

EXAMPLE 275

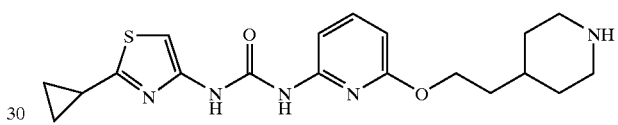

1-(2-Cyclopropyl-thiazol-4-yl)-3-[6-(2-piperidin-4-yl-ethoxy)-pyridin-2-yl]-urea In a manner similar to that described in Example 2,2-cyclopropylthiazole-4-carbonylazide (133.0 mg, 0.686 mmol) and tert-butyl 4-[2-(6-amino-pyridin-2-yloxy)-ethyl]-piperidine-1-carboxylate (220.0 mg, 0.686 mmol) were heated in toluene (20 mL) to give the BOC-protected product as a yellow oil. In a similar manner to Example 274, tert-butyl 4-(2-{6-[3-(2-cyclopropyl-thiazol-4-yl)-ureido]-pyridin-2-yloxy}-ethyl)-piperidine-1-carboxylate (7.6 mg, 0.016 mmol) was heated in $CH_2Cl_2$ (10 mL) in the presence of TFA (2 mL) to give the product as yellow oil. MS m/z: 388.3 (M+H). Calc'd. for $C_{19}H_{26}N_5O_2S$-388.2.

EXAMPLE 276

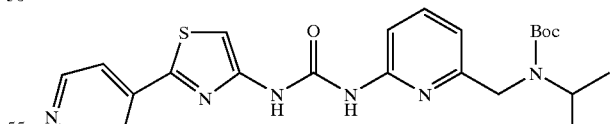

Isopropyl-{6-[3-(2-pyridin-4-yl-thiazol-4-yl)-ureido]-pyridin-2-ylmethyl}-carbamic Acid Tert-Butyl Ester The compound was prepared in a manner similar to Example 1 using 2-pyridin-4-yl-thiazole-4-carbonyl azide and (6-amino-pyridin-2-ylmethyl)-isopropyl-carbamic acid tert-butyl ester to afford a white solid. MS m/z: 469.2 (M+H). Calc'd for $C_{23}H_{28}N_6O_3S$: 468.19.

EXAMPLE 277

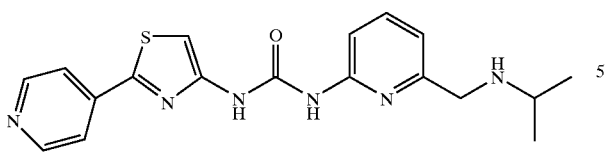

1-[6-(Isopropylamino-methyl)-pyridin-2-yl]-3-(2-pyridin-4-yl-thiazol-4-yl)-urea

The compound was prepared in a manner similar to Example 2 to give a white solid. EI-MS m/z: 368.2 (M+H). Calc'd for $C_{18}H_{20}N_6OS$: 368.14.

EXAMPLE 278

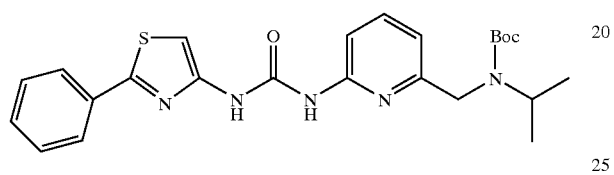

Isopropyl-{6-[3-(2-phenyl-thiazol-4-yl)-ureido]-pyridin-2-ylmethyl}-carbamic Acid Tert-Butyl Ester The compound was prepared in a manner similar to Example 1 using 2-phenyl-thiazole-4-carbonyl azide to afford a white solid. MS m/z: 468.4 (M+H). Calc'd for $C_{24}H_{29}N_5O_3S$: 467.20.

EXAMPLE 279

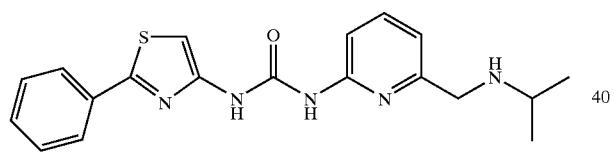

1-[6-(Isopropylamino-methyl)-pyridin-2-yl]-3-(2-phenyl-thiazol-4-yl)-urea

The compound was prepared in a manner similar to Example 2 to give a white solid. EI-MS m/z: 368.2 (M+H). Calc'd for $C_{19}H_{21}N_5OS$: 367.15.

EXAMPLE 280

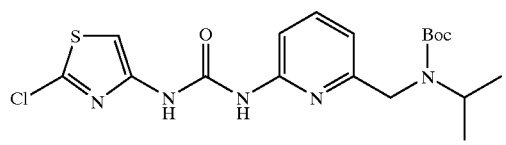

{6-[3-(2-Chloro-thiazol-4-yl)-ureido]-pyridin-2-ylmethyl}-isopropyl-carbamic Acid Tert-Butyl Ester The compound was prepared in a manner similar to Example 1 using 2-chloro-thiazole-4-carbonyl azide to afford a white solid. MS m/z: 426.3 (M+H). Calc'd for $C_{18}H_{24}ClN_5O_3S$: 425.13.

EXAMPLE 281

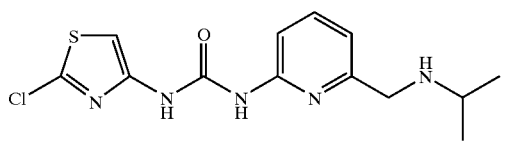

1-(2-Chloro-thiazol-4-yl)-3-[6-(isopropylamino-methyl)-pyridin-2-yl]-urea

The compound was prepared in a manner similar to Example 2 to give a white solid. EI-MS m/z: 326.1 (M+H). Calc'd for $C_{13}H_{16}ClN_5OS$: 325.08.

EXAMPLE 282

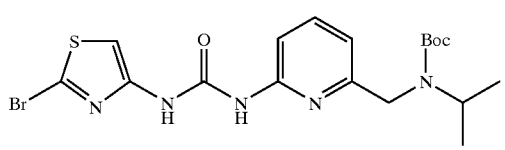

{6-[3-(2-Bromo-thiazol-4-yl)-ureido]-pyridin-2-ylmethyl)-isopropyl-carbamic Acid Tert-Butyl Ester The compound was prepared in a manner similar to Example 1 to give a white solid. EI-MS m/z: 470.0 (M+H). Calc'd for $C_{18}H_{24}BrN_5O_3S$: 469.08.

EXAMPLE 283

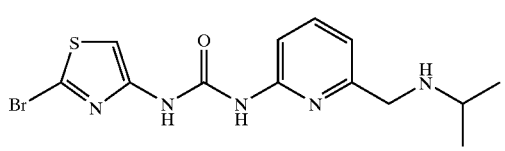

1-(2-Bromo-thiazol-4-yl)-3-[6-(isopropylamino-methyl)-pyridin-2-yl]-urea

The compound was prepared in a manner similar to Example 2 to give a white solid. EI-MS m/z: 370.2 (M+H). Calc'd for $C_{13}H_{16}BrN_5OS$: 369.03.

EXAMPLE 284

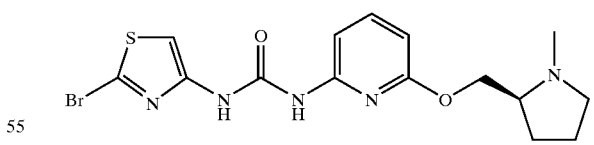

1-(2-Bromo-thiazol-4-yl)-3-[6-(1-methyl-pyrrolidin-2-ylmethoxy)-pyridin-2-yl]-urea A stirred solution of 2-bromo-thiazole-4-carbonyl azide (0.10 g, 0.43 mmol) in dry toluene (15 mL) was heated at 85° C. for 20 min followed by the addition of 6-(1-methyl-pyrrolidin-2-ylmethoxy)-pyridin-2-ylamine (0.09 g, 0.43 mmol). The resulting mixture was heated at 90° C. for 15 h. The mixture was cooled to RT and concentrated. The residue obtained was washed with MeOH at RT. The impurities were

EXAMPLE 285 dissolved in MeOH yielding a white precipitate as the desired product. MS m/z: 412.2 (M+H). Calc'd for $C_{15}H_{18}BrN_5O_2S$: 411.04.

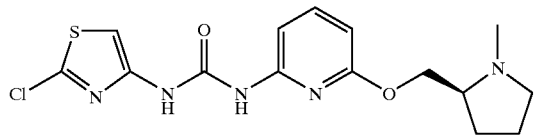

1-(2-Chloro-thiazol-4-yl)-3-[6-(1-methyl-pyrrolidin-2-ylmethoxy)-pyridin-2-yl]-urea The compound was prepared in a manner similar to Example 15 using 2-chloro-thiazole-4-carbonyl azide to afford a white solid. EI-MS m/z: 368.2 (M+H). Calc'd for $C_{15}H_{18}ClN_5O_2S$: 367.09.

EXAMPLE 286

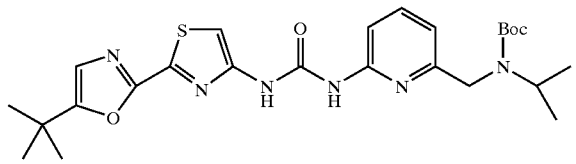

(6-{3-[2-(5-tert-Butyl-oxazol-2-yl)-thiazol-4-yl]-ureido}-pyridin-2-ylmethyl)-isopropyl-carbamic Acid Tert-Butyl Ester A stirred solution of 2-(5-tert-butyl-oxazol-2-yl)-thiazole-4-carbonyl azide (0.22 g, 0.79 mmol) was heated at 85° C. for 25 min followed by the addition of (6-amino-pyridin-2-ylmethyl)-isopropyl-carbamic acid tert-butyl ester. The resulting solution was heated at 90° C. for 15 h. The mixture was brought to RT, concentrated and purified by chromatography on silica gel using 2:1 Hexanes/EtOAc as eluent to afford a yellow solid as the desired product. MS m/z: 515.4 (M+H) Calc'd for $C_{25}H_{34}N_6O_4S$: 514.24.

EXAMPLE 287

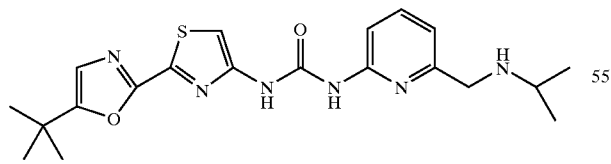

1-[2-(5-tert-Butyl-oxazol-2-yl)-thiazol-4-yl]-3-[6-(isopropylamino-methyl)-pyridin-2-yl]-urea The compound was prepared in a manner similar to Example 2 to give a white solid. EI-MS m/z: 415.30 (M+H). Calc'd for $C_{20}H_{26}N_6O_2S$: 414.18.

EXAMPLE 288

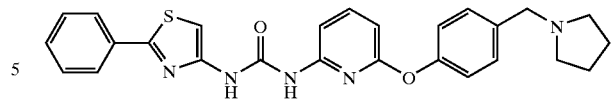

1-(2-phenylthiazol-4-yl)-3-(6-p-pyrrolidin-1-ylmethylphenoxypyridin-2-yl)urea

2-Phenyl-4-thiazolcarbonylazide (200 mg, 0.87 mmol) in dry toluene (5 mL) was heated to 105° C. under $N_2$ and maintained at for 5 min. 2-Amino-6-(4-pyrrolidin-1-ylmethylphenoxy)pyridine was added and the resulting mixture was heated at 105° C. for 4 h. After cooling to RT, the solid was filtered and rinsed with $Et_2O$. The product was purified by chromatography on silica gel eluting with MeOH/$CH_2Cl_2$ (5%) to form a white solid. MS m/z: 472.3 (M+H). Calc'd for $C_{26}H_{25}N_5O_2S$: 471.17.

EXAMPLE 289

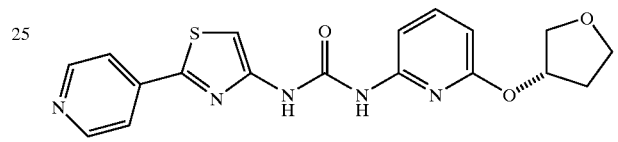

1-(2-Pyridin-4-yl-thiazol-4-yl)-3-[6-(tetrahydro-furan-3-yloxy)-pyridin-2-yl]-urea In a manner similar to Example 234, 2-(4-pyridinyl)-4-thiazolcarbonylazide and 6-(Tetrahydro-furan-3-yloxy)-pyridin-2-ylamine were heated together in toluene to give 1-(2-pyridin-4-yl-thiazol-4-yl)-3-[6-(tetrahydro-furan-3-yloxy)-pyridin-2-yl]-urea as a white solid. MS m/z: 384.3 (M+H). Calc'd for $C_{18}H_{17}N_5O_3S$ 383.43.

EXAMPLE 290

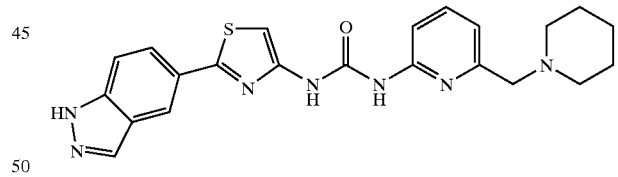

1-[2-(1H-Indazol-5-yl)-thiazol-4-yl]-3-(6-piperidin-1-ylmethyl-pyridin-2-yl)-urea In manner similar to Example 234, 2-(1-acetyl-1H-indazol-5-yl)thiazole-4-carbonyl azide and 6-piperidin-1-ylmethyl-pyridin-2-ylamine were heated in toluene to give 1-[2-(1-acetyl-1H-indazol-5-yl)-thiazol-4-yl]-3-(6-piperidin-1-ylmethyl-pyridin-2-yl)-urea as a yellow solid (62 mg, 100%) which was next dissolved in EtOH (5 mL), treated with 1 N HCl (0.1 mL) and heated to 70° C. After 1 h, the reaction mixture was concentrated in vacuo and extracted with EtOAc, washed with saturated $NaHCO_3$ and brine, dried ($MgSO_4$) and concentrated in vacuo to give the desired compound as a tan solid. MS m/z: 434.3 (M+H). Calc'd for $C_{22}H_{23}N_7OS$-433.53.

EXAMPLE 291

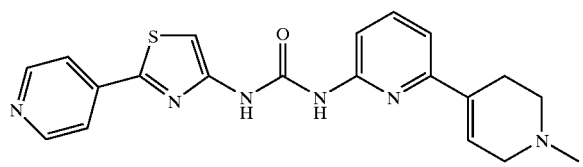

1(1'-Methyl-1',2',3',6'-tetrahydro-[2,4']bipyridinyl-6-yl)-3-(2-pyridin-4-yl-thiazol-4-yl)-urea In a manner similar to Example 234, 2-(4-pyridinyl)-4-thiazolcarbonylazide and 1'-methyl-1',2,3',6'-tetrahdyro-[2,4']bipyridinyl-6yl amine were heated together in toluene to give 1-(1'-methyl-1',2',3',6'-tetrahydro-[2,4']bipyridinyl-6-yl)-3-(2-pyridin-4-yl-thiazol-4-yl)-urea as a tan solid. MS m/z: 393.0 (M+H). Calc'd. for $C_{20}H_{20}N_6OS$—392.48.

EXAMPLE 292

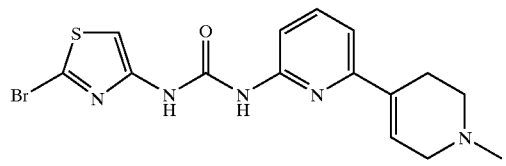

1-(2-Bromo-thizol-4-yl)-3-(1'-methyl-1',2',3',6'-tetreahydro-[2,4']bipyridinyl-6-yl)-urea In a manner similar to Example 234, 2-bromo-thiazole-4-carbonyl azide and 1'-methyl-1',2,3',6'-tetrahdyro-[2,4']bipyridinyl-6yl amine were heated together in toluene to give 1-(2-bromo-thizol-4-yl)-3-(1'-methyl-1',2',3',6'-tetrahydro-[2,4']bipyridinyl-6-yl)-urea as a tan solid. MS m/z: 395.1 (M+H). Calc'd for $C_{15}H_{16}BrN_5OS$ 394.29.

EXAMPLE 293

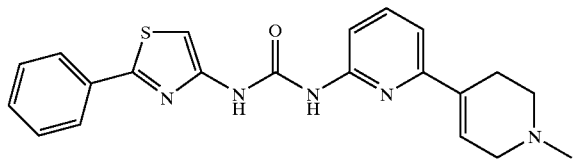

1-(1'-Methyl-1',2',3',6'-tetrahydro-2[2,4]bipyridinyl-6-yl)-3-(2-phenyl-thiazol-4-yl)-urea In a manner similar to Example 234 2-phenyl-thiazole-4-carbonyl azide and 1'-methyl-1',2,3',6'-tetrahdyro-[2,4'] bipyridinyl-6yl amine were heated together in toluene to give 1-(1'-methyl-1',2',3',6'-tetrahydro-2[2,4]bipyridinyl-6-yl)-3-(2-phenyl-thiazol-4-yl)-urea as a tan solid. MS m/z: 392.3 (M+H). Calc'd for $C_{21}H_{21}N_5OS$ 391.49.

EXAMPLE 294

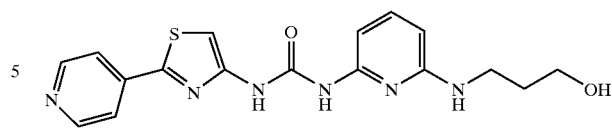

1-[6-(3-Hydroxy-propylamino)-pyridin-2-yl]-3-(2-pyridin-4-yl-thizol-4-yl)-urea

In a manner similar to Example 234, 2-(4-pyridinyl)-4-thiazolcarbonylazide and N-[3-(tetrahydro-pyran-2-yloxy)-propyl]-pyridine-2,6-diamine were heated together in toluene to give 1-[6-(3-hydroxy-propylamino)-pyridin-2-yl]-3-(2-pyridin-4-yl-thizol-4-yl)-urea as a yellow solid (65 mg, 16%) which was dissolved in MeOH (15 mL) and treated with 10 mg of TsOH. The reaction was heated to reflux for 2 h, quenched with saturated $NaHCO_3$, extracted with EtOAc, washed with brine then dried ($MgSO_4$)and concentrated in vacuo to give 1-[6-(3-hydroxy-propylamino)-pyridin-2-yl]-3-(2-pyridin-4-yl-thizol-4-yl)-urea as a yellow solid. MS m/z: 371.2 (M+H). Calc'd for $C_{17}H_{18}N_6O_2S$-370.43.

EXAMPLE 295

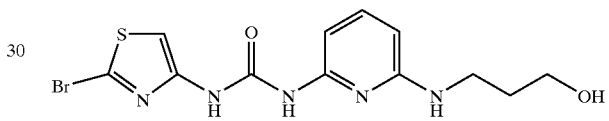

1-(2-Bromo-thiazol-4-yl)-3-[6(3-hydroxy-propylamino)-pyridin-2-yl]-urea

In a manner similar to example 299, 2-bromo-thiazole-4-carbonyl azide and N-[3-(tetrahydro-pyran-2-yloxy)-propyl]-pyridine-2,6-diamine were heated together in toluene to give 1-(2-bromo-thiazol-4-yl)-3-{6-[3-(tetrahydro-pyran-2-yloxy)-propylamino]-pyridin-2-yl}-urea as a yellow solid (150 mg, 75%) which was then dissolved in MeOH (15 mL) and treated with 10 mg of TsOH. Heated to reflux for 2 h, quenched with saturated $NaHCO_3$, extracted with EtOAc and washed with brine then dried ($MgSO_4$)and concentrated in vacuo to give 1-(2-bromo-thiazol-4-yl)-3-[6 (3-hydroxy-propylamino)-pyridin-2-yl]-urea as a white solid. MS m/z: 373.2 (M+H). Calc'd for $C_{12}H_{14}BrN_5O_2S$-372.24.

EXAMPLE 296

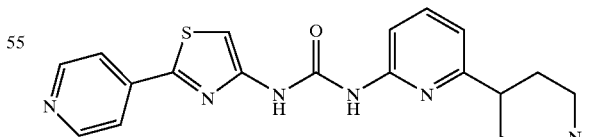

1-(1'-Methyl-1',2',3',4',5',6'-hexahydro-[2,4'] bipydrinyl-6-yl)-3-(2-pyridin-4-yl-thiazol-4-yl)-urea In a manner similar to Example 234, 2-(4-pyridinyl)-4-thiazolcarbonylazide and 1'-methyl-1',2',3',4',5',6'-hexahydro-[2,4']bipyridinyl-6-ylamine were heated together in toluene to give 1-(1'-methyl-1',2',3',4',5',6'-hexahydro-[2,4']bipydrinyl-6-yl)-3-(2-pyridin-4-yl-thiazol-4-yl)-urea as a yellow solid. MS m/z: 395.0 (M+H). Calc'd. for C$_{20}$H$_{22}$N$_6$OS-394.49.

EXAMPLE 297

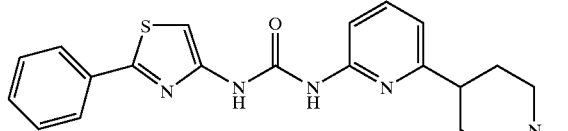

1-(1'-Methyl-1',2',3',4',5',6'-hexahydro-[2,4']bipyridinyl-6-yl)-3-(2-phenyl-thiazol-4-yl)-urea In a manner similar to Example 234 2-phenyl-thiazole-4-carbonyl azide and 1'-methyl-1',2',3',4',5',6'-hexahydro-[2,4']bipyridinyl-6-ylamine were heated together in toluene to give 1-(1'-methyl-1',2',3',4',5',6'-hexahydro-[2,4']bipyridinyl-6-yl)-3-(2-phenyl-thiazol-4-yl)-urea as a white solid. MS m/z: 394.3 (M+H). Calc'd for C$_{21}$H$_{23}$N$_5$OS-393.51.

EXAMPLE 298

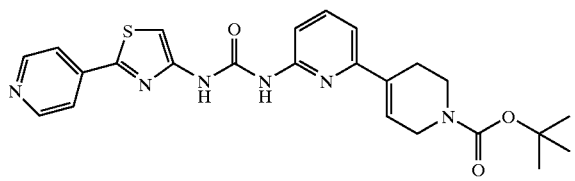

6-[3-(2-Pyridin-4-yl-thizol-4-yl)-ureido]-3',6'-dihydro-2'H-[2,4]bipyridinyl-1'-carboxylic acid tert-butylester In a manner similar to Example 234, 2-(4-pyridinyl)-4-thiazolcarbonylazide and 6-amino-3',6'-dihydro-2'H-[2,4']bipyridinyl-1'-carboxylic acid tert-butyl ester were heated together in toluene to give 6-[3-(2-pyridin-4-yl-thizol-4-yl)-ureido]-3',6'-dihydro-2'H-[2,4]bipyridinyl-1'-carboxylic acid tert-butyl ester as a yellow solid. MS m/z: 479.1 (M+H). Calc'd for C$_{24}$H$_{26}$N$_6$O$_3$S 478.57.

EXAMPLE 299

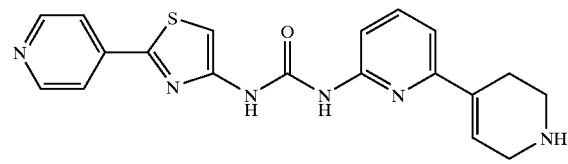

1-(2-Pyridin-4-yl-thiazol-4-yl)-3-(1',2',3',6'-tetrahydro-[2,4']bipyridinyl-6-yl)-urea 6-[3-(2-Pyridin-4-yl-thizol-4-yl)-ureido]-3',6'-dihydro-2'H-[2,4]bipyridinyl-1'-carboxylic acid tert-butyl ester was suspended in CH$_2$Cl$_2$ (10 mL) and treated with TFA (5 mL). Stirred at RT for 30 min. Quenched with saturated NaHCO$_3$ and filtered yellow solid. Washed solid with H$_2$O and MeOH to give 1-(2-pyridin-4-yl-thiazol-4-yl)-3-(1',2',3',6'-tetrahydro-[2,4']bipyridinyl-6-yl)-urea as a yellow solid. MS m/z: 379.1 (M+H). Calc'd for C$_{19}$H$_{18}$N$_6$OS-378.45.

EXAMPLE 300

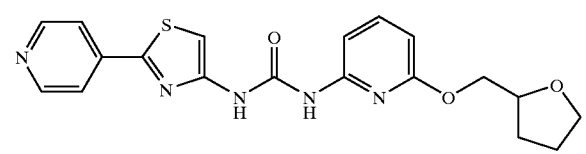

1-(2-Pyridin-4-yl-thiazol-4-yl)-3-[6-(tetrahydro-furan-2-ylmethoxy)-pyridin-2-yl]-urea In a manner similar to Example 234 2-(4-pyridinyl)-4-thiazolcarbonylazide and 6-(tetrahydro-furan-2ylmethoxy)-pyridin-2ylamine were heated together in toluene to give 1-(2-pyridin-4-yl-thiazol-4-yl)-3-[6-(tetrahydro-furan-2-ylmethoxy)-pyridin-2-yl]-urea as a yellow solid. MS m/z: 398.4 (M+H). Calc'd for C$_{19}$H$_{19}$N$_5$O$_3$S-397.45.

EXAMPLE 301

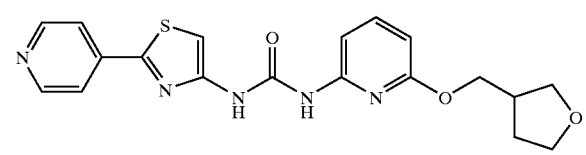

1-(2-Pyridin-4-yl-thizol-4-yl)-3-[6-(tetrahydro-furan-3-ylmethoxy)-pyridin-2-yl]-urea In a manner similar to Example 234, 2-(4-pyridinyl)-4-thiazolcarbonylazide and 6-(tetrahydro-furan-3ylmethoxy)-pyridin-2ylamine were heated together in toluene to give 1-(2-pyridin-4-yl-thizol-4-yl)-3-[6-(tetrahydro-furan-3-ylmethoxy)-pyridin-2-yl]-urea as a yellow solid. MS m/z: 398.3 (M+H). Calc'd. for C$_{19}$H$_{19}$N$_5$O$_3$S-397.45.

EXAMPLE 302

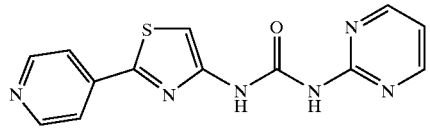

1-(2-Pyridin-4-yl-thiazol-4-yl)-3-pyrimidin-2-yl-urea

In a manner similar to Example 234 2-(4-pyridinyl)-4-thiazolcarbonylazide and 2-aminopyrimidine were heated together in toluene to give 1-(2-pyridin-4-yl-thiazol-4-yl)-3-pyrimidin-2-yl-urea as a yellow solid. MS m/z: 299.1 (M+H). Calc'd for C$_{13}$H$_{10}$N$_6$OS-298.32.

EXAMPLE 303

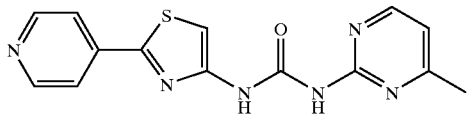

1-(4-Methyl-pyrimidin-2-yl)-3-(2-pyridin-4-yl-thiazol-4-yl)-urea

In a manner similar to Example 234, 2-(4-pyridinyl)-4-thiazolcarbonylazide and 2-amino-4-methyl-pyrimidine

EXAMPLE 304

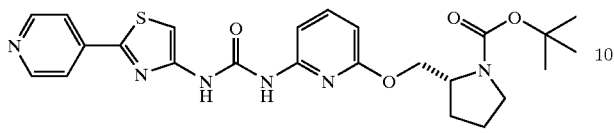

2-[6-[3-(2-Pyridin-4-yl-thiazol-4-yl)-ureido]-pyridin-2-yloxymethyl]-pyrrolidine-1-carboxylic Acid Tert-Butyl Ester In a manner similar to Example 234, 2-(4-pyridinyl)-4-thiazolcarbonylazide and 2-(6-amino-pyridin-2yloxymethyl)-pyrrolidine-1-carboxylic acid tert-butyl ester were heated together in toluene to give 1-(2-pyridin-4-yl-thiazol-4-yl)-3-[6-(tetrahydro-furan-3-yloxy)-pyridin-2-yl]-urea as a yellow solid. MS m/z: 497.4 (M+H). Calc'd for $C_{24}H_{28}N_6O_4S$-496.58.

EXAMPLE 305

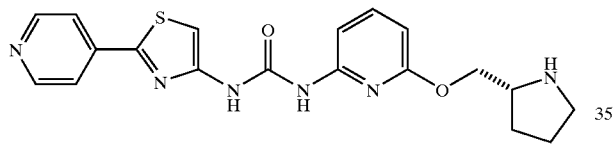

1-(2-Pyridin-4-yl-thiazol-4-yl)-3-[6-(pyrrolidin-2-ylmethoxy)-pyridin-2-yl]-urea To a solution of 1-(2-pyridin-4-yl-thiazol-4-yl)-3-[6-(tetrahydro-furan-3-yloxy)-pyridin-2-yl]-urea and 150 ml of $CH_2Cl_2$ was added 50 mL of TFA. Stirred at RT for 30 min, then concentrated in vacuo. Neutralized with saturated $NaHCO_3$ and basified to pH 9. Filtered white precipitate and washed with $H_2O$ and $Et_2O$. Dried on high-vacuum to give 1-(2-pyridin-4-yl-thiazol-4-yl)-3-[6-(pyrrolidin-2-ylmethoxy)-pyridin-2-yl]-urea as an off-white solid. MS m/z: 497.4 (M+H). Calc'd for $C_{19}H_{20}N_6O_2S$-396.47.

EXAMPLE 306

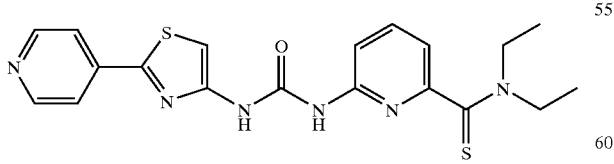

6-[3-(2-Pyridin-4-yl-thiazol-4-yl)-ureido]-pyridine-2-carbothioic acid diethylamide MS m/z: 413.0 (M+H). Calc'd. for $C_{19}H_{20}N_6OS_2$-412.11.

EXAMPLE 307

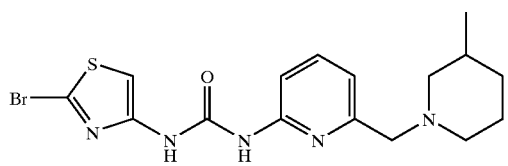

1-(2-Bromo-thiazol-4-yl)-3-[6-(3-methyl-piperidin-1-ylmethyl)-pyridin-2-yl]-urea MS m/z: 410.3 (M+H). Calc'd. for $C_{16}H_{20}BrN_5OS$-409.06.

EXAMPLE 308

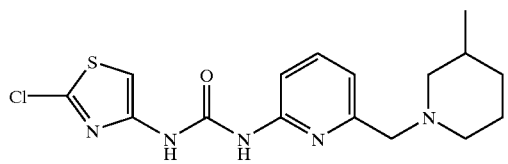

1-(2-Chloro-thiazol-4-yl)-3-[6-(3-methyl-piperidin-1-ylmethyl)-pyridin-2-yl]-urea MS m/z: 366.2 (M+H). Calc'd. for $C_{16}H_{20}ClN_5OS$-365.1.

EXAMPLE 309

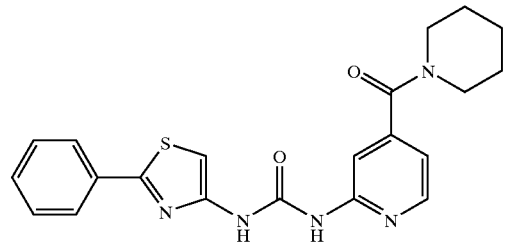

1-(2-Phenyl-thiazol-4-yl)-3-[4-(piperidine-1-carbonyl)-pyridin-2-yl]-urea

MS m/z: 408.3 (M+H). Calc'd for $C_{21}H_{21}N_5O_2S$-407.49.

EXAMPLE 310

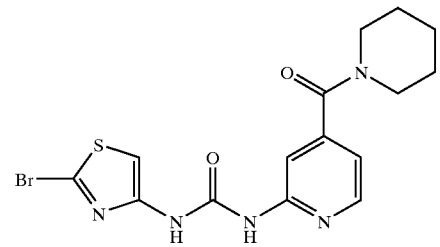

1-(2-Bromo-thiazol-4-yl)-3-[4-(piperidine-1-carbonyl)-pyridin-2-yl]-urea

MS m/z: 412.0 (M+2H). Calc'd. for $C_{15}H_{16}BrN_5O_2S$-410.29.

EXAMPLE 311

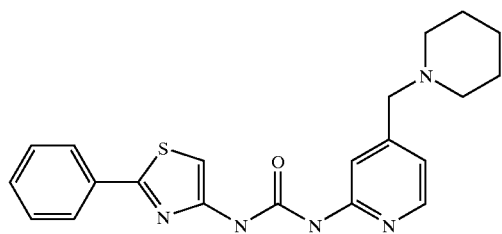

1-(2-Phenyl-thiazol-4-yl)-3-(4-piperidin-1-ylmethyl-pyridin-2-yl)-urea

MS m/z: 394.3 (M+H). Calc'd for $C_{21}H_{23}N_5OS$-393.51.

EXAMPLE 312

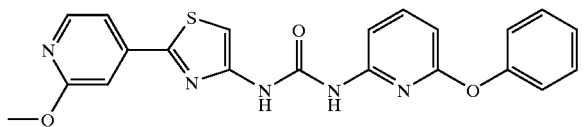

1-[2-(2-Methoxy-pyridin-4-yl)-thiazol-4-yl]-3-(6-phenoxy-pyridin-2-yl)-urea

MS m/z: 420.1 (M+H). Calc'd for $C_{21}H_{17}N_5O_3S$-419.46.

EXAMPLE 313

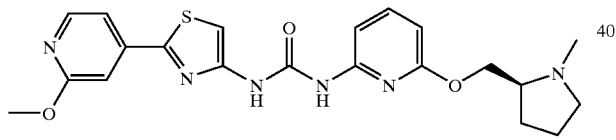

1-[2-(2-Methoxy-pyridin-4-yl)-thiazol-4-yl]-3-[6-(1-methyl-pyrrolidin-2-ylmethoxy)-pyridin-2-yl]-urea MS m/z: 441.0 (M+H). Calc'd for $C_{21}H_{24}N_6O_3S$-440.52.

EXAMPLE 314

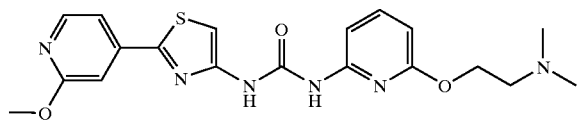

1-[6-(2-Dimethylamino-ethoxy)-pyridin-2-yl]-3-[2-(2-methoxy-pyridin-4-yl)-thiazol-4-yl]-urea MS m/z: 415.0 (M+H). Calcld for $C_{19}H_{22}N_6O_3S$-414.48.

EXAMPLE 318

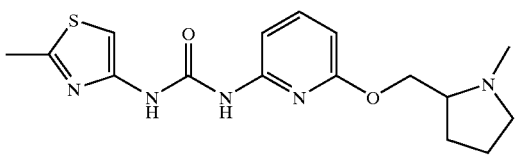

1-[6-(1-Methyl-pyrrolidin-2-ylmethoxy)-pyridin-2-yl]-3-(2-methyl-thiazol-4-yl)-urea MS m/z: 348.1 (M+H). Calc'd for $C_{16}H_{21}N_5O_2S$-347.44.

EXAMPLE 316

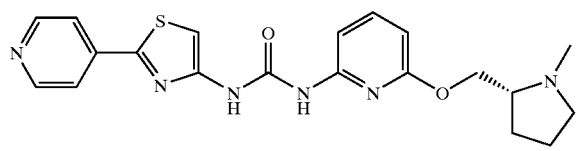

1-[6-(1-Methyl-pyrrolidin-2-ylmethoxy)-pyridin-2-yl]-3-(2-pyridin-4-yl-thiazol-4-yl)-urea MS m/z: 411.1 (M+H). Calc'd for $C_{20}H_{22}N_6O_2S$-410.49.

EXAMPLE 317

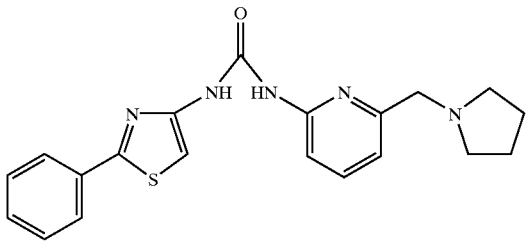

1-(2-phenylthiazol-4-yl)-3-(6-pyrrolidin-1-ylmethyl-pyridin-2-yl)urea

EI-MS m/z 380.4 (M+H). Calc'd for $C_{20}H_{21}N_5OS$: 379.15.

EXAMPLE 318

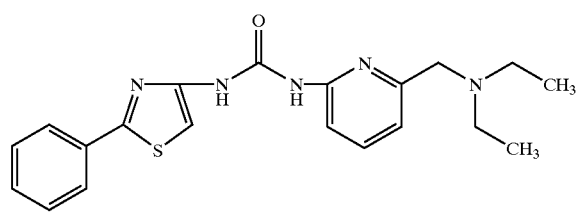

1-(6-Diethylaminomethylpyridin-2-yl)-3-(2-phenylthiazol-4-yl)urea

EI-MS m/z 382.2(M+H). Calc'd for $C_{20}H_{23}N_5OS$: 381.16.

EXAMPLE 319

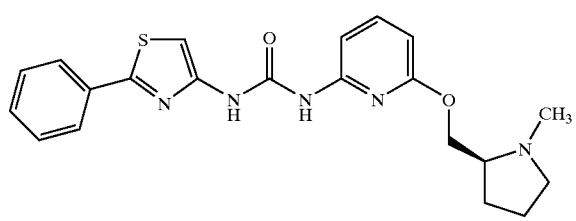

(S)-1-[6-(1-Methylpyrrolidin-2-ylmethoxy)pyridin-2-yl]-3-(2-phenylthiazol-4-yl)urea EI-MS m/z 410.0 (M+H). Calc'd for $C_{21}H_{23}N_5O_2S$: 409.16.

EXAMPLE 320

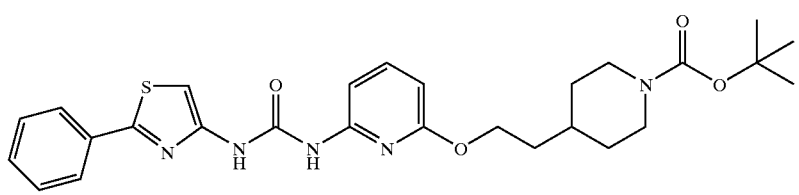

tert-Butyl 4-(2-(6-[3-(2-phenylthiazol-4-yl)-ureido]pyridin-2-yloxy}ethyl)piperidine-1-carboxylate MS m/z: 524.3 (M+H) Calc'd for $C_{27}H_{33}N_5O_4S$: 523.23.

EXAMPLE 321

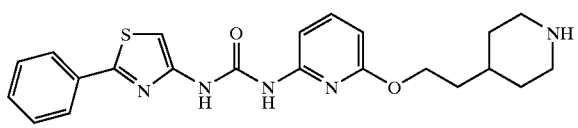

1-[6-(2-Piperidin-4-yl-ethoxy)pyridin-2-yl]-3-[2-phenylthiazol-4-yl]urea

MS m/z: 424.1 (M+1). Calc'd for $C_{22}H_{25}N_5O_2S$: 423.17.

EXAMPLE 322

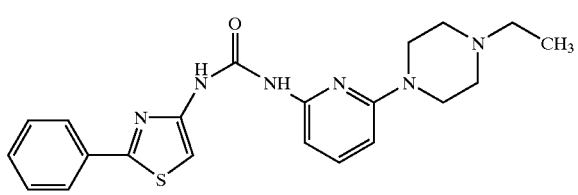

1-[6-(4-Ethylpiperazin-1-yl)-pyridin-2-yl]-3-(2-phenylthiazol-4-yl)urea

EI-MS m/z 419.3 (M+H). Calc'd for $C_{21}H_{24}N_6OS$: 408.17.

EXAMPLE 323

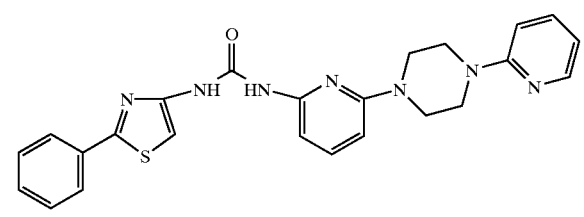

1-[6-(4-Pyridin-2-yl-piperazin-1-yl)pyridin-2-yl]-3-(2-phenylthiazol-4-yl) urea

EI-MS m/z 458.2 (M+H). Calc'd for $C_{24}H_{23}N_7OS$: 457.17.

EXAMPLE 324

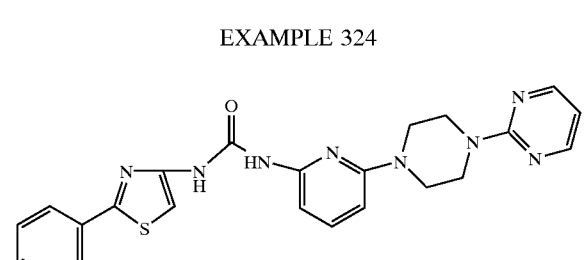

1-(2-phenylthiazol-4-yl)-3-[6-(4-pyrimidin-2-yl-piperazin-1-yl)pyridin-2-yl]urea EI-MS m/z 459.4 (M+H). Calc'd for $C_{23}H_{22}N_8OS$: 458.16.

EXAMPLE 325

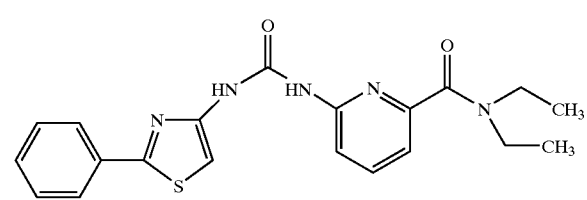

Diethyl 6-[3-(2-phenylthiazol-4-yl)ureido]-pyridine-2-carboxamide

EI-MS m/z 396.3 (M+H). Calc'd for $C_{20}H_{21}N_5O_2S$: 395.14.

EXAMPLE 326

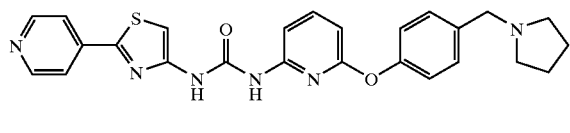

1-(2-Pyridin-4-yl-thiazol-4-yl)-3-(6-p-pyrrolidin-1-ylmethylphenoxypyridin-2-yl)urea EI-MS m/z 473.3(M+H). Calc'd for $C_{25}H_{24}N_5O_2S$: 472.17.

EXAMPLE 327

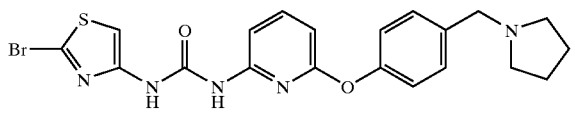

1-(2-Bromothiazol-4-yl)-3-(6-p-pyrrolidin-1-ylmethylphenoxypyridin-2-yl)urea

MS m/z: 473.9 (M+H). Calc'd for $C_{20}H_{20}BrN_5O_2S$: 473.05.

EXAMPLE 328

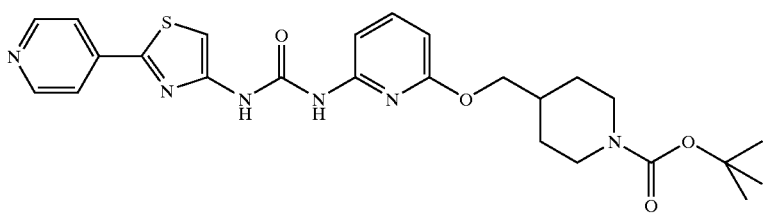

4-(6-[3-(2-Pyridin-4-yl-thiazol-4-yl)-ureido]-pyridin-2-yloxymethyl}-piperidine-1-carboxylic Acid Tert-Butyl Ester MS m/z: 511.2 (M+H). Calc'd for $C_{25}H_{30}N_6O_4S$-510.61.

EXAMPLE 329

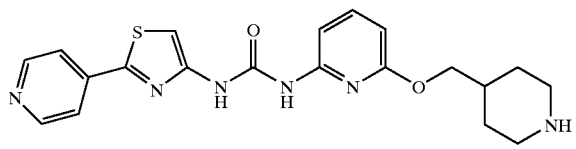

1-[6-(Piperidin-4-ylmethoxy)-pyridin-2-yl]-3-(2-pyridin-4-yl-thiazol-4-yl)-urea

MS m/z: 411.0 (M+H). Calc'd for $C_{20}H_{22}N_6O_2S$-410.49.

EXAMPLE 330

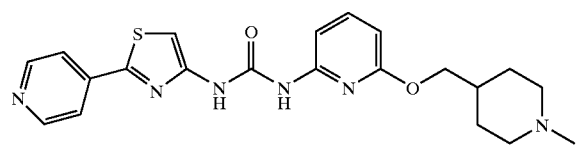

1-[6-(1-Methyl-piperidin-4-ylmethoxy)-pyridin-2-yl]-3-(2-pyridin-4-yl-thiazol-4-yl)-urea MS m/z: 425.2 (M+H). Calc'd for $C_{21}H_{24}N_6O_2S$-424.52.

EXAMPLE 331

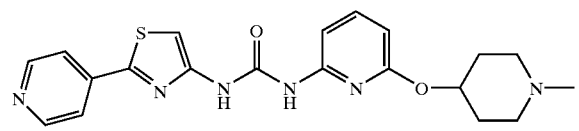

1-[6-(1-Methyl-piperidin-4-yloxy)-pyridin-2-yl]-3-(2-pyridin-4-yl-thiazol-4-yl)-urea MS m/z: 411.0 (M+H). Calc'd for $C_{20}H_{22}N_6O_2S$-410.49.

EXAMPLE 332

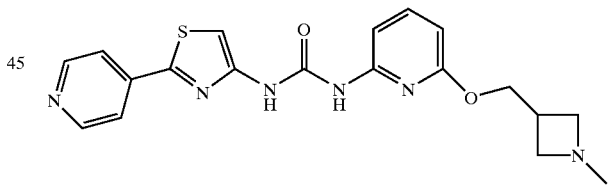

1-[6-(1-Methyl-azetidin-3-ylmethoxy)-pyridin-2-yl]-3-(2-pyridin-4-yl-thiazol-4-yl)-urea
MS m/z: 397.3 (M+H). Calc'd for $C_{19}H_{20}N_6O_2S$-396.47.

EXAMPLE 333

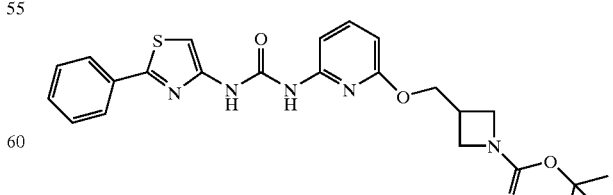

3-(6-[3-(2-Phenyl-thiazol-4-yl)-ureido]-pyridin-2-yloxymethyl)-azetidine-1-carboxylic Acid Tert-Butyl Ester MS m/z: 482.4 (M+H). Calc'd for $C_{24}H_{27}N_5O_4S$-481.57.

EXAMPLE 334

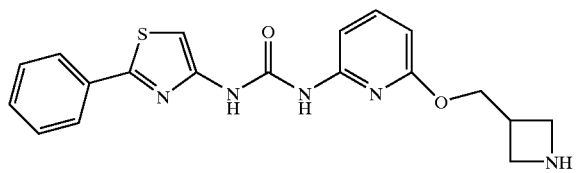

1-[6-(Azetidin-3-ylmethoxy)-pyridin-2-yl]-3-(2-phenyl-thiazol-4-yl)-urea

MS m/z: 382.3 (M+H). Calc'd for $C_{19}H_{19}N_5O_2S$-381.45.

EXAMPLE 335

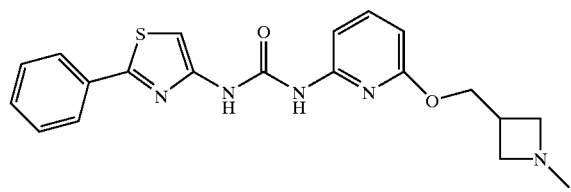

1-[6-(1-Methyl-azetidin-3-ylmethoxy)-pyridin-2-yl]-3-(2-phenyl-thiazol-4-y¹)-urea MS m/z: 396.3 (M+H). Calc'd for $C_{20}H_{21}N_5O_2S$-395.48.

EXAMPLE 336

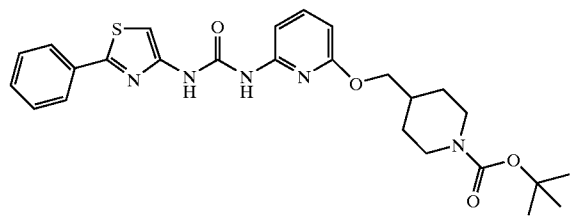

4-{6-[3-(2-Phenyl-thiazol-4-yl)-ureido]pyridin-2-yloxymethyl)-piperidine-1-carboxylic Acid Tert-Butyl Ester MS m/z: 510.3 (M+H). Calc'd for $C_{26}H_{31}N_5S$-509.62.

EXAMPLE 337

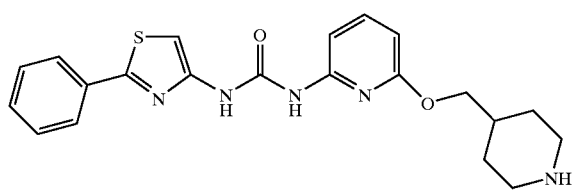

1-(2-Phenyl-thiazol-4-yl)-3-[6-(piperidin-4-ylmethoxy)-pyridin-2-yl]-urea

MS m/z: 410.3 (M+H). Calc'd for $C_{21}H_{23}N_5O_4S$-409.51.

EXAMPLE 338

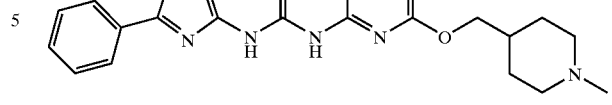

1-[6-(1-Methyl-piperidin-4-ylmethoxy)-pyridin-2-yl]-3-(2-phenyl-thiazol-4-yl)-urea MS m/z: 424.2 (M+H). Calc'd for $C_{22}H_{25}N_5O_2S$-423.53.

EXAMPLE 339

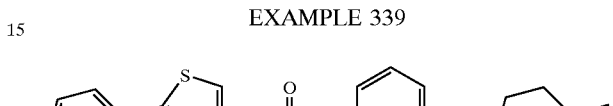

1-[6-(1-Methyl-piperidin-4-yloxy)-pyridin-2-yl]-3-(2-phenyl-thiazol-4-yl)-urea

MS m/z: 410.4 (M+H). Calc'd for $C_{21}H_{23}N_5O_2S$-409.51.

EXAMPLE 340

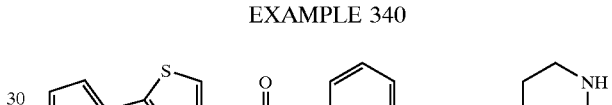

1-[6-(2-Piperidin-4-yl-ethoxy)-pyridin-2-yl]-3-(2-thiophen-2-yl-thiazol-4-yl)-urea MS m/z: 430.1 (M+H). Calc'd for $C_{20}H_{23}N_5O_2S_2$-429.56.

EXAMPLE 341

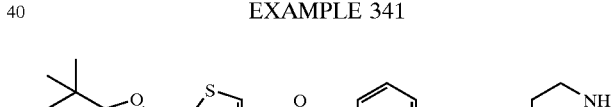

1-[2-(5-tert-Butyl-oxazol-2-yl)-thiazol-4-yl]-3-[6-(2-piperidin-4-yl-ethoxy)-pyridin-2-yl]-urea MS m/z: 471.1 (M+H). Calc'd for $C_{23}H_{30}N_6O_3S$-470.59.

EXAMPLE 342

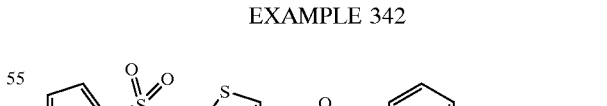

1-[6-(1-Methyl-pyrrolidin-2-ylmethoxy)-pyridin-2-yl]-3-[2-(thiophene-2-sulfonylmethyl)-thiazol-4-yl]-urea MS m/z: 494.0 (M+H). Calc'd for $C_{20}H_{23}N_5O_4S_3$—493.63.

EXAMPLE 343

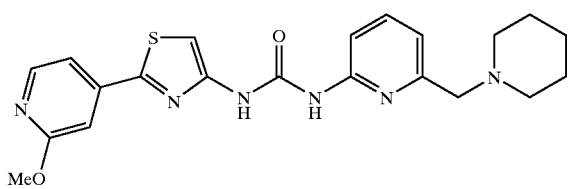

1-[2-(2-Methoxy-pyridin-4-yl)-thiazol-4-yl]-3-(6-piperdin-1-ylmethyl-pyridin-2-yl)-urea MS m/z: 425.1 (M+H). Calc'd for $C_{21}H_{24}N_6O_2S$-424.52.

EXAMPLE 344

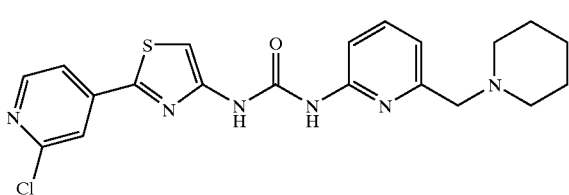

[2-(2-Chloropyridin-4-yl)-thiazol-4-yl]-3-(6-piperdin-1-ylmethyl-pyridin-2-yl)-urea MS m/z: 429.1 (M+H). Calc'd for $C_{20}H_{21}ClN_6OS$-428.9.

The following compounds can be made by procedures similar to those previously described:

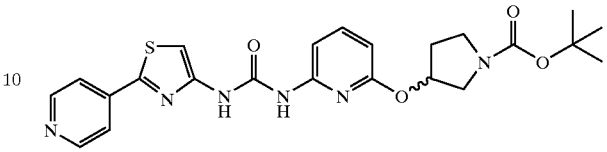

tert-Butyl 3-{6-[3-(2-pyridin-4-yl-thiazol-4yl)-ureido]-pyridin-2-yloxy}-pyrrolidine-1-carboxylate

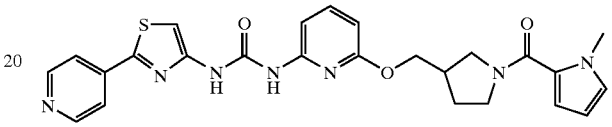

1-{6-[1-(1-Methyl-1H-pyrrole-2-carbonyl)-pyrrolidin-3-ylmethoxy]-pyridin-2yl}-3-(2-pyridin-4-yl-thiazol-4-yl)-urea

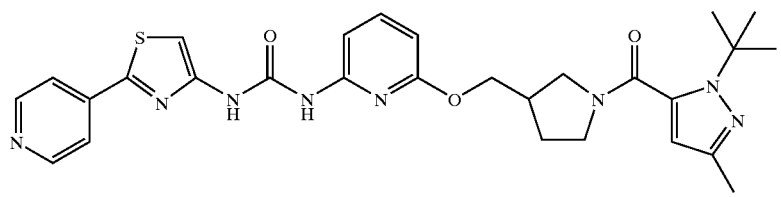

1-{6-[1-(2-tert-Butyl-5-methyl-2H-pyrazole-3-carbonyl)-pyrrolidin-3-ylmethoxy]-pyridin-2-yl}-3-(2-pyridin-4-yl-thiazol-4-yl)-urea

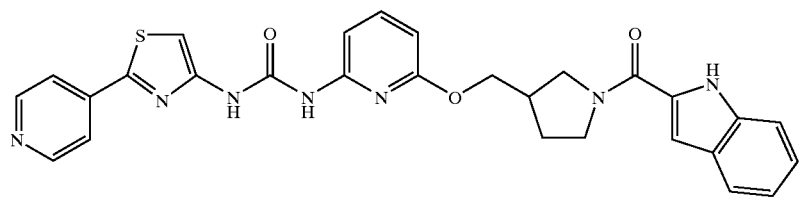

1-{6-[1-(1H-Indole-2-carbonyl)-pyrrolidin-3-ylmethoxy]-pyridin-2-yl}-3-(2-pyridin-4-yl-thiazol-4-yl)-urea

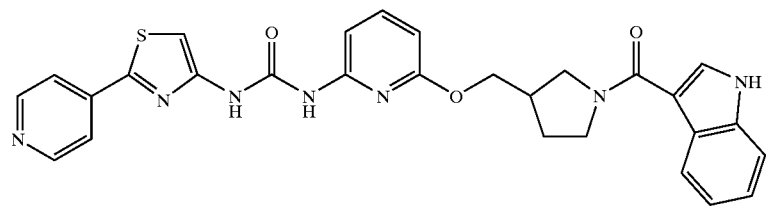

1-{6-[1-(1-Indole-3-carbonyl)-pyrrolidin-3-ylmethoxy]-pyridin-2-yl}-3-(2-pyridin-4-yl-thiazol-4-yl)-urea

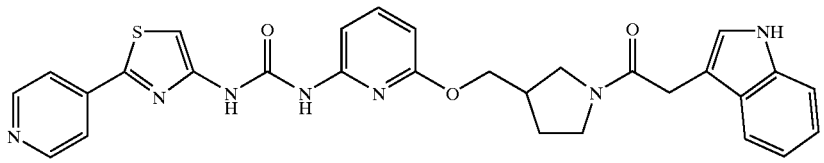

1-{6-[1-(2-1H-Indol-3-yl-acetyl)-pyrrolidin-3-ylmethoxy]-pyridin-2-yl}-3-(2-pyridin-4-yl-thiazol-4-yl)-urea

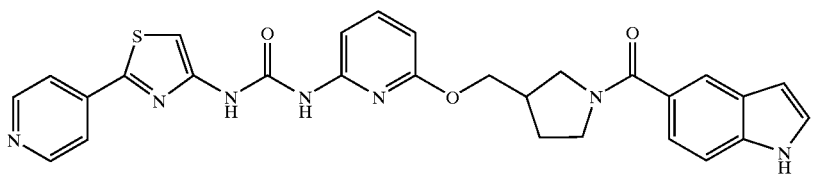

1-{6-[1-(1H-Indole-5-carbonyl)-pyrrolidin-3-ylmethoxy]-pyridin-2-yl}-3-(2-pyridin-4-yl-thiazol-4-yl)-urea

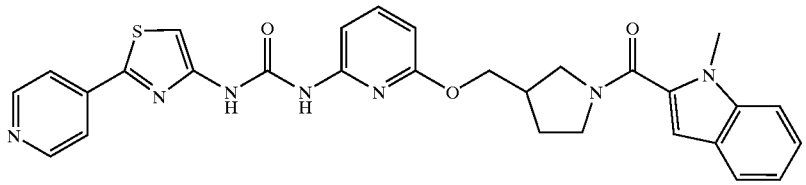

1-(6-[1-(1-Methyl-1H-indole-2-carbonyl)-pyrrolidin-3-ylmethoxy]-pyridin-2-yl}-3-(2-pyridin-4-yl-thiazol-4-yl)-urea

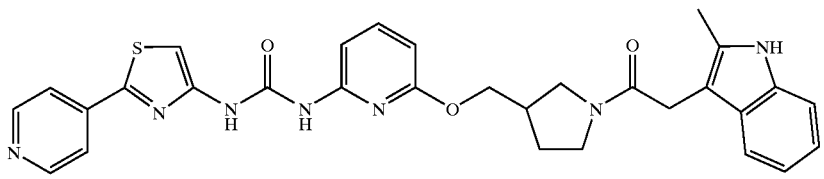

1-(6-{1-[2-(2-Methyl-1H-indol-3-yl)-acetyl]-pyrrolidin-3-ylmethoxy}-pyridin-2-yl)-3-(2-pyridin-4-yl-thiazol-4-yl)-urea

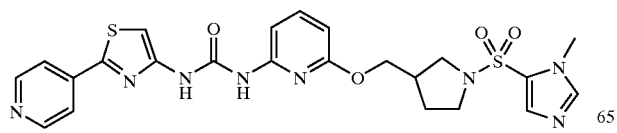

1-(6-[1-(3-Methyl-3H-imidazole-4-sulfonyl)-pyrrolidin-3-ylmethoxy]-pyridin-2-yl}-3-(2-pyridin-4-yl-thiazol-4-yl)-urea

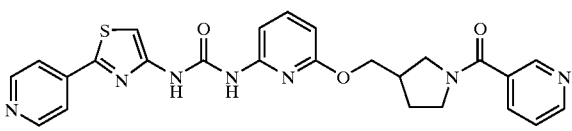

1-{6-[1-(Pyridine-3-carbonyl)-pyrrolidin-3-
ylmethoxy]-pyridin-2-yl}-3-(2-pyridin-4-yl-thiazol-
4-yl)-urea

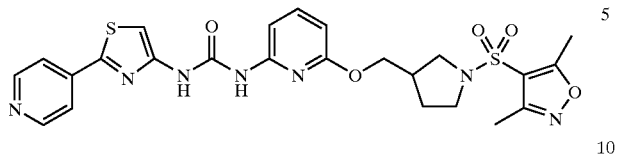

1-{6-[1-(3,5-Dimethyl-isoxazole-4-sulfonyl)-
pyrrolidin-3-ylmethoxy]-pyridin-2-yl}-3-(2-pyridin-
4-y-thiazol-4-yl)-urea

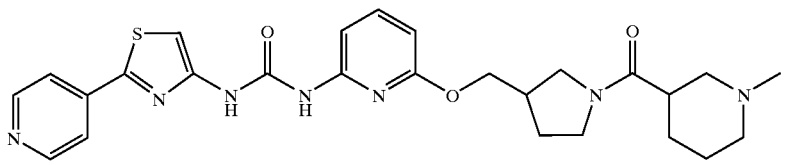

1-{6-[1-(1-Methyl-piperidine-3-carbonyl)-
pyrrolidin-3-ylmethoxy]-pyridin-2-yl}-3-(2-pyridin-
4-yl-thiazol-4-yl)-urea

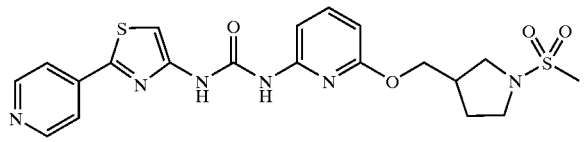

1-[6-(1-Methanesulfonyl-pyrrolidin-3-ylmethoxy)-
pyridin-2-yl]-3-(2-pyridin-4-yl-thiazol-4-yl)-urea

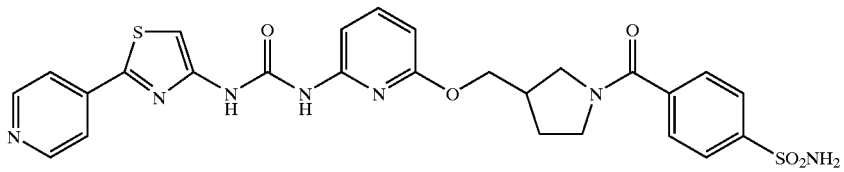

4-(3-{6-[3-(2-Pyridin-4-yl-thiazol-4-yl)-ureido]-
pyridin-2-yloxymethyl}-pyrrolidine-1-carbonyl)-
benzenesulfonamide

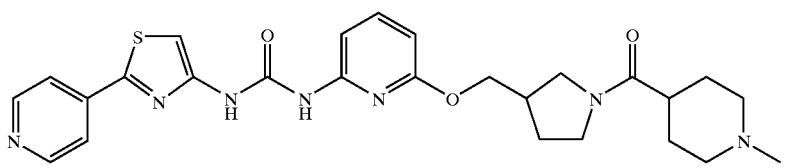

1-{6-[1-(1-Methyl-piperidine-4-carbonyl)-
pyrrolidin-3-ylmethoxy]-pyridin-2-yl}-3-(2-pyridin-
4-yl-thiazol-4-yl)-urea

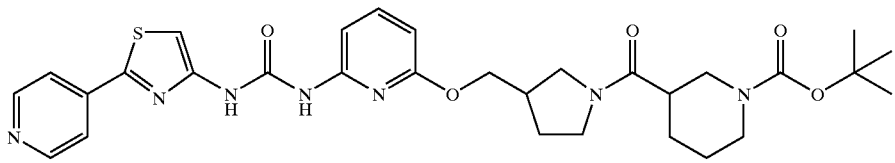

tert-Butyl 3-(3-{6-[3-(2-pyridin-4-yl]-thiazol-4-yl)-
ureido]-pyridin-2-yloxymethyl}-pyrrolidine-1-
carbonyl)-piperidine-1-carboxylate

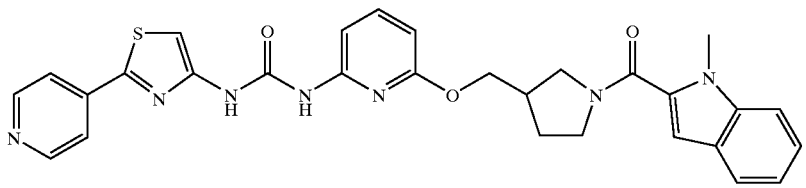

1-{6-[1-(1-Methyl-1H-indole-2-carbonyl)-
pyrrolidin-3-ylmethoxy]-pyridin-2-yl}-3-(2-pyridin-
4-yl-thiazol-4-yl)-urea

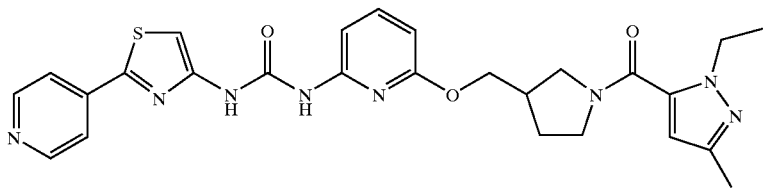

1-{6-[1-(2-Ethyl-5-methyl-2H-pyrazole-3-carbonyl)-
pyrrolidin-3-ylmethoxyl-pyridin-2-yl}-3-(2-pyridin-
4-yl]-thiazol-4-yl)-urea

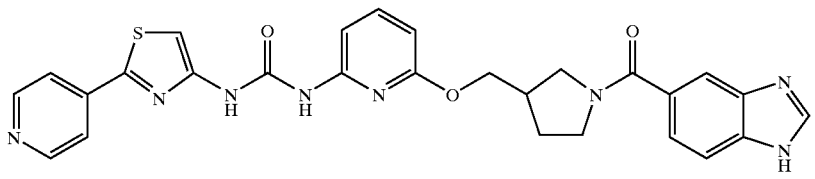

1-{6-[1-(1H-Benzoimidazole-5-carbonyl)-
pyrrolidin-3-ylmethoxy]-pyridin-2-yl}-3-(2-pyridin-
4-yl-thiazol-4-yl)-urea

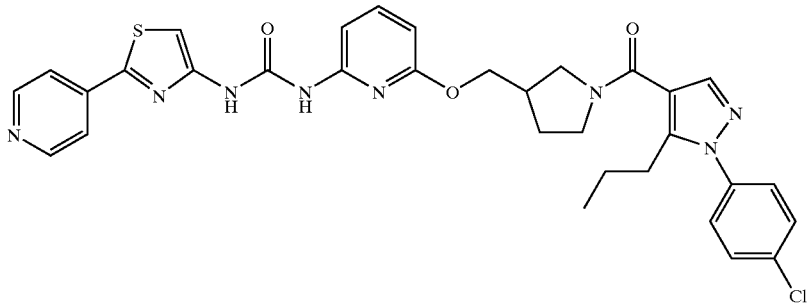

1-(6-{1-[1-(4-Chloro-phenyl)-5-propyl-1H-pyrazole-
4-carbonyl]-pyrrolidin-3-ylmethoxy}-pyridin-2-yl)-
3-(2-pyridin-4-yl-thiazol-4-yl)-urea

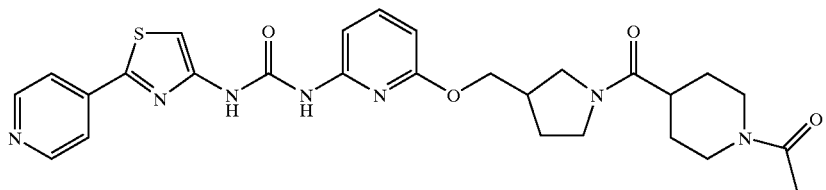

1-{6-[1-(1-Acetyl-piperidine-4-carbonyl)-pyrrolidin-
3-ylmethoxy]-pyridin-2-yl}-3-(2-pyridin-4-yl-
thiazol-4-yl)-urea

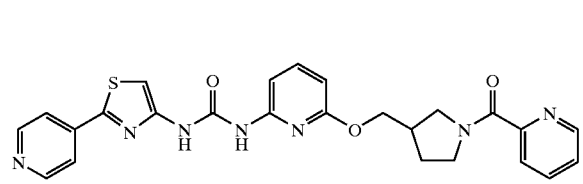

1-{6-[1-(Pyridine-2-carbonyl)-pyrrolidin-3-
ylmethoxy]-pyridin-2-yl}-3-(2-pyridin-4-yl-thiazol-
4-yl)-urea

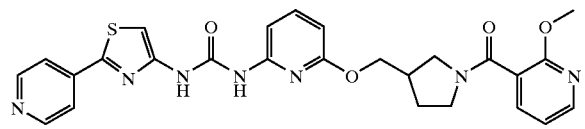

1-{6-[1-(2-Methoxy-pyridine-3-carbonyl)-
pyrrolidin-3-ylmethoxy]-pyridin-2-yl}-3-(2-pyridin-
4-yl-thiazol-4-yl)-urea

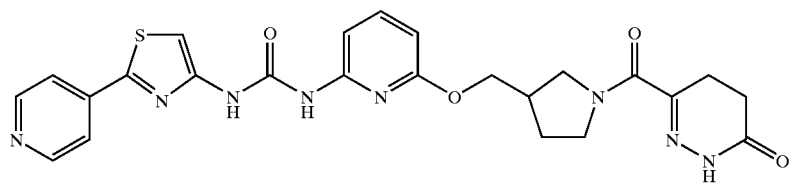

1-{6-[1-(6-Oxo-1,4,5,6-tetrahydro-pyridazine-3-
carbonyl)-pyrrolidin-3-ylmethoxy]-pyridin-2-yl}-3-
(2-pyridin-4-yl-thiazol-4-yl)-urea

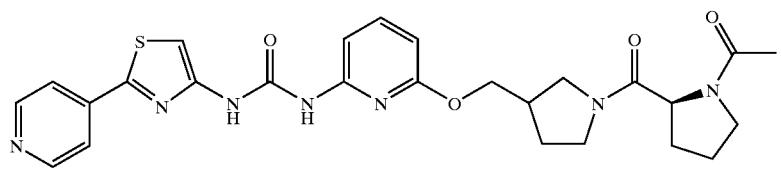

203

1-{6-[l-(1-Acetyl-pyrrolidine-2-carbonyl)-pyrrolidin-3-ylmethoxy]-pyridin-2-yl}-3-(2-pyridin-4-yl-thiazol-4-yl)-urea

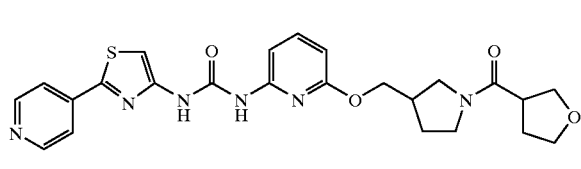

1-(2-Pyridin-4-yl-thiazol-4-yl)-3-{6-[1-(tetrahydro-furan-3-carbonyl)-pyrrolidin-3-ylmethoxy]-pyridin-2-yl}-urea

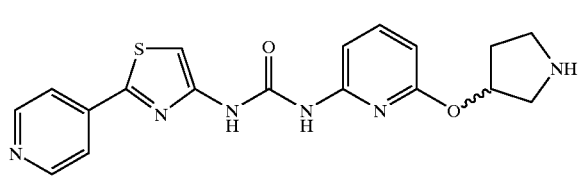

1-(2-Pyridin-4-yl-thiazol-4-yl)-3-[6-(pyrrolidin-3-yloxy)-pyridin-2-yl]-urea

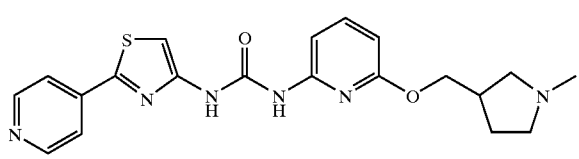

1-[6-(1-Methyl-pyrrolidin-3-ylmethoxy)-pyridin-2-yl]-3-(2-pyridin-4-yl-thiazol-4-yl)-urea

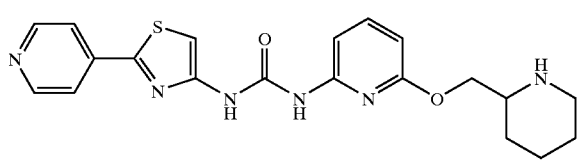

1-[6-(Piperidin-2-ylmethoxy)-pyridin-2-yl]-3-(2-pyridin-4-yl-thiazol-4-yl)-urea

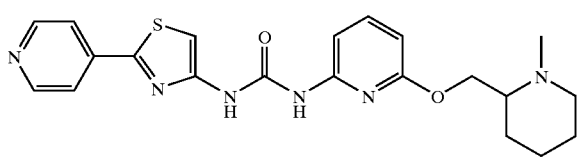

204

1-[6-(1-Methyl-piperidin-2-ylmethoxy)-pyridin-2-yl3-3-(2-pyridin-4-yl-thiazol-4-yl)-urea

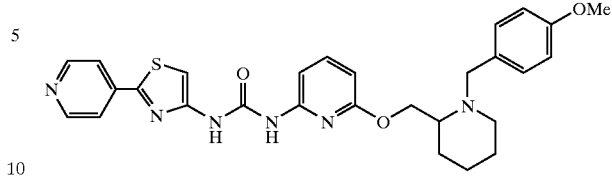

1-(6-[1-(4-Methoxy-benzyl)-piperidin-2-ylmethoxy]-pyridin-2-yl)-3-(2-pyridin-4-yl-thiazol-4-yl)-urea

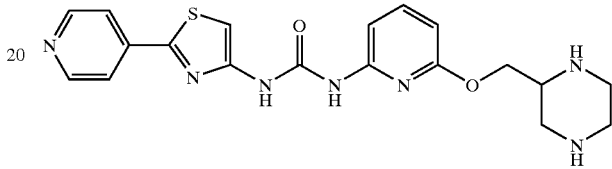

1-[6-(Piperazin-2-ylmethoxy)-pyridin-2-yl]-3-(2-pyridin-4-yl-thiazol-4-yl)-urea

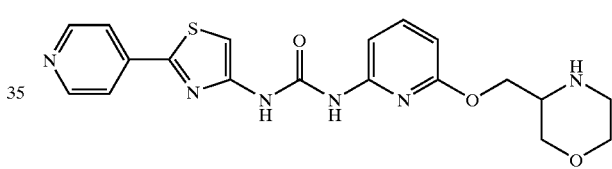

1-[6-(Morpholin-3-ylmethoxy)-pyridin-2-yl]-3-(2-pyridin-4-yl-thiazol-4-yl)-urea

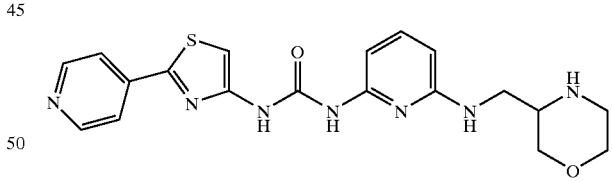

1-{6-[(Morpholin-3-ylmethyl)-amino]-pyridin-2-yl}-3-(2-pyridin-4-yl-thiazol-4-yl)-urea

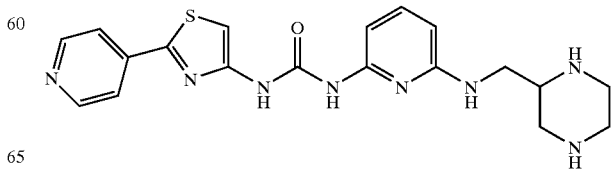

205

1-{6-[(Piperazin-2-ylmethyl)-amino]-pyridin-2-yl}-
3-(2-pyridin-4-yl-thiazol-4-yl)-urea

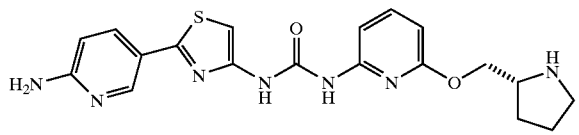

1-[2-(6-Amino-pyridin-3-yl)-thiazol-4-yl]-3-[6-
(pyrrolidin-2-ylmethoxy)-pyridin-2-yl]-urea

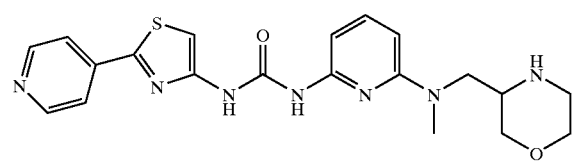

1-[6-(Methyl-morpholin-3-ylmethyl-amino)-pyridin-
2-yl]-3-(2-pyridin-4-yl-thiazol-4-yl)-urea

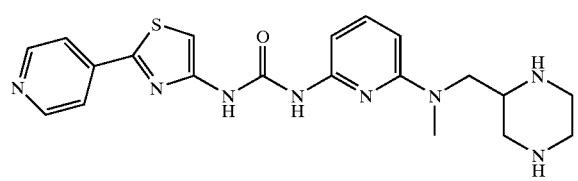

1-[6-(Methyl-piperazin-2-ylmethyl-amino)-pyridin-
2-yl]-3-(2-pyridin-4-yl-thiazol-4-yl)-urea

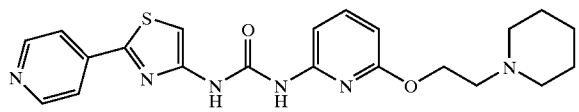

1-[6-(2-Piperidin-1-yl-ethoxy)-pyridin-2-yl]-3-(2-
pyridin-4-yl-thiazol-4-yl)-urea

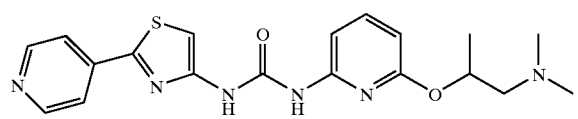

1-[6-(2-Dimethylamino-1-methyl-ethoxy)-pyridin-2-
yl]-3-(2-pyridin-4-yl-thiazol-4-yl)-urea

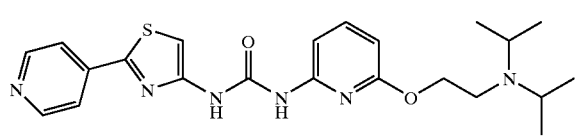

206

1-[6-(2-Diisopropylamino-ethoxy)-pyridin-2-yl]-3-
(2-pyridin-4-yl-thiazol-4-yl)-urea

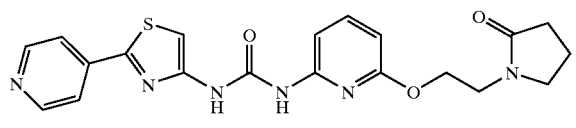

1-{6-[2-(2-Oxo-pyrrolidin-1-yl)-ethoxy]-pyridin-2-
yl}-3-(2-pyridin-4-yl-thiazol-4-yl)-urea

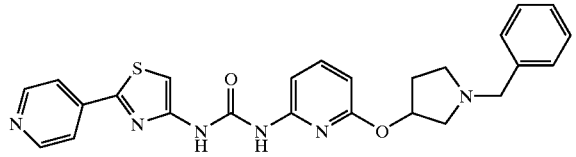

1-[6-(1-Benzyl-pyrrolidin-3-yloxy)-pyridin-2-yl]-3-
(2-pyridin-4-yl-thiazol-4-yl)-urea

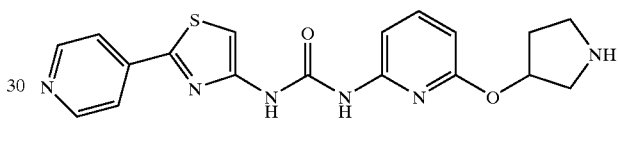

1-(2-Pyridin-4-yl-thiazol-4-yl)-3-[6-(pyrrolidin-3-
yloxy)-pyridin-2-yl]-urea

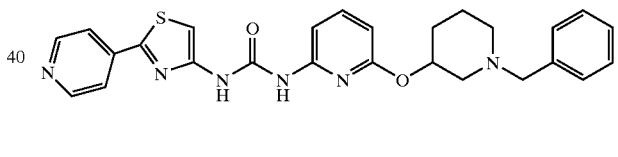

1-[6-(1-Benzyl-piperidin-3-yloxy)-pyridin-2-yl]-3-
(2-pyridin-4-yl-thiazol-4-yl)-urea

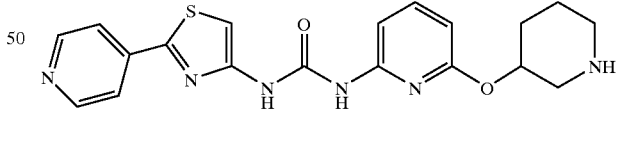

1-[6-(Piperidin-3-yloxy)-pyridin-2-yl]-3-(2-pyridin-
4-yl-thiazol-4-yl)-urea

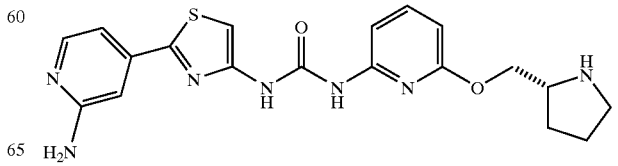

1-[2-(2-Amino-pyridin-4-yl)-thiazol-4-yl]-3-[6-(pyrrolidin-2-ylmethoxy)-pyridin-2-yl]-urea

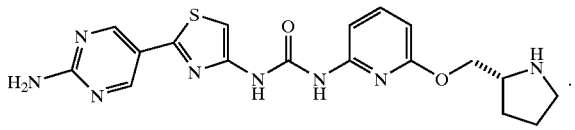

1-[2-(2-Amino-pyrimidin-5-yl)-thiazol-4-yl]-3-[6-(pyrrolidin-2-ylmethoxy)-pyridin-2-yl]-urea.

The pharmacological properties of the compounds of this invention may be confirmed by a number of pharmacological assays. The exemplified pharmacological assays which follow have been carried out with the compounds according to the invention and their salts. The compounds of invention exhibited more than 10% cdk5/p25 or cdk2/cyclin inhibition at 10 μM.

Biological Evaluation
Protocols for Cyclin E2/CDK2
Cloning of Cdk2 and cyclin 2/Generation of Cdk2 and Cyclin 2 Recombinant Baculovirus The following oligonucleotide primers flanking the coding sequence of the human Cdk2 cDNA clone were used to amplify the gene and place EcoRI and HindIII restriction sites at the 5' and 3' ends of the gene respectively. [5' oligo-5'-AAGCGCGCGGAATTCATAAATATGGAGAACTTCCAAAAGGTGGAA-3'; 3' oligo-5'-CTCGACAAGCTTATTAGAGTCGAAGATGGGGTAC-3']

The following oligonucleotide primers flanking the coding sequence of the human CycE2 cDNA clone were used to amplify the gene and place XhoI and SphI restriction sites at the 5' and 3' ends of the gene respectively. A His tag was also placed at the N-terminus of the CycE2 protein. [5' oligo-5'-CCCGGGATCTCGAGATAAATATGCATCATCATCATCATTCAAGACGAAGTAGCCGTTTACAA-3'; 3' oligo-5'-CCCGGTACCGCATGCTTAGTGTTTTCCTGGTGGTTTTTC-3']

CycE-2 and Cdk2 PCR fragments were subcloned into the vector pFastBacDual (Gibco/LifeTechnologies) using the restriction sites indicated above. Recombinant virus was made following protocols supplied by the manufacturer.
Expression of Cyclin 2/CDK2 in Insect Cells Hi5 cells were grown to a cell density of 1×10⁶ cells per ml in 800 ml of Excell 405 media (JRH). Cells were infected with virus at a multiplicity of 1. Infected cultures were incubated with shaking at 28° C. Cells were harvested by centrifugation.
Cloning of Cdk5 and p25/Generation of CDK5 and p25 Recombinant Baculovirus Based on the reported sequences of human CDK5 and p35, GenBank accession numbers X66364 and X80343 respectively, oligonucleotide primers flanking the coding sequence of each gene were used to amplify CDK5 (5'-GCGATGCAGAAATACGAGAAACT-3'; 5'-CCCCACTGTCTCACCCTCTCAA-3') and p35 (5'-CGGTGAGCGGTTTTATCCC-TCC-3'; 5'-GCATTGAATCCTTGAGCCATGACG-3') from a human fetal brain cDNA library (Clontech). p25, a C-terminal proteolytic fragment corresponding to amino acids 99–307 of full-length p35 (Lew, et. al), was PCR subcloned from the p35 sequence using oligonucleotide primers (5'-CGGGATCCATGGCCCAGCCCCCACCGGCCCA-3'; 5'-CCAAGCTTTCACCGATCCAGGCCTAG-3'). The p25 PCR product (629 bp) was cloned into the pFastBacHTb baculovirus expression vector (Gibco BRL) using BamHI and HindIII. CDK5 was PCR subcloned using oligonucleotide primers (5'-CGGGATCC-GCCACCATGCAGAAATACGAGAAACTGG-3'; 5'-GGACTAGTCTAGGGCGGAC-AGAAGTCG-3'). The CDK5 PCR product (879 bp) was cloned into the pFastBacl baculovirus expression vector (Gibco BRL) using BamHI and SpeI. Recombinant baculovirus expressing human Cdk5 and N-terminally six histidine tagged p25 were generated using the Bac-to-Bac system (Gibco BRL).
Expression of P25/CDK5 in Insect Cells Coinfections of Hi5 cells by recombinant baculovirus containing the P25 gene and another containing the CDK5 gene were done at a multiplicity of infection of 5 (each virus). The Hi5 cultures were set to a cell concentration of 1×10⁶ cells per ml in 800 ml of Excell media by JRH. The cultures were grown in 2.6L fernbach flasks with shaking (110 rpm) at 27° C. for 60 h. The cells were harvested by centrifugation.
Purification of Complexes All steps were performed at 4° C. Insect cells expressing either cyclin E2/CDK2 or p25/CDK5 were lysed using a microfluidizer (Microfluidics Corporation.) The lysis buffer contained 10 mM Hepes, 150 mM NaCl, 20 mM MgCl₂, 20 mm imidazole, 0.5 mM EDTA, 10% glycerol, 25 μg/ml Aprotinin, 25 μg/ml Leupeptin, 1 mM Pefabloc, pH 7.5). Total protein was determined on the resulting lysate using the Bradford method with a BSA standard curve. Protamine sulfate was added to the lysate to give a final 30:1 protein::protamine sulfate, incubated for 15–20 min and centrifuged at 14000× g for 30 min to remove insoluble material. Ni-NTA superflow resin (Qiagen Inc) was equilibrated in lysis buffer and incubated with the centrifugation supernatant for 1 h while rotating. The slurry was packed in a glass column and washed until a stable UV baseline was reached. Proteins were eluted with a linear gradient of 20–300 mM imidazole over 15 column volumes. Fractions were analyzed by SDS-PAGE and Western blot. Appropriate fractions were pooled, total protein determined, and submitted for kinase assay.
CDK2 Kinase Assay CDK2 kinase assays were carried out with inhibitor (dissolved in DMSO) in a total volume of 50 μl with 1 nM enzyme (His-tagged cyclin 2/CDK2), 1 μM Histone-H1 (Gibco), 25 μM ATP, 20 μCi/ml ³³P-ATP (Amersham; 2500 Ci/mmole) in kinase buffer (50 mM Tris-HCl, pH 7.5, 5 mM MgCl₂, 1 mM EGTA, 5 mM DTT, 200 μg/ml BSA and 20 mM β-glycerophosphate for 60 min at 25° C. Reactions were stopped by the addition of an equal volume of 30% trichloroacetic acid (Sigma). Precipitates were formed by incubation at 4° C. for 60 min then collected by filtration on Millipore® filter plates (MAFC NOB10). MicroScint-20 (40 μL, Packard) was added, and counted on a Packard TopCount®. Raw cpms were analyzed with a four-parameter logistic fit using the Levenburg Marquardt algorithm (Xlfit software IDBS LTD). Kinetic parameters were calculated by non-linear regression analysis using Grafit (Erithacus Software LTD). Riscovitine (BIOMOL Research Labs Inc., Plymouth Meeting, Pa.) and staurosporin (Sigma, St. Louis Mo.) were used as standards.
CDK5 Kinase Assay CDK5 kinase assays were carried out with inhibitor (dissolved in DMSO) in a total volume of 50 μl with 1 nM enzyme (His-tagged p25/CDK5), 1 μM Histone-Hl (Gibco), 25 μM ATP, 20 μCi/ml ³³P-ATP (Amersham; 2500

Ci/mmole) in kinase buffer (50 mM Tris-HCl, pH 7.5, 5 mM MgCl2, 1 mM EGTA, 5 mM DTT, 200 μg/ml BSA and 20 mM β-glycerophosphate) for 60 min at 25° C. Reactions were stopped by the addition of an equal volume of 30% trichloroacetic acid (Sigma). Precipitates were formed by incubation at 4° C. for 60 min then collected by filtration on Millipore® filter plates (MAFC NOB10). MicroScint-20 (40 μL, Packard) was added, and counted on a Packard Top-Count®. Raw cpms were analyzed with a four-parameter logistic fit using the Levenburg Marquardt algorithm (Xlfit software IDBS LTD). Kinetic parameters were calculated by non-linear regression analysis using Grafit (Erithacus Software LTD). Riscovitine (BIOMOL Research Labs Inc., Plymouth Meeting, Pa.) and staurosporin (Sigma) were used as standards.

Examples 235–236, 238, 242, 245, 247–251, 258, 263–268, 270, 273–275, 279, 280–282, 287–288, 291–302, 304, 307–311, 316–317, 319–322, 324–325, 327–330, 332–335, 337–338, 340–343, and 346–347 exhibited cdk2/cyclin kinase activity with $IC_{50}$ values less than 0.5 μM. The compounds of examples 235–240, 242, 245, 247–251, 258, 263–268, 273–275, 280, 282, 286–288, 291–302, 304, 307–313, 315–317, 319–322, 324–325, 328–330, 332–335, 337–338, 340–343, and 345–347 exhibited cdk5/p25 kinase activity with $IC_{50}$ values less than 0.5 μM.

Cell Proliferation Assay

Cell proliferation was measured using a calorimetric immunoassay (B/M Roche #164 7229), based on the measurement of pyrimidine analog BrdU incorporation during DNA synthesis in proliferating cells. Cells, e.g., human PC-3 prostate carconima cells, huFSF normal human foreskin fibroblast cells, HCT 116 human colon carcinoma cells or HT 29 human colon carcinoma cells, were cultured in a 96-well plate for 24 h, until a cell count of $3 \times 10^3$ to $6 \times 10^3$ cells per well in duplicate wells were achieved, in a well volume of 200 μl. The media was changed and 1 μl of 200× control inhibitors or compounds was added to each well. Cells are incubated for 48 h at 37° C. The cells were labeled with BrdU for 4 h at 37° C. The labeling medium was removed and in one step, the cells were fixed and the DNA was denatured (30 min at RT). Anti-BrdU-POD antibody was added to bind to the BrdU incorporated in newly synthesized cellular DNA (60–90 min at RT). The cells were washed 3× with washing buffer, substrate (100 μl) was added and the cells were incubated for 10 min at RT. The substrate reaction was stopped by adding 25 μl of 1M $H_2SO_4$. The amount of BrdU incorporated was quantified by measuring the absorbance at 450 nm using ELISA reader. $IC_{50}$'s were calculated using GraFit (Sigma).

Ischemic Stroke Model: Middle Cerebral Artery Occlusion (MCAO) In Vivo

The compounds' effect on treating stroke was measured in a MCAO rat model. (L. Belayev et al., Stroke, 27, 1616–23 (1996). Male Sprague-Dawley rats (300–330 g body weight) were anesthetized with halothane and MCAO was induced by inserting a poly-L-lysine coated monofilament suture to the beginning of the middle cerebral artery (MCA). After various time points (60, 90 or 120 min), the intraluminal suture was carefully removed to start reperfusion. Physiological conditions (blood $O_2$, $CO_2$, pH, glucose, blood pressure) were monitored and kept stable during the surgery. The compound was dissolved in 20% Captisol in phosphate buffered saline and administered (orally, IV or IP) 90 min after ischemia onset, at the beginning of reperfusion. Further dosing occurred at 4–8 h and twice a day thereafter.

The use of behavioral tests was directly analogous to the clinical neurological examination for assessing ischemic deficits and rates of behavioral recovery. The battery consisted of four tests: (1) postural reflex test, (2) forelimb placing test (JB Bederson et al., Stroke, 17:472–76 (1986) (L. Belayev et al., Stroke, 26:2313–20 (1995), (3) contralateral foot fault index (A. Tamura et al., J. Cereb Blood Flow Metab., 1:53–60 (1981) (DM Freeney, Science, 217:855–57 (1982), and (4) cylinder asymmetry (TA Jones and T. Schallert, J. Neurosci., 14:2140–52 (1994). Tests were performed once a day for three days and then once a week for a period of 30 days. These tests are useful in assessing neurological deficits for short-term studies; the cylinder asymmetry test appeared to be the most useful for long term experiments.

At the end of the experiment, the infarct volume was measured (JB Bederson et al., Stroke, 17:1304–8 (1986) (KA Osborne et al, J. Neurol Neurosurg. Psychiatry, 50:402 (1987) (RA Swanson et al., J. Cereb. Blood Flow Metab., 10:290–3 (1990). The brains were removed and sliced coronally at 1 mm thickness. The brain slices were stained with 2% (w/vol) 2,3,5-triphenyltetrazolium chloride (TTC) which stains the infarcted areas of the brain in white and allows for the measurement of infarct volume by an image-analysis system. Edema volume that contributes to infarct volume was subtracted by comparison with the total volume of the contralateral hemisphere.

Formulations

Also embraced within this invention is a class of pharmaceutical compositions comprising the active compounds of Formula I–V in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg body weight, preferably between about 0.5 and about 50 mg/kg body weight and most preferably between about 0.1 to 20 mg/kg body weight, may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyinylpyrrolidone, and/or polyinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie.Captisol), cosolvent solubilization (ie. propylene glycol) or micellar solubilization (ie. tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

All mentioned references, patents, applications and publications, are hereby incorporated by reference in their entirety, as if here written.

What is claimed is:

1. A compound of formula VI

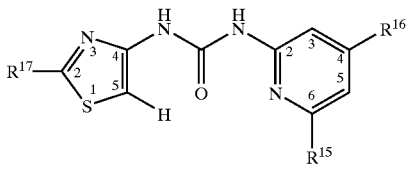

wherein $R^{15}$ is one or more substituents selected from H, optionally substituted 6-membered nitrogen-containing heterocyclyl, phenyl, $C_1$–$C_3$-alkyl, $C_1$–$C_2$-haloalkyl, $C_1$–$C_4$-hydroxyalkyl, amino, $C_1$–$C_4$-azidoalkyl, $C_1$–$C_4$-cyanoalkyl, $C_1$–$C_4$-aminoalkyl, halo, hydroxy, (optionally substituted 6-membered nitrogen-containingheterocyclyl)-$C_1$–$C_4$-alkyl, optionally substituted phenoxy-$C_1$–$C_2$-alkyl, $C_1$–$C_4$-alkoxy-$C_1$–$C_4$-alkyl, $C_1$–$C_4$-alkylamino-$C_1$–$C_4$-alkyl, $C_1$–$C_4$-hydroxyalkylamino, amino-$C_1$–$C_4$-alkoxy-$C_1$–$C_4$-alkyl, optionally substituted 6-membered nitrogen-containing heterocyclyloxy, optionally substituted 6-membered nitrogen-containing heterocyclyl-$C_1$–$C_4$-alkoxy, $C_1$–$C_4$-alkylamino-$C_1$–$C_4$-alkoxy, optionally substituted phenoxy, $C_1$–$C_4$-alkoxycarbonyl, 6-membered heterocyclyl-$C_1$–$C_4$-alkylaminocarbonyl, 6-membered N-containing heterocyclylcarbonyl, $C_1$–$C_4$-alkylaminocarbonyl, $C_1$–$C_4$-alkylaminothiocarbonyl, $C_1$–$C_4$-alkylamino-$C_1$–$C_4$-alkylaminocarbonyl, aminocarbonyl, 6-membered N-containing heterocyclyl-sulfonyl-$C_1$–$C_4$-alkyl, 6-membered N-containing heterocyclyl-$C_1$–$C_4$-alkylamino, $C_1$–$C_4$-alkylamino, $C_1$–$C_4$-alkylamino-$C_1$–$C_4$-alkylamino-$C_1$–$C_4$-alkyl, and $C_1$–$C_4$-alkylamino-$C_1$–$C_4$-alkylamino;

wherein $R^{16}$ is selected from H, 6-membered nitrogen-containingheterocyclylcarbonyl, alkylaminocarbonyl, alkylaminomethyl, and 6-membered nitrogen-containing heterocyclylmethyl; and wherein $R^{17}$ is selected from halo, $C_1$–$C_6$-alkyl, cycloalkylalkynyl, cycloalkyl, optionally substituted phenoxy, optionally substituted 6-membered nitrogen-containing heteroarylsulfonyl-$C_1$–$C_4$-alkyl, unsubstituted 6-membered nitrogen-containing heterocyclyl, phenyl optionally substituted with one or two substituents selected from halo, $C_1$–$C_4$-alkylamino, amino, nitro, $C_1$–$C_4$-alkoxy, $C_1$–$C_2$-haloalkyl, hydroxy, $C_1$–$C_4$-alkylthio, $C_1$–$C_4$-alkylcarbonylamino, (optionally substituted phenyl)sulfonylamino, cyano, $C_1$–$C_2$-haloalkoxy, 5- or 6-membered N-containing heterocyclyl, aminosulfonyl, (6-membered N-containing heterocyclyl)sulfonyl, $C_1$–$C_2$-haloalkylcarbonylaminosulfonyl and (optionally substituted phenyl)aminosulfonyl, and 6-membered nitrogen-containing heterocyclyl substituted with one or more substituents independently selected from pyridyl, phenyl, $C_1$–$C_4$ alkyl, $C_1$–$C_2$ haloalkyl, $C_1$–$C_2$ alkoxy, amino, halo, piperidinyl, morpholinyl, $C_1$–$C_2$ alkylpiperazinyl, $C_1$–$C_3$ alkylaminothiocarbonyl, N,N-di-$C_1$–$C_2$alkylamino-$C_1$–$C_4$-alkylenyl, N—$C_1$–$C_2$alkylamino-$C_1$–$C_4$-alkylenyl, morpholinyl-$C_1$–$C_4$-alkylenylaminocarbonyl, aminocarbonyl, $C_1$–$C_2$-haloalkylcarbonylamino, morpholinyl-$C_1$–$C_4$-alkylenylamino, N,N-di-$C_1$–$C_2$alkylamino and N,N-di-$C_1$–$C_2$alkylamino-$C_1$–$C_4$-alkylenylamino;

and pharmaceutically acceptable salts thereof;

provided only one of $R^{15}$ and $R^{16}$ is H.

2. A compound of claim 1 wherein $R^{15}$ is selected from H, optionally substituted piperidinyl, 1,2,3,6-tetrahydropyridinyl, (optionally substituted piperidinyl)-$C_1$–$C_2$-alkyl, $C_1$–$C_4$-alkylamino-$C_1$–$C_4$-alkyl, $C_1$–$C_4$-hydroxyalkylamino, (optionally substituted piperidinyl)-$C_1$–$C_2$-alkylamino, optionally substituted piperidinyl-$C_1$–$C_4$-alkoxy, $C_1$–$C_4$-alkylamino-$C_1$–$C_4$-alkoxy, optionally substituted piperidinyloxy, optionally substituted phenoxy, $C_1$–$C_4$-alkylaminocarbonyl and $C_1$–$C_4$-alkylaminothiocarbonyl; wherein $R^{16}$ is selected from H, 6-membered nitrogen containing heterocyclylcarbonyl, $C_1$–$C_4$-alkylaminocarbonyl, $C_1$–$C_4$-alkylaminomethyl, and 6-membered nitrogen containing heterocyclylmethyl; and wherein $R^{17}$ is selected from halo, $C_1$–$C_2$-alkyl, optionally substituted 6-membered nitrogen containing heteroarylsulfonyl-$C_1$–$C_2$-alkyl, optionally substituted phenoxy, and $C_3$–$C_6$-cycloalkyl-$C_2$–$C_4$-alkynyl; and pharmaceutically acceptable salts thereof.

3. A compound of claim 2 wherein $R^{15}$ is selected from H, 4-piperidinylmethoxy, 1-Boc-piperidin-4-ylmethoxy, 1-Boc-piperidin-4-ylethoxy, piperidin-4-ylethoxy, 1-methyl-piperidin-4-ylmethoxy, 1-methyl-piperidin-4-yloxy, phenyloxy, dimethylaminoethoxy, 1-piperidinylmethyl, 1-(piperidin-1-yl)ethyl, 3-methylpiperidin-1-ylmethyl, 2,2,6,6-tetramethylpiperidin-1-ylmethyl, 2,6-dimethylpiperidin-1-ylmethyl, dimethylaminomethyl, diethylaminomethyl, diethylaminothiocarbonyl, diethylaminocarbonyl, N-Boc-N-isopropylaminomethyl, isopropylaminomethyl, hydroxypropylamino, 4-ethyl-piperidin-1-yl, 4-(2-pyridyl)piperidin-1-yl, 1-methylpiperidin-4-yl, 4-(2-pyrazinyl)piperidin-1-yl, 1-methyl-1,2,3,6-tetrahydro-pyridin-4-yl, 1,2,3,6-tetrahydro-pyridin-4-yl, and 1-Boc-1,2,3,6-tetrahydro-pyridin-4-yl; wherein $R^{16}$ is selected from H, 1-piperidinylcarbonyl, diethylaminocarbonyl, diethylaminomethyl, and 1-piperidinylmethyl; and wherein $R^{17}$ is selected from chloro, bromo, methyl and cyclopropylethynyl; and pharmaceutically acceptable derivatives thereof.

4. A compound of claim 3 wherein $R^{17}$ is chloro or bromo; and pharmaceutically acceptable salts thereof.

5. A compound of claim 1 wherein $R^{15}$ is selected from H, optionally substituted piperidinyl, 1,2,3,6-tetrahydropyridinyl, (optionally substituted piperidinyl)-$C_1$–$C_2$-alkyl, (optionally substituted piperidinyl)-$C_1$–$C_2$-alkylamino, $C_1$–$C_4$-alkylamino-$C_1$–$C_4$-alkyl, $C_1$–$C_4$-hydroxyalkylamino, optionally substituted piperidinyl-$C_1$–$C_4$-alkoxy, $C_1$–$C_4$-alkylamino-$C_1$–$C_4$-alkoxy, optionally substituted piperidinyloxy, optionally substituted phenoxy, $C_1$–$C_4$-alkylaminocarbonyl and $C_1$–$C_4$-alkylaminothiocarbonyl; wherein $R^{16}$ is selected from H, 6-membered nitrogen containing heterocyclylcarbonyl, $C_1$–$C_4$-alkylaminocarbonyl, $C_1$–$C_4$-alkylaminomethyl, and 6-membered nitrogen containing heterocyclylmethyl; and wherein $R^{17}$ is selected from $C_3$–$C_6$-cycloalkyl and phenyl optionally substituted with one or two substituents selected from halo, $C_1$–$C_4$-alkylamino, amino, nitro, $C_1$–$C_4$-alkoxy, $C_1$–$C_2$-haloalkyl, hydroxy, $C_1$–$C_4$-alkylthio, $C_1$–$C_4$-alkylcarbonylamino, (optionally substituted phenyl) sulfonylamino, cyano, $C_1$–$C_2$-haloalkoxy, 5- or 6-membered N-containing heterocyclyl, aminosulfonyl, (6-membered N-containing heterocyclyl)sulfonyl, $C_1$–$C_2$-haloalkylcarbonylaminosulfonyl and (optionally substituted phenyl)aminosulfonyl;

and pharmaceutically acceptable salts thereof.

6. A compound of claim 5 wherein $R^{15}$ is selected from H, 4-piperidinylmethoxy, 1-Boc-piperidin-4-ylmethoxy, 1-Boc-piperidin-4-ylethoxy, piperidin-4-ylethoxy, 1-methyl-piperidin-4-ylmethoxy, 1-methyl-piperidin4-yloxy, phenyloxy, 4-(pyrrolidin-1-ylmethyl)phenoxy, dimethylaminoethoxy, 1-piperidinylmethyl, 1-(piperidin-1-yl)ethyl, 3-methylpiperidin-1-ylmethyl, 2,2,6,6-tetramethylpiperidin-1-ylmethyl, 2,6-dimethylpiperidin-1-ylmethyl, dimethylaminomethyl, diethylaminomethyl, diethylaminothiocarbonyl, diethylaminocarbonyl, N-Boc-N-isopropylaminomethyl, isopropylaminomethyl, hydroxypropylamino, 4-ethyl-piperidin-1-yl, 4-(2-pyridyl)piperidin-1-yl, 1-methylpiperidin-4-yl, 4-(2-pyrazinyl)piperidin-1-yl, 1-methyl-1,2,3,6-tetrahydro-pyridin-4-yl, 1,2,3,6-tetrahydro-pyridin-4-yl, and 1-Boc-1,2,3,6-tetrahydro-pyridin-4-yl; wherein $R^{16}$ is selected from H, 1-piperidinylcarbonyl, diethylaminocarbonyl, diethylaminomethyl, and 1-piperidinylmethyl; and wherein $R^{17}$ is selected from cyclopropyl and phenyl optionally substituted with aminosulfonyl; and pharmaceutically acceptable salts thereof.

7. A compound of claim 6 wherein $R^{17}$ is unsubstituted phenyl; and pharmaceutically acceptable salts thereof.

8. Compound of claim 1 wherein $R^{15}$ is selected from H, optionally substituted piperidinyl, 1,2,3,6-tetrahydropyridinyl, (optionally substituted piperidinyl)-$C_1$–$C_2$-alkyl, (optionally substituted piperidinyl)-$C_1$–$C_2$-alkylamino, $C_1$–$C_4$-alkylamino-$C_1$–$C_4$-alkyl, $C_1$–$C_4$-hydroxyalkylamino, optionally substituted piperidinyl-$C_1$–$C_4$-alkoxy, $C_1$–$C_4$-alkylamino-$C_1$–$C_4$-alkoxy, optionally substituted piperidinyloxy, optionally substituted phenoxy, $C_1$–$C_4$-alkylaminocarbonyl and $C_1$–$C_4$-alkylaminothiocarbonyl; wherein $R^{16}$ is selected from H, 6-membered nitrogen containing heterocyclylcarbonyl, $C_1$–$C_4$-alkylaminocarbonyl, $C_1$–$C_4$-alkylaminomethyl, and 6-membered nitrogen containing heterocyclylmethyl; and wherein $R^{17}$ is selected from unsubstituted 6-membered nitrogen-containing heterocyclyl, and 6-membered nitrogen-containing heterocyclyl substituted with one or more substituents independently selected from pyridyl, phenyl, $C_1$–$C_4$ alkyl, $C_1$–$C_2$ haloalkyl, $C_1$–$C_2$ alkoxy, amino, halo, piperidinyl, morpholinyl, $C_1$–$C_2$ alkylpiperazinyl, $C_1$–$C_3$ alkylaminothiocarbonyl, N,N-di-$C_1$–$C_2$-alkylamino-$C_1$–$C_4$-alkylenyl, N—$C_1$–$C_2$alkylamino-$C_1$–$C_4$-alkylenyl, morpholinyl-$C_1$–$C_4$-alkylenylaminocarbonyl, aminocarbonyl, $C_1$–$C_2$-haloalkylcarbonylamino, morpholinyl-$C_1$–$C_4$-alkylenylamino, N,N-di-$C_1$–$C_2$alkylamino and N,N-di-$C_1$–$C_2$alkylamino-$C_1$–$C_4$-alkylenylamino;

and pharmaceutically acceptable salts thereof.

9. Compound of claim 8 wherein $R^{15}$ is selected from H, 4-piperidinylmethoxy, 1-Boc-piperidin-4-ylmethoxy, 1-Boc-piperidin-4-ylethoxy, piperidin-4-ylethoxy, 1-methyl-piperidin-4-ylmethoxy, 1-methyl-piperidin4-yloxy, phenyloxy, 4-(pyrrolidin-1-ylmethyl)phenoxy, dimethylaminoethoxy, 2,2,6,6-tetramethylpiperidin-1-ylmethyl, 2,6-dimethylpiperidin-1-ylmethyl, dimethylaminomethyl, diethylaminomethyl, diethylaminothiocarbonyl, diethylaminocarbonyl, N-Boc-N-isopropylaminomethyl, isopropylaminomethyl, hydroxypropylamino, 4-ethyl-piperidin-1-yl, 4-(2-pyridyl)piperidin-1-yl, 1-methylpiperidin4-yl, 4-(2-pyrazinyl)piperidin-1-yl, 1-methyl-1,2,3,6-tetrahydro-pyridin-4-yl, 1,2,3,6-tetrahydro-pyridin-4-yl, and 1-Boc-1,2,3,6-tetrahydro-pyridin4-yl; wherein $R^{16}$ is selected from H, 1-piperidinylcarbonyl, diethylaminocarbonyl, diethylaminomethyl, and 1-piperidinylmethyl; and wherein $R^{17}$ is 4-pyridyl substituted with one or more substituents independently selected from methoxy and chloro and pharmaceutically acceptable salts thereof.

10. A compound of claim 9 wherein $R^{17}$ is 4-pyridyl; and pharmaceutically acceptable salts thereof.

11. A pharmaceutical composition comprising a pharmaceutically acceptable carrier and a compound of any of claims 1–10 or 1–11.

12. A compound of Formula II

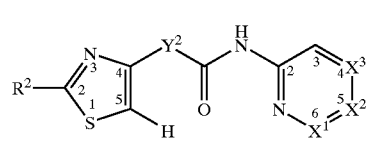

II wherein $X^1$ is $CR^1$; wherein $X^2$ is $CR^1$; wherein $X^3$ is CH; wherein $R^1$ is one or more substituents selected from H, optionally substituted piperidinyl, pyridyl, phenyl, $C_1$–$C_6$-alkyl, $C_1$–$C_2$-haloalkyl, $C_1$–$C_4$-hydroxyalkyl, amino, $C_1$–$C_4$-azidoalkyl, $C_1$–$C_4$-cyanoalkyl, $C_1$–$C_4$-aminoalkyl, halo, hydroxy, (optionally substituted piperidinyl)-$C_1$–$C_2$-alkyl, optionally substituted phenoxy-$C_1$–$C_2$-alkyl, $C_1$–$C_4$-alkylaminothiocarbonyl, $C_1$–$C_4$-alkoxy-$C_1$–$C_4$-alkyl, $C_1$–C4-alkylamino-$C_1$–C4-alkyl, $C_1$–$C_4$-hydroxyalkylamino-$C_1$–C4-alkyl, amino-$C_1$–C4-alkoxy-$C_1$–$C_4$-alkyl, optionally substituted piperidinyl-$C_1$–C4-alkoxy, $C_1$–C4-alkylamino-$C_1$–C4-alkoxy, optionally substituted pyridyloxy, optionally substituted phenoxy, $C_1$–C4-alkoxycarbonyl, (6-membered N-containing heterocyclyl)-$C_1$–$C_4$-alkylaminocarbonyl, (6-membered N-containing heterocyclyl)carbonyl, $C_1$–$C_4$-alkylaminocarbonyl, $C_1$–$C_4$-alkylamino-$C_1$–$C_4$-alkylaminocarbonyl, aminocarbonyl, (6-membered N-containing heterocyclyl)-$C_1$–$C_4$-alkylamino, $C_1$–$C_4$-alkylamino, $C_1$–$C_4$-alkylamino-$C_1$–$C_4$-alkylamino-$C_1$–C4-alkyl, and $C_1$–$C_4$-alkylamino-$C_1$–$C_4$-alkylamino;

wherein R² is selected from halo, C₁–C₄-alkyl, C₁–C₄-alkylamino-C₂–C₄-alkynyl, C₃–C₆-cycloalkyl, optionally substituted benzodioxolyl, optionally substituted phenoxy, unsubstituted 6-membered nitrogen-containing heterocyclyl, phenyl optionally substituted with one or two substituents selected from halo, C₁–C₄-alkylamino, amino, nitro, C₁–C₄-alkoxy, C₁–C₂-haloalkyl, hydroxy, C₁–C₄-alkylthio, C₁–C₄-alkylcarbonylamino, (optionally substituted phenyl)sulfonylamino, cyano, C₁–C₂-haloalkoxy, 5- or 6-membered N-containing heterocyclyl, aminosulfonyl, (6-membered N-containing heterocyclyl)sulfonyl, C₁–C₂-haloalkylcarbonylaminosulfonyl and (optionally substituted phenyl)aminosulfonyl, and 6-membered nitrogen-containing heterocyclyl substituted with one or more substituents independently selected from pyridyl, phenyl, C₁–C₄ alkyl, C₁–C₂ haloalkyl, C₁–C₂ alkoxy, amino, halo, piperidinyl, morpholinyl, C₁–C₂ alkylpiperazinyl, C₁–C₃ alkylaminothiocarbonyl, N,N-di-C₁–C₂alkylamino-C₁–C₄-alkylenyl, N—C₁–C₂alkylamino-C₁–C₄-alkylenyl, morpholinyl-C₁–C₄-alkylenylaminocarbonyl, aminocarbonyl, C₁–C₂-haloalkylcarbonylamino, morpholinyl-C₁–C₄-alkylenylamino, N,N-di-C₁–C₂alkylamino and N,N-di-C₁–C₂alkylamino-C₁–C₄-alkylenylamino; and wherein Y² is NH;

and pharmaceutically acceptable salts thereof.

13. A compound of Formula V

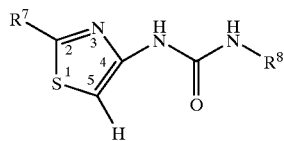

wherein R⁷ is selected from halo, C₁–C₄-alkyl, C₃–C₆-cycloalkyl, optionally substituted benzodioxolyl, optionally substituted phenoxy, 6-membered nitrogen-containing heterocyclyl, phenyl optionally substituted with one or two substituents selected from halo, C₁–C₄-alkylamino, amino, C₁–C₄-alkoxy, C₁–C₂-haloalkyl, hydroxy, C₁–C₄-alkylthio, cyano, C₁–C₂-haloalkyloxy, aminosulfonyl, (6-membered N-containing heterocyclyl)sulfonyl, C₁–C₂-haloalkylcarbonylaminosulfonyl, and (optionally substituted phenyl)aminosulfonyl, and 6-membered nitrogen-containing heterocyclyl substituted with one or more substituents independently selected from pyridyl, phenyl, C₁–C₄ alkyl, C₁–C₂ haloalkyl, C₁–C₂ alkoxy, halo, piperidinyl, morpholinyl, C₁–C₂ alkylpiperazinyl, C₁–C₃ alkylaminothiocarbonyl, N,N-di-C₁–C₂-alkylamino-C₁–C₄-alkylenyl, N—C₁–C₂-alkylamino-C₁–C₄-alkylenyl, morpholinyl-C₁–C₄-alkylenylaminocarbonyl, aminocarbonyl, morpholinyl-C₁–C₄-alkylenylamino, N,N-di-C₁–C₂alkylamino and N,N-di-C₁–C₂alkylamino-C₁–C₄-alkylenylamino;

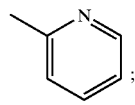

wherein R⁸ is optionally substituted with one or two substituents independently selected from H, optionally substituted piperidinyl, pyridyl, phenyl, C₁–C₆-alkyl, C₁–C₂-haloalkyl, C₁–C₄-hydroxyalkyl, amino, C₁–C₄-azidoalkyl, C₁–C₄-cyanoalkyl, C₁–C₄-aminoalkyl, halo, hydroxy, (optionally substituted piperidinyl)-C₁–C₂-alkyl, optionally substituted phenoxy-C₁–C₂-alkyl, C₁–C₄-alkylaminothiocarbonyl, C₁–C₄-alkoxy-C₁–C₄-alkyl, C₁–C₄-alkylamino-C₁–C₄-alkyl, C₁–C₄-hydroxyalkylamino-C₁–C₄-alkyl, amino-C₁–C₄-alkoxy-C₁–C₄-alkyl, optionally substituted piperidinyl-C₁–C₄-alkoxy, C₁–C₄-alkylamino-C₁–C₄-alkoxy, optionally substituted pyridyloxy, optionally substituted phenoxy, C₁–C₄-alkoxycarbonyl, (6-membered N-containing heterocyclyl)-C₁–C₄-alkylaminocarbonyl, (6-membered N-containing heterocyclyl)carbonyl, C₁–C₄-alkylaniinocarbonyl, C₁–C₄-alkylamino-C₁–C₄-alkylaminocarbonyl, aminocarbonyl, (6-membered N-containing heterocyclyl)-C₁–C₄-alkylamino, C₁–C₄-alkylamino, C₁–C₄-alkylamino-C₁–C₄-alkylamino-C₁–C₄-alkyl, and C₁–C₄-alkylamino-C₁–C₄-alkylamino;

and pharmaceutically acceptable salts thereof.

14. Compound of claim 13 wherein R⁷ is selected from halo, C₁–C₄-alkyl, C₃–C₆-cycloalkyl, optionally substituted piperidinyl, optionally substituted benzodioxolyl, optionally substituted phenoxy, phenyl optionally substituted with one or two substituents selected from halo, C₁–C₄-alkylamino, Boc-amino, amino, C₁–C₄-alkoxy, C₁–C₂-haloalkyl, hydroxy, C₁–C₄-alkylthio, cyano, C₁–C₂-haloalkyloxy, aminosulfonyl, (6-membered N-containing heterocyclyl)sulfonyl, C₁–C₂-haloalkylcarbonylaminosulfonyl, and (optionally substituted phenyl)aminosulfonyl, and pyridyl optionally substituted with one or two substituents selected from C₁–C₃ alkyl, C₁–C₄-alkoxy and halo;

wherein R⁸ is selected from

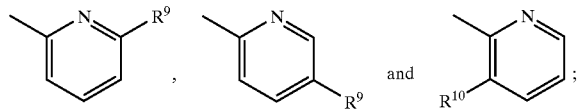

wherein R⁹ is selected from optionally substituted piperidinyl, pyridyl, phenyl, C₁–C₄ alkyl, C₁–C₂ haloalkyl, C₁–C₂ hydroxyalkyl, amino, C₁–C₂ azidoalkyl, C₁–C₂ cyanoalkyl, C₁–C₂ aminoalkyl, halo, (optionally substituted piperidinyl)-CH₂—, optionally substituted phenoxy-CH₂—, C₁–C₄-alkylaminothiocarbonyl, C₁–C₄-alkoxy-C₁–C₄-alkyl, C₁–C₄-alkylamino-C₁–C₄-alkyl, C₁–C₄-hydroxyalkylamino-C₁–C₄-alkyl, Boc-aminoethoxymethylenyl, amino-C₁–C₄-alkoxy-C₁–C₄-alkyl, optionally substituted piperidinyl-C₁–C₄-alkoxy, C₁–C₄-alkylamino-C₁–C₄-alkoxy, optionally substituted phenoxy, C₁–C₄-alkoxycarbonyl, (6-membered N-containing heterocyclyl)-C₁–C₄-alkylaminocarbonyl, 1-piperidinylcarbonyl, C₁–C₄alkylaminocarbonyl, C₁–C₄-alkylamino-C₁–C₄-alkylaminocarbonyl, aminocarbonyl, C₁–C₄-alkylamino, C₁–C₄-alkylamino-C₁–C₄-alkylamino- $C_1$–$C_4$-alkyl, and $C_1$–$C_4$-alkylamino-$C_1$–$C_4$-alkylamino; and wherein $R^{10}$ is selected from H, hydroxy, and amino.

15. Compound of claim 14 wherein $R^7$ is selected from bromo, chloro, fluoro, $C_1$–$C_3$-alkyl, $C_3$–$C_6$-cycloalkyl, piperidinyl, benzodioxolyl, phenoxy, phenyl optionally substituted with one or two substituents selected from fluoro, N,N-dimethylamino, amino, methoxy, trifluoromethyl, Boc-amino, hydroxy, ethoxy, methylthio, cyano, trifluoromethoxy, aminosulfonyl, 4-morpholinylsulfonyl, trifluoroacetylaminosulfonyl, and (4-chlorophenyl)aminosulfonyl, and pyridyl optionally substituted with one or two substituents selected from $C_1$-$C_3$ alkyl, methoxy, ethoxy and chloro;

wherein $R^8$ is selected from

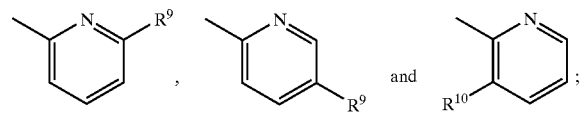

and wherein $R^9$ is selected from 4-amino-1-piperidinyl, 4-(N-hydroxyethylamino)-1-piperidinyl, 4-(N-propylamino)-1-piperidinyl, 4-(N-benzylamino)-1-piperidinyl, 4-oxo-piperidinyl, 4-(hydroxyimino)-piperidinyl, pyridyl, phenyl, methyl, ethyl, propyl, amino, azidomethyl, hydroxymethyl, trifluoromethyl, fluoro, chloro, bromo, aminoethyl, aminomethyl, cyanomethyl, 1-piperidinyl-$CH_2$—, 4-methyl-1-piperidinyl-$CH_2$—, 3-methyl-1-piperidinyl-$CH_2$—, 2-methyl-1-piperidinyl-$CH_2$—, 3,5-dimethyl-1-piperidinyl-$CH_2$—, 4-oxo-1-piperidinyl-$CH_2$—, 4-hydroxy-1-piperidinyl-$CH_2$—, 3-hydroxy-1-piperidinyl-$CH_2$—, 2-ethoxycarbonyl-1-piperidinyl-$CH_2$—, 3-ethoxycarbonyl-1-piperidinyl-$CH_2$—, 3-carboxy-1-piperidinyl-$CH_2$—, 4-ethoxycarbonyl-1-piperidinyl-$CH_2$—, 4-carboxy-1-piperidinyl-$CH_2$—, 4-(1-pyrrolidinyl)-1-piperidinyl-$CH_2$—, 4-(N-hydroxyethylamino)-1-piperidinyl-$CH_2$—, 4-(N-propylamino)-1-piperidinyl-$CH_2$—, 3-(N,N-diethylamino)carbonyl-1-piperidinyl-$CH_2$—, 4-(methyl)phenoxymethylenyl, 4-(N,N-dimethylaminomethylenyl)-phenoxymethylenyl, methylaminothiocarbonyl, methoxymethylenyl, ethylaminothiocarbonyl, N,N-dimethylaminoethylenyl, N,N-diethylaminomethylenyl, N-methylaminomethylenyl, N-(hydroxypropyl)aminomethylenyl, N-ethylaminomethylenyl, Boc-aminoethoxymethylenyl, aminoethoxymethylenyl, N—Boc-piperidin-4-ylethoxy, 1-methyl-4-piperidinylethoxy, 4-piperidinylethoxy, 4-piperidinylmethoxy, N,N-dimethylaminoethoxy, 4-methylphenoxy, 4-(aminoethyl)phenoxy, 4-(1-imidazolyl)phenoxy, 2,4-dimethylphenoxy, phenoxy, 4-cyanophenoxy, 4-[1,3]dioxolan-2-ylphenoxy, 4-fluorophenoxy, 3,4-difluorophenoxy, ethoxycarbonyl, 1-piperidinylcarbonyl, methylaminocarbonyl, ethylaminocarbonyl, N,N-diethylaminocarbonyl, aminocarbonyl, N,N-diethylamino, N-(N',N'-dimethylaminoethylenyl)aminocarbonyl, N,N-diethylamino(2-propylenyl)aminomethylenyl, N,N-diethylamino(1-propylenyl)-aminomethylenyl and N-(N',N'-dimethylaminoethylenyl)amino.

16. Compound of claim 13 wherein $R^7$ is selected from bromo, methyl, ethyl, cyclopropyl, cyclohexyl, 3-fluorophenyl, 4-fluorophenyl, 4-(N,N-dimethylamino)phenyl, phenyl, 3-trifluoromethylphenyl, 4-trifluoromethylphenyl, 4-aminophenyl, 3-aminophenyl, 4-Boc-aminophenyl, 4-aminosulfonylphenyl, 4-(4-morpholinylsulfonyl)phenyl, 4-(trifluoroacetylaminosulfonyl)phenyl, 4-[(4-chlorophenyl)aminosulfonyl]phenyl, 2,4-difluorophenyl, 5-benzodioxolyl, 2,4-dimethoxyphenyl, 3-hydroxyphenyl, 3-ethoxyphenyl, 3,4-dimethoxyphenyl, 4-methylthiophenyl, 4-cyanophenyl, 4-trifluoromethoxyphenyl, 4-methoxyphenyl, 3-methoxyphenyl, 2-methoxyphenyl, phenoxy, 4-piperidinyl, 6-methoxy-3-pyridyl, 2-methoxy-3-pyridyl, 2-ethoxy-3-pyridyl, 3,4-dichloro-4-pyridyl, 3,5-dichloro-4

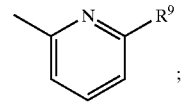

and pyridyl, 2-chloro-4-pyridyl, 3-pyridyl and 4-pyridyl; wherein $R^8$ is and wherein $R^9$ is selected from 4-amino-1-piperidinyl, 4-(N-hydroxyethylamino)-1-piperidinyl, 4-(N-propylamino)-1-piperidinyl, 4-(N-benzylamino)-1-piperidinyl, 4-oxo-piperidinyl, 4-(hydroxyimino)-piperidinyl, pyridyl, phenyl, methyl, ethyl, propyl, amino, azidomethyl, hydroxymethyl, trifluoromethyl, fluoro, chloro, bromo, aminoethyl, aminomethyl, cyanomethyl, 1-piperidinyl-$CH_2$—, 4-methyl-1-piperidinyl-$CH_2$—, 3-methyl-1-piperidinyl-$CH_2$—, 2-methyl-1-piperidinyl-$CH_2$—, 3,5-dimethyl-1-piperidinyl-$CH_2$—, 4-oxo-1-piperidinyl-$CH_2$—, 4-hydroxy-1-piperidinyl-$CH_2$—, 3-hydroxy-1-piperidinyl-$CH_2$—, 2-ethoxycarbonyl-1-piperidinyl-$CH_2$—, 3-ethoxycarbonyl-1-piperidinyl-$CH_2$—, 3-carboxy-1-piperidinyl-$CH_2$—, 4-ethoxycarbonyl-1-piperidinyl-$CH_2$—, 4-carboxy-1-piperidinyl-$CH_2$—, 4-(1-pyrrolidinyl)-1-piperidinyl-$CH_2$—, 4-(N-hydroxyethylamino)-1-piperidinyl-$CH_2$—, 4-(N-propylamino)-1-piperidinyl-$CH_2$—, 3-(N,N-diethylamino)carbonyl-1-piperidinyl-$CH_2$—, 4-(methyl)phenoxymethylenyl, 4-(N,N-dimethylaminomethylenyl)-phenoxymethylenyl, methylaminothiocarbonyl, methoxymethylenyl, ethylaminothiocarbonyl, N,N-dimethylaminoethylenyl, N,N-diethylaminomethylenyl, N-methylaminomethylenyl, N-(hydroxypropyl)aminomethylenyl, N-ethylaminomethylenyl, Boc-aminoethoxymethylenyl, aminoethoxymethylenyl, N-Boc-piperidin-4-ylethoxy, 1-methyl-4-piperidinylethoxy, 4-piperidinylethoxy, 4-piperidinylmethoxy, N,N-dimethylaminoethoxy, 4-methylphenoxy, 4-(aminoethyl)phenoxy, 4-(1-imidazolyl)phenoxy, 2,4-dimethyiphenoxy, phenoxy, 4-cyanophenoxy, 4-[1,3]dioxolan-2-ylphenoxy, 4-fluorophenoxy, 3,4-difluorophenoxy, ethoxycarbonyl, 1-piperidinylcarbonyl, methylaminocarbonyl, ethylaminocarbonyl, N,N-diethylaminocarbonyl, aminocarbonyl, N,N-diethylamino, N-(N',N'-dimethylaminoethylenyl)aminocarbonyl, N,N diethylamino (2-propylenyl)aminomethylenyl, N,N-diethylamino(1-propylenyl)-aminomethylenyl and N-(N',N'-dimethylaminoethylenyl)amino.

17. Compound of claim 1 and pharmaceutically acceptable derivatives thereof selected from:

1-[6-(3-Methyl-piperidin-1-ylmethyl)-pyridin-2-yl]-3-(2-phenyl-thiazol-4-yl)-urea;

1-[4-(Piperidine-1-carbonyl)-pyridin-2-yl]-3-(2-pyridin-4-yl-thiazol4-yl)-urea;

1-(2-Chloro-thiazol-4-yl)-3-[4-(piperidine-1-carbonyl)-pyridin-2-yl]-urea;

N,N-Diethyl-2-[3-(2-pyridin4-yl-thiazol-4-yl)-ureido]-isonicotinamide;

N,N-Diethyl-2-[3-(2-phenyl-thiazol-4-yl)-ureido]-isonicotinamide;
2-[3-(2-Bromo-thiazol-4-yl)-ureido]-N,N-diethyl-isonicotinamide;
1-(4-Diethylaminomethyl-pyridin-2-yl)-3-(2-pyridin-4-yl-thiazol-4-yl)-urea;
1-[6-(2,6-Dimethyl-piperidin-1-ylmethyl)-pyridin-2-yl]-3-(2-pyridin-4-yl-thiazol-4-yl)-urea;
1-[6-(1-Piperidin-1-yl-ethyl)-pyridin-2-yl]-3-(2-pyridin-4-yl-thiazol4-yl)-urea;
2-({6-[3-(2-Pyridin-4-yl-thiazol-4-yl)-ureido]-pyridin-2-ylamino]-methyl)-piperidine-1-carboxylic acid tert-butyl ester;
1-{6-[(Piperidin-2-ylmethyl)-aminol-pyridin-2-yl}-3-(2-pyridin-4-yl-thiazol-4-yl)-urea;
(S)-1-[6-(3-Methyl-piperidin-1-ylmethyl)-pyridin-2-yl]-3-(2-pyridin-4-yl-thiazol-4-yl)-urea;
(R)-1-[6-(3-Methyl-piperidin-1-ylmethyl)-pyridin-2-yl]-3-(2-pyridin-4-yl-thiazol-4-yl)-urea;
1-(2-Chloro-thiazol-4-yl)-3-(6-piperidin-1-ylmethyl-pyridin-2-yl)-urea;
1-(2-Bromo-thiazol-4-yl)-3-[6-(2-piperidin-4-yl-ethoxy)-pyridin-2-yl]-urea;
1-(2-Chloro-thiazol-4-yl)-3-[6-(2-piperidin4-yl-ethoxy)-pyridin-2-yl]-urea;
1-(2-Bromo-thiazol-4-yl)-3-[6-(piperidin4-ylmethoxy)-pyridin-2-yl]-urea;
1-(2-Chloro-thiazol-4-yl)-3-[6-(piperidin-4-ylmethoxy)-pyridin-2-yl]-urea;
1-(2-Cyclopropyl-thiazol-4-yl)-3-[6-(2-piperidin-4-yl-ethoxy)-pyridin-2-yl]-urea;
1-[6-(Isopropylamino-methyl)-pyridin-2-yl]-3-(2-pyridin-4-yl-thiazol4-yl)-urea;
1-[6-(Isopropylamino-methyl)-pyridin-2-yl]-3-(2-phenyl-thiazol-4-yl)-urea;
1-(2-Bromo-thiazol-4-yl)-3-[6-(isopropylamino-methyl)-pyridin-2-yl]-urea;
1-(1'-Methyl-1,2',3',6'-tetrahydro-[2,4]-bipyridinyl-6-yl)-3-(2-pyridin-4-yl-thiazol-4-yl)-urea;
1-(2-Bromo-thizol-4-yl)-3-(1'-methyl-1',2',3',6'-tetrahydro-[2,4']bipyridinyl-6-yl)-urea;
1-(1'-Methyl-1,2',3',6'-tetrahydro-2 [2,4]bipyridinyl-6-yl)-3-(2-phenyl-thiazol-4-yl)-urea;
1-[6-(3-Hydroxy-propylamino)-pyridin-2-yl]-3-(2-pyridin-4-yl-thizol-4-yl)-urea;
1-(2-Bromo-thiazol-4-yl)-3-[6-(3-hydroxy-propylamino)-pyridin-2-yl]-urea;
1-(1'-Methyl-1',2',3',4',5',6'-hexahydro-[2,4']bipydrinyl-6-yl)-3-(2-pyridin-4-yl-thiazol-4-yl)-urea;
1-(1'-Methyl-1',2',3',4',5',6'-hexahydro-[2,4']bipyridinyl-6-yl)-3-(2-phenyl-thiazol4-yl)-urea;
6-[3-(2-Pyridin-4-yl-thizol-4-yl)-ureido]-3',6'-dihydro-2'H-[2,4]bipyridinyl-1'-carboxylic acid tert-butyl ester;
1-(2-Pyridin-4-yl-thiazol4-yl)-3-(1',2',3',6'-tetrahydro-[2,4']bipyridinyl-6-yl)-urea;
6-[3-(2-Pyridin-4-yl-thiazol-4-yl)-ureido]-pyridine-2-carbothioic acid diethylamide;
1-(2-Bromo-thiazol-4-yl)-3-[6-(3-methyl-piperidin-1-ylmethyl)-pyridin-2-yl]-urea;
1-(2-Chloro-thiazol-4-yl)-3-[6-(3-methyl-piperidin-1-ylmethyl)-pyridin-2-yl]-urea;
1-(2-Phenyl-thiazol-4-yl)-3-[4-(piperidine-1-carbonyl)-pyridin-2-yl]-urea;
1-(2-Bromo-thiazol-4-yl)-3-[4-(piperidine-1-carbonyl)-pyridin-2-yl]-urea;
1-[2-(2-Methoxy-pyridin-4-yl)-thiazol-4-yl]-3-(6-phenoxy-pyridin-2-yl)-urea;
1-[6-(2-Dimethylamino-ethoxy)-pyridin-2-yl]-3-[2-(2-methoxy-pyridin-4-yl)-thiazol4-yl]-urea;
1-(6-Diethylaminomethylpyridin-2-yl)-3-(2-phenylthiazol4-yl)urea;
1-[6-(2-Piperidin-4-yl-ethoxy)pyridin-2-yl]-3-[2-phenylthiazol-4-yl]urea;
Diethyl 6-[3-(2-phenylthiazol-4-yl)ureido]-pyridine-2-carboxamide;
1-[6-(Piperidin-4-ylmethoxy)-pyridin-2-yl]-3-(2-pyridin-4-yl-thiazol-4-yl)-urea;
1-[6-(1-Methyl-piperidin-4-ylmethoxy)-pyridin-2-yl]-3-(2-pyridin-4-yl-thiazol-4-yl)-urea;
1-[6-(1-Methyl-piperidin-4-yloxy)-pyridin-2-yl]-3-(2-pyridin-4-yl-thiazol-4-yl)-urea;
1-(2-Phenyl-thiazol-4-yl)-3-[6-(piperidin-4-ylmethoxy)-pyridin-2-yl]-urea;
1-[6-(1-Methyl-piperidin-4-ylmethoxy)-pyridin-2-yl]-3-(2-phenyl-thiazol-4-yl)-urea;
1-[6-(1-Methyl-piperidin-4-yloxy)-pyridin-2-yl]-3-(2-phenyl-thiazol4-yl)-urea;
1-[2-(2-Methoxy-pyridin-4-yl)-thiazol-4-yl]-3-(6-piperidin-1-ylmethyl-pyridin-2-yl)-urea; and
[2-(2-Chloro-pyridin-4-yl)-thiazol-4-yl]-3-(6-piperidin-1-ylmethyl-pyridin-2-yl)-urea.

18. Compound of claim 1 and pharmaceutically acceptable derivatives thereof selected from:
1-[6-(3-Methyl-piperidin-1-ylmethyl)-pyridin-2-yl]-3-(2-phenyl-thiazol-4-yl)-urea;
1-[4-(Piperidine-1-carbonyl)-pyridin-2-yl]-3-(2-pyridin-4-yl-thiazol4-yl)-urea;
N,N-Diethyl-2-[3-(2-pyridin-4-yl-thiazol-4-yl)-ureido]-isonicotinamide;
1-(4-Diethylaminomethyl-pyridin-2-yl)-3-(2-pyridin-4-yl-thiazol-4-yl)-urea;
1-[6-(2,6-Dimethyl-piperidin-1-ylmethyl)-pyridin-2-yl]-3-(2-pyridin-4-yl-thiazol-4-yl)-urea;
1-[6-(1-Piperidin-1-yl-ethyl)-pyridin-2-yl]-3-(2-pyridin-4-yl-thiazol-4-yl)-urea;
2-({6-[3-(2-Pyridin-4-yl-thiazol4-yl)-ureido]-pyridin-2-ylamino}-methyl)-piperidine-1-carboxylic acid tert-butyl ester;
1-{6-[(Piperidin-2-ylmethyl)-amino]-pyridin-2-yl}-3-(2-pyridin-4-yl-thiazol-4-yl)-urea;
(S)-1-[6-(3-Methyl-piperidin-1-ylmethyl)-pyridin-2-yl]-3-(2-pyridin4-yl-thiazol-4-yl)-urea;
(R)-1-[6-(3-Methyl-piperidin-1-ylmethyl)-pyridin-2-yl]-3-(2-pyridin-4-yl-thiazol-4-yl)-urea;
1-(2-Chloro-thiazol-4-yl)-3-(6-piperidin-1-ylmethyl-pyridin-2-yl)-urea;
1-(2-Bromo-thiazol-4-yl)-3-[6-(2-piperidin-4-yl-ethoxy)-pyridin-2-yl]-urea;
1-(2-Chloro-thiazol-4-yl)-3-[6-(2-piperidin-4-yl-ethoxy)-pyridin-2-yl]-urea;
1-(2-Bromo-thiazol-4-yl)-3-[6-(piperidin4-ylmethoxy)-pyridin-2-yl]-urea;
1-(2-Chloro-thiazol-4-yl)-3-[6-(piperidin-4-ylmethoxy)-pyridin-2-yl]-urea;
1-(2-Cyclopropyl-thiazol-4-yl)-3-[6-(2-piperidin4-yl-ethoxy)-pyridin-2-yl]-urea;

Isopropyl-{6-[3-(2-pyridin-4-yl-thiazol-4-yl)-ureido]-pyridin-2-ylmethyl}-carbamic acid tert-butyl ester;

1-[6-(Isopropylamino-methyl)-pyridin-2-yl]-3-(2-pyridin-4-yl-thiazol-4-yl)-urea;

Isopropyl-{6-[3-(2-phenyl-thiazol-4-yl)-ureido]-pyridin-2-ylmethyl}-carbamic acid tert-butyl ester;

1-[6-(Isopropylamino-methyl)-pyridin-2-yl]-3-(2-phenyl-thiazol-4-yl)-urea;

1-(1'-Methyl-1',2',3',6'-tetrahydro-[2,4']bipyridinyl-6-yl)-3-(2-pyridin-4-yl-thiazol4-yl)-urea;

1-(2-Bromo-thizol-4-yl)-3-(1'-methyl-1',2',3',6'-tetrahydro-[2,4']bipyridinyl-6-yl)-urea;

1-(1'-Methyl-1',2',3',6'-tetrahydro-2,2,4']bipyridinyl-6-yl)-3-(2-phenyl-thiazol-4-yl)-urea;

1-[6-(3-Hydroxy-propylamino)-pyridin-2-yl]-3-(2-pyridin-4-yl-thizol-4-yl)-urea;

1-(2-Bromo-thiazol-4-yl)-3-[6-(3-hydroxy-propylamino)-pyridin-2-yl]-urea;

1-(1'-Methyl-1',2',3',4',5',6'-hexahydro-[2,4']bipydrinyl-6-yl)-3-(2-pyridin-4-yl-thiazol-4-yl)-urea;

1-(1'-Methyl-1',2',3',4',5',6'-hexahydro-[2,4']bipyridinyl-6-yl)-3-(2-phenyl-thiazol4-yl)-urea;

6-[3-(2-Pyridin-4-yl-thizol-4-yl)-ureido]-3',6'-dihydro-2,4'-[2,4]bipyridinyl-1'-carboxylic acid tert-butyl ester;

1-(2-Pyridin4-yl-thiazol-4-yl)-3-(1',2',3',6'-tetrahydro-[2,4']bipyridinyl-6-yl)-urea;

6-[3-(2-Pyridin-4-yl-thiazol4-yl)-ureido]-pyridine-2-carbothioic acid diethylamide;

1-(2-Bromo-thiazol-4-yl)-3-[6-(3-methyl-piperidin-1-ylmethyl)-pyridin-2-yl]-urea;

1-(2-Chloro-thiazol-4-yl)-3-[6-(3-methyl-piperidin-1-ylmethyl)-pyridin-2-yl]-urea;

1-[6-(2-Dimethylamino-ethoxy)-pyridin-2-yl]-3-[2-(2-methoxy-pyridin-4-yl)-thiazol-4-yl]-urea;

1-(6-Diethylaminomethylpyridin-2-yl)-3-(2-phenylthiazol-4-yl)urea;

1-[6-(2-Piperidin-4-yl-ethoxy)pyridin-2-yl]-3-[2-phenylthiazol-4-yl]urea;

Diethyl 6-[3-(2-phenylthiazol-4-yl)ureido]-pyridine-2-carboxamide;

1-[6-(Piperidin-4-ylmethoxy)-pyridin-2-yl]-3-(2-pyridin-4-yl-thiazol4-yl)-urea;

1-[6-(1-Methyl-piperidin-4-ylmethoxy)-pyridin-2-yl]-3-(2-pyridin-4-yl-thiazol-4-yl)-urea;

1-[6-(1-Methyl-piperidin4-yloxy)-pyridin-2-yl]-3-(2-pyridin-4-yl-thiazol-4-yl)-urea;

1-(2-Phenyl-thiazol-4-yl)-3-[6-(piperidin-4-ylmethoxy)-pyridin-2-yl]-urea;

1-[6-(1-Methyl-piperidin-4-ylmethoxy)-pyridin-2-yl]-3-(2-phenyl-thiazol-4-yl)-urea;

1-[6-(1-Methyl-piperidin-4-yloxy)-pyridin-2-yl]-3-(2-phenyl-thiazol-4-yl)-urea;

1-[2-(2-Methoxy-pyridin-4-yl)-thiazol-4-yl]-3-(6-piperidin-1-ylmethyl-pyridin-2-yl)-urea; and

[2-(2-Chloro-pyridin-4-yl)-thiazol-4-yl]-3-(6-piperidin-1-ylmethyl-pyridin-2-yl)-urea.

\* \* \* \* \*